United States Patent
Reznik et al.

(10) Patent No.: US 11,865,135 B2
(45) Date of Patent: Jan. 9, 2024

(54) ß-1,6-GLUCAN THERAPEUTIC ANTIBODY CONJUGATES

(71) Applicant: Innate Biotherapeutics, LLC, Newton, MA (US)

(72) Inventors: Gabriel Oscar Reznik, Bedford, MA (US); John James Kane, Cambridge, MA (US); James Michael Siedlecki, Burlington, MA (US); Zuzana Dostalova, Cambridge, MA (US); Isabelle Sansal-Castellano, Jamaica Plain, MA (US); Ifat Rubin-Bejerano, Newton, MA (US); Hua Miao, Newton, MA (US); Eric Steven Furfine, Lincoln, MA (US)

(73) Assignee: Innate Biotherapeutics, LLC, Newton, MA (US)

( * ) Notice: Subject to any disclaimer, the term of this patent is extended or adjusted under 35 U.S.C. 154(b) by 238 days.

(21) Appl. No.: 16/466,927

(22) PCT Filed: Dec. 5, 2017

(86) PCT No.: PCT/US2017/064631
§ 371 (c)(1),
(2) Date: Jun. 5, 2019

(87) PCT Pub. No.: WO2018/106645
PCT Pub. Date: Jun. 14, 2018

(65) Prior Publication Data
US 2020/0030360 A1    Jan. 30, 2020

Related U.S. Application Data

(60) Provisional application No. 62/431,362, filed on Dec. 7, 2016.

(51) Int. Cl.
| | | |
|---|---|---|
| *A61K 31/716* | (2006.01) | |
| *A61K 47/61* | (2017.01) | |
| *C07K 16/28* | (2006.01) | |
| *C07K 16/32* | (2006.01) | |

(52) U.S. Cl.
CPC ............ *A61K 31/716* (2013.01); *A61K 47/61* (2017.08); *C07K 16/2863* (2013.01); *C07K 16/32* (2013.01); *C07K 2317/24* (2013.01); *C07K 2317/73* (2013.01); *C07K 2317/90* (2013.01)

(58) Field of Classification Search
None
See application file for complete search history.

(56) References Cited

U.S. PATENT DOCUMENTS

| | | | |
|---|---|---|---|
| 2005/0095250 A1 | 5/2005 | Yvin et al. | |
| 2006/0009419 A1 | 1/2006 | Ross et al. | |
| 2007/0141084 A1* | 6/2007 | Lee | A61K 39/00 424/236.1 |
| 2011/0014189 A1 | 1/2011 | Soula et al. | |
| 2012/0288495 A1 | 11/2012 | Vasilakos | |
| 2014/0308238 A1 | 10/2014 | Rubin-Bejerano et al. | |
| 2014/0370046 A1 | 12/2014 | Bose et al. | |
| 2020/0030360 A1 | 1/2020 | Reznik et al. | |

FOREIGN PATENT DOCUMENTS

| | | |
|---|---|---|
| WO | WO-2009/134891 A2 | 11/2009 |
| WO | WO-2011011617 A1 | 1/2011 |
| WO | WO 2014/124316 * | 8/2014 |
| WO | WO-2015/172040 A2 | 11/2015 |
| WO | WO-2016/118654 A1 | 7/2016 |
| WO | WO-2016/196682 A1 | 12/2016 |
| WO | WO-2018/106644 A1 | 6/2018 |

OTHER PUBLICATIONS

Badescu et al., Bioconjugate Chemistray, 24:1124-1136, May 2014.*
Ayoub et al., "Correct primary structure assessment and extensive glyco-profiling of cetuximab by a combination of intact, middle-up, middle-down and bottom-up ESI and MALDI mass spectrometry techniques," mAbs Supplemental, 5:699-710 (2013).
Ayoub et al., "Correct primary structure assessment and extensive glyco-profiling of cetuximab by a combination of intact, middle-up, middle-down and bottom-up ESI and MALDI mass spectrometry techniques," mAbs, 5:699-710 (2013).
Benvenuti et al., "Oncogenic activation of the RAS/RAF signaling pathways impairs the response to metastatic colorectal cancers to anti-epidermal growth factor receptor antibody therapies," Cancer Research, 67"2643-2648 (2007).
Bonner et al., "Radiotherapy plus cetuximab for squamous-cell carcinoma of the head and neck," New England Journal of Medicine, 354:567-578 (2006).
Jain et al., "Current ADC Linker Chemistry," Pharm Res, 32:3526-3540 (2015).
Rodriguez et al., "Fc gamma receptor polymorphisms as predictive markers of Cetuximab efficacy in epidermal growth factor receptor downstream-mutated metastatic colorectal cancer," Journal of Cancer, 48:1774-1780 (2012).
Rubin-Bejerano et al., "MAbXcite: a novel immunotherapy platform that initiates a robust anti-cancer immune response by recruiting and activating neutrophils," Journal for Immunotherapy of Cancer, 2(Suppl3):p. 262 (2014).
Wan et al., "A potentially valuable advance in the synthesis of carbohydrate-based anticancer vaccines through extended cycloaddition chemistry," Journal of Organic Chemistry, 71:8244-8249 (2006).

(Continued)

*Primary Examiner* — Marianne P Allen
(74) *Attorney, Agent, or Firm* — FOLEY HOAG LLP

(57) ABSTRACT

The present invention encompasses embodiments in which a therapeutic antibody is conjugated to β-1,6-glucan oligomers. Thus, the present invention includes, among other things, compositions including a therapeutic antibody conjugated to one or more β-1,6-glucan oligomers. The present invention further includes, among other things, methods of making and/or using such β-1,6-glucan conjugates. In certain embodiments, a β-1,6-glucan conjugate of the present invention is useful as a therapeutic or in a method of therapy.

17 Claims, 73 Drawing Sheets

Specification includes a Sequence Listing.

(56) References Cited

OTHER PUBLICATIONS

"β-Glucans: bittersweet ligands of Dectin-1," InvivoGen Insight, pp. 1-8 (2013).
Extended European Search Report for EP Application No. 16804366.9 dated Jan. 16, 2019.
International Preliminary Report on Patentability for International Application No. PCT/US16/35346, dated Jul. 25, 2017.
International Preliminary Report on Patentability for International Application No. PCT/US2017/064630 dated Jun. 11, 2019.
International Preliminary Report on Patentability for International Application No. PCT/US2017/064631 dated Jun. 20, 2019.
International Search Report and Written Opinion for International Application No. PCT/US16/35346, dated Sep. 13, 2016.
International Search Report and Written Opinion for International Application No. PCT/US17/64630, dated Mar. 15, 2018.
International Search Report and Written Opinion for International Application No. PCT/US17/64631, dated Mar. 6, 2018.
InvivoGen Product Information, Pustulan: Beta-glucan from Lasallia pustulata—Dectin-1 ligand, created Dec. 9, 2013 [http://www.invivogen.com/PDF/Pustulan_TDS.pdf].
Liu et al., "Combined yeast-derived beta-glucan with anti-tumor monoclonal antibody for cancer immunotherapy," Experimental and Molecular Pathology, 86(3):208-214 (2009).
Sansal-Castellano et al., "The mAbXcite platform modifies the tumor microenvironment when applied to an immune-oncology anti-CTLA4 antibody," J Immunother Cancer, 3(Suppl 2): p. 414 (2015).
Extended European Search Report for EP Application No. 17879636.3 dated Jul. 22, 2020.
Mitdeshpandecenter: "Ifat Rubin-Bejerano—IdeaStream 2015" Retrieved from the Internet <https://www.youtube.com/watch?v=y-MuV0wl6S4>: (2015).

* cited by examiner

FIG. 18  Evaluate anti-β 1,6 Glucan IgG2 binding to carbohydrate conjugated to Cetuximab
Carbohydrate: same size – various load Evaluate anti-β 1,6 Glucan IgG2 binding to carbohydrate conjugated to Cetuximab
Comparison: same carbohydrate size – various

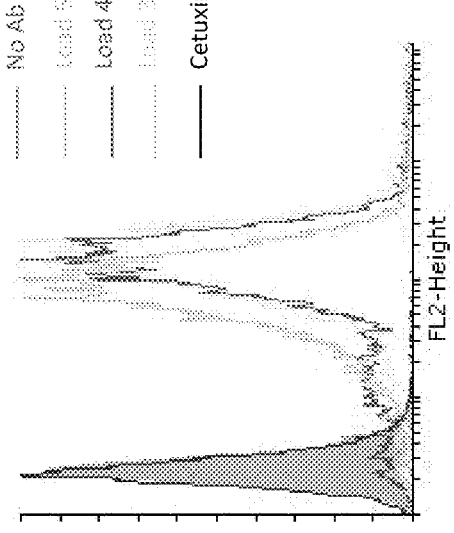
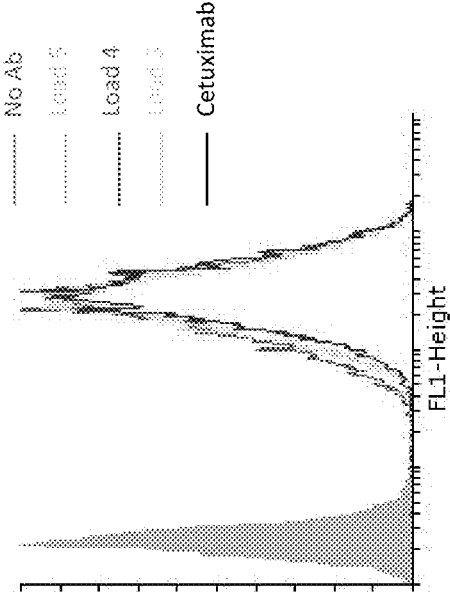
FIG. 24

FIG. 25  mAbXcite-cetuximab is stable in human serum

FIG. 27
mAbXcite-cetuximab is stable in human serum
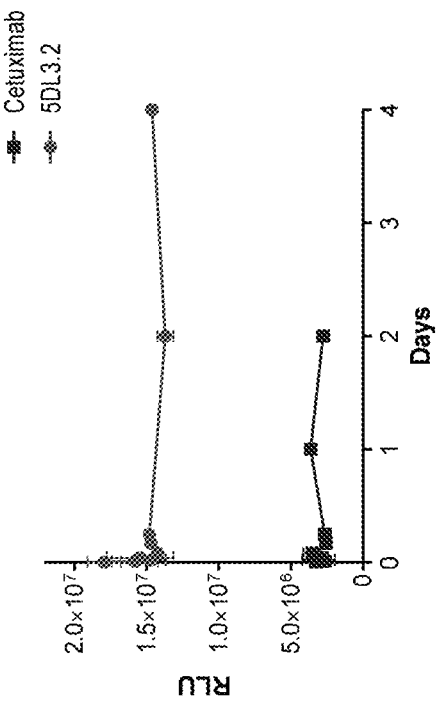
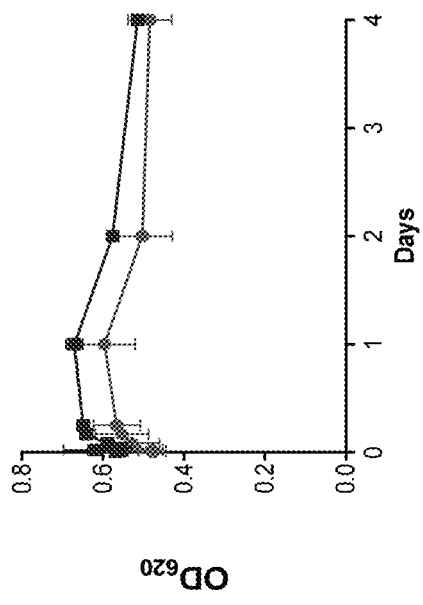

mAbXcite-cetuximab is stable in heat inactivated human serum
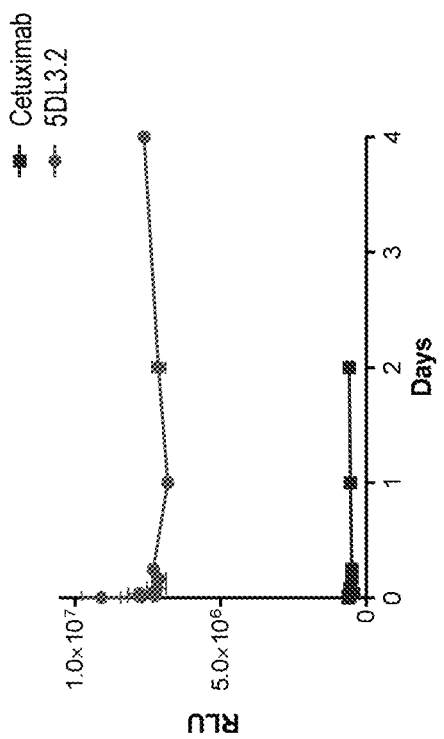
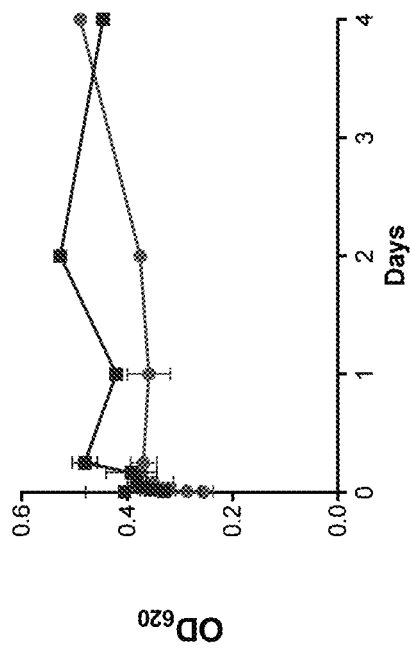
FIG. 28

FIG. 37  Pharmacokinetic of mAbXcite-cetuximab in absence of tumor
-- Antibody stability --
Carbohydrate: same load—various sizes FIG. 44
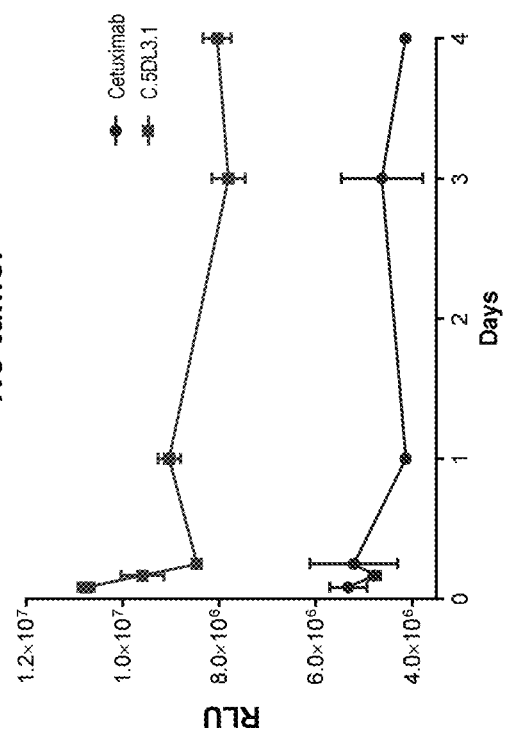
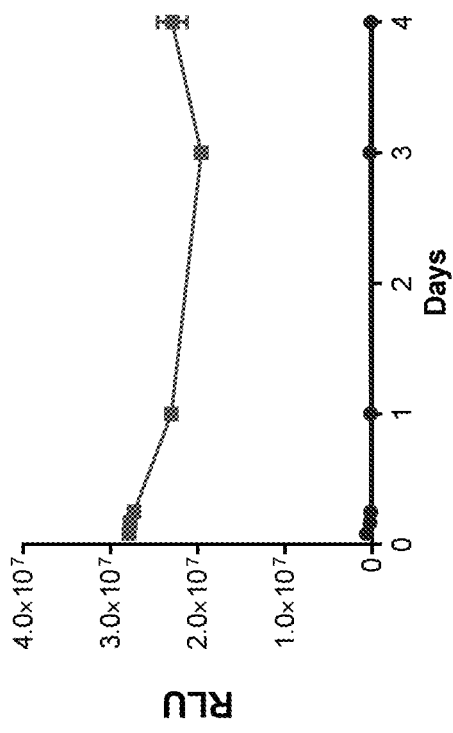

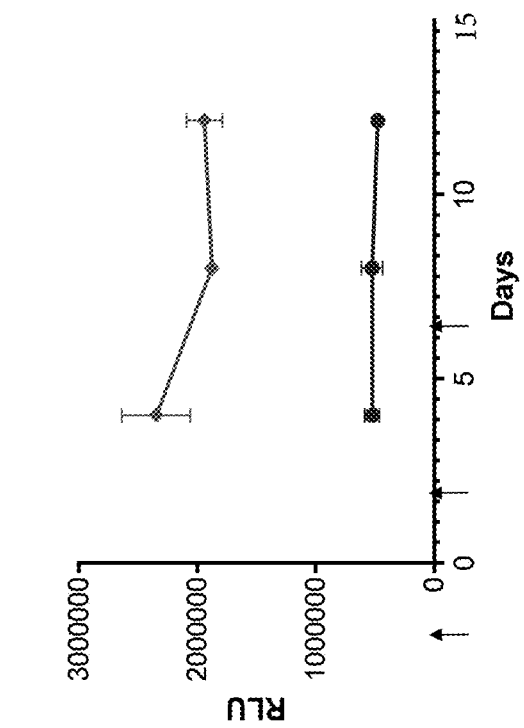
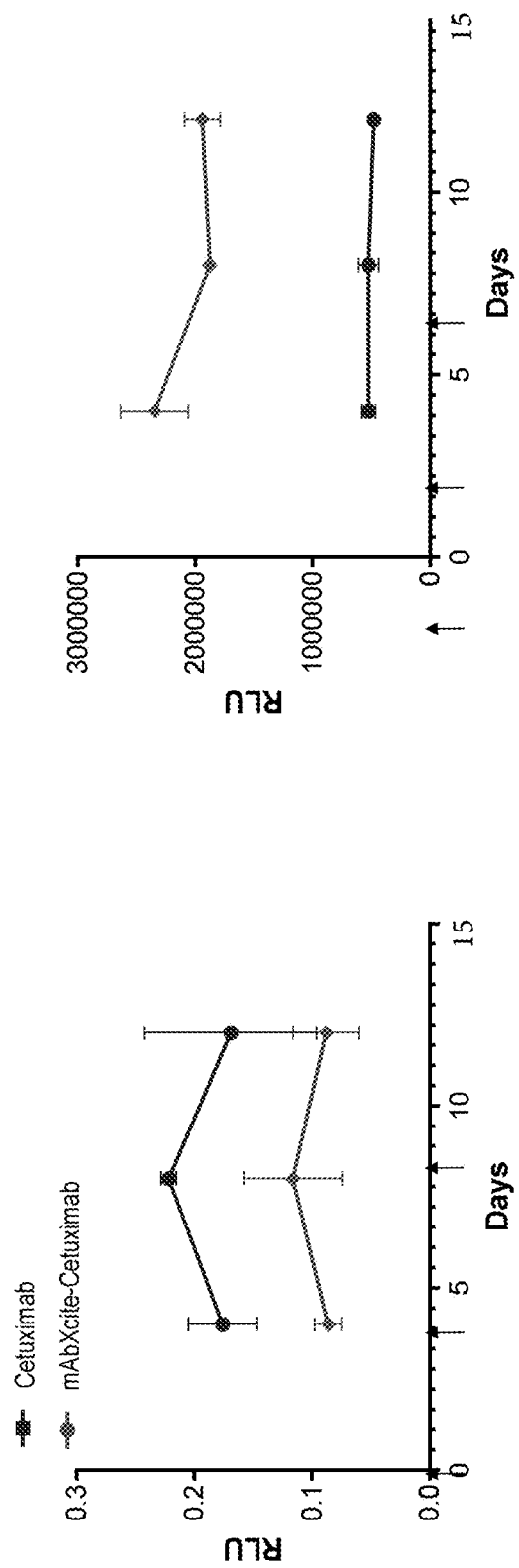
FIG. 46

FIG. 47  Pharmacokinetics of mAbXcite-cetuximab in tumor bearing animals
Antibody and β 1,6 Glucan detection --
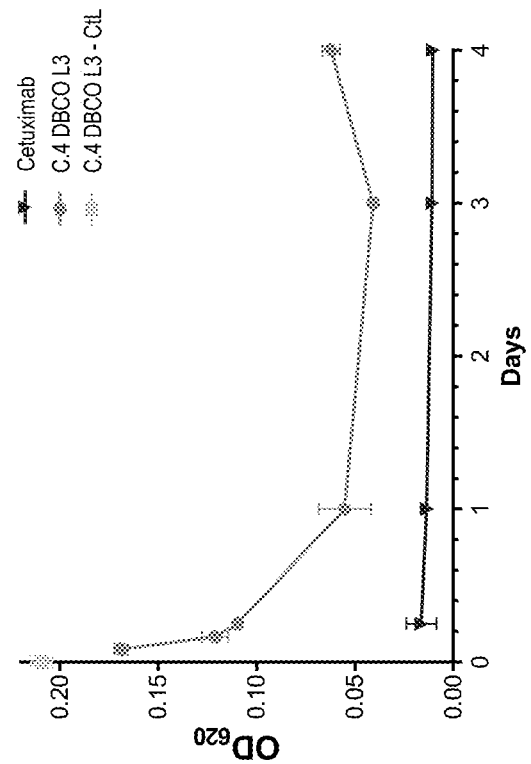
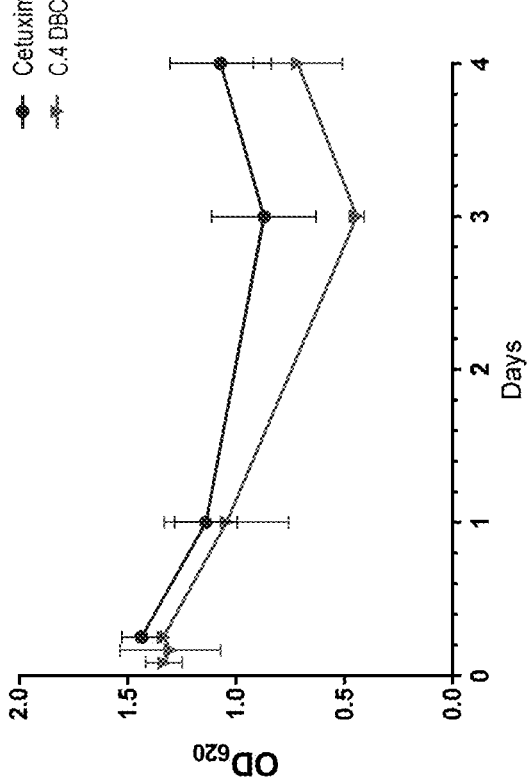

FIG. 48
Pharmacokinetic of mAbXcite-cetuximab in absence of tumor or in tumor bearing mice
-- Antibody stability --
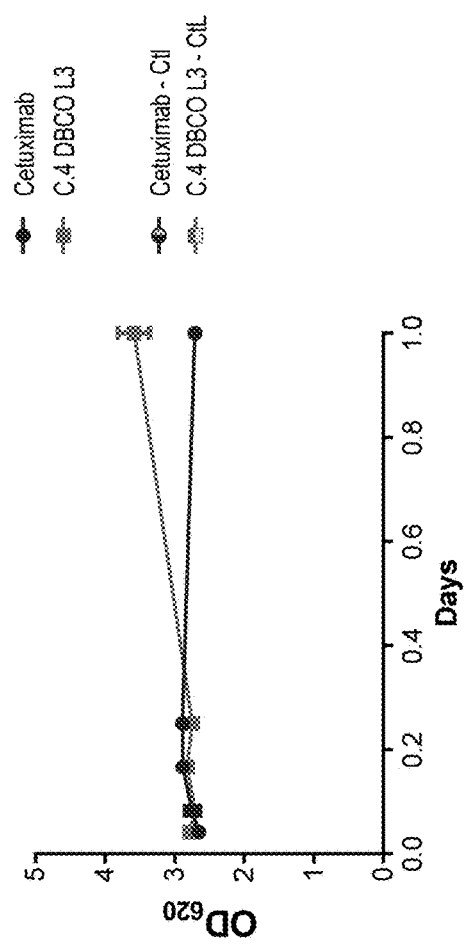
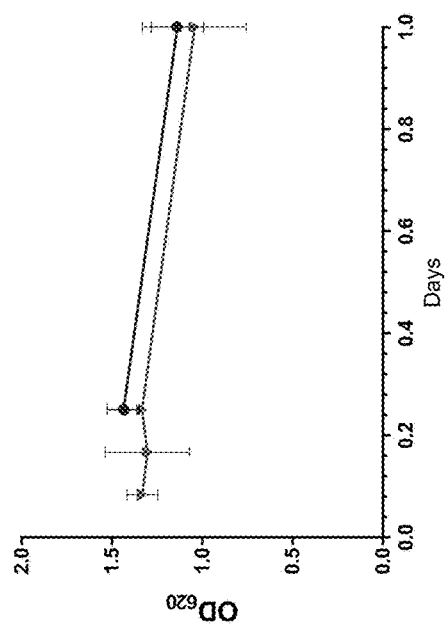

FIG. 49
Pharmacokinetic of mAbXcite-cetuximab in absence of tumor or in tumor bearing mice
— β 1,6 Glucan detection —
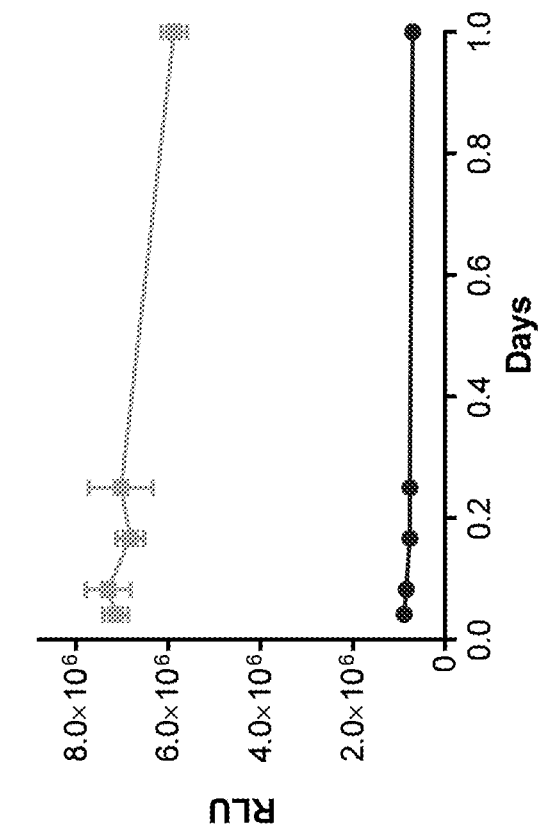
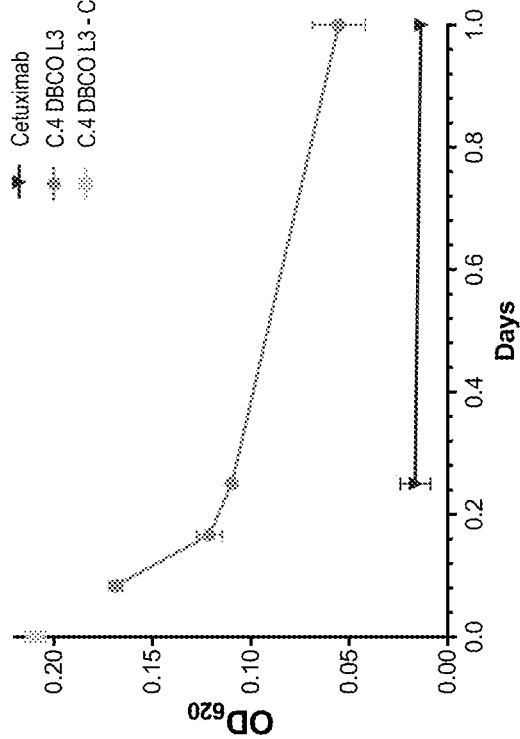

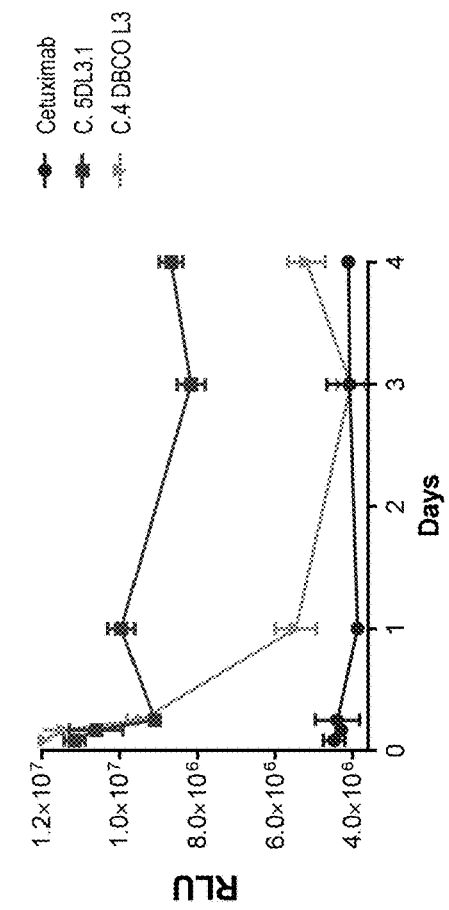
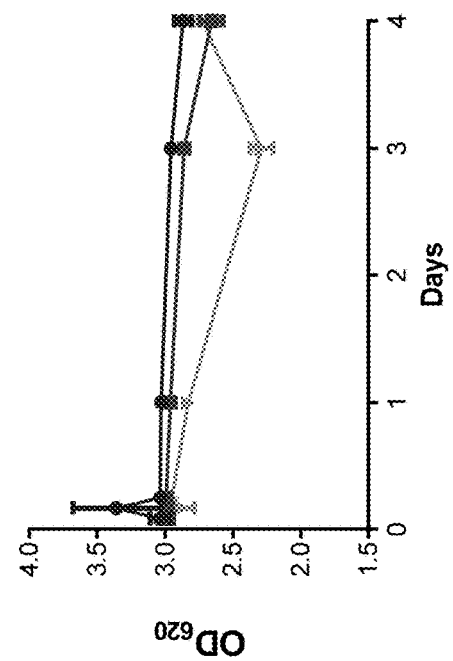
FIG. 50

FIG. 53  mAbXcite-cetuximab efficacy in BRAF mutant colorectal tumor model

FIG. 54  mAbXcite-cetuximab efficacy in KRAS mutant colorectal tumor model — DBCO: comparison 4 and 6 mer FIG. 55  mAbXcite-cetuximab efficacy in KRAS mutant colorectal tumor model
-- Compare DBCO & direct conjugation --

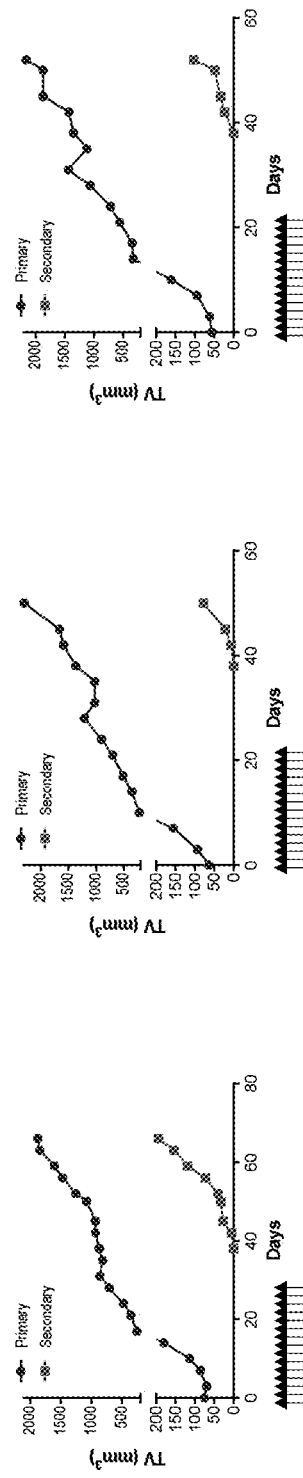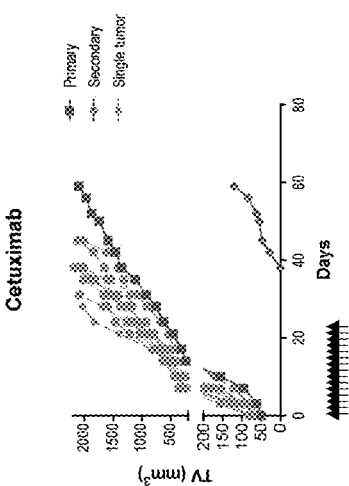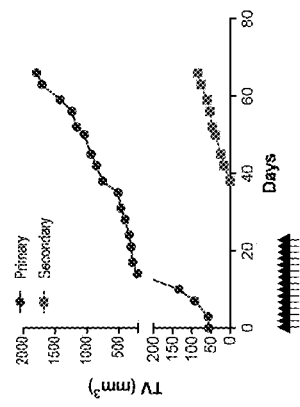
FIG. 66 ic
β-1,6-GLUCAN THERAPEUTIC ANTIBODY CONJUGATES

CROSS-REFERENCE TO RELATED APPLICATIONS

This application is a national-stage filing under 35 U.S.C. § 371 of PCT International Application No. PCT/US2017/064631, filed Dec. 5, 2017, which claims priority and benefit of U.S. Provisional Application No. 62/431,362 filed on Dec. 7, 2016.

SEQUENCE LISTING

The instant application contains a Sequence Listing which has been filed electronically in ASCII format and is hereby incorporated by reference in its entirety. Said ASCII copy, created on Sep. 24, 2019, is named INQ-00601_(35024-00601)_SL.txt and is 140,423 bytes in size.

BACKGROUND

Therapeutic antibodies have been used for the treatment of various cancers. While these antibodies have efficacy for the treatment of many cancers, there remain a number of patients for whom these treatments are not effective. There is therefore a need for new forms of therapeutic antibodies that have improved efficacy in patients and/or efficacy across a broader set of cancer patients.

For example, trastuzumab is a HER2 inhibitor monoclonal antibody used for the treatment of breast and gastric cancers. Kadcyla® (ado-trastuzumab emtansine) is an antibody-drug conjugate consisting of the monoclonal antibody trastuzumab linked to the cytotoxic agent emtansine (DM1), and is approved for the treatment of metastatic breast cancer. While HER-2 overexpression (score 2/3+) and amplification occurs most often in breast cancers, it is also seen in 18 other tumor entities including cancers of the urinary bladder, stomach, endometrium, lung and ovary (Modern Pathology (2007) 20:192-198) as well as prostate cancer (Am J Clin Pathol (2001) 116:234-239). Trastuzumab and Kadcyla® have efficacy for the treatment of these types of cancer in some but not all patients and/or under some but not all conditions. There is therefore a need for new forms of trastuzumab antibodies that have improved efficacy in cancer patients and/or efficacy across a broader set of cancer patients.

In another example, cetuximab is an epidermal growth factor receptor (EGFR) inhibitor used for the treatment of squamous cell Carcinoma of the head and neck (SCCHN) and colorectal cancer (e.g., KRAS wild-type EGFR-expressing colorectal cancer). Cetuximab has efficacy for the treatment of these types of cancer in some but not all patients and/or under some but not all conditions. There is therefore a need for new forms of cetuximab antibodies that have improved efficacy in patients and/or efficacy across a broader set of cancer patients.

Many other antibodies, including, but not limited to cergutuzumab; ibritumomab tiuxetan; rituximab; tositumomab; gemtuzumab; alemtuzumab; panitumumab; depatuxizumab; sibrotuzumab; codrituzumab; patritumab; figitumumab; ganitumab; cantuzumab; ABX-MA1; bavituximab; J591; palivizumab; or bevacizumab have efficacy for the treatment of cancers, in some, but not all patients and/or under some but not all conditions. There is therefore a need for new forms of these, and other, therapeutic antibodies that have improved efficacy in patients and/or efficacy across a broader set of cancer patients.

SUMMARY

The present invention encompasses embodiments in which a therapeutic antibody is conjugated to β-1,6-glucan oligomers. Thus, the present invention includes, among other things, compositions including a therapeutic antibody conjugated to one or more β-1,6-glucan oligomers. The present invention further includes, among other things, methods of making and/or using these β-1,6-glucan conjugates. In certain embodiments, a β-1,6-glucan conjugate of the present invention is useful as a therapeutic or in a method of therapy.

In certain embodiments, the present invention encompasses a composition including a therapeutic antibody conjugated to between 1 and 6 β-1,6-glucan oligomers (e.g., between 1 and 5, 1 and 4, or 1 and 3 β-1,6-glucan oligomers), wherein each β-1,6-glucan oligomer is independently comprised of between 2 and 10 glucose monomer units. In certain embodiments, each of the β-1,6-glucan oligomers is independently comprised of between 2 and 8 glucose monomer units, each of the β-1,6-glucan oligomers is independently comprised of between 2 and 6 glucose monomer units, each of the β-1,6-glucan oligomers is independently comprised of between 4 and 6 glucose monomer units, each of the β-1,6-glucan oligomers is comprised of 8 glucose monomer units, each of the β-1,6-glucan oligomers is comprised of 7 glucose monomer units, each of the β-1,6-glucan oligomers is comprised of 6 glucose monomer units, each of the β-1,6-glucan oligomers is comprised of 5 glucose monomer units, each of the β-1,6-glucan oligomers is comprised of 4 glucose monomer units, each of the β-1,6-glucan oligomers is comprised of 3 glucose monomer units, or each of the β-1,6-glucan oligomers is comprised of 2 glucose monomer units. In certain embodiments, the therapeutic antibody is conjugated to between 2 and 4 β-1,6-glucan oligomers, e.g., to 3 β-1,6-glucan oligomers.

In certain particular embodiments, the therapeutic antibody is conjugated to between 2 and 4 β-1,6-glucan oligomers, and the β-1,6-glucan oligomers are each independently comprised of between 2 and 10 glucose monomer units. In certain particular embodiments, the therapeutic antibody is conjugated to between 2 and 4 β-1,6-glucan oligomers, and the β-1,6-glucan oligomers are each independently comprised of between 2 and 8 glucose monomer units. In certain particular embodiments, the therapeutic antibody is conjugated to between 2 and 4 β-1,6-glucan oligomers, and the β-1,6-glucan oligomers are each independently comprised of between 2 and 6 glucose monomer units. In certain particular embodiments, the therapeutic antibody is conjugated to between 2 and 4 β-1,6-glucan oligomers, and the β-1,6-glucan oligomers are each independently comprised of between 4 and 6 glucose monomer units. In certain particular embodiments, the therapeutic antibody is conjugated to between 2 and 4 β-1,6-glucan oligomers, and the β-1,6-glucan oligomers are each independently comprised of 8 glucose monomer units. In certain particular embodiments, the therapeutic antibody is conjugated to between 2 and 4 β-1,6-glucan oligomers, and the β-1,6-glucan oligomers are each independently comprised of 7 glucose monomer units. In certain particular embodiments, the therapeutic antibody is conjugated to between 2 and 4 β-1,6-glucan oligomers, and the β-1,6-glucan oligomers are each independently comprised of 6 glucose monomer units. In certain particular embodiments, the therapeutic antibody is conjugated to between 2 and 4 β-1,6-glucan oligomers, and the β-1,6-glucan oligomers are each independently comprised of 5 glucose monomer units. In certain particular embodiments, the therapeutic antibody is conjugated to between 2 and 4 β-1,6-glucan oligomers, and the β-1,6-glucan oligomers are each independently comprised of 4 glucose monomer units. In certain particular embodiments, the therapeutic antibody is conjugated to between 2 and 4 β-1,6-glucan oligomers, and the β-1,6-glucan oligomers are each independently comprised of 3 glucose monomer units. In certain particular embodiments, the therapeutic antibody is conjugated to between 2 and 4 β-1,6-glucan oligomers, and the β-1,6-glucan oligomers are each independently comprised of 2 glucose monomer units.

In certain particular embodiments, the therapeutic antibody is conjugated to 3 β-1,6-glucan oligomers, and the β-1,6-glucan oligomers are each independently comprised of between 2 and 10 glucose monomer units. In certain particular embodiments, the therapeutic antibody is conjugated to 3 β-1,6-glucan oligomers, and the β-1,6-glucan oligomers are each independently comprised of between 2 and 8 glucose monomer units. In certain particular embodiments, the therapeutic antibody is conjugated to 3 β-1,6-glucan oligomers, and the β-1,6-glucan oligomers are each independently comprised of between 2 and 6 glucose monomer units. In certain particular embodiments, the therapeutic antibody is conjugated to 3 β-1,6-glucan oligomers, and the β-1,6-glucan oligomers are each independently comprised of between 4 and 6 glucose monomer units. In certain particular embodiments, the therapeutic antibody is conjugated to 3 β-1,6-glucan oligomers, and the β-1,6-glucan oligomers are each independently comprised of 8 glucose monomer units. In certain particular embodiments, the therapeutic antibody is conjugated to 3 β-1,6-glucan oligomers, and the β-1,6-glucan oligomers are each independently comprised of 7 glucose monomer units. In certain particular embodiments, the therapeutic antibody is conjugated to 3 β-1,6-glucan oligomers, and the β-1,6-glucan oligomers are each independently comprised of 6 glucose monomer units. In certain particular embodiments, the therapeutic antibody is conjugated to 3 β-1,6-glucan oligomers, and the β-1,6-glucan oligomers are each independently comprised of 5 glucose monomer units. In certain particular embodiments, the therapeutic antibody is conjugated to 3 β-1,6-glucan oligomers, and the β-1,6-glucan oligomers are each independently comprised of 4 glucose monomer units. In certain particular embodiments, the therapeutic antibody is conjugated to 3 β-1,6-glucan oligomers, and the β-1,6-glucan oligomers are each independently comprised of 3 glucose monomer units. In certain particular embodiments, the therapeutic antibody is conjugated to 3 β-1,6-glucan oligomers, and the β-1,6-glucan oligomers are each independently comprised of 2 glucose monomer units.

In certain embodiments of the present invention, the therapeutic antibody is conjugated to the β-1,6-glucan oligomers according to Formula II:

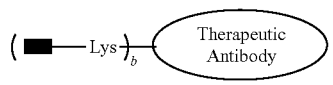

II wherein: Lys is a lysine residue; b is between 1 and 6, 1 and 5, 1 and 4, or 1 and 3; and ■ is a compound of Formula I:

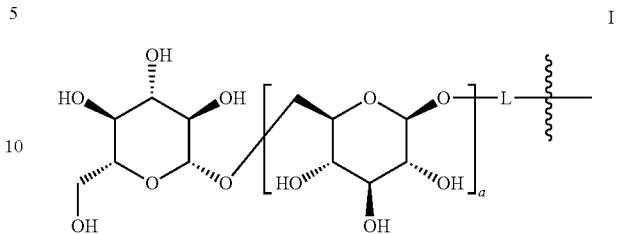

I wherein: a is between 1 and 9, 1 and 8, 1 and 7, 1 and 6, 1 and 5, 1 and 4 or 1 and 3; L is a linker; and "∼∼∼" represents a point of attachment between two atoms.

In certain embodiments of the present invention, ■ is a compound of Formula Ia:

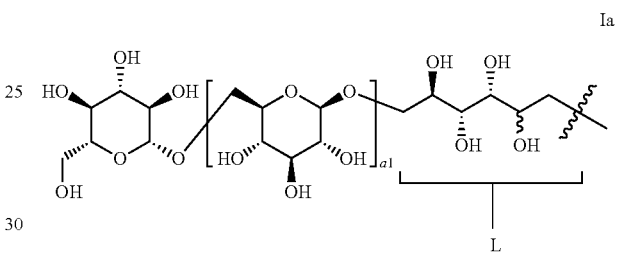

Ia wherein: $a^1$ is between 1 and 9, 1 and 8, 1 and 7, 1 and 6, 1 and 5, 1 and 4 or 1 and 3; and "∼∼∼" represents a point of attachment between two atoms.

In some embodiments of the present invention, a therapeutic antibody is cergutuzumab; ibritumomab tiuxetan; rituximab; tositumomab; gemtuzumab; alemtuzumab; cetuximab; panitumumab; depatuxizumab; sibrotuzumab; codrituzumab; trastuzumab; patritumab; figitumumab; ganitumab; cantuzumab; ABX-MA1; bavituximab; J591; palivizumab; or bevacizumab.

In some embodiments of the present invention, a therapeutic antibody is cergutuzumab; ibritumomab tiuxetan; rituximab; tositumomab; gemtuzumab; alemtuzumab; panitumumab; depatuxizumab; sibrotuzumab; codrituzumab; trastuzumab; patritumab; figitumumab; ganitumab; cantuzumab; ABX-MA1; bavituximab; J591; palivizumab; or bevacizumab.

In some embodiments of the present invention, a therapeutic antibody is cergutuzumab; ibritumomab tiuxetan; rituximab; tositumomab; gemtuzumab; alemtuzumab; panitumumab; depatuxizumab; sibrotuzumab; codrituzumab; patritumab; figitumumab; ganitumab; cantuzumab; ABX-MA1; bavituximab; J591; palivizumab; or bevacizumab.

In some embodiments of the present invention, a therapeutic antibody is a cergutuzumab antibody; a ibritumomab tiuxetan antibody; a rituximab antibody; a tositumomab antibody; a gemtuzumab antibody; an alemtuzumab antibody; a cetuximab antibody; a panitumumab antibody; a depatuxizumab antibody; a sibrotuzumab antibody; a codrituzumab antibody; a trastuzumab antibody; a patritumab antibody; a figitumumab antibody; a ganitumab antibody; a cantuzumab antibody; an ABX-MA1 antibody; a bavituximab antibody; a J591 antibody; a palivizumab antibody; a bevacizumab antibody, as defined herein.

In some embodiments of the present invention, a therapeutic antibody is a cergutuzumab antibody; a ibritumomab tiuxetan antibody; a rituximab antibody; a tositumomab antibody; a gemtuzumab antibody; an alemtuzumab antibody; a panitumumab antibody; a depatuxizumab antibody; a sibrotuzumab antibody; a codrituzumab antibody; a trastuzumab antibody; a patritumab antibody; a figitumumab antibody; a ganitumab antibody; a cantuzumab antibody; an ABX-MA1 antibody; a bavituximab antibody; a J591 antibody; a palivizumab antibody; a bevacizumab antibody, as defined herein.

In some embodiments of the present invention, a therapeutic antibody is a cergutuzumab antibody; a ibritumomab tiuxetan antibody; a rituximab antibody; a tositumomab antibody; a gemtuzumab antibody; an alemtuzumab antibody; a panitumumab antibody; a depatuxizumab antibody; a sibrotuzumab antibody; a codrituzumab antibody; a patritumab antibody; a figitumumab antibody; a ganitumab antibody; a cantuzumab antibody; an ABX-MA1 antibody; a bavituximab antibody; a J591 antibody; a palivizumab antibody; a bevacizumab antibody, as defined herein.

In some embodiments of the present invention, a therapeutic antibody includes a sequence having at least 80% identity with a sequence listed in Table I. In some embodiments of the present invention, a therapeutic antibody includes a sequence having at least 80% identity with a portion of a sequence listed in Table I.

In some embodiments of the present invention, a therapeutic antibody includes a variable domain comprising a sequence having at least 80% identity with at least a portion of a sequence listed in Table I. In some embodiments of the present invention, a therapeutic antibody includes a heavy chain variable domain comprising a sequence having at least 80% identity with at least a portion of a sequence listed in Table I. In some embodiments of the present invention, a therapeutic antibody includes a light chain variable domain comprising a sequence having at least 80% identity with at least a portion of a sequence listed in Table I.

In some embodiments of the present invention, a therapeutic antibody includes a CDR comprising a sequence having at least 80% identity with at least a portion of a sequence listed in Table I. In some embodiments of the present invention, a therapeutic antibody includes a heavy chain CDR comprising a sequence having at least 80% identity with at least a portion of a sequence listed in Table I. In some embodiments of the present invention, a therapeutic antibody includes a light chain CDR comprising a sequence having at least 80% identity with at least a portion of a sequence listed in Table I. In some embodiments of the present invention, a therapeutic antibody includes a heavy chain CDR comprising a sequence having at least 80% identity with at least a portion of a sequence listed in Table I.

In some embodiments of the present invention, a therapeutic antibody includes a constant region comprising a sequence having at least 80% identity with at least a portion of a sequence listed in Table I. In some embodiments of the present invention, a therapeutic antibody includes a light chain constant region comprising a sequence having at least 80% identity with at least a portion of a sequence listed in Table I. In some embodiments of the present invention, a therapeutic antibody includes a heavy chain constant region comprising a sequence having at least 80% identity with at least a portion of a sequence listed in Table I. In some embodiments of the present invention, a therapeutic antibody includes a hinge domain comprising a sequence having at least 80% identity with at least a portion of a sequence listed in Table I.

In some embodiments, a therapeutic antibody competes with its parent therapeutic antibody for binding to its target. For example, in some embodiments a cergutuzumab antibody competes with cergutuzumab for binding to CEACAM5, etc.

In various embodiments, the β-1,6-glucan oligomers are chemically synthesized. In various embodiments, at least 90% of the dry weight of glucan contained in the composition is β-1,6-glucan. In various embodiments, less than 10% of the dry weight of glucan contained in the composition is β-1,3-glucan. In various embodiments, the composition is substantially free of β-1,3-glucan.

The present invention further provides methods of treating a cancer associated with expression of a tumor antigen (e.g., CEACAM5, etc.) which involves administering a composition of the present invention to a subject in need thereof. For example, in some embodiments, the methods involve administering a therapeutically effective amount of a composition that includes a therapeutic antibody conjugated to between 1 and 6 β-1,6-glucan oligomers (e.g., between 1 and 5, 1 and 4, or 1 and 3 β-1,6-glucan oligomers), where each β-1,6-glucan oligomer is independently comprised of between 2 and 10 glucose monomer units.

In some embodiments, the cancer is breast cancer. In some embodiments, the cancer is ovarian cancer. In some embodiments, the cancer is bladder cancer. In some embodiments, the cancer is salivary gland cancer. In some embodiments, the cancer is endometrial cancer. In some embodiments, the cancer is pancreatic cancer. In some embodiments, the cancer is non-small-cell lung cancer (NSCLC). In some embodiments, the cancer is prostate cancer. In some embodiments the cancer is metastatic.

Definitions

As used herein, "antibody" means an immunoglobulin molecule that recognizes and specifically binds to a target through at least one antigen recognition site within a variable, optimized, or selected region of an immunoglobulin molecule. As used herein, the term "antibody" encompasses intact polyclonal antibodies, intact monoclonal antibodies, antibody fragments (such as Fab, Fab', Fab'2, $Fab_2$, $Fab_3$, $F(ab')_2$, Fd, Fv, Feb, scFv, SMIP, antibody, diabody, triabody, tetrabody, minibody, maxibody, tandab, DVD, BiTe, TandAb, or the like, or any combination thereof), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as glucans, toxins, radioisotopes, and the like. As used herein, an antibody can be, e.g., an "intact antibody" or an "antibody fragment." As used herein, "antibody" additionally encompasses various alternative formats as may be known in the art, e.g., camelid antibodies. As used herein, an antibody or intact antibody can be an immunoglobulin molecule comprising four polypeptide chains, two heavy (H) chains and two light (L) chains inter-connected by disulfide bonds.

Each heavy chain comprises a heavy chain variable ($V_H$) region and a heavy chain constant region ($C_H$). The heavy chain constant region comprises three domains, $C_H1$, $C_H2$ and $C_H3$. Each light chain comprises a light chain variable ($V_L$) region and a light chain constant region ($C_L$). The $V_H$ and $V_L$ regions can be further subdivided into regions of hypervariability, termed complementarity determining regions (CDR), interspersed with regions that are more conserved, termed framework regions (FR). Other intact antibodies, e.g., intact camelid antibodies, are known in the art.

As used herein, the term "antibody fragment" means a molecule comprising at least a portion derived from or having significant identity to all or a portion of an immunoglobulin protein, such as, for example, an antigen-binding or variable region of an antibody. Examples of antibody fragments include Fab, Fab', F(ab')$_2$, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

As used herein, the term glucan means any polymeric or oligomeric molecule composed largely or entirely of glucose monomer units. A glucan can be a free molecule or may be a molecule that is conjugated with one or more other molecules, such as an antibody.

As used herein, the term "conjugate" refers to an antibody that is covalently linked to one or more glucans. The terms "glucan-conjugated" or "glucan-linked" as well as grammatical equivalents thereof refer to an antibody molecule that is covalently linked to one or more glucans.

As used herein, the term "identity" refers to the overall relatedness between a reference nucleic acid or amino acid sequence and one or more other nucleic acid or amino acid sequences. Identity may be expressed as a percentage. Methods for calculating percent identity are known in the art. Calculation of identity does not require that sequences be of same or similar length. Calculation of the percent identity can be performed by aligning the two sequences for optimal comparison purposes (e.g., gaps can be introduced in one or both of a first and a second nucleic acid sequences for optimal alignment and non-identical sequences can be disregarded for comparison purposes); nucleotides at corresponding nucleotide positions can then be compared. When a position in a first sequence is occupied by the same nucleotide as the corresponding position in a second sequence, then the sequences are identical at that position. The percent identity between the two sequences is a function of the number of identical positions shared by the sequences, typically taking into account, e.g., the number and/or length of any gaps introduced for optimal alignment of the sequences. The comparison of sequences and determination of percent identity between two sequences can be accomplished using a mathematical algorithm, such as BLAST®.

As used herein, the term "linker" refers to that portion of a multi-element agent that connects different elements to one another. A linker may be derived from or synthesized from any source and/or by any procedure, e.g., any source and/or by any procedure known in the art. In some embodiments, a linker joins a therapeutic antibody (e.g., one selected from Table I) and a β-1,6-glucan oligomer. In some embodiments, a linker is characterized in that it tends not to adopt a rigid three-dimensional structure, but rather provides flexibility between the joined elements.

As used herein, the term "treatment" (also "treat" or "treating") refers to any administration of a therapeutic molecule (e.g., a conjugate) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

As used herein, the term "therapeutically effective amount" is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular subject. Rather, a therapeutically effective amount may be that amount that provides a particular desired pharmacological response in a significant number of subjects when administered to subjects in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular conjugate may be formulated and/or administered in a single dose. In some embodiments, a therapeutically effective amount of a particular conjugate may be formulated and/or administered in a plurality of doses, for example, as part of a dosing regimen.

In some embodiments, the present invention involves compounds (e.g., β-1,6-glucan oligomers and optional linkers) including those described generally for Formula I, above, and which are further illustrated by the classes, subclasses, and species disclosed herein. It will be appreciated that preferred subsets described for each variable herein can be used for any of the structural subsets as well. As used herein, the following definitions shall apply to these compounds unless otherwise indicated.

As described herein, compounds used in the present invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. In some embodiments, a stable compound or chemically feasible compound is one in which the chemical structure is not substantially altered when kept at a temperature from about −80° C. to about +25°. In some embodiments, a stable compound or chemically feasible compound is one in which the chemical structure is not substantially altered when kept at a temperature from about −80° C. to about +4°.

The phrase "one or more substituents", as used herein, refers to a number of substituents that equals from one to the maximum number of substituents possible based on the number of available bonding sites, provided that the above conditions of stability and chemical feasibility are met.

The term "aliphatic" or "aliphatic group", as used herein, means an optionally substituted straight-chain or branched $C_{1-12}$ hydrocarbon which is completely saturated or which contains one or more units of unsaturation. For example, suitable aliphatic groups include optionally substituted linear or branched alkyl, alkenyl, and alkynyl groups. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms, e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms. Exemplary alkenyl groups include vinyl, prop-1-enyl, prop-2-enyl, allenyl, 2-methylprop-2-enyl, 3-methylbut-2-enyl, butadienyl, and the like.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms. Exemplary alkynyl groups include $CH_3$—C≡C—, $CH_3$—C≡C—$CH_2$—, H—C≡C—$CH_2CH_2$—, H—C≡C—$CH(CH_3)CH_2$—, H—C≡C—$CH_2$—C≡C—$CH_2$—, The term "alkylene" refers to a bivalent alkyl group. An "alkylene chain" is a polymethylene group, e.g., —$(CH_2)_n$—, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one triple bond in which one or more hydrogen atoms are replaced with a substituent. Suitable substituents include those described below for a substituted aliphatic group.

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. For example, the aryl group is a $C_{6-10}$aryl group (e.g., phenyl and naphthyl). Aryl groups include, without limitation, optionally substituted phenyl, naphthyl, anthracenyl, and phenanthrenyl. The terms "aryl" and "ar-", as used herein, also include groups in which an aryl ring is fused to one or more cycloaliphatic rings to form an optionally substituted cyclic structure (e.g., 2,3-dihydroindenyl; 1,2,3,4-tetrahydroaphetalenyl; 1,2-dihydronaphthalenyl; 2,3-dihydronaphthalenyl; 8,10-dihydroanthracenyl, fluorenyl, and the like.

The term "heteroalkyl," as used herein, refers to straight, branched and cyclic alkyl groups, as defined herein, which are optionally substituted with one or more functional groups, and that contain one or more oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, for example, mono-, bi-, or tricyclic, (e.g., mono- or bicyclic). The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR°, —S(O)R°, —SO$_2$R°, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R°, —NR$^+$CO$_2$R$^+$, —NR$^+$SO$_2$R°, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R°, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R°)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R° is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

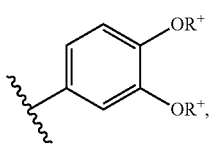

these two occurrences of R$^+$ are taken together with the oxygen atoms to which they are bound to form a fused 6-membered oxygen containing ring:

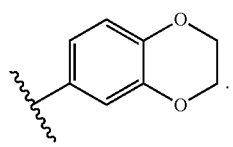 [SMILES: *c1ccc2c(c1)OCCO2]

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}C$- or $^{14}C$-enriched carbon are within the scope of this invention. Such compounds are useful, as a nonlimiting example, as analytical tools or probes in biological assays.

BRIEF DESCRIPTION OF THE DRAWING

FIG. 22 is a graph showing an evaluation of anti-β-1,6-glucan IgG2 binding to a mAbXcite-cetuximab.

FIG. 24 is a set of two graphs showing the effect of β-1,6-glucan conjugation on antibody binding to EGF receptor and on anti-β-1,6-glucan IgG2 binding to β-1,6-glucan. Graph 1 of FIG. 18 shows the effect of conjugation on antibody binding to EGF receptor. Graph 2 of FIG. 18 shows the effect of conjugation on anti-β-1,6-glucan IgG2 binding to β-1,6-glucan.

FIG. 27 is a set of two graphs showing that a mAbXcite-cetuximab is stable in human serum. The left graph of FIG. 21 shows antibody detection in human serum. The right graph of FIG. 21 shows β-1,6-glucan detection in human serum.

FIG. 28 is a set of two graphs showing that a mAbXcite-cetuximab is stable in heat inactivated human serum. The left graph of FIG. 22 shows antibody detection in heat inactivated human serum. The right graph of FIG. 22 shows β-1,6-glucan detection in heat inactivated human serum.

The graph shows that conjugation with β-1,6-glucan 5-mer does not affect cetuximab PK.

Figure 32:
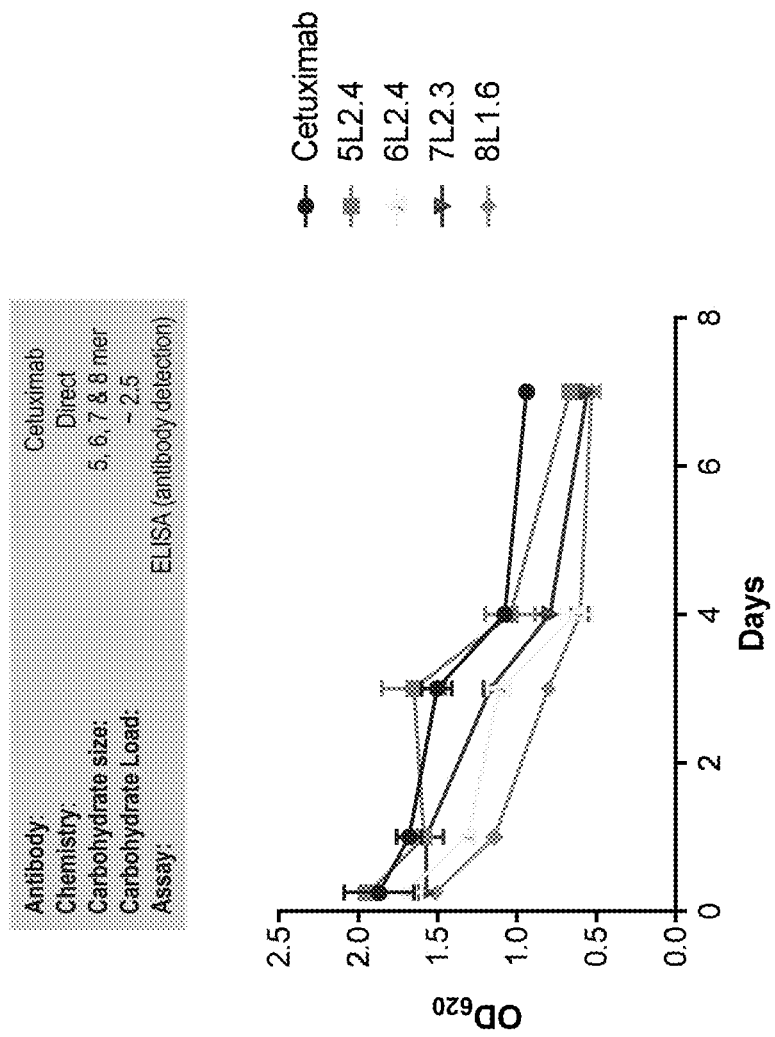

FIG. 32 is a graph showing pharmacokinetic antibody stability of a mAbXcite-cetuximab in the absence of tumor. The graph shows that conjugation with β-1,6-glucan 5-mer does not affect cetuximab PK.

Figure 33:
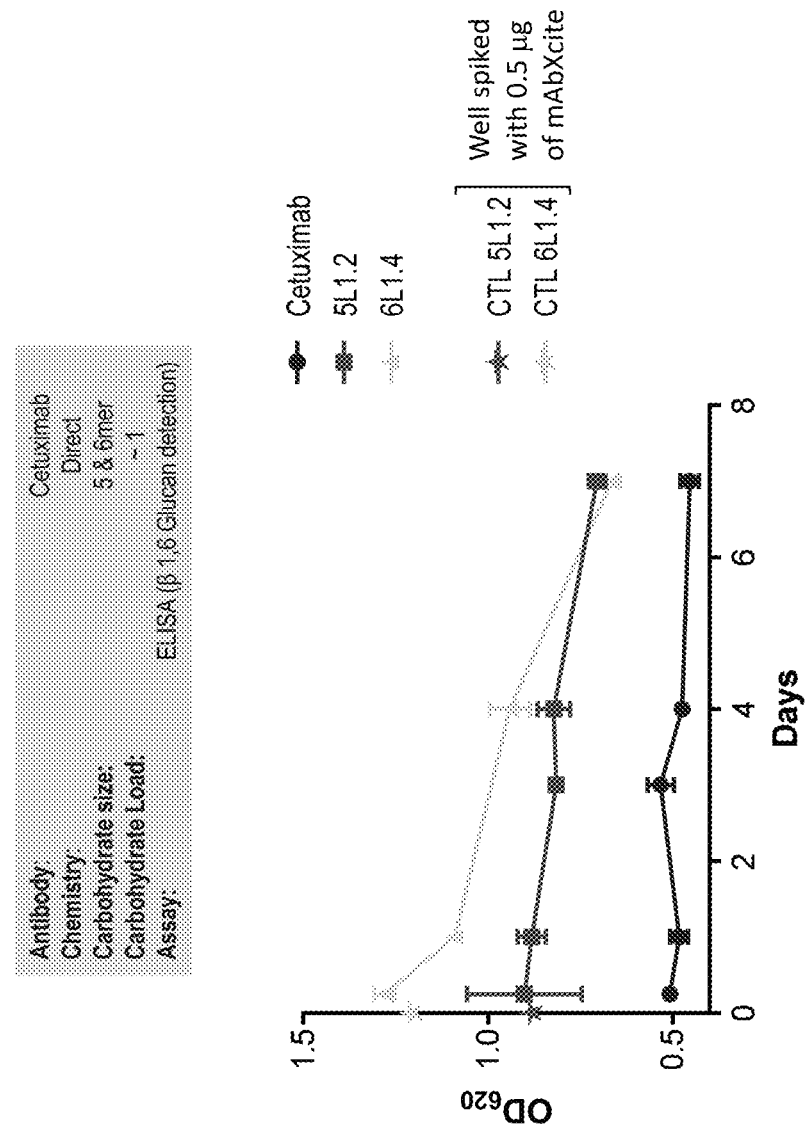

FIG. 33 is a graph showing pharmacokinetic analysis of β-1,6-glucan detection in the absence of tumor.

Figure 34:
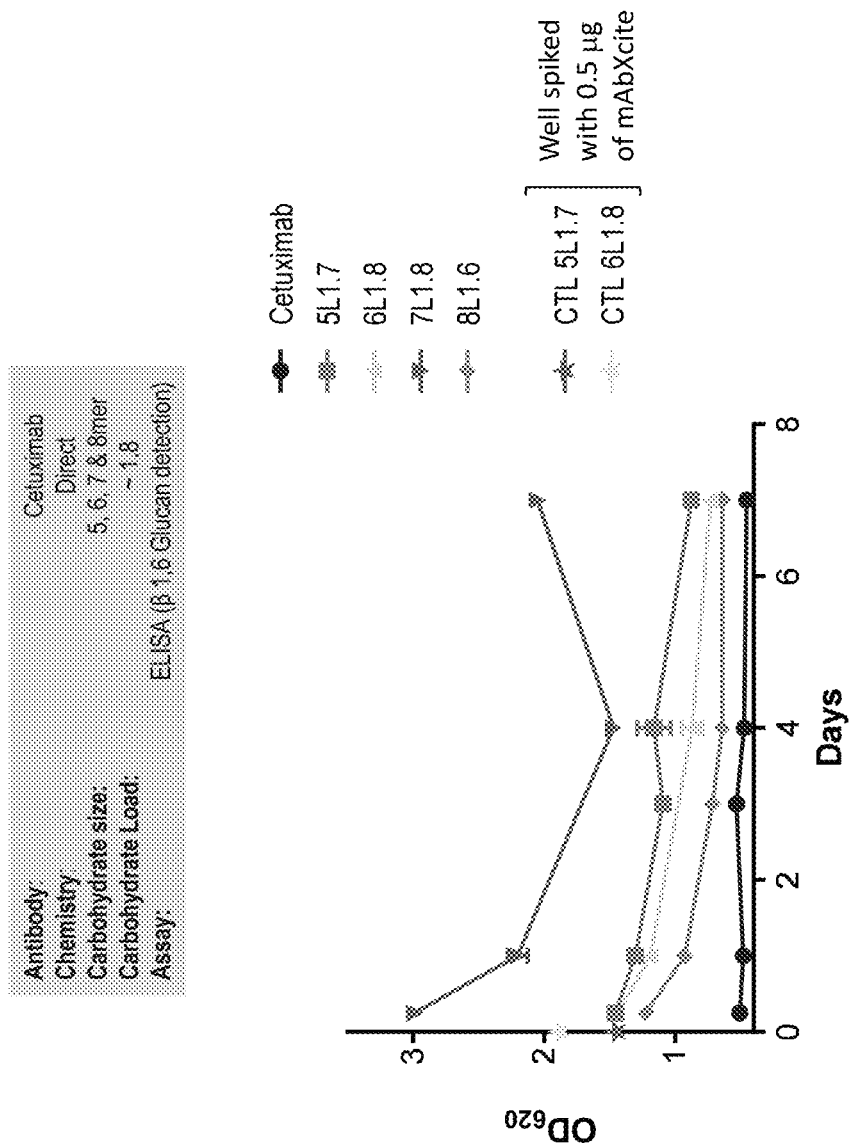

FIG. 34 is a graph showing pharmacokinetic analysis of β-1,6-glucan detection in the absence of tumor.

Figure 35:
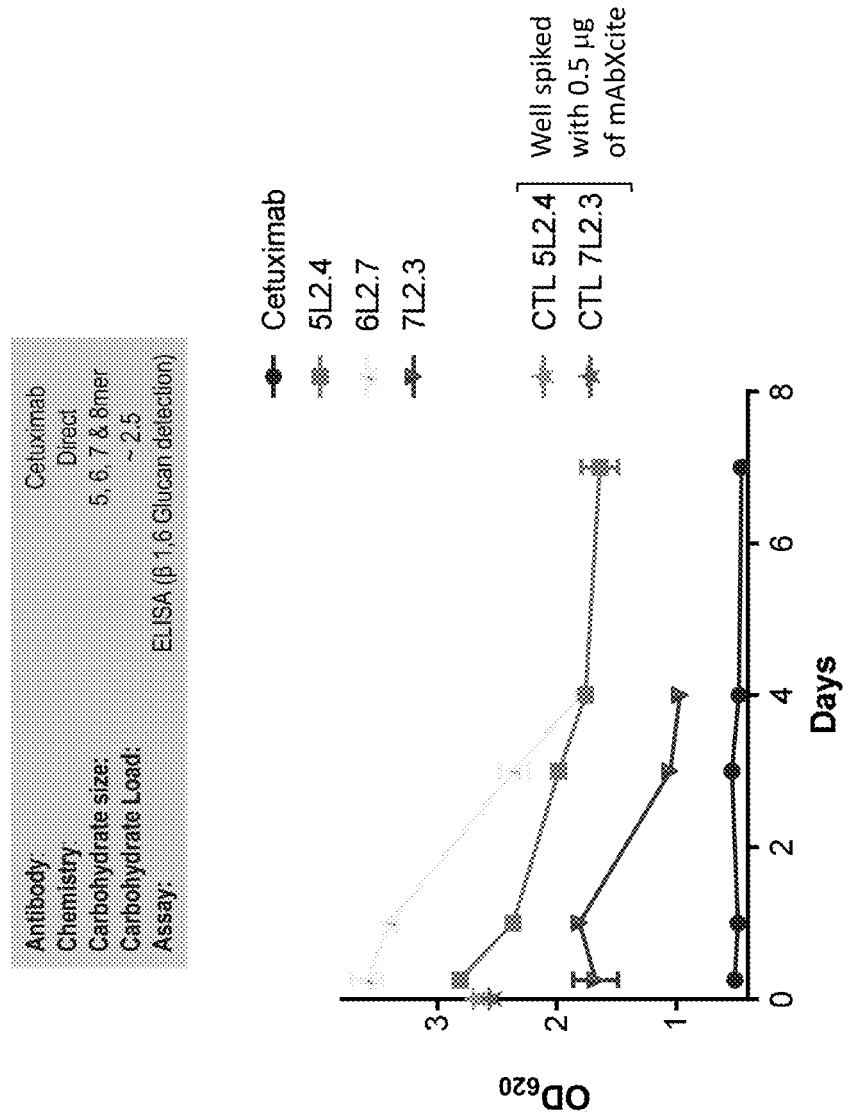

FIG. 35 is a graph showing pharmacokinetic analysis of β-1,6-glucan detection in the absence of tumor.

Figure 36:
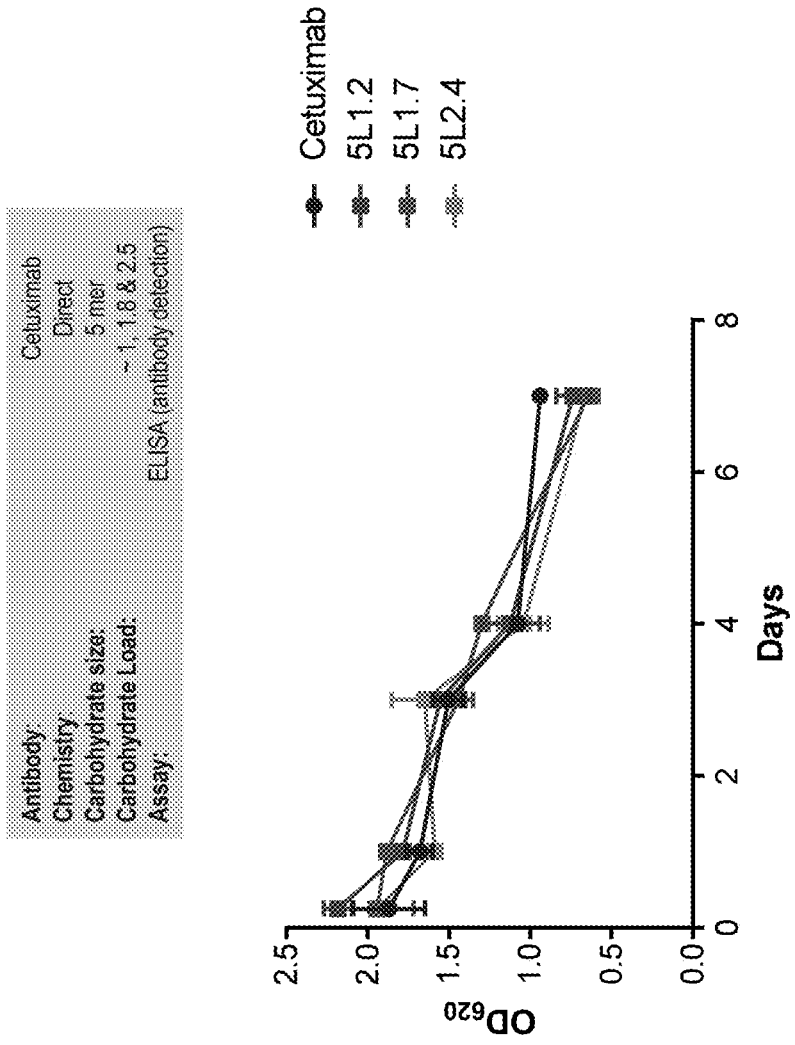

FIG. 36 is a graph showing pharmacokinetic analysis of mAbXcite-cetuximab stability in the absence of tumor. A mAbXcite-cetuximab loaded with β-1,6-glucan 5-mer was stable based on PK with load up to 2.4.

Figure 37:
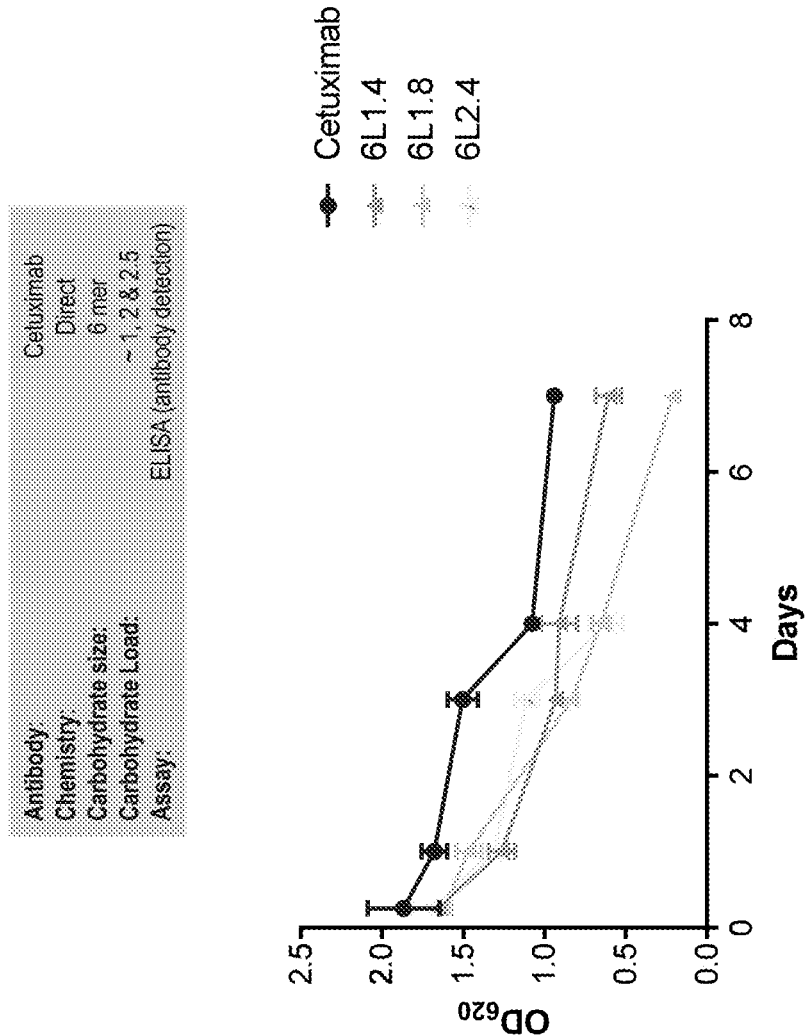

FIG. 37 is a graph showing pharmacokinetic analysis of mAbXcite-cetuximab stability in the absence of tumor.

Figure 38:
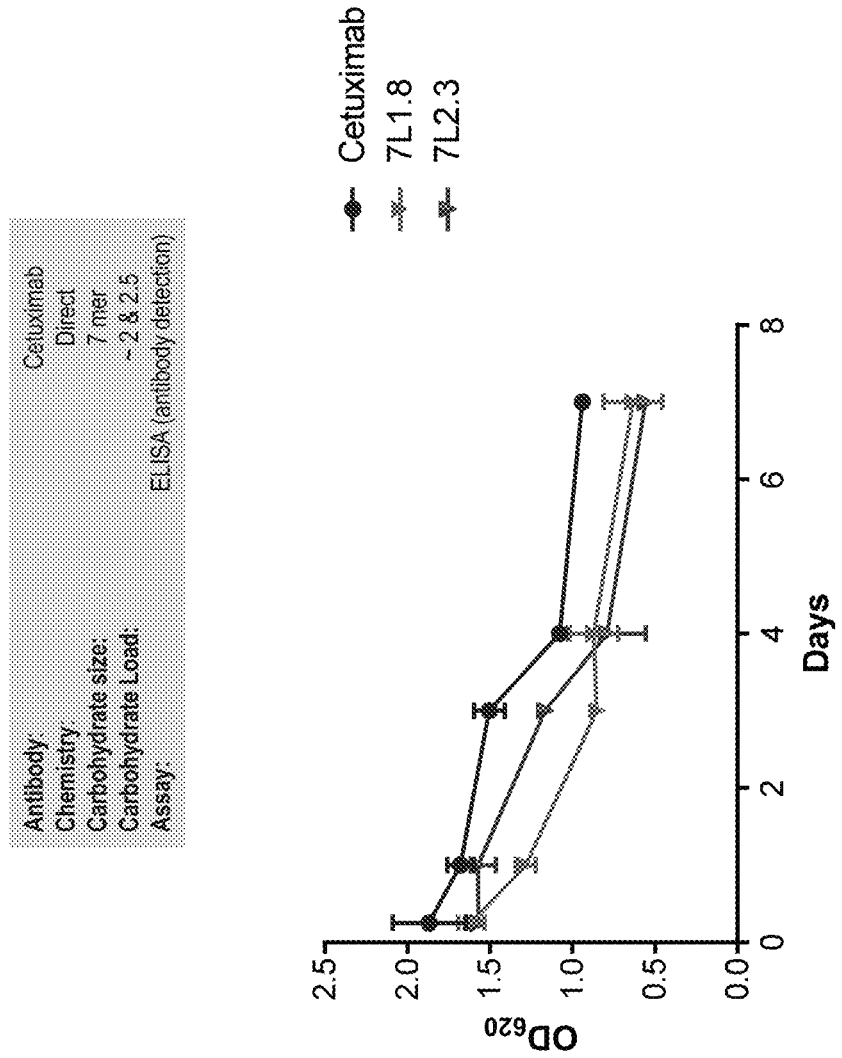

FIG. 38 is a graph showing pharmacokinetic analysis of mAbXcite-cetuximab stability in the absence of tumor.

Figure 39:
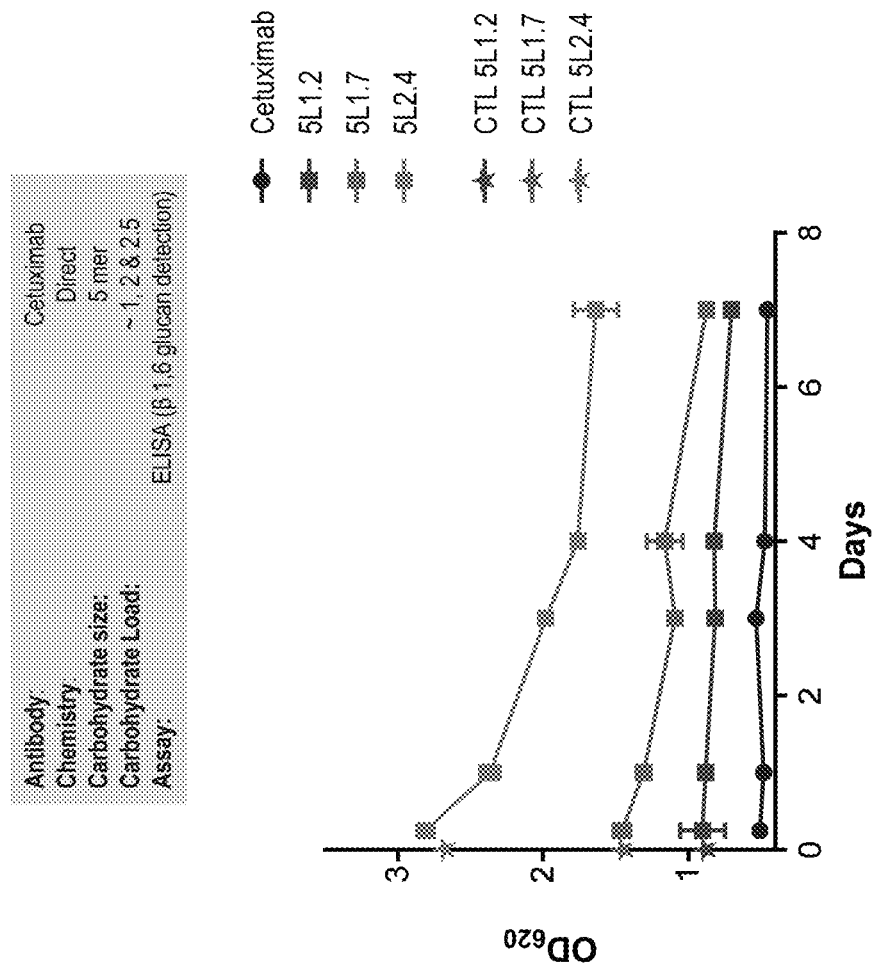

FIG. 39 is a graph showing pharmacokinetic analysis of β-1,6-glucan detection in the absence of tumor.

Figure 40:
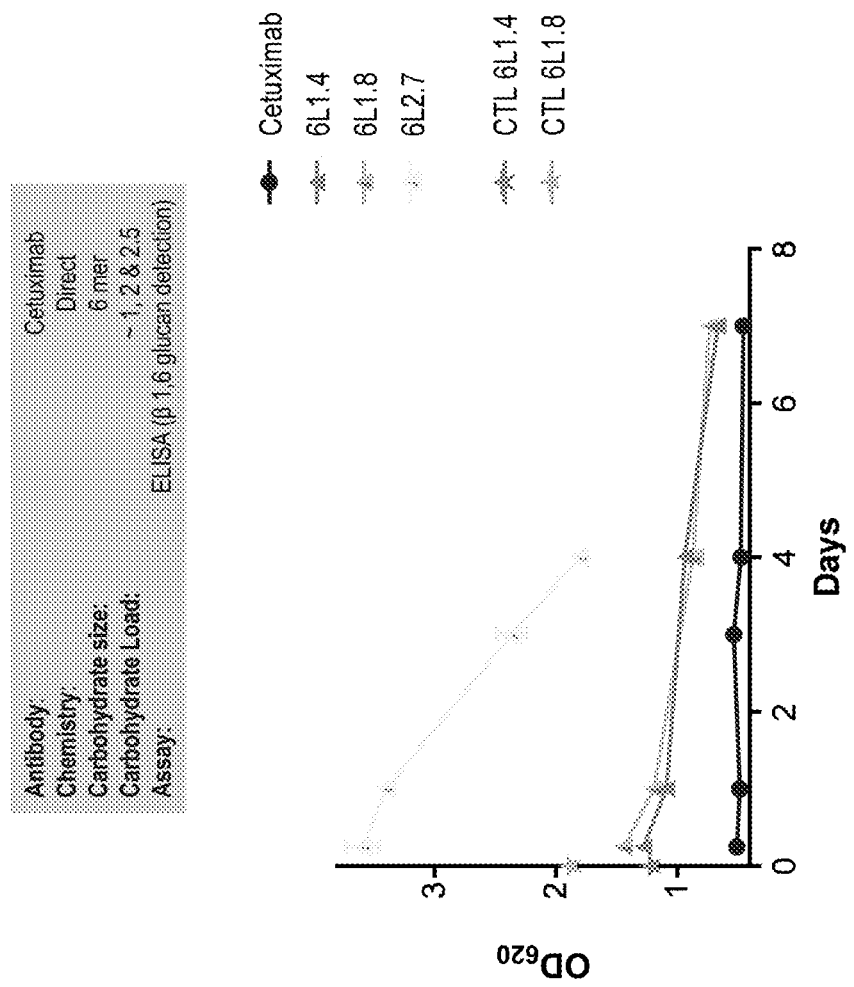

FIG. 40 is a graph showing pharmacokinetic analysis of β-1,6-glucan detection in the absence of tumor.

Figure 41:
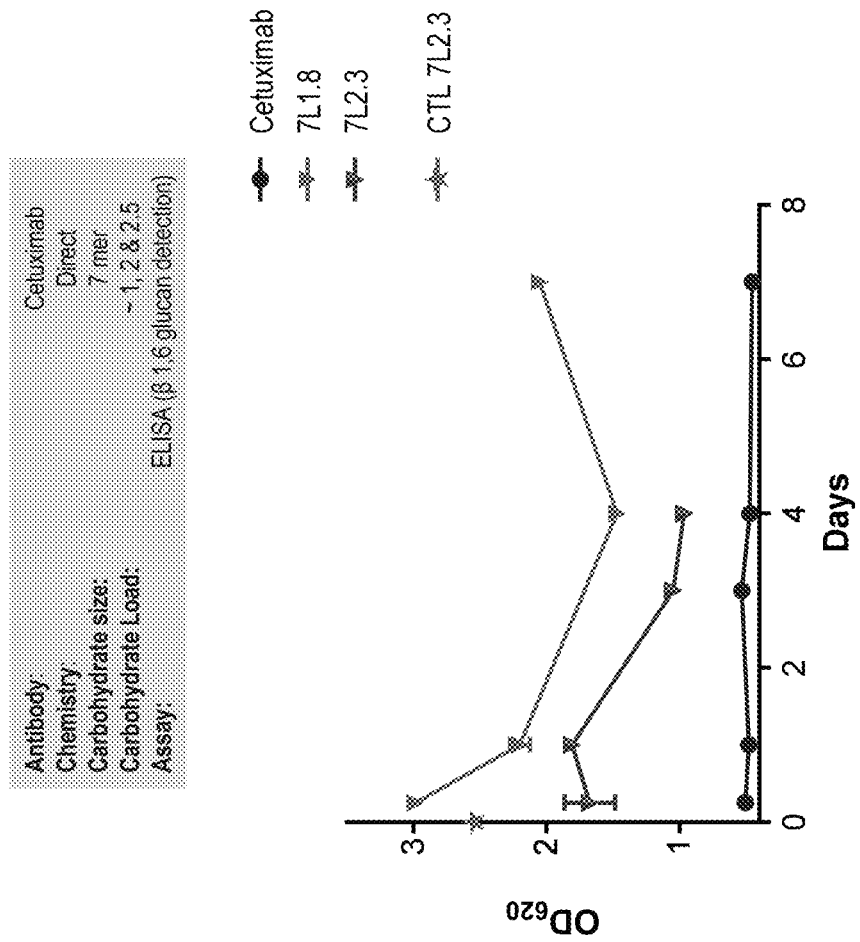

FIG. 41 is a graph showing pharmacokinetic analysis of β-1,6-glucan detection in the absence of tumor.

Figure 42:
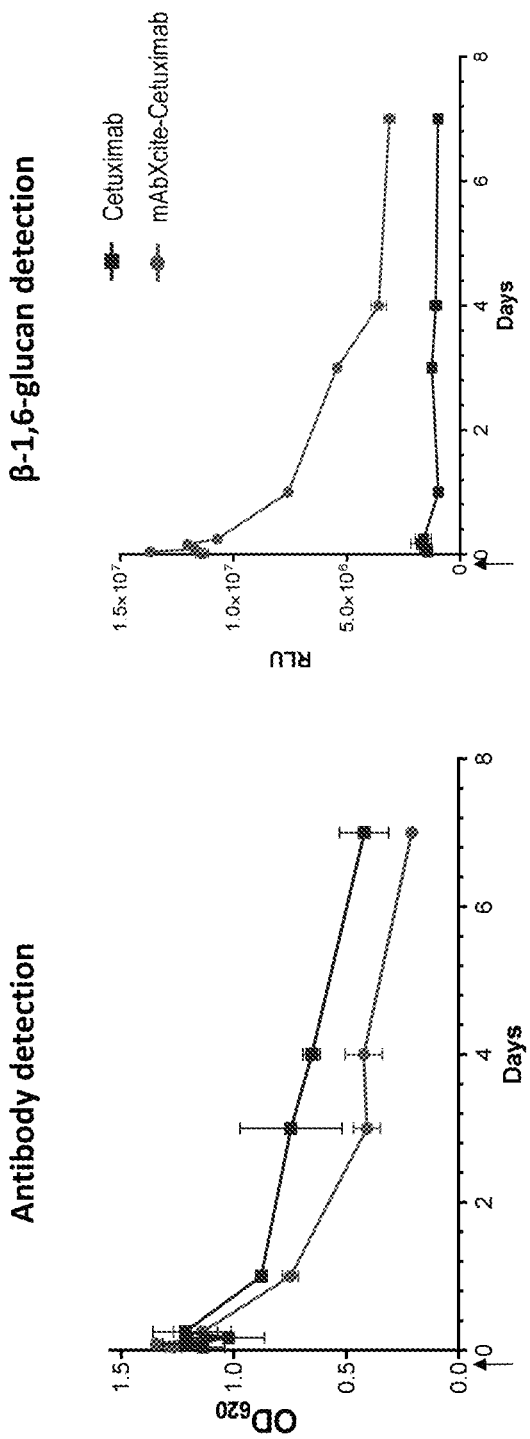

FIG. 42 is a set of two graphs showing pharmacokinetics of a mAbXcite-cetuximab in tumor bearing animals. The left graph shows mAbXcite-cetuximab antibody detection in tumor bearing animals. The right graph shows β-1,6-glucan detection in tumor bearing animals.

Figure 43:
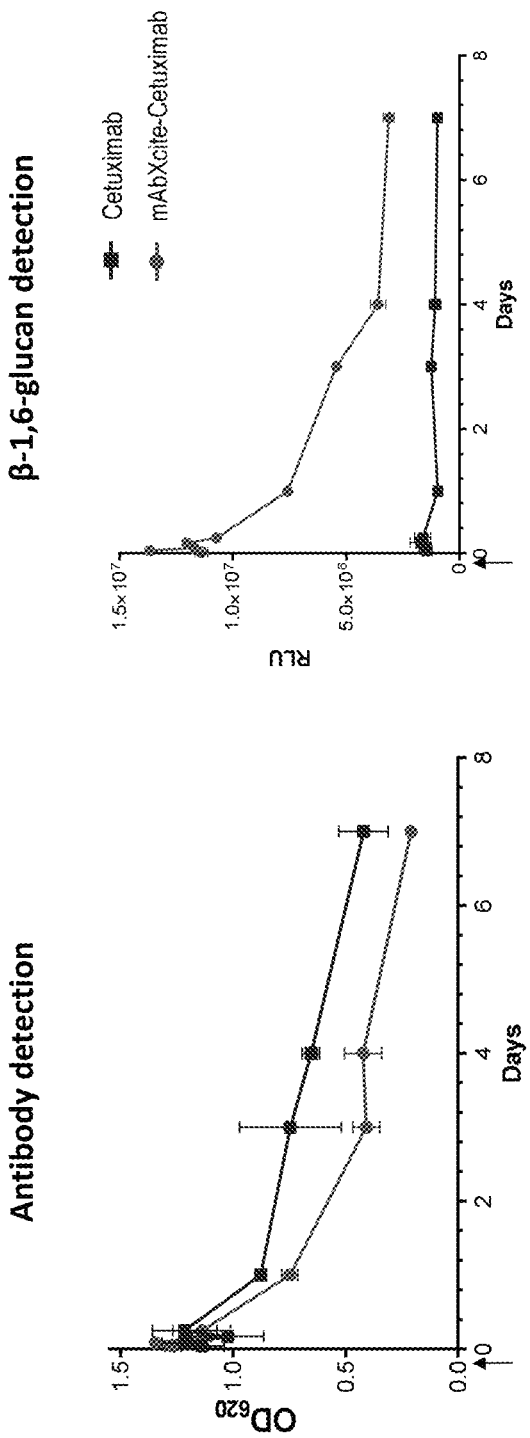

FIG. 43 is a set of two graphs showing pharmacokinetics of a mAbXcite-cetuximab in tumor bearing animals. The left graph shows mAbXcite-cetuximab antibody detection in tumor bearing animals. The right graph shows β-1,6-glucan detection in tumor bearing animals.

FIG. 44 is a set of two graphs showing pharmacokinetic analysis of β-1,6-glucan detection in absence of tumor or in tumor bearing mice. The left graph shows pharmacokinetic analysis of β-1,6-glucan detection in tumor bearing mice. The left graph shows pharmacokinetic analysis of β-1,6-glucan detection in absence of tumor.

Figure 45:
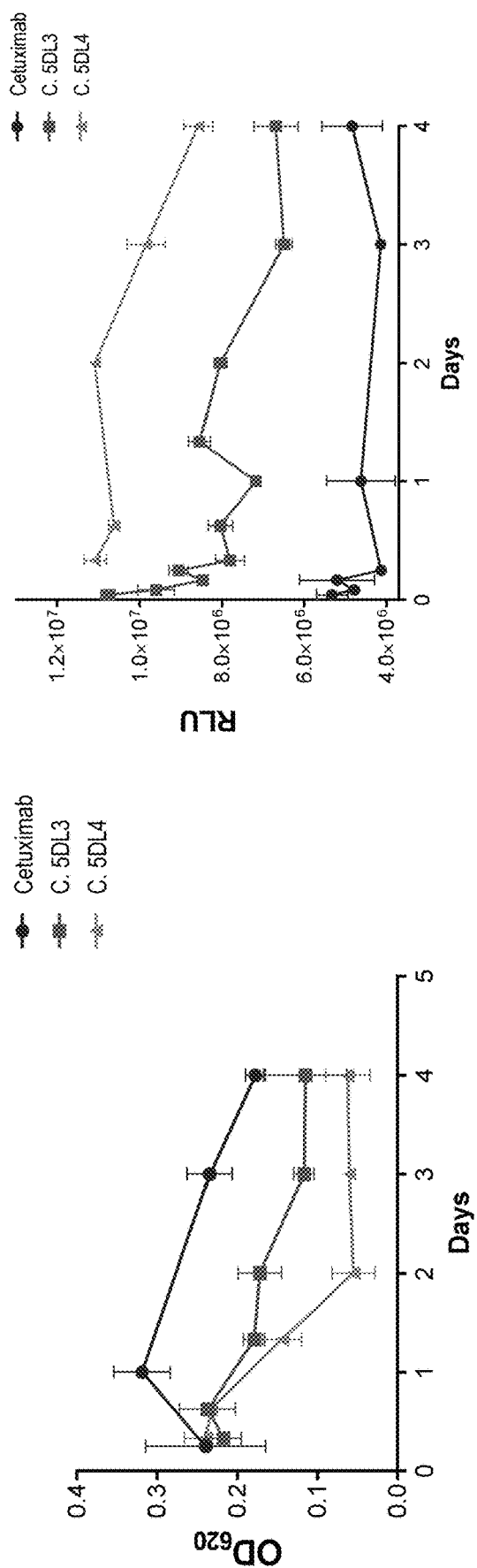

FIG. 45 is a set of two graphs showing pharmacokinetic analysis of a mAbXcite-cetuximab. The left graph shows mAbXcite-cetuximab antibody detection. The right graph shows β-1,6-glucan detection.

FIG. 46 is a set of two graphs showing a pharmacokinetic analysis of mAbXcite-cetuximab accumulation with twice weekly treatment. The left graph shows mAbXcite-cetuximab antibody detection. The right graph shows β-1,6-glucan detection. No accumulation was observed with twice weekly treatment.

FIG. 47 is a set of two graphs showing a pharmacokinetic analysis of a mAbXcite-cetuximab in tumor bearing animals. The left graph shows antibody stability. The right graph shows β-1,6-glucan detection.

FIG. 48 is a set of two graphs showing a pharmacokinetic analysis of mAbXcite-cetuximab stability in absence of tumor or in tumor bearing mice. The left graph shows antibody stability in mice with tumor. The right graph shows antibody stability in absence of tumor.

FIG. 49 is a set of two graphs showing a pharmacokinetic analysis of mAbXcite-cetuximab in absence of tumor or in tumor bearing mice. The left graph shows β-1,6-glucan detection in tumor bearing mice. The right graph shows β-1,6-glucan detection in absence of tumor.

FIG. 50 is a set of two graphs showing a pharmacokinetic analysis comparing mAbXcite-cetuximab having DBCO or direct conjugation chemistry. The left graph shows antibody stability. The right graph shows β-1,6-glucan detection.

Figure 51:
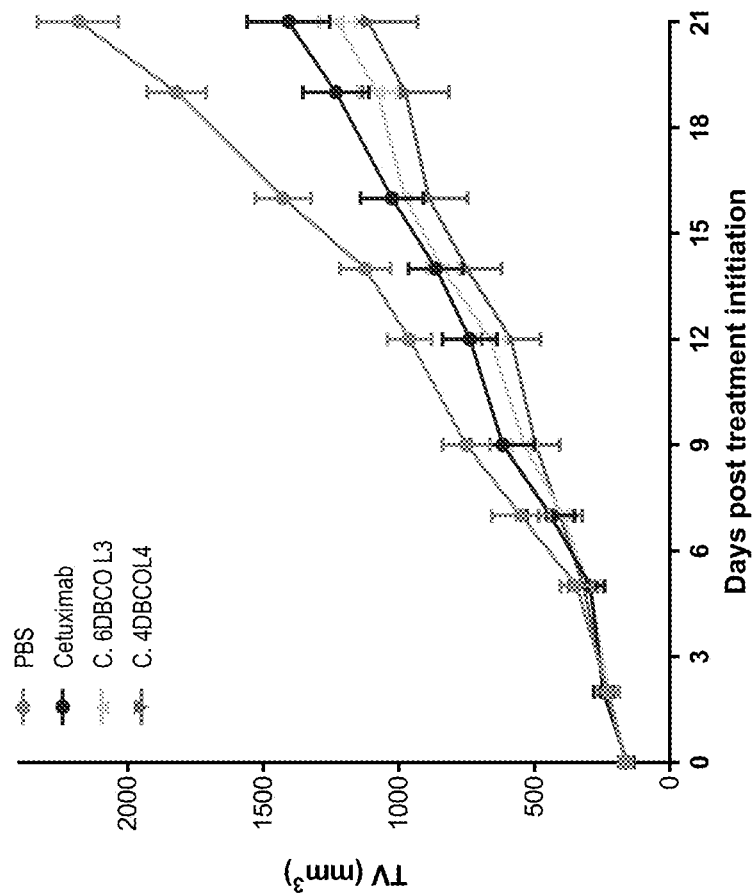

FIG. 51 is a graph showing mAbXcite-cetuximab efficacy in a BRAF mutant colorectal tumor model.

Figure 52:
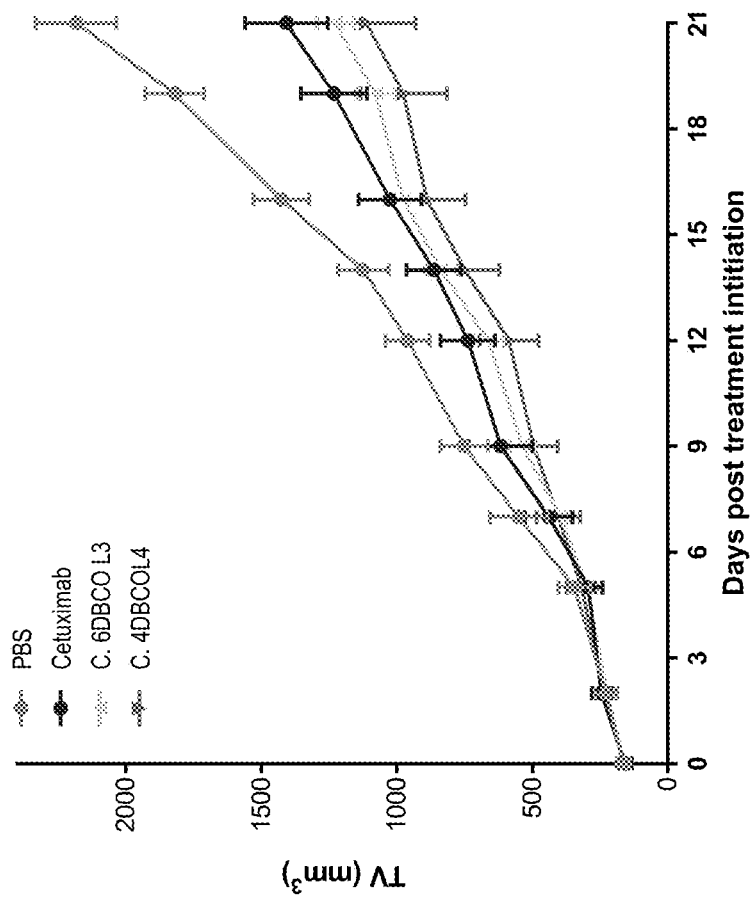

FIG. 52 is a graph showing mAbXcite-cetuximab efficacy in a BRAF mutant colorectal tumor model.

Figure 53:
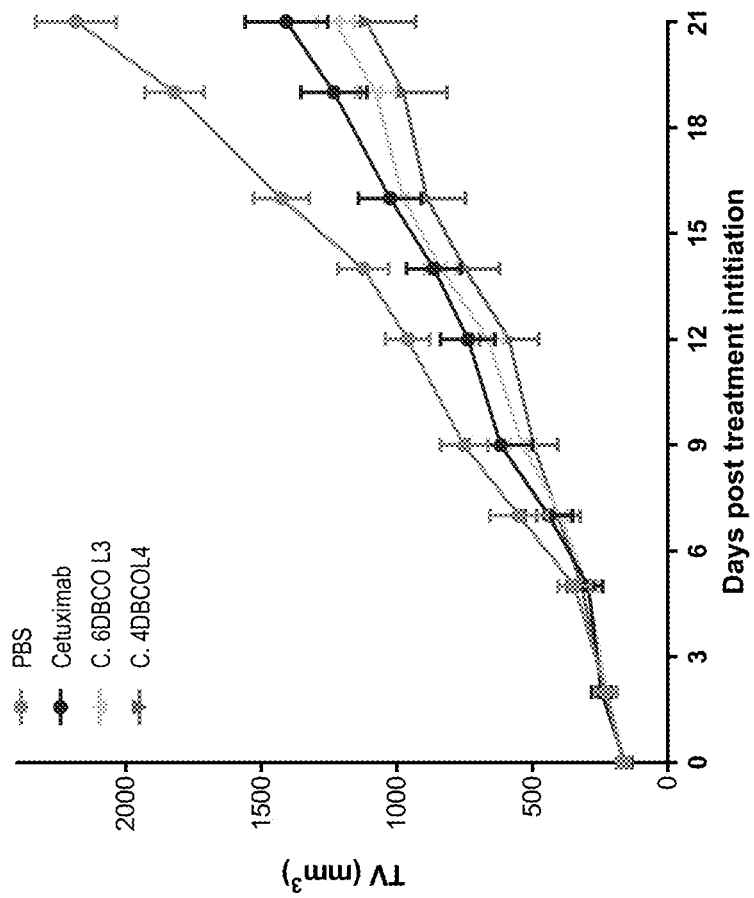

FIG. 53 is a graph showing mAbXcite-cetuximab efficacy in a BRAF mutant colorectal tumor model.

Figure 54:
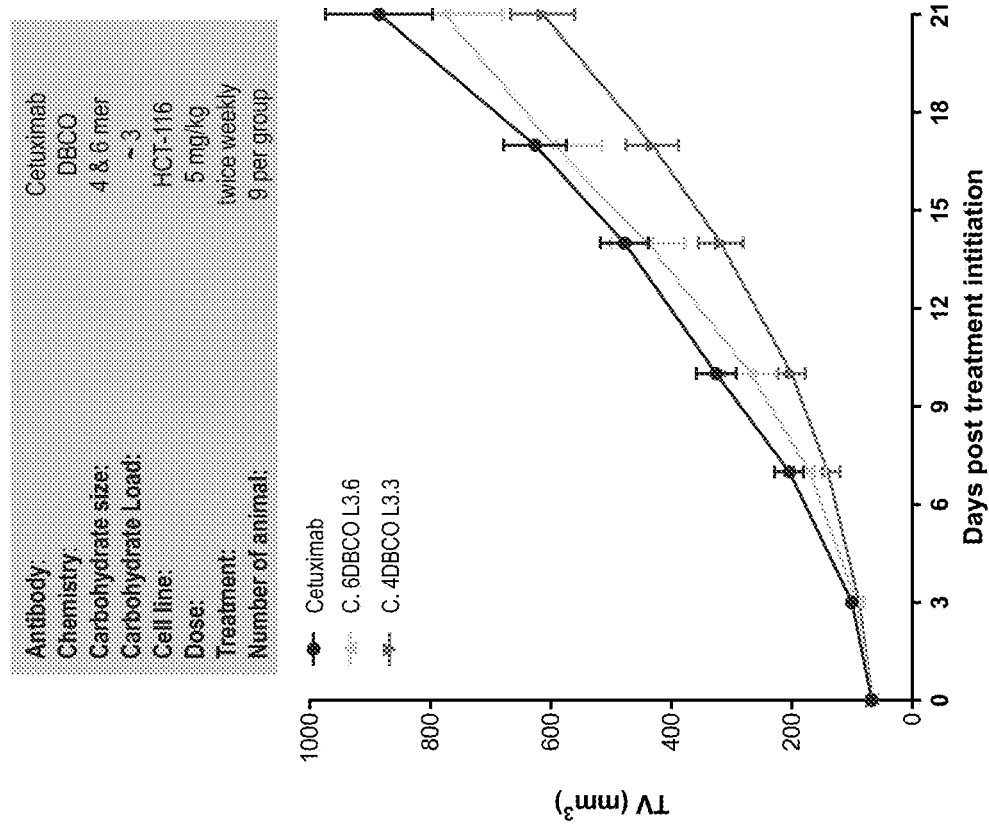

FIG. 54 is a graph showing mAbXcite-cetuximab efficacy in a KRAS mutant colorectal tumor model.

Figure 55:
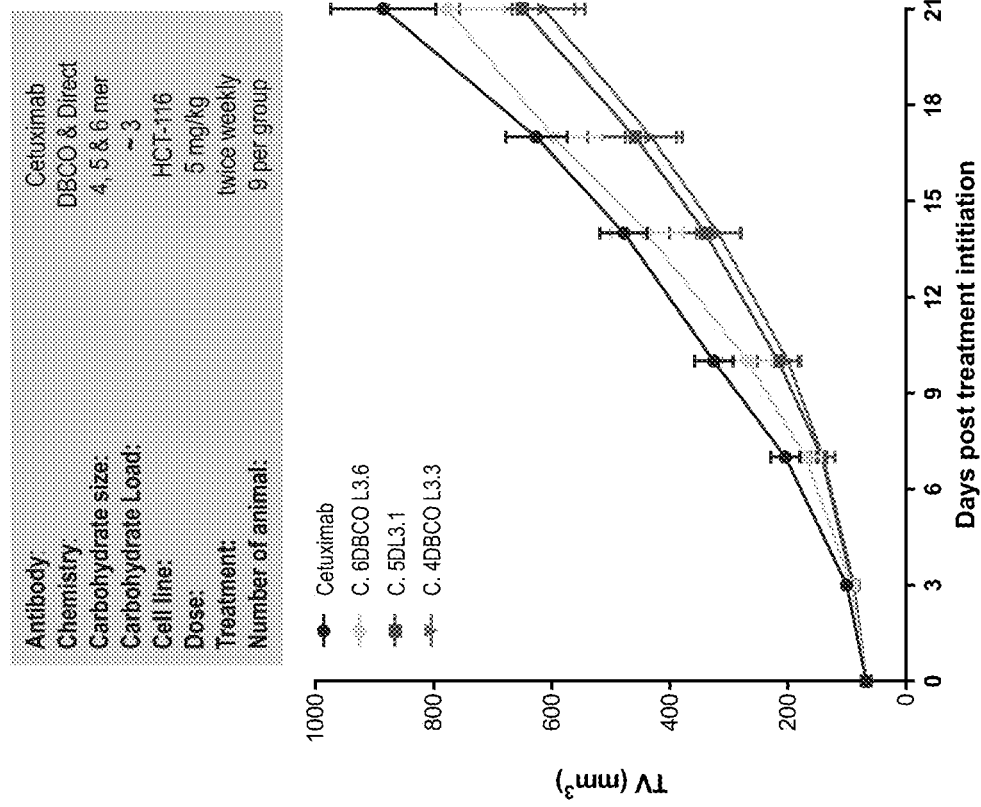

FIG. 55 is a graph showing mAbXcite-cetuximab efficacy in a KRAS mutant colorectal tumor model.

Figure 56:
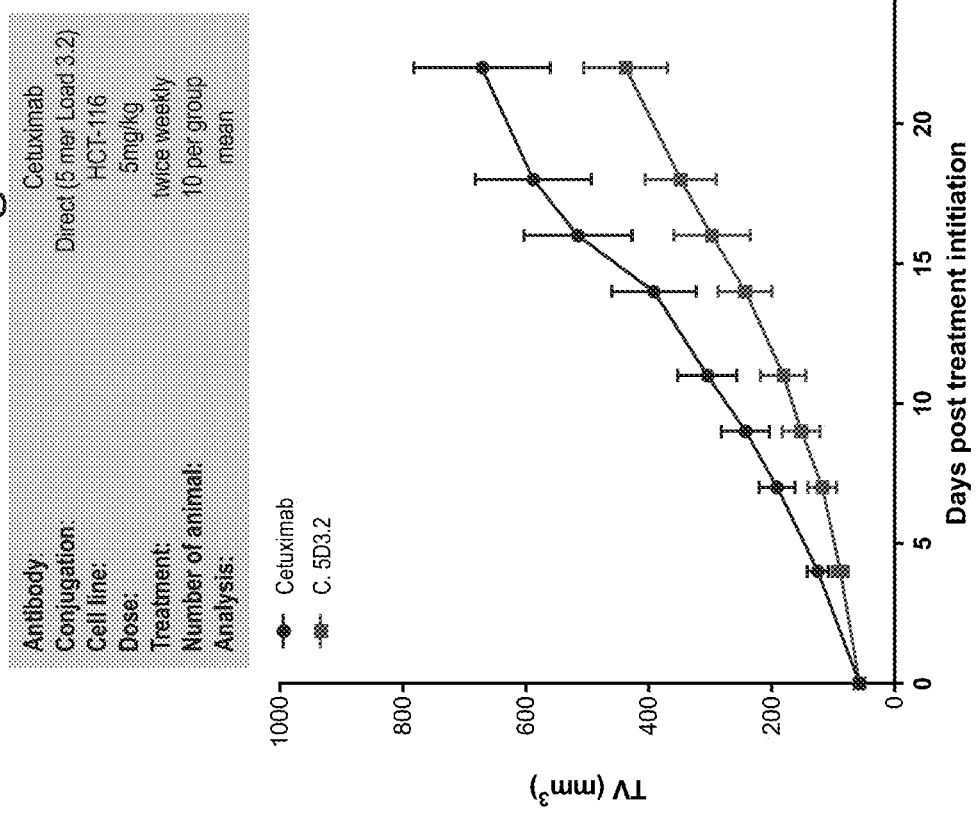

FIG. 56 is a graph showing that a mAbXcite-cetuximab inhibits KRAS mutant colorectal tumor growth.

Figure 57:
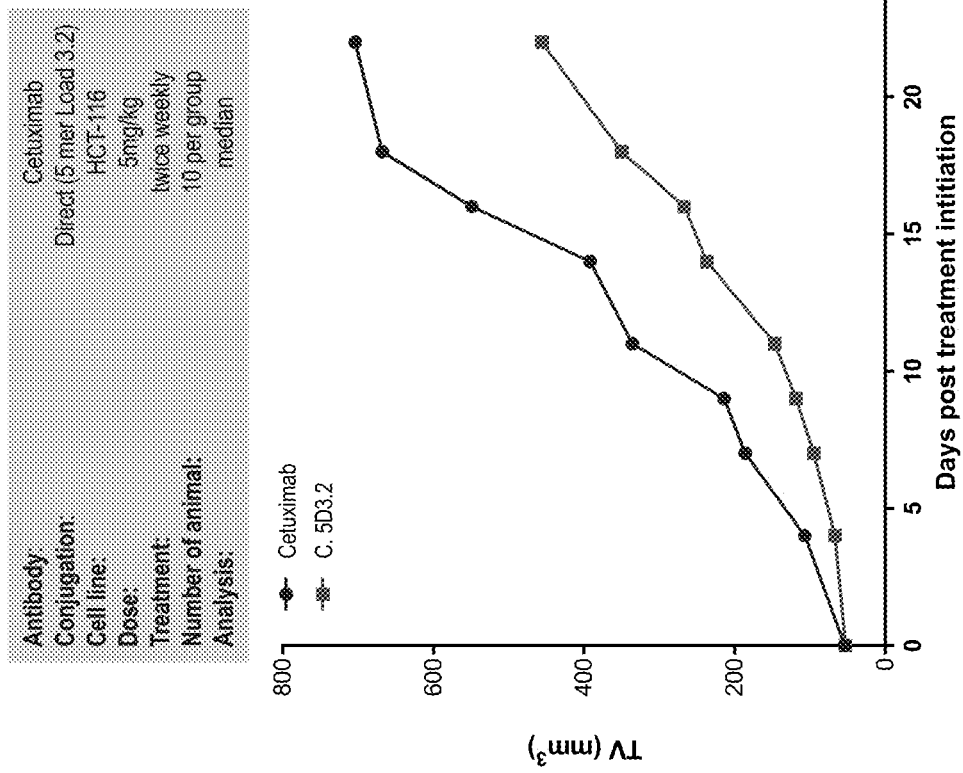

FIG. 57 is a graph showing that a mAbXcite-cetuximab inhibits KRAS mutant colorectal tumor growth.

Figure 58:
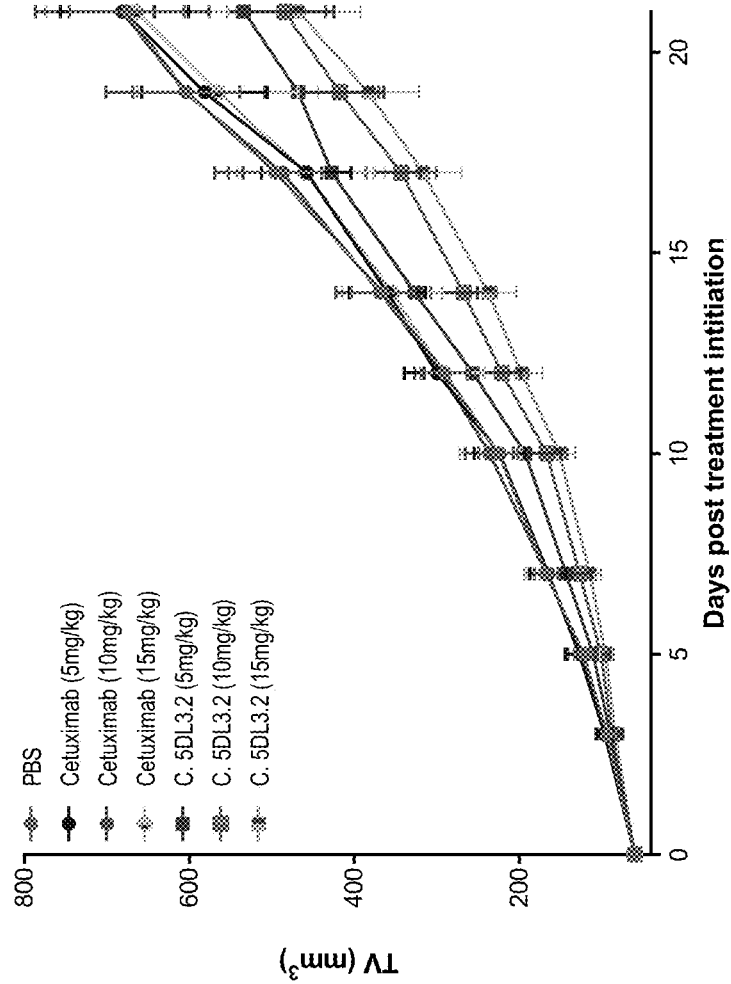

FIG. 58 is a graph showing that a mAbXcite-cetuximab inhibits KRAS mutant colorectal tumor growth.

Figure 59:
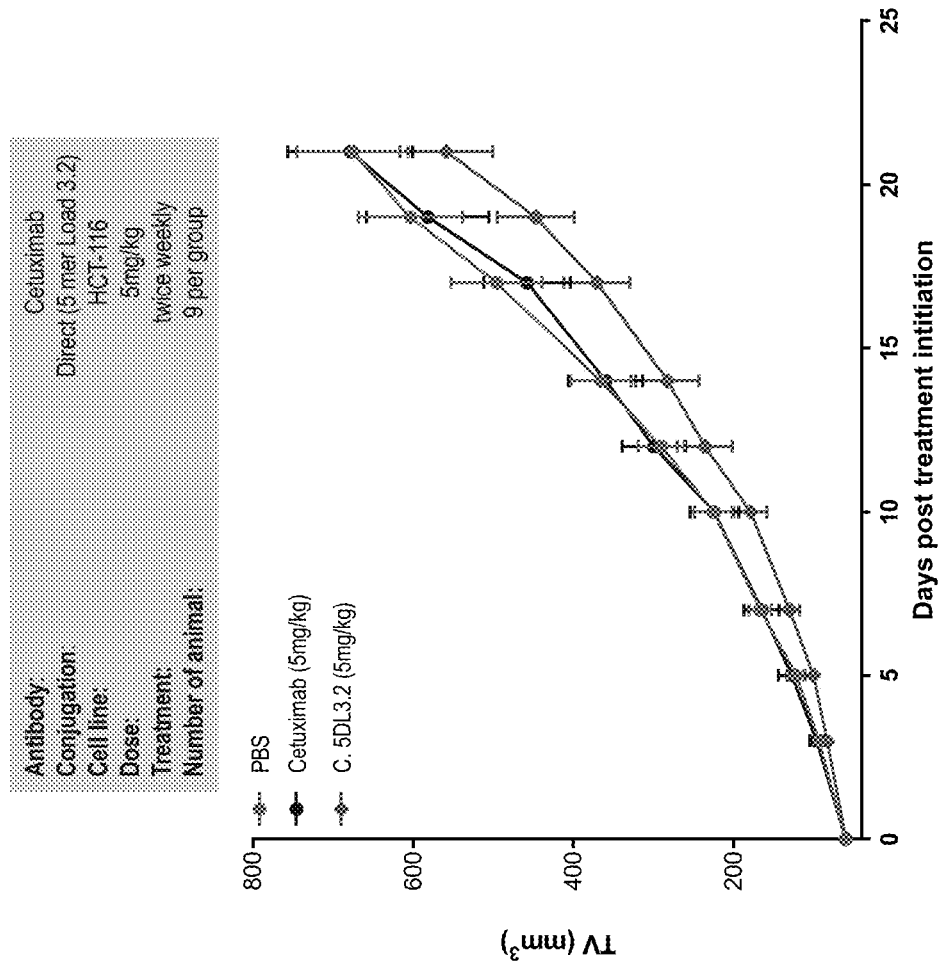

FIG. 59 is a graph showing that a mAbXcite-cetuximab inhibits KRAS mutant colorectal tumor growth.

Figure 60:
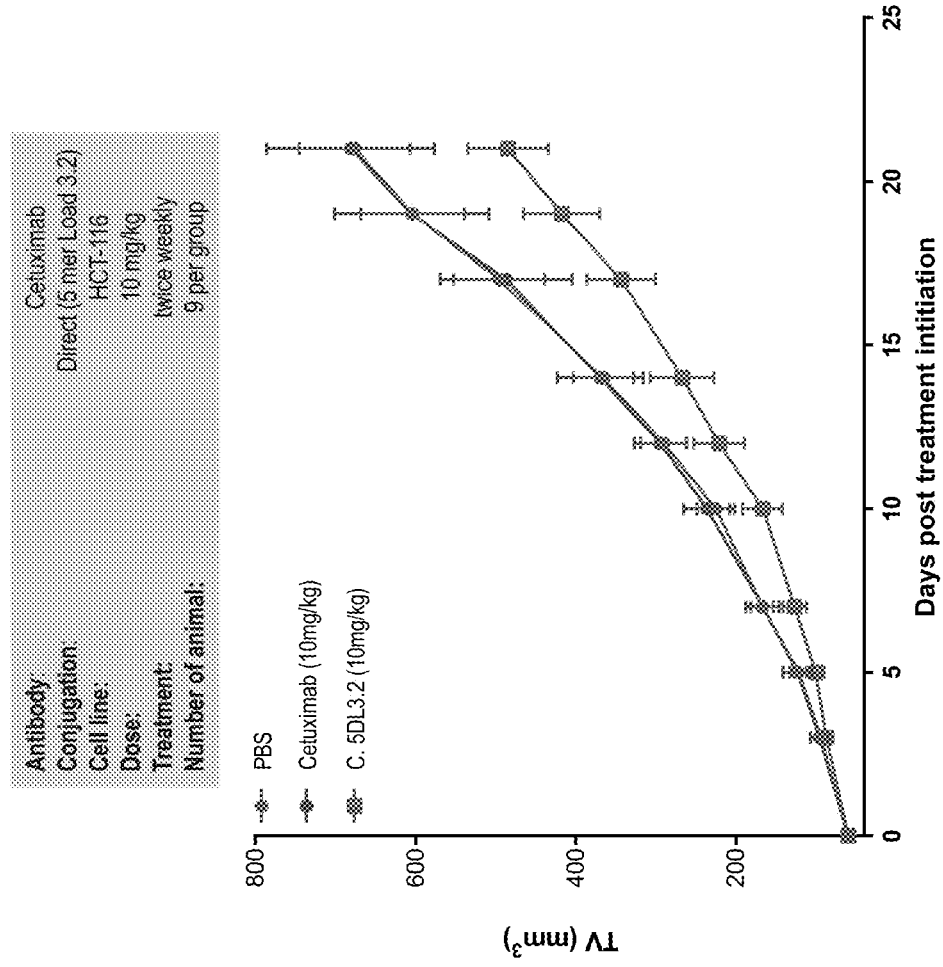

FIG. 60 is a graph showing that a mAbXcite-cetuximab inhibits KRAS mutant colorectal tumor growth.

Figure 61:
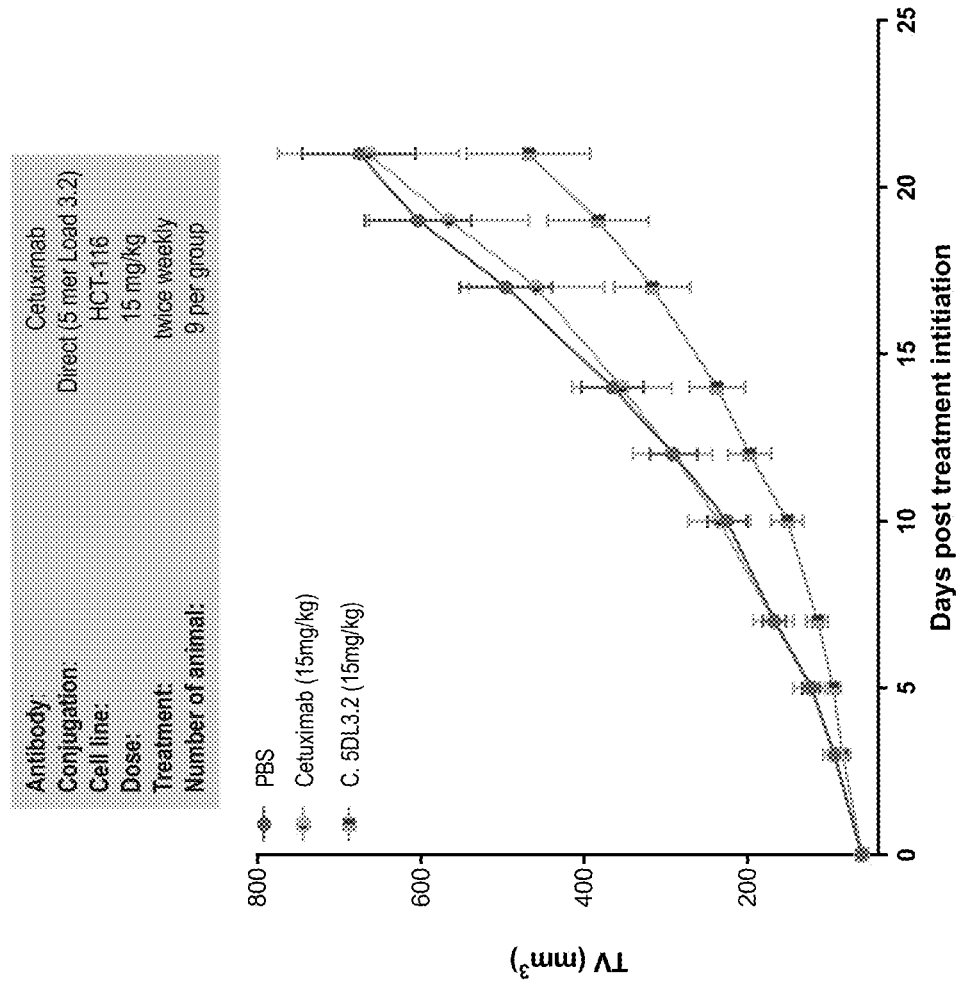

FIG. 61 is a graph showing that a mAbXcite-cetuximab inhibits KRAS mutant colorectal tumor growth.

Figure 62:
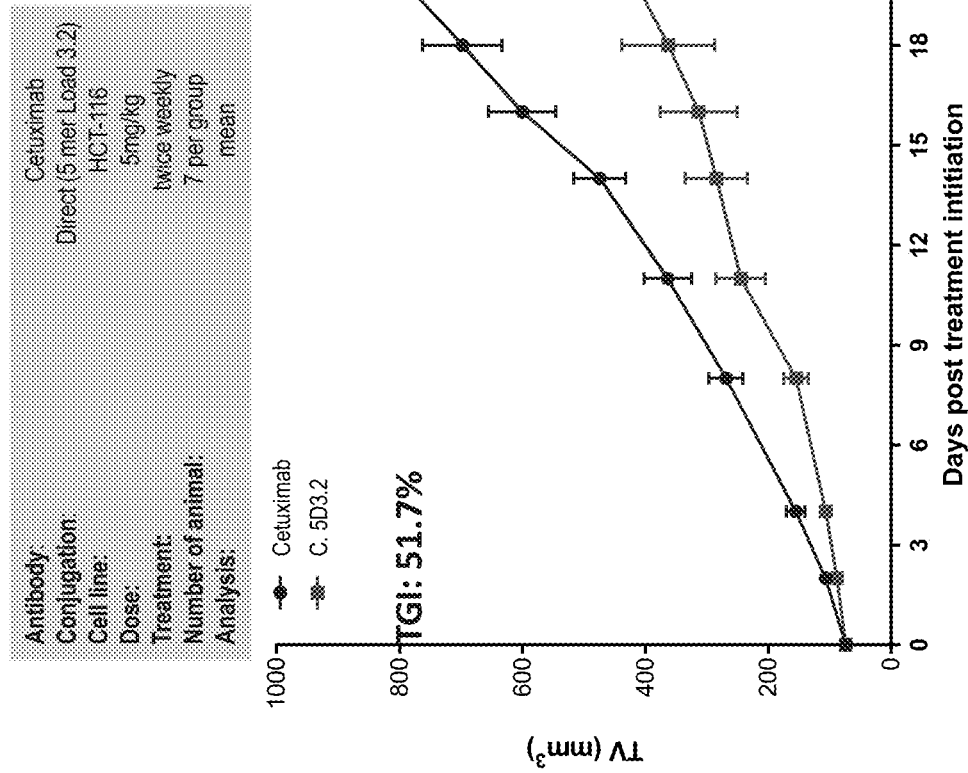

FIG. 62 is a graph showing that a mAbXcite-cetuximab inhibits KRAS mutant colorectal tumor growth (mean).

Figure 63:
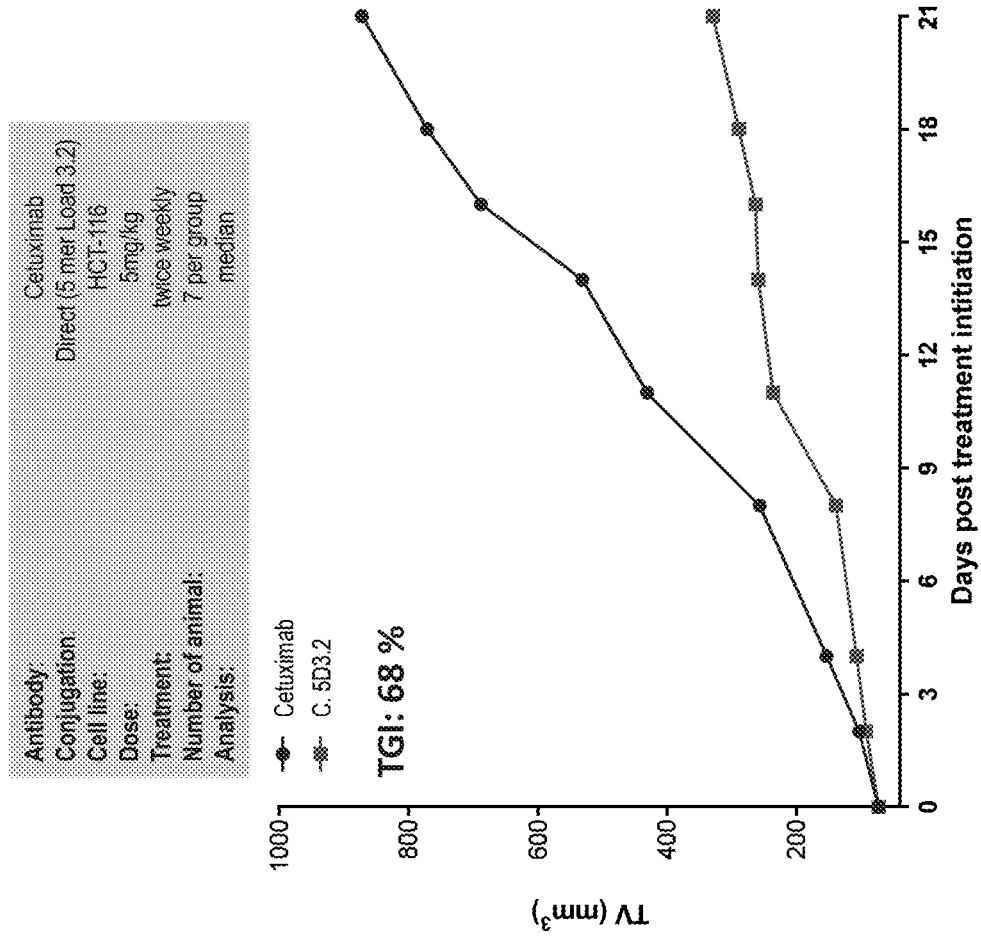

FIG. 63 is a graph showing that a mAbXcite-cetuximab inhibits KRAS mutant colorectal tumor growth (median).

Figure 64:
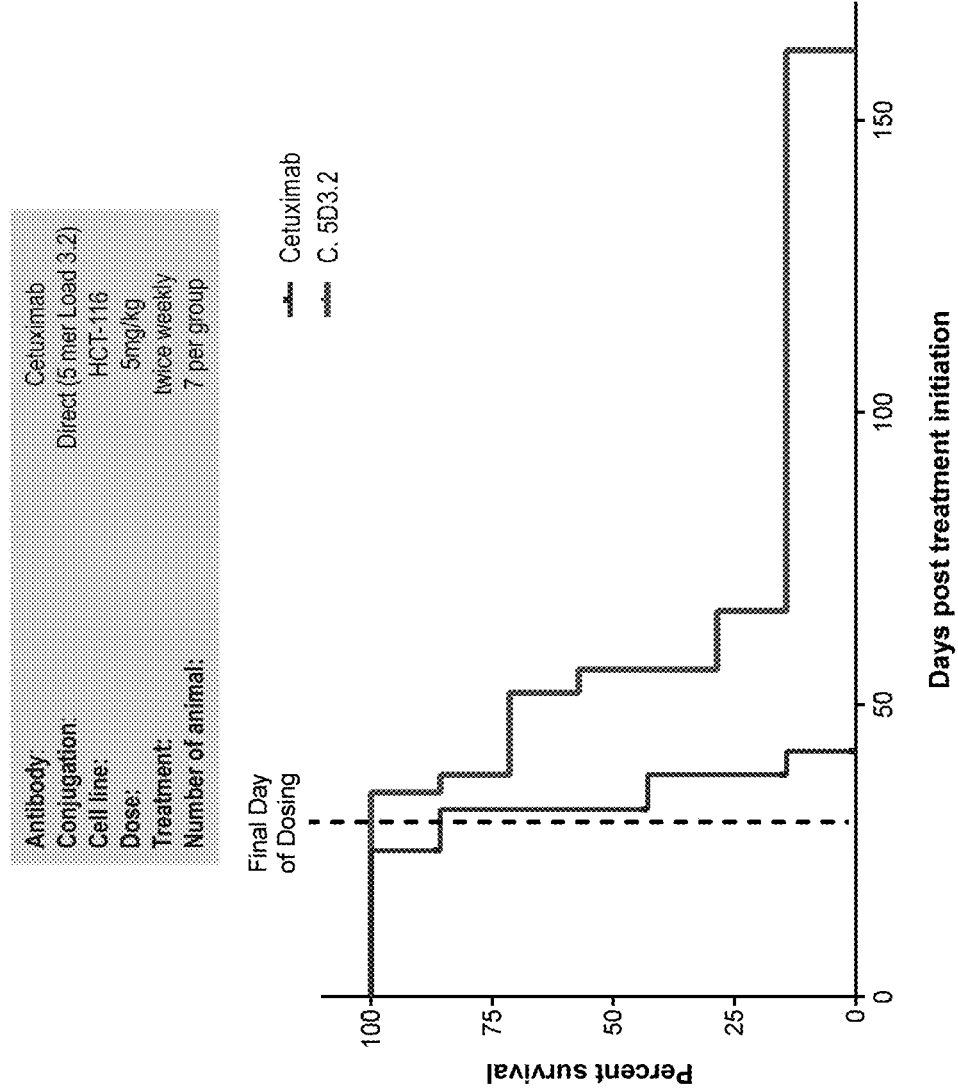

FIG. 64 is a graph showing that a mAbXcite-cetuximab increases survival in a KRAS mutant colorectal cancer xenograft model.

Figure 65:
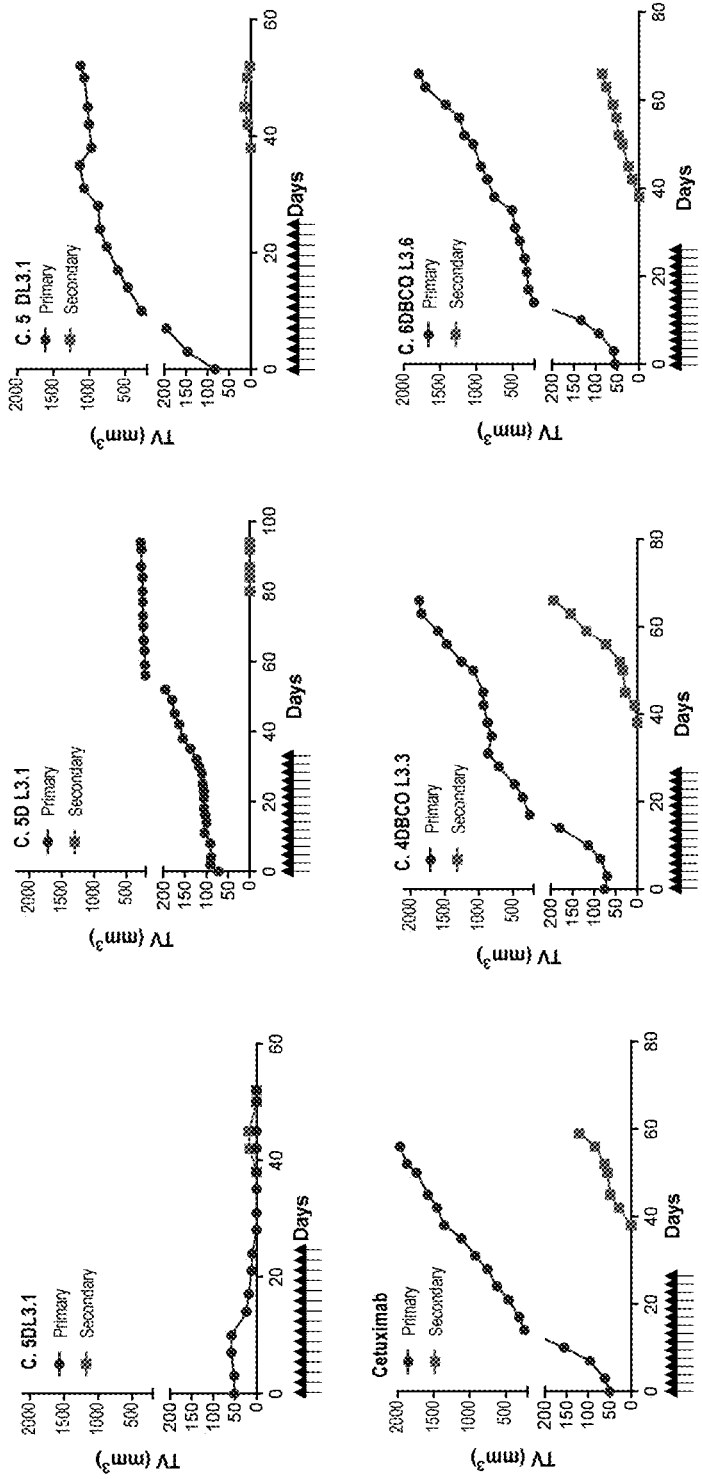

FIG. 65 is a set of six graphs showing tumor regression or stasis is observed with direct conjugate mAbXcite-cetuximab and correlates with immune memory. Individual graphs represent individual mice.

FIG. 66 is a set of five graphs showing no tumor regression or stasis with 4-mer DBCO mAbXcite-cetuximab conjugates. Individual graphs represent individual mice.

Figure 67:
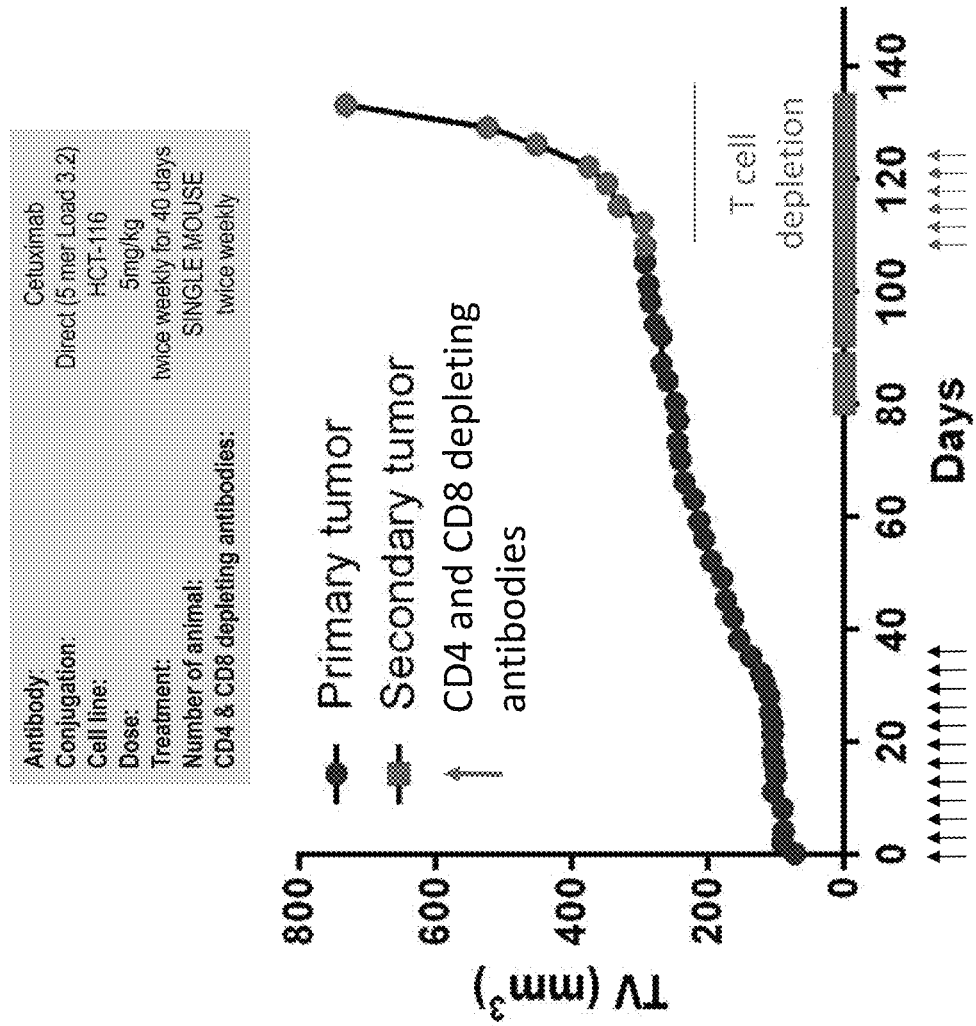

FIG. 67 is a graph showing evidence for involvement of T cells in stasis.

Figure 68:
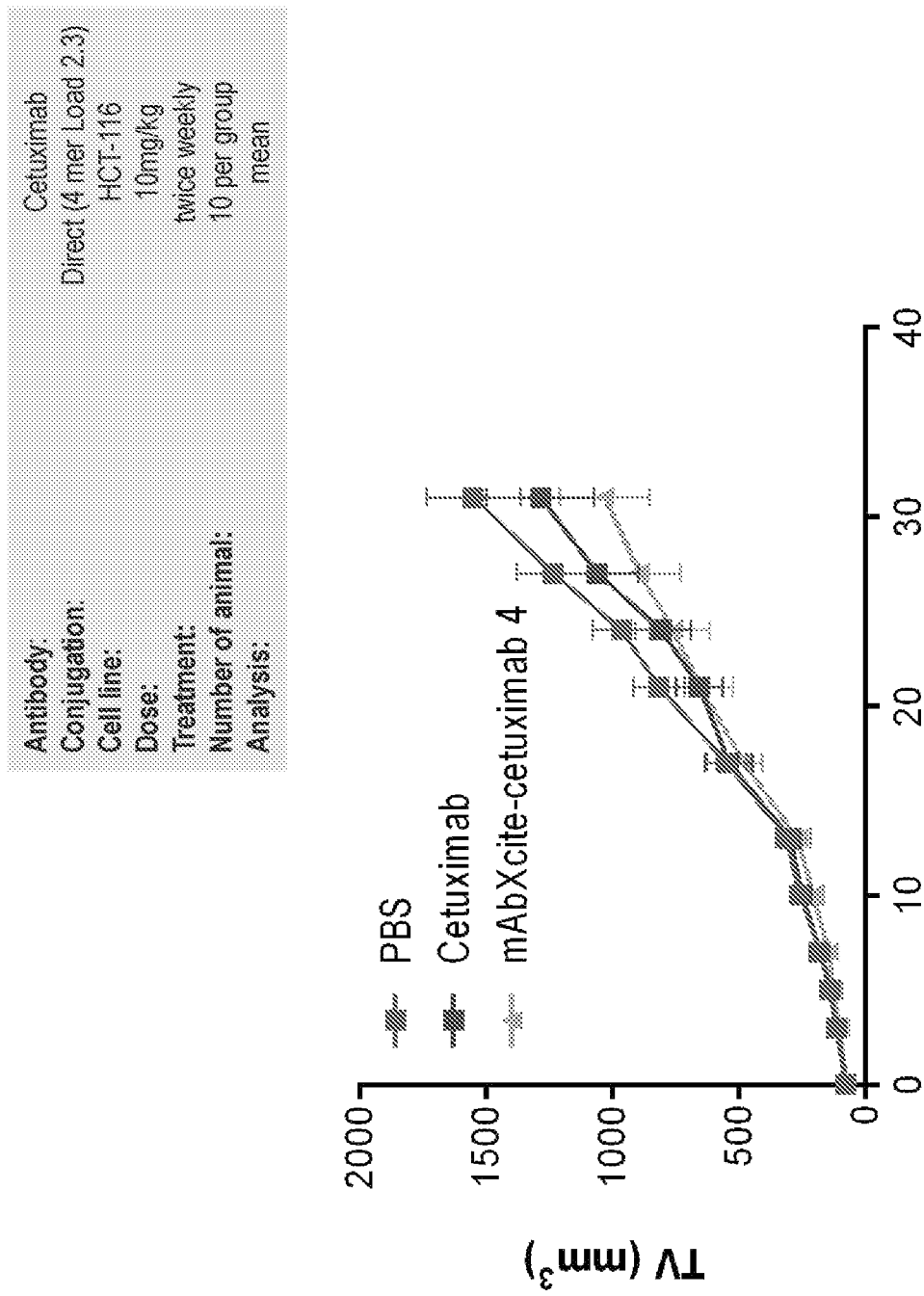

FIG. 68 is a graph showing KRAS mutant colorectal tumor growth.

Figure 69:
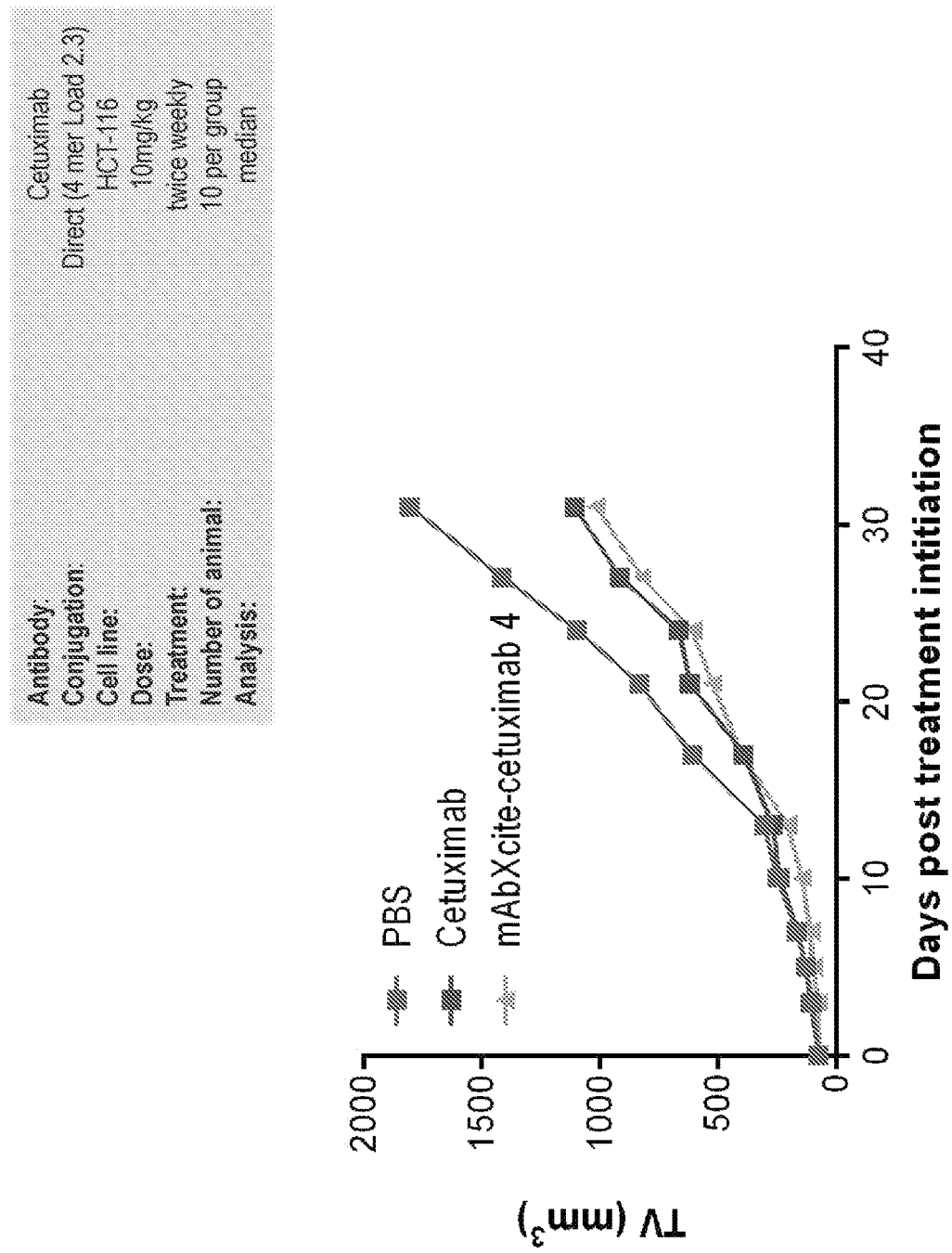

FIG. 69 is a graph showing KRAS mutant colorectal tumor growth.

Figure 70:
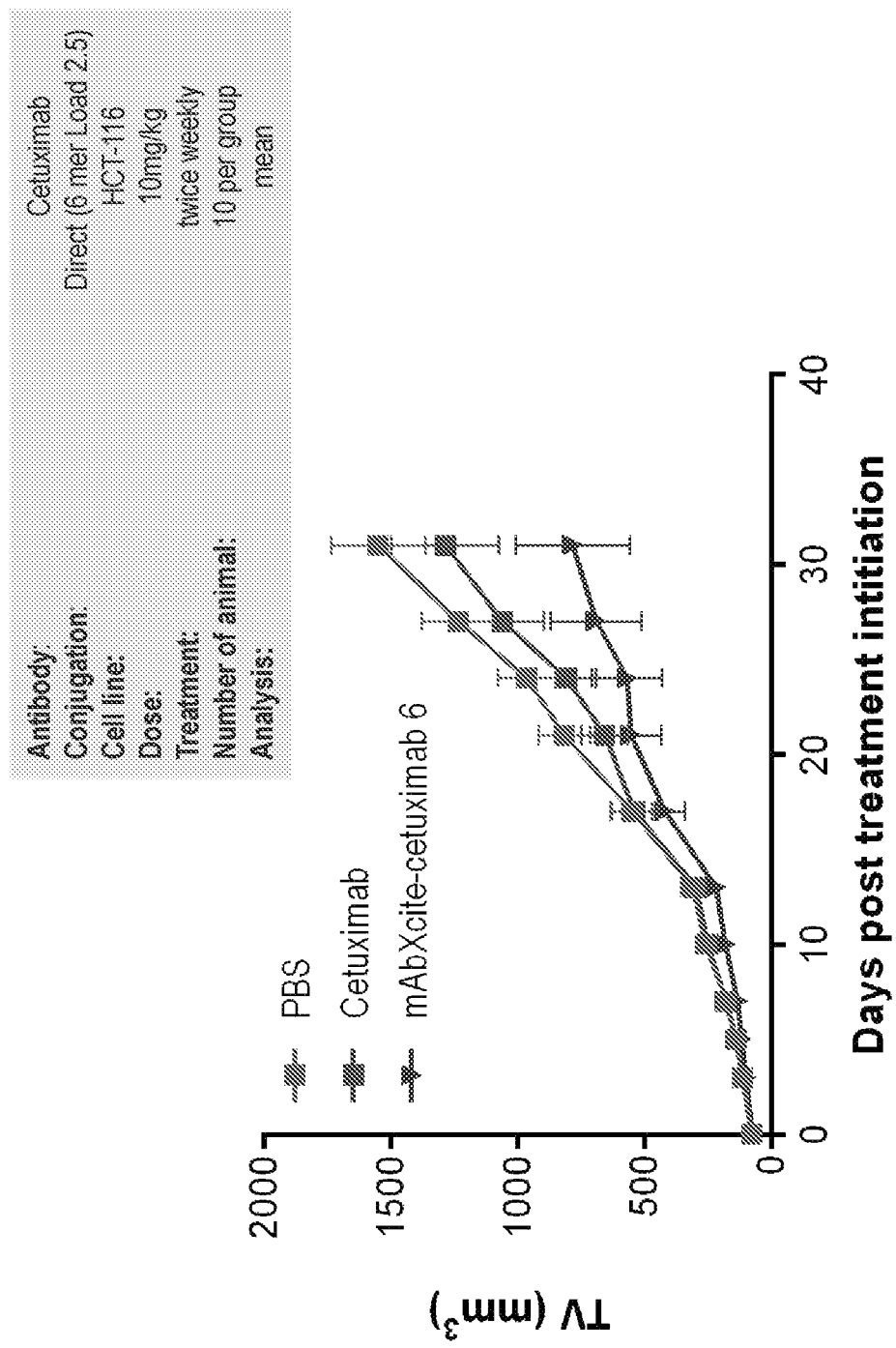

FIG. 70 is a graph showing KRAS mutant colorectal tumor growth.

Figure 71:
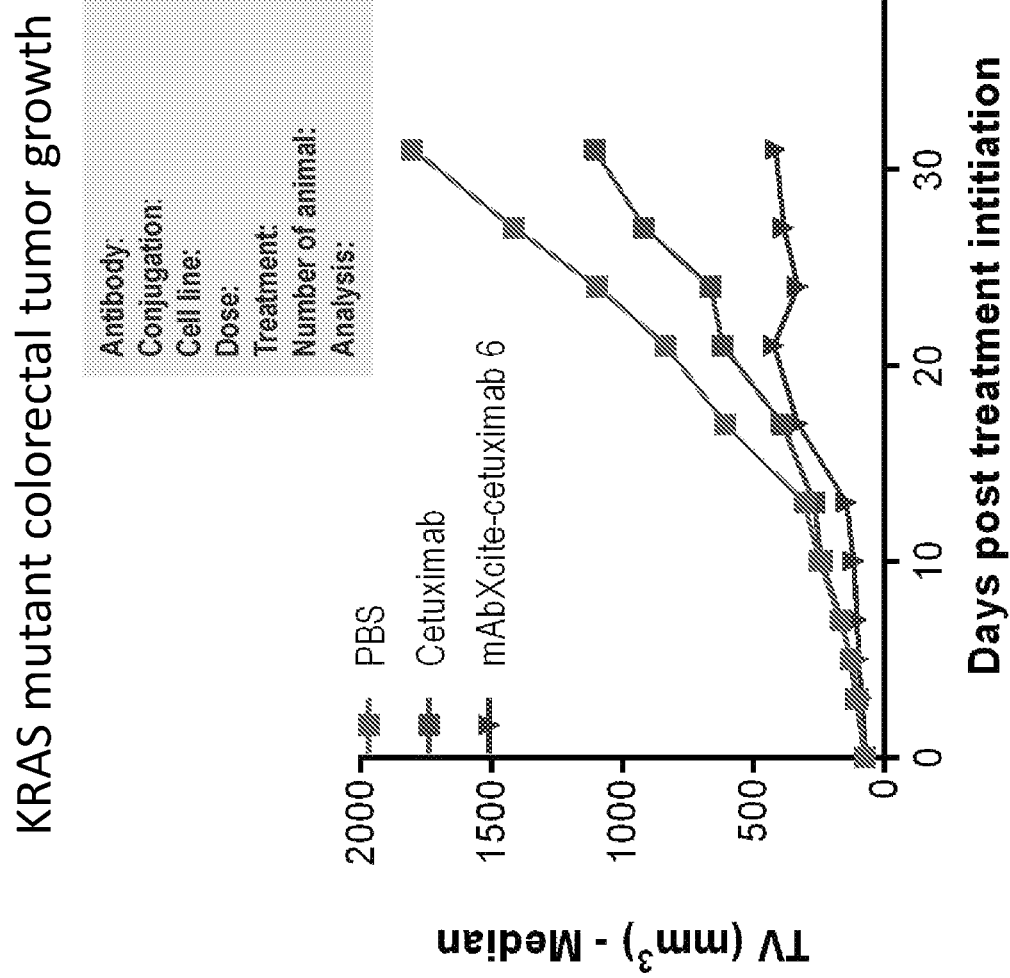

FIG. 71 is a graph showing KRAS mutant colorectal tumor growth.

Figure 72:
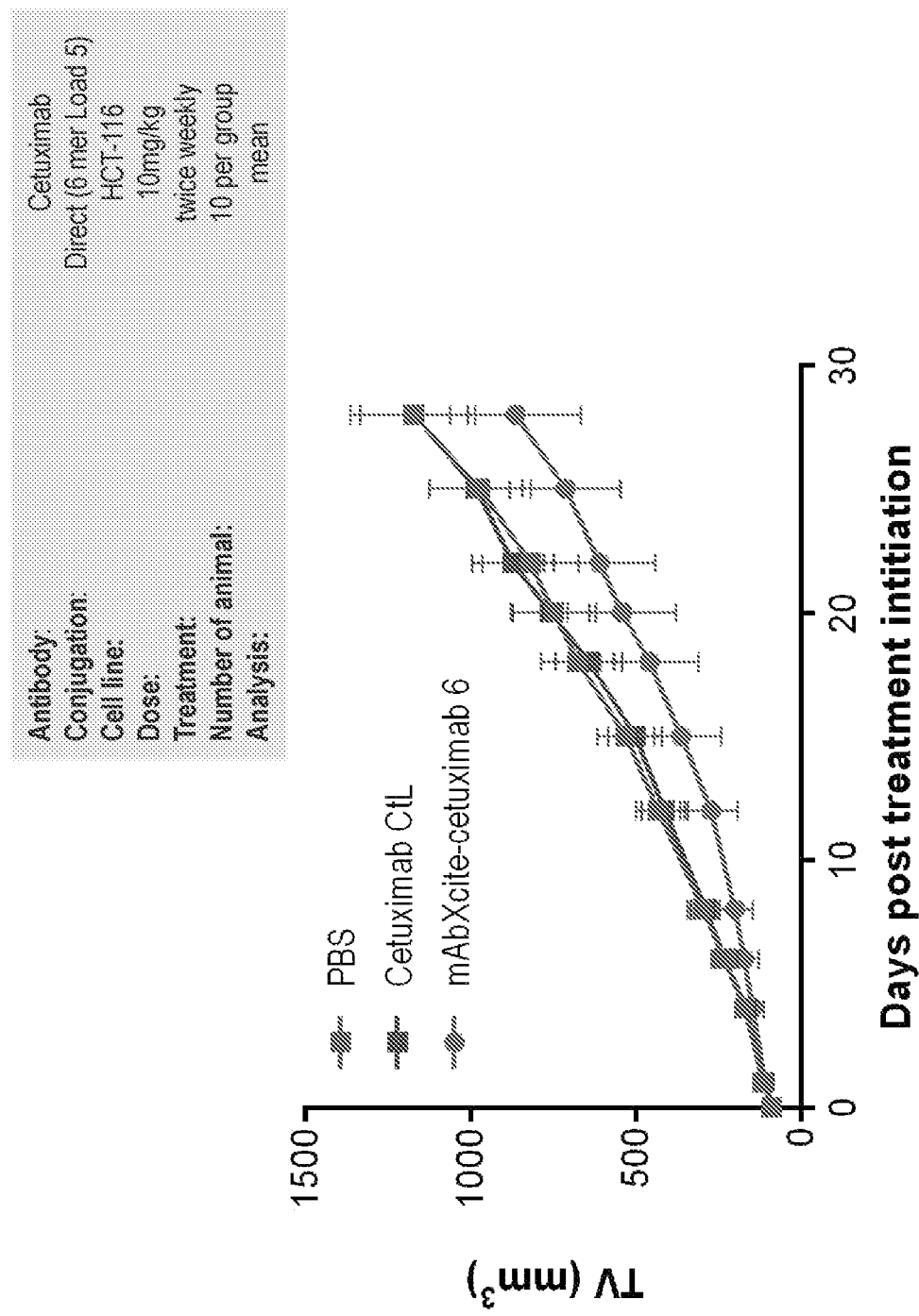

FIG. 72 is a graph showing mean tumor growth.

Figure 73:
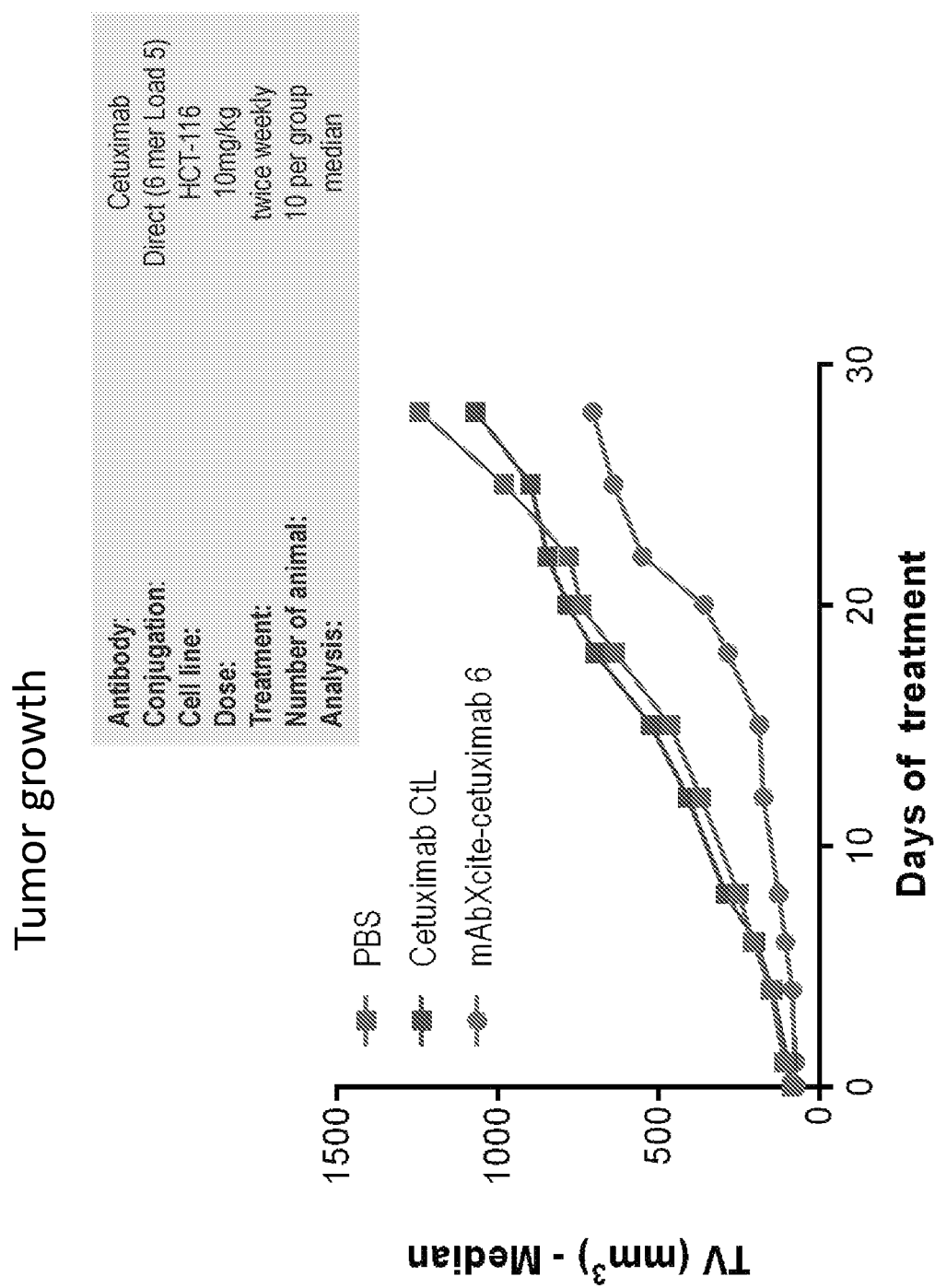

FIG. 73 is a graph showing median tumor growth.

DETAILED DESCRIPTION

The present invention encompasses embodiments in which a therapeutic antibody is conjugated to β-1,6-glucan oligomers. Thus, the present invention includes, among other things, compositions including a therapeutic antibody conjugated to one or more β-1,6-glucan oligomers. The present invention further includes, among other things, methods of making and/or using these β-1,6-glucan conjugates. In certain embodiments, a β-1,6-glucan conjugate of the present invention is useful as a therapeutic or in a method of therapy.

Therapeutic Antibodies

Monoclonal antibodies are useful in the treatment of various cancers. Some antibodies target cell surface moieties. Some antibodies include two heavy chains and two light chains. The heavy chain and light chain sequences listed in Table I are known in the art. Moreover, the various domains in the heavy and light chain domains, such as the variable domains, constant domains, CDRs and FWs are known in the art. Table I provides some sources for the sequences listed therein. The contents of all of these are herein incorporated by reference in their entireties.

TABLE I

Exemplary Therapeutic Antibody Sequences

| Antibody (Proprietary Name) | Target | Sequences |
|---|---|---|
| Cergutuzumab | CEACAM5 | Source: drugspider.com/drug/cergutuzumab-amunaleukin<br>Heavy chain, SEQ ID NO: 49<br>QVQLVQSGAEVKKPGASVKVSCKASGYTFTEFGMNW<br>VRQAPGQGLEWMGWINTKTGEATYVEEFKGRVTFTT<br>DTSTSTAYMELRSLRSDDTAVYYCARWDFAYYVEAM<br>DYWGQGTTVTVSSASTKGPSVFPLAPSSKSTSGGTA<br>ALGCLVKDYFPEPVTVSWNSGALTSGVHTFPAVLQS<br>SGLYSLSSVVTVPSSSLGTQTYICNVNHKPSNTKVD<br>KKVEPKSCDKTHTCPPCPAPEAAGGPSVFLFPPKPK<br>DTLMISRTPEVTCVVVDVSHEDPEVKFNWYVDGVEV<br>HNAKTKPREEQYNSTYRVVSVLTVLHQDWLNGKEYK<br>CKVSNKALGAPIEKTISKAKGQPREPQVCTLPPSRD<br>ELTKNQVSLSCAVKGFYPSDIAVEWESNGQPENNYK<br>TTPPVLDSDGSFFLVSKLTVDKSRWQQGNVFSCSVM<br>HEALHNHYTQKSLSLSPGK<br>Light chain, SEQ ID NO: 50<br>DIQMTQSPSSLSASVGDRVTITCKASAAVGTYVAWY<br>QQKPGKAPKLLIYSASYRKRGVPSRFSGSGSGTDFT<br>LTISSLQPEDFATYYCHQYYTYPLFTFGQGTKLEIK<br>RTVAAPSVFIFPPSDEQLKSGTASVVCLLNNFYPRE<br>AKVQWKVDNALQSGNSQESVTEQDSKDSTYSLSSTL<br>TLSKADYEKHKVYACEVTHQGLSSPVTKSFNRGEC |
| Ibritumomab tiuxetan (Zevalin®) | CD20 | Source: www.drugbank.ca/drugs/DB00078<br>Heavy chain, SEQ ID NO: 51<br>QAYLQQSGAELVRPGASVKMSCKASGYTFTSYNMHW<br>VKQTPRQGLEWIGAIYPGNGDTSYNQKFKGKATLTV<br>DKSSSTAYMQLSSLTSEDSAVYFCARVVYYSNSYWY<br>FDVWGTGTTVTVSAPSVYPLAPVCGDTTGSSVTLGC<br>LVKGYFPEPVTLTWNSGSLSSGVHTFPAVLQSDLYT<br>LSSSVTVTSSTWPSQSITCNVAHPASSTKVDKKIEP<br>RGPTIKPCPPCKCPAPNLLGGPSVFIFPPKIKDVLM<br>ISLSPIVTCVVVDVSEDDPDVQISWFVNNVEVHTAQ<br>TQTHREDYNSTLRVVSALPIQHQDWMSGKEFKCKVN<br>NKDLPAPIERTISKPKGSVRAPQVYVLPPPEEEMTK<br>KQVTLTCMVTDFMPEDIYVEWTNNGKTELNYKNTEP<br>VLDSDGSYFMYSKLRVEKKNWVERNSYSCSVVHEGL<br>HNHHTTKSFSR<br>Light chain, SEQ ID NO: 52<br>QIVLSQSPAILSASPGEKVTMTCRASSSVSYMHWYQ<br>QKPGSSPKPWIYAPSNLASGVPARFSGSGSGTSYSL<br>TISRVEAEDAATYYCQQWSFNPPTFGAGTKLELKRA<br>DAAPTVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFN |
| Rituximab (Rituxan®) | CD20 | Source: Error! Hyperlink reference not valid. www.drugbank.ca/drugs/DB00073<br>Heavy chain, SEQ ID NO: 53<br>QVQLQQPGAELVKPGASVKMSCKASGYTFTSYNMHW<br>VKQTPGRGLEWIGAIYPGNGDTSYNQKFKGKATLTA<br>DKSSSTAYMQLSSLTSEDSAVYYCARSTYYGGDWYF<br>NVWGAGTTVTVSAASTKGPSVFPLAPSSKSTSGGTA<br>ALGCLVKDYFPEPVTVSWNSGALTSGVHTFPAVLQS<br>SGLYSLSSVVTVPSSSLGTQTYICNVNHKPSNTKVD<br>KKAEPKSCDKTHTCPPCPAPELLGGPSVFLFPPKPK<br>DTLMISRTPEVTCVVVDVSHEDPEVKFNWYVDGVEV<br>HNAKTKPREEQYNSTYRVVSVLTVLHQDWLNGKEYK<br>CKVSNKALPAPIEKTISKAKGQPREPQVYTLPPSRD<br>ELTKNQVSLTCLVKGFYPSDIAVEWESNGQPENNYK<br>TTPPVLDSDGSFFLYSKLTVDKSRWQQGNVFSCSVM<br>HEALHNHYTQKSLSLSPGK |

TABLE I-continued

Exemplary Therapeutic Antibody Sequences

| Antibody (Proprietary Name) | Target | Sequences |
|---|---|---|
| | | Light chain, SEQ ID NO: 54<br>QIVLSQSPAILSASPGEKVTMTCRASSSVSYIHWFQ<br>QKPGSSPKPWIYATSNLASGVPVRFSGSGSGTSYSL<br>TISRVEAEDAATYYCQQWTSNPPTFGGGTKLEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC |
| Tositumomab (Bexxar®) | CD20 | Source: www.drugbank.ca/drugs/DB00081<br>Heavy Chain, SEQ ID NO: 55<br>QAYLQQSGAELVRPGASVKMSCKASGYTFTSYNMHW<br>VKQTPRQGLEWIGAIYPGNGDTSYNQKFKGKATLTV<br>DKSSSTAYMQLSSLTSEDSAVYFCARVVYYSNSYWY<br>FDVWGTGTTVTVSGPSVFPLAPSSKSTSGGTAALGC<br>LVKDYFPEPVTVSWNSGALTSGVHTFPAVLQSSGLY<br>SLSSVVTVPSSSLGTQTYICNVNHKPSNTKVDKKAE<br>PKSCDKTHTCPPCPAPELLGGPSVFLFPPKPKDTLM<br>ISRTPEVTCVVVDVSHEDPEVKFNWYVDGVEVHNAK<br>TKPREEQYNSTYRVVSVLTVLHQDWLNGKEYKCKVS<br>NKALPAPIEKTISKAKGQPREPQVYTLPPSRDELTK<br>NQVSLTCLVKGFYPSDIAVEWESNGQPENNYKTTPP<br>VLDSDGSFFLYSKLTVDKSRWQQGNVFSCSVMHEAL<br>HNHYTQKSLSLSPGK<br>Light Chain, SEQ ID NO: 56<br>QIVLSQSPAILSASPGEKVTMTCRASSSVSYMHWYQ<br>QKPGSSPKPWIYAPSNLASGVPARFSGSGSGTSYSL<br>TISRVEAEDAATYYCQQWSFNPPTFGAGTKLELKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNR |
| Gemtuzumab ozogamicin (Mylotarg®) Monoclonal antibody to CD33 linked to a cytotoxic agent from the class of calicheamicin | CD33 | Source: www.drugbank.ca/drugs/DB00056<br>Heavy Chain No. 1, SEQ ID NO: 57<br>QVQLQQSGAELAKPGASVKMSCKASGYTFTSYRMHW<br>VKQRPGQGLEWIGYINPSTGYTEYNQKFKDKATLTA<br>DKSSSTAYMQLSSLTFEDSAVYYCARGGGVFDYWGQ<br>GTTLTVSS<br>Heavy Chain No. 2, SEQ ID NO: 58<br>QVQLVQSGAEVKKPGSSVKVSCKASGGTFSRSAIIW<br>VRQAPGQGLEWMGGIVPMFGPPNYAQKFQGRVTITA<br>DESTNTAYMELSSLRSEDTAFYFCAGGYGIYSPEEY<br>NGGLVTVSS<br>Light Chain No. 1, SEQ ID NO: 59<br>QIVLTQSPAIMSASPGEKVTITCSASSSISYMHWFQ<br>QKPGTSPKLWIYTTSNLASGVPARFSGSGSGTSYSL<br>TISRMEAEDAATYYCHQRSTYPLTFGSGTKLELK<br>Light Chain No. 2, SEQ ID NO: 60<br>DIQMTQSPSTLSASVGDRVTITCRASQSINTWLAWY<br>QQKPGKAPKLLMYKASSLESGVPSRFIGSGSGTEFT<br>LTISSLQPDDFATYYCQQYNSDSKMFGQGTKVEVK |
| Alemtuzumab (Campath®) | CD52 a protein present on the surface of mature lymphocytes, but not on the stem cells from which these lymphocytes are derived | Source: www.drugbank.ca/drugs/DB00087<br>Heavy chain, SEQ ID NO: 61<br>QVQLQESGPGLVRPSQTLSLTCTVSGFTFTDFYMNW<br>VRQPPGRGLEWIGFIRDKAKGYTTEYNPSVKGRVTM<br>LVDTSKNQFSLRLSSVTAADTAVYYCAREGHTAAPF<br>DYWGQGSLVTVSSASTKGPSVFPLAPSSKSTSGGTA<br>ALGCLVKDYFPEPVTVSWNSGALTSGVHTFPAVLQS<br>SGLYSLSSVVTVPSSSLGTQTYICNVNHKPSNTKVD<br>KKVEPKSCDKTHTCPPCPAPELLGGPSVFLFPPKPK<br>DTLMISRTPEVTCVVVDVSHEDPEVKFNWYVDGVEV<br>HNAKTKPREEQYNSTYRVVSVLTVLHQDWLNGKEYK<br>CKVSNKALPAPIEKTISKAKGQPREPQVYTLPPSRD<br>ELTKNQVSLTCLVKGFYPSDIAVEWESNGQPENNYK<br>TTPPVLDSDGSFFLYSKLTVDKSRWQQGNVFSCSVM<br>HEALHNHYTQKSLSLSPGK<br>Light Chain, SEQ ID NO: 62<br>DIQMTQSPSSLSASVGDRVTITCKASQNIDKYLNWY<br>QQKPGKAPKLLIYNTNNLQTGVPSRFSGSGSGTDFT<br>FTISSLQPEDIATYYCLQHISRPRTFGQGTKVEIKR<br>TVAAPSVFIFPPSDEQLKSGTASVVCLLNNFYPREA |

TABLE I-continued

Exemplary Therapeutic Antibody Sequences

| Antibody (Proprietary Name) | Target | Sequences |
|---|---|---|
| | | KVQWKVDNALQSGNSQESVTEQDSKDSTYSLSSTLT<br>LSKADYEKHKVYACEVTHQGLSSPVTKSFNR |
| Cetuximab (Erbitux®) | EGFR | See Table II |
| Panitumumab (Vectibix®) | EGFR | Source: PTE application for U.S. Pat. No. 6,235,883<br>Heavy chain, SEQ ID NO: 63<br>QVQLQESGPGLVKPSETLSLTCTVSGGSVSSGDYYW<br>TWIRQSPGKGLEWIGHIYYSGNTNYNPSLKSRLTIS<br>IDTSKTQFSLKLSSVTAADTAIYYCVRDRVTGAFDI<br>WGQGTMVTVSSASTKGPSVFPLAPCSRSTSESTAAL<br>GCLVKDYFPEPVTVSWNSGALTSGVHTFPAVLQSSG<br>LYSLSSVVTVPSSNFGTQTYTCNVDHKPSNTKVDKT<br>VERKCCVECPPCPAPPVAGPSVFLFPPKPKDTLMIS<br>RTPEVTCVVVDVSHEDPEVQFNWYVDGVEVHNAKTK<br>PREEQFNSTFRVVSVLTVVHQDWLNGKEYKCKVSNK<br>GLPAPIEKTISKTKGQPREPQVYTLPPSREEMTKNQ<br>VSLTCLVKGFYPSDIAVEWESNGQPENNYKTTPPML<br>DSDGSFFLYSKLTVDKSRWQQGNVFSCSVMHEALHN<br>HYTQKSLSLSPG<br>Light chain, SEQ ID NO: 64<br>DIQMTQSPSSLSASVGDRVTITCQASQDISNYLNWY<br>QQKPGKAPKLLIYDASNLETGVPSRFSGSGSGTDFT<br>FTISSLQPEDIATYFCQHFDHLPLAFGGGTKVEIKR<br>TVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC |
| Depatuxizumab | EGFR VIII | Source: drugspider.com/drug/depatuxizumab<br>Heavy chain, SEQ ID NO: 65<br>QVQLQESGPGLVKPSQTLSLTCTVSGYSISSDFAWN<br>WIRQPPGKGLEWMGYISYSGNTRYQPSLKSRITISR<br>DTSKNQFFLKLNSVTAADTATYYCVTAGRGFPYWGQ<br>GTLVTVSSASTKGPSVFPLAPSSKSTSGGTAALGCL<br>VKDYFPEPVTVSWNSGALTSGVHTFPAVLQSSGLYS<br>LSSVVTVPSSSLGTQTYICNVNHKPSNTKVDKKVEP<br>KSCDKTHTCPPCPAPELLGGPSVFLFPPKPKDTLMI<br>SRTPEVTCVVVDVSHEDPEVKFNWYVDGVEVHNAKT<br>KPREEQYNSTYRVVSVLTVLHQDWLNGKEYKCKVSN<br>KALPAPIEKTISKAKGQPREPQVYTLPPSRDELTKN<br>QVSLTCLVKGFYPSDIAVEWESNGQPENNYKTTPPV<br>LDSDGSFFLYSKLTVDKSRWQQGNVFSCSVMHEALH<br>NHYTQKSLSLSPGK<br>Light chain, SEQ ID NO: 66<br>DIQMTQSPSSMSVSVGDRVTITCHSSQDINSNIGWL<br>QQKPGKSFKGLIYHGTNLDDGVPSRFSGSGSGTDYT<br>LTISSLQPEDFATYYCVQYAQFPWTFGGGTKLEIKR<br>TVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC |
| Sibrotuzumab | FAP | Sources: www.imgt.org/mAb-DB/mAbcard?AbId=285; U.S. Pat. application Publication No. 20030103968 and PCT Pat. application Publication No. WO 99/57151<br>Heavy chain, SEQ ID NO: 67<br>QVQLVQSGAEVKKPGASVKVSCKTSRYTFTEYTIHW<br>VRQAPGQRLEWIGGINPNNGIPNYNQKFKGRVTITV<br>DTSASTAYMELSSLRSEDTAVYYCARRRIAYGYDEG<br>HAMDYWGQGTLVTVSSASTKGPSVFPLAPSSKSTSG<br>GTAALGCLVKDYFPEPVTVSWNSGALTSGVHTFPAV<br>LQSSGLYSLSSVVTVPSSSLGTQTYICNVNHKPSNT<br>KVDKKVEPKSCDKTHTCPPCPAPELLGGPSVFLFPP<br>KPKDTLMISRTPEVTCVVVDVSHEDPEVKFNWYVDG<br>VEVHNAKTKPREEQYNSTYRVVSVLTVLHQDWLNGK<br>EYKCKVSNKALPAPIEKTISKAKGQPREPQVYTLPP<br>SREEMTKNQVSLTCLVKGFYPSDIAVEWESNGQPEN<br>NYKTTPPVLDSDGSFFLYSKLTVDKSRWQQGNVFSC<br>SVMHEALHNHYTQKSLSLSPGK |

TABLE I-continued

Exemplary Therapeutic Antibody Sequences

| Antibody (Proprietary Name) | Target | Sequences |
|---|---|---|
| | | Light chain, SEQ ID NO: 68<br>DIVMTQSPDSLAVSLGERATINCKSSQSLLYSRNQK<br>NYLAWYQQKPGQPPKLLIFWASTRESGVPDRFSGSG<br>FGTDFTLTISSLQAEDVAVYYCQQYFSYPLTFGQGT<br>KVEIKRTVAAPSVFIFPPSDEQLKSGTASVVCLLNN<br>FYPREAKVQWKVDNALQSGNSQESVTEQDSKDSTYS<br>LSSTLTLSKADYEKHKVYACEVTHQGLSSPVTKSFN<br>RGEC |
| Codrituzumab | Glycipan-3 | Sources: www.imgt.org/mAb-DB/<br>mAbcard?AbId=466; U.S.<br>Pat. No. 7,867,734<br>Heavy chain, SEQ ID NO: 69<br>QVQLVQSGAEVKKPGASVKVSCKASGYTFTDYEMHW<br>VRQAPGQGLEWMGALDPKTGDTAYSQKFKGRVTLTA<br>DKSTSTAYMELSSLTSEDTAVYYCTRFYSYTYWGQG<br>TLVTVSSASTKGPSVFPLAPSSKSTSGGTAALGCLV<br>KDYFPEPVTVSWNSGALTSGVHTFPAVLQSSGLYSL<br>SSVVTVPSSSLGTQTYICNVNHKPSNTKVDKKVEPK<br>SCDKTHTCPPCPAPELLGGPSVFLFPPKPKDTLMIS<br>RTPEVTCVVVDVSHEDPEVKFNWYVDGVEVHNAKTK<br>PREEQYNSTYRVVSVLTVLHQDWLNGKEYKCKVSNK<br>ALPAPIEKTISKAKGQPREPQVYTLPPSRDELTKNQ<br>VSLTCLVKGFYPSDIAVEWESNGQPENNYKTTPPVL<br>DSDGSFFLYSKLTVDKSRWQQGNVFSCSVMHEALHN<br>HYTQKSLSLSPGK<br>Light chain, SEQ ID NO: 70<br>DVVMTQSPLSLPVTPGEPASISCRSSQSLVHSNRNT<br>YLHWYLQKPGQSPQLLIYKVSNRFSGVPDRFSGSGS<br>GTDFTLKISRVEAEDVGVYYCSQNTHVPPTFGQGTK<br>LEIKRTVAAPSVFIFPPSDEQLKSGTASVVCLLNNF<br>YPREAKVQWKVDNALQSGNSQESVTEQDSKDSTYSL<br>SSTLTLSKADYEKHKVYACEVTHQGLSSPVTKSFNR<br>GEC |
| Trastuzumab (Herceptin®) | HER2/neu | See Table III |
| Patritumab | Her3 | Source:<br>www.ebi.ac.uk/chembl/compound/<br>inspect/CHEMBL2109406<br>Heavy chain, SEQ ID NO: 71<br>QVQLQQWGAGLLKPSETLSLTCAVYGGSFSGYYWSW<br>IRQPPGKGLEWIGEINHSGSTNYNPSLKSRVTISVE<br>TSKNQFSLKLSSVTAADTAVYYCARDKWTWYFDLWG<br>RGTLVTVSSASTKGPSVFPLAPSSKSTSGGTAALGC<br>LVKDYFPEPVTVSWNSGALTSGVHTFPAVLQSSGLY<br>SLSSVVTVPSSSLGTQTYICNVNHKPSNTKVDKRVE<br>PKSCDKTHTCPPCPAPELLGGPSVFLFPPKPKDTLM<br>ISRTPEVTCVVVDVSHEDPEVKFNWYVDGVEVHNAK<br>TKPREEQYNSTYRVVSVLTVLHQDWLNGKEYKCKVS<br>NKALPAPIEKTISKAKGQPREPQVYTLPPSREEMTK<br>NQVSLTCLVKGFYPSDIAVEWESNGQPENNYKTTPP<br>VLDSDGSFFLYSKLTVDKSRWQQGNVFSCSVMHEAL<br>HNHYTQKSLSLSPGK<br>Light chain, SEQ ID NO: 72<br>DIEMTQSPDSLAVSLGERATINCRSSQSVLYSSSNR<br>NYLAWYQQNPGQPPKLLIYWASTRESGVPDRFSGSG<br>SGTDFTLTISSLQAEDVAVYYCQQYYSTPRTFGQGT<br>KVEIKRTVAAPSVFIFPPSDEQLKSGTASVVCLLNN<br>FYPREAKVQWKVDNALQSGNSQESVTEQDSKDSTYS<br>LSSTLTLSKADYEKHKVYACEVTHQGLSSPVTKSFN<br>RGEC |
| Figitumumab | IGF1R (insulin-like growth factor-1 receptor) | Source:<br>www.ebi.ac.uk/chembl/compound/<br>inspect/CHEMBL1743019<br>Heavy chain, SEQ ID NO: 73<br>EVQLLESGGGLVQPGGSLRLSCTASGFTFSSYAMNW<br>VRQAPGKGLEWVSAISGSGGTTFYADSVKGRFTISR<br>DNSRTTLYLQMNSLRAEDTAVYYCAKDLGWSDSYYY<br>YYGMDVWGQGTTVTVSSASTKGPSVFPLAPCSRSTS<br>ESTAALGCLVKDYFPEPVTVSWNSGALTSGVHTFPA<br>VLQSSGLYSLSSVVTVPSSNFGTQTYTCNVDHKPSN |

TABLE I-continued

Exemplary Therapeutic Antibody Sequences

| Antibody (Proprietary Name) | Target | Sequences |
|---|---|---|
| | | TKVDKTVERKCCVECPPCPAPPVAGPSVFLFPPKPK<br>DTLMISRTPEVTCVVVDVSHEDPEVQFNWYVDGVEV<br>HNAKTKPREEQFNSTFRVVSVLTVVHQDWLNGKEYK<br>CKVSNKGLPAPIEKTISKTKGQPREPQVYTLPPSRE<br>EMTKNQVSLTCLVKGFYPSDIAVEWESNGQPENNYK<br>TTPPMLDSDGSFFLYSKLTVDKSRWQQGNVFSCSVM<br>HEALHNHYTQKSLSLSPG<br>Light chain, SEQ ID NO: 74<br>DIQMTQFPSSLSASVGDRVTITCRASQGIRNDLGWY<br>QQKPGKAPKRLIYAASRLHRGVPSRFSGSGSGTEFT<br>LTISSLQPEDFATYYCLQHNSYPCSFGQGTKLEIKR<br>TVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC |
| Ganitumab | IGF1R | Source: www.genome.jp/dbget-bin/<br>www_bget?dr:D09908<br>Heavy chain, SEQ ID NO: 75<br>QVQLQESGPGLVKPSGTLSLTCAVSGGSISSSNWWS<br>WVRQPPGKGLEWIGEIYHSGSTNYNPSLKSRVTISV<br>DKSKNQFSLKLSSVTAADTAVYYCARWTGRTDAFDI<br>WGQGTMVTVSSASTKGPSVFPLAPSSKSTSGGTAAL<br>GCLVKDYFPEPVTVSWNSGALTSGVHTFPAVLQSSG<br>LYSLSSVVTVPSSSLGTQTYICNVNHKPSNTKVDKK<br>VEPKSCDKTHTCPPCPAPELLGGPSVFLEPPKPKDT<br>LMISRTPEVTCVVVDVSHEDPEVKFNWYVDGVEVHN<br>AKTKPREEQYNSTYRVVSVLTVLHQDWLNGKEYKCK<br>VSNKALPAPIEKTISKAKGQPREPQVYTLPPSRDEL<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK<br>Light chain, SEQ ID NO: 76<br>DVVMTQSPLSLPVTPGEPASISCRSSQSLLHSNGYN<br>YLDWYLQKPGQSPQLLIYLGSNRASGVPDRFSGSGS<br>GTDFTLKISRVEAEDVGVYYCMQGTHWPLTFGQGTK<br>VEIKRTVAAPSVFIFPPSDEQLKSGTASVVCLLNNF<br>YPREAKVQWKVDNALQSGNSQESVTEQDSKDSTYSL<br>SSTLTLSKADYEKHKVYACEVTHQGLSSPVTKSFNR<br>GEC |
| Cantuzumab | Muc1 (CanAg) | Source: www.kegg.jp/dbget-bin/<br>www_bget?dr:D10454<br>Heavy chain, SEQ ID NO: 77<br>XVQLVQSGAEVKKPGETVKISCKASDYTFTYYGMNW<br>VKQAPGQGLKWMGWIDTTTGEPTYAQKFQGRIAFSL<br>ETSASTAYLQIKSLKSEDTATYFCARRGPYNWYFDV<br>WGQGTTVTVSSASTKGPSVFPLAPSSKSTSGGTAAL<br>GCLVKDYFPEPVTVSWNSGALTSGVHTFPAVLQSSG<br>LYSLSSVVTVPSSSLGTQTYICNVNHKPSNTKVDKK<br>VEPKSCDKTHTCPPCPAPELLGGPSVFLFPPKPKDT<br>LMISRTPEVTCVVVDVSHEDPEVKFNWYVDGVEVHN<br>AKTKPREEQYNSTYRVVSVLTVLHQDWLNGKEYKCK<br>VSNKALPAPIEKTISKAKGQPREPQVYTLPPSRDEL<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK<br>Light chain, SEQ ID NO: 78<br>DIVMTQSPLSVPVTPGEPVSISCRSSKSLLHSNGNT<br>YLYWFLQRPGQSPQLLIYRMSNLVSGVPDRFSGSGS<br>GTAFTLRISRVEAEDVGVYYCLQHLEYPFTFGPGTK<br>LELKRTVAAPSVFIFPPSDEQLKSGTASVVCLLNNF<br>YPREAKVQWKVDNALQSGNSQESVTEQDSKDSTYSL<br>SSTLTLSKADYEKHKVYACEVTHQGLSSPVTKSFNR<br>GEC |
| ABX-MA1 | MUC18 | Source: U.S. Pat. No. 6,924,360<br>Heavy chain, SEQ ID NO: 79<br>QVQLQESGPGLVKPSETLSLTCTVSGGSISSYYWSW<br>IRQPPGKGLEWIGYIYYTWTSNYNPSLKSRVTISVD<br>TSKNQFSLRLSSVTAADTAVYYCARDQGQWLLPDAF<br>DIWGQGTMVTVSS<br>Light chain, SEQ ID NO: 80<br>DIVMTQSPLSLPVTPGEPASISCRSSQSLLRSNGYN<br>YLDWYLQKPGQSPHLLIYLGSNRASGVPDRFSGSGS |

TABLE I-continued

Exemplary Therapeutic Antibody Sequences

| Antibody (Proprietary Name) | Target | Sequences |
|---|---|---|
| | | GTDFTLKISRVEAEDVGVYYCMQAQQSPITFGQGTR<br>LEIK |
| Bavituximab | Phosphatidyl Serine (PS) | Source: Error! Hyperlink reference not valid. www.drugbank.ca/drugs/DB05136<br>Heavy chain, SEQ ID NO: 81<br>EVQLQQSGPELEKPGASVKLSCKASGYSFTGYNMNW<br>VKQSHGKSLEWIGHIDPYYGDTSYNQKFRGKATLTV<br>DKSSSTAYMQLKSLTSEDSAVYYCVKGGYYGHWYFD<br>VWGAGTTVTVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDK<br>KVEPKSCDKTHTCPPCPAPELLGGPSVFLFPPKPKD<br>TLMISRTPEVTCVVVDVSHEDPEVKFNWYVDGVEVH<br>NAKTKPREEQYNSTYRVVSVLTVLHQDWLNGKEYKC<br>KVSNKALPAPIEKTISKAKGQPREPQVYTLPPSRDE<br>LTKNQVSLTCLVKGFYPSDIAVEWESNGQPENNYKT<br>TPPVLDSDGSFFLYSKLTVDKSRWQQGNVFSCSVMH<br>EALHNHYTQKSLSLSPGK<br>Light chain, SEQ ID NO: 82<br>DIQMTQSPSSLSASLGERVSLTCRASQDIGSSLNWL<br>QQGPDGTIKRLIYATSSLDSGVPKRFSGSRSGSDYS<br>LTISSLESEDFVDYYCLQYVSSPPTFGAGTKLELKR<br>ADAAPSVFIFPPSDEQLKSGTASVVCLLNNFYPREA<br>KVQWKVDNALQSGNSQESVTEQDSKDSTYSLSKADY<br>EKHKVYACEVTHQGLSSPVTKSFNRGEC |
| J591 | PSMA (prostate specific membrane antigen) | Source: U.S. Pat. No. 7,666,414<br>Heavy chain, SEQ ID NO: 83<br>EVQLQQSGPELKKPGTSVRISCKTSWVKQSHGKSLE<br>WIGKATLTVDKSSSTAYMELRSLTSEDSAVYYCAAW<br>GQGTTLTVSS<br>Light chain, SEQ ID NO: 84<br>DIVMTQSHKFMSTSVGDRVSIICWYQQKPGQSPKLL<br>IYGVPDRFTGSGSGTDFTLTITNVQSEDLADYFCFG<br>AGTMLDLK |
| Palivizumab (Synagis®) | RSV (A antigenic site of the F protein) | Source: U.S. Pat. No. 6,955,717<br>Heavy chain, SEQ ID NO: 85<br>QVTLRESGPALVKPTQTLTLTCTFSGFSLSTSGMSV<br>GWIRQPPGKALEWLADIWWDDKKDYNPSLKSRLTIS<br>KDTSKNQVVLKVTNMDPADTATYYCARSMITNWYFD<br>VWGAGTTVTVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDK<br>RVEPKSCDKTHTCPPCPAPELLGGPSVFLFPPKPKD<br>TLMISRTPEVTCVVVDVSHEDPEVKFNWYVDGVEVH<br>NAKTKPREEQYNSTYRVVSVLTVLHQDWLNGKEYKC<br>KVSNKALPAPIEKTISKAKGQPREPQVYTLPPSREE<br>MTKNQVSLTCLVKGFYPSDIAVEWESNGQPENNYKT<br>TPPVLDSDGSFFLYSKLTVDKSRWQQGNVFSCSVMH<br>EALHNHYTQKSLSLSPGK<br>Light chain, SEQ ID NO: 86<br>DIQMTQSPSTLSASVGDRVTITCKCQLSVGYMHWYQ<br>QKPGKAPKLLIYDTSKLASGVPSRFSGSGSGTEFTL<br>TISSLQPDDFATYYCFQGSGYPFTFGGGTKLEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC |
| Bevacizumab (Avastin®) | VEGF-A | Source: www.drugbank.ca/drugs/DB00112<br>Heavy chain, SEQ ID NO: 87<br>EVQLVESGGGLVQPGGSLRLSCAASGYTFTNYGMNW<br>VRQAPGKGLEWVGWINTYTGEPTYAADFKRRFTFSL<br>DTSKSTAYLQMNSLRAEDTAVYYCAKYPHYYGSSHW<br>YFDVWGQGTLVTVSSASTKGPSVFPLAPSSKSTSGG<br>TAALGCLVKDYFPEPVTVSWNSGALTSGVHTFPAVL<br>QSSGLYSLSSVVTVPSSSLGTQTYICNVNHKPSNTK<br>VDKKVEPKSCDKTHTCPPCPAPELLGGPSVFLFPPK<br>PKDTLMISRTPEVTCVVVDVSHEDPEVKFNWYVDGV<br>EVHNAKTKPREEQYNSTYRVVSVLTVLHQDWLNGKE<br>YKCKVSNKALPAPIEKTISKAKGQPREPQVYTLPPS |

TABLE I-continued

Exemplary Therapeutic Antibody Sequences

| Antibody (Proprietary Name) | Target | Sequences |
|---|---|---|
| | | REEMTKNQVSLTCLVKGFYPSDIAVEWESNGQPENN YKTTPPVLDSDGSFFLYSKLTVDKSRWQQGNVFSCS VMHEALHNHYTQKSLSLSPGK<br>Light chain, SEQ ID NO: 88<br>DIQMTQSPSSLSASVGDRVTITCSASQDISNYLNWY QQKPGKAPKVLIYFTSSLHSGVPSRFSGSGSGTDFT LTISSLQPEDFATYYCQQYSTVPWTFGQGTKVEIKR TVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |

As used herein, the term "therapeutic antibody" encompasses a therapeutic antibody (e.g., one described in Table I) and any antibody or antibody fragment that recognizes and specifically binds the same target as a therapeutic antibody, and has at least a heavy chain variable domain or light chain variable domain having at least 80% identity (e.g., at least 85%, 90%, 91%, 92%, 93%, 94%, 95%, 96%, 97%, 98%, 99%, or 100% identity) to a corresponding sequence of a therapeutic antibody listed in Table I. In some instances, a therapeutic antibody includes two such variable domains, three such variable domains, four such variable domains, two such heavy chain variable domains, two such light chain variable domains, and/or two such heavy chain variable domains and two such light chain variable domains. In some instances, a therapeutic antibody includes a heavy chain or light chain having at least 80% identity (e.g., at least 85%, 90%, 91%, 92%, 93%, 94%, 95%, 96%, 97%, 98%, 99%, or 100% identity) to a corresponding sequence of therapeutic (e.g., one or more of the sequences or a portion of the sequences listed in Table I). In some instances, a therapeutic antibody includes two such chains, three such chains, four such chains, two such heavy chains, two such light chains, and/or two such heavy chains and two such light chains. Thus, a therapeutic antibody may be, e.g., an intact antibody, antibody fragment (such as a Fab, Fab', F(ab')$_2$, Fd, or Fv), single chain Fv (scFv), or multispecific antibody such as a bispecific antibody.

In some embodiments, a therapeutic antibody comprises a heavy chain sequence listed in Table I. In some embodiments, a therapeutic antibody comprises a portion of a heavy chain sequence listed in Table I. In some embodiments, a heavy chain sequence listed in Table I includes a heavy chain variable domain. In some embodiments, a heavy chain sequence listed in Table I includes a heavy chain CDR1. In some embodiments, a heavy chain sequence listed in Table I includes a heavy chain CDR2. In some embodiments, a heavy chain sequence listed in Table I includes a heavy chain CDR3. In some embodiments, a heavy chain sequence listed in Table I includes a heavy chain FW1. In some embodiments, a heavy chain sequence listed in Table I includes a heavy chain FW2. In some embodiments, a heavy chain sequence listed in Table I includes a heavy chain FW3. In some embodiments, a heavy chain sequence listed in Table I includes a heavy chain FW4. In some embodiments, a heavy chain sequence listed in Table I includes a heavy chain CH1 constant domain. In some embodiments, a heavy chain sequence listed in Table I includes a heavy chain CH2 constant domain. In some embodiments, a heavy chain sequence listed in Table I includes a heavy chain CH3 constant domain.

In some embodiments, a light chain sequence listed in Table I includes a light chain variable domain. In some embodiments, a therapeutic antibody comprises a portion of a light chain sequence listed in Table I. In some embodiments, a light chain sequence listed in Table I includes a light chain CDR1. In some embodiments, a light chain sequence listed in Table I includes a light chain CDR2. In some embodiments, a light chain sequence listed in Table I includes a light chain CDR3. In some embodiments, a light chain sequence listed in Table I includes a light chain FW1. In some embodiments, a light chain sequence listed in Table I includes a light chain FW2. In some embodiments, a light chain sequence listed in Table I includes a light chain FW3. In some embodiments, a light chain sequence listed in Table I includes a light chain FW4. In some embodiments, a light chain sequence listed in Table I includes a light chain constant domain. In some embodiments, a therapeutic antibody comprises a kappa light chain. In some embodiments, a therapeutic antibody comprises a lambda light chain.

In various instances of the present invention, a therapeutic antibody includes a heavy chain having at least 80%, at least 85%, at least 90%, at least 91%, at least 92%, at least 93%, at least 94%, at least 95%, at least 96%, at least 97%, at least 98%, or at least 99% identity to a heavy chain sequence listed in Table I.

In various instances of the present invention, a therapeutic antibody includes a light chain having at least 80%, at least 85%, at least 90%, at least 91%, at least 92%, at least 93%, at least 94%, at least 95%, at least 96%, at least 97%, at least 98%, or at least 99% identity to a light chain sequence listed in Table I.

In various instances of the present invention, a therapeutic antibody includes a heavy chain that includes at least one heavy chain variable domain having at least 80%, at least 85%, at least 90%, at least 91%, at least 92%, at least 93%, at least 94%, at least 95%, at least 96%, at least 97%, at least 98%, or at least 99% identity to a heavy chain variable domain included in a heavy chain sequence listed in Table I.

In various instances of the present invention, a therapeutic antibody includes a light chain that includes at least one light chain variable domain having at least 80%, at least 85%, at least 90%, at least 91%, at least 92%, at least 93%, at least 94%, at least 95%, at least 96%, at least 97%, at least 98%, or at least 99% identity to a light chain variable domain included in a light chain sequence listed in Table I.

In various instances of the present invention, a therapeutic antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence of a CDR sequence included in a heavy chain sequence listed in Table I. In certain instances a therapeutic antibody includes a heavy chain including such a CDR sequence. In certain instances a therapeutic antibody includes two such heavy chains.

In various instances of the present invention, a therapeutic antibody includes CDR sequences having at least 80%, at least 85%, at least 90%, at least 91%, at least 92%, at least 93%, at least 94%, at least 95%, at least 96%, at least 97%, at least 98%, or at least 99% identity to two CDR sequences included the same heavy chain sequence listed in Table I. In certain instances a therapeutic antibody includes a heavy chain including such CDR sequences. In certain instances a therapeutic antibody includes two such heavy chains.

In various instances of the present invention, a therapeutic antibody includes CDR sequences having at least 80%, at least 85%, at least 90%, at least 91%, at least 92%, at least 93%, at least 94%, at least 95%, at least 96%, at least 97%, at least 98%, or at least 99% identity to three CDR sequences included in the same heavy chain sequence listed in Table I. In certain instances a therapeutic antibody includes a heavy chain including such CDR sequences. In certain instances a therapeutic antibody includes two such heavy chains.

In various instances of the present invention, a therapeutic antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence included in a light chain sequence listed in Table I. In certain instances a therapeutic antibody includes a light chain including such a CDR sequence. In certain instances a therapeutic antibody includes two such light chains.

In various instances of the present invention, a therapeutic antibody includes CDR sequences having at least 80%, at least 85%, at least 90%, at least 91%, at least 92%, at least 93%, at least 94%, at least 95%, at least 96%, at least 97%, at least 98%, or at least 99% identity to a CDR sequence included in a light chain sequence listed in Table I. In certain instances a therapeutic antibody includes a light chain including such CDR sequences. In certain instances a therapeutic antibody includes two such light chains.

In various instances of the present invention, a therapeutic antibody includes CDR sequences having at least 80%, at least 85%, at least 90%, at least 91%, at least 92%, at least 93%, at least 94%, at least 95%, at least 96%, at least 97%, at least 98%, or at least 99% identity to two CDR sequences included in the same light chain sequence listed in Table I. In certain instances a therapeutic antibody includes a light chain including such CDR sequences. In certain instances a therapeutic antibody includes two such light chains.

In various instances of the present invention, a therapeutic antibody includes CDR sequences having at least 80%, at least 85%, at least 90%, at least 91%, at least 92%, at least 93%, at least 94%, at least 95%, at least 96%, at least 97%, at least 98%, or at least 99% homology or identity to three CDR sequences included in the same light chain sequence listed in Table I. In certain instances a therapeutic antibody includes a light chain including such CDR sequences. In certain instances a therapeutic antibody includes two such light chains.

In various instances of the present invention, a therapeutic antibody includes a heavy chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of a FW domain included in a heavy chain sequence listed in Table I.

In various instances of the present invention, a therapeutic antibody includes a light chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of a FW domain included in a light chain sequence listed in Table I.

In various instances of the present invention, a therapeutic antibody includes a heavy chain that includes at least one constant or hinge domain having at least 80%, at least 85%, at least 90%, at least 91%, at least 92%, at least 93%, at least 94%, at least 95%, at least 96%, at least 97%, at least 98%, or at least 99% identity to the sequence of one or more of a constant or hinge domain of a heavy chain listed in Table I.

In various instances of the present invention, a therapeutic antibody includes a light chain that includes at least one constant domain having at least 80%, at least 85%, at least 90%, at least 91%, at least 92%, at least 93%, at least 94%, at least 95%, at least 96%, at least 97%, at least 98%, or at least 99% identity to the sequence of a constant domain included in a light chain listed in Table I.

Various antibodies or antibody fragments as described herein incorporate one or more amino acid mutations, e.g., one or more amino acid substitutions, in a sequence corresponding to any of the sequences or portions of the sequences listed in Table I. In some embodiments the one or more amino acid substitutions may be conservative substitutions as is known in the art. Various heavy chains and light chains described herein can be utilized in the production of an antibody, e.g., a monoclonal antibody including two heavy chains and light chains.

It is to be understood that this definition of "therapeutic antibody" applies equally to the specific therapeutic antibodies described herein, e.g., where a "cergutuzumab antibody" corresponds to both cergutuzumab and also the types of antibodies and antibody fragments described above under the definition of "therapeutic antibody" when based on the sequences of cergutuzumab as set forth in Table I. The same applies to the definition of a "ibritumomab tiuxetan antibody"; a "rituximab antibody"; a "tositumomab antibody"; a "gemtuzumab antibody"; a "alemtuzumab antibody"; a "cetuximab antibody"; a "panitumumab antibody"; a "depatuxizumab antibody"; a "sibrotuzumab antibody"; a "codrituzumab antibody"; a "trastuzumab antibody"; a "patritumab antibody"; a "figitumumab antibody"; a "ganitumab antibody"; a "cantuzumab antibody"; an "ABX-MA1 antibody"; a "bavituximab antibody"; a "J591 antibody"; a "palivizumab antibody"; a "bevacizumab antibody". Below we illustrate these definitions in more detail for "cetuximab antibody" and "trastuzumab antibody".

In some embodiments, the conjugates of the present invention do not include conjugates of cetuximab antibodies. In some embodiments, the conjugates of the present invention do not include conjugates of trastuzumab antibodies. In some embodiments, the conjugates of the present invention do not include conjugates of cetuximab antibodies or conjugates of trastuzumab antibodies.

Cetuximab and Cetuximab Antibodies

Cetuximab is an IgG1 mouse-human chimeric monoclonal antibody that targets epidermal growth factor receptor (EGFR). Cetuximab is used for the treatment of metastatic colorectal cancer, metastatic non-small cell lung cancer and head and neck cancer.

Cetuximab includes two heavy chains and two light chains. Cetuximab heavy chain and light chain sequences are known in the art. For instance, a cetuximab heavy chain or light chain can have a cetuximab heavy chain sequence or cetuximab light chain sequence as disclosed in any of (1) Li et al., *Cancer Cell* 7:301-11, 2005; (2) Dubois et al., *Anal. Chem.*; 80:1737-45, 2008; (3) the art-recognized IMGT database, sequence available online at www.imgt.org/3Dstructure-DB/cgi/details.cgi?pdbcode=7906; and/or (4) Ayoub et al., *mAbs* 5(5): 699-710, 2013 (inclusive of supplemental material); each of which is hereby incorporated by reference in its entirety. Table II provides certain cetuximab sequences that were obtained from these sources. Of note, SEQ ID NO: 2 is a cetuximab kappa light chain sequence from the IMGT database (supra) while SEQ ID NO: 3 is an alternative cetuximab kappa light chain sequence from Ayoub et al. (supra). SEQ ID NOs: 24 and SEQ ID NO: 25 are, respectively, the constant domains of SEQ ID NO: 2 and SEQ ID NO: 3.

TABLE II

Cetuximab Sequences

| SEQ ID NO. | Sequence |
| --- | --- |
| Cetuximab IgG1 Heavy Chain (SEQ ID NO: 1) | QVQLKQSGPGLVQPSQSLSITCTVS GFSLTNYGVHWVRQSPGKGLEWLGV IWSGGNTDYNTPFTSRLSINKDNSK SQVFFKMNSLQSNDTAIYYCARALT YYDYEFAYWGQGTLVTVSAASTKGP SVFPLAPSSKSTSGGTAALGCLVKD YFPEPVTVSWNSGALTSGVHTFPAV LQSSGLYSLSSVVTVPSSSLGTQTY ICNVNHKPSNTKVDKRVEPKSCDKT HTCPPCPAPELLGGPSVFLFPPKPK DTLMISRTPEVTCVVVDVSHEDPEV KFNWYVDGVEVHNAKTKPREEQYNS TYRVVSVLTVLHQDWLNGKEYKCKV SNKALPAPIEKTISKAKGQPREPQV YTLPPSREEMTKNQVSLTCLVKGFY PSDIAVEWESNGQPENNYKTTPPVL DSDGSFFLYSKLTVDKSRWQQGNVF SCSVMHEALHNHYTQKSLSLSPGK |
| Cetuximab Kappa Light Chain (IMGT) (SEQ ID NO: 2) | DILLTQSPVILSVSPGERVSFSCRA SQSIGTNIHWYQQRTNGSPRLLIKY ASESISGIPSRFSGSGSGTDFTLSI NSVESEDIADYYCQQNNNWPTTFGA GTKLELKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC |
| Cetuximab Kappa Light Chain (Ayoub et al.) (SEQ ID NO: 3) | DILLTQSPVILSVSPGERVSFSCRA SQSIGTNIHWYQQRTNGSPRLLIKY ASESISGIPSRFSGSGSGTDFTLSI NSVESEDIADYYCQQNNNWPTTFGA GTKLELKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGAC |
| Cetuximab Heavy chain variable domain (1-119) (SEQ ID NO: 4) | QVQLKQSGPGLVQPSQSLSITCTVS GFSLTNYGVHWVRQSPGKGLEWLGV IWSGGNTDYNTPFTSRLSINKDNSK SQVFFKMNSLQSNDTAIYYCARALT YYDYEFAYWGQGTLVTVSA |
| Cetuximab Kappa Light Chain Variable Domain (1-108) (SEQ ID NO: 5) | DILLTQSPVILSVSPGERVSFSCRA SQSIGTNIHWYQQRTNGSPRLLIKY ASESISGIPSRFSGSGSGTDFTLSI NSVESEDIADYYCQQNNNWPTTFGA GTKLELK |

TABLE II-continued

Cetuximab Sequences

| SEQ ID NO. | Sequence |
| --- | --- |
| Cetuximab Heavy Chain CDR1 (SEQ ID NO: 6) | GFSLTNYG |
| Cetuximab Heavy Chain CDR2 (SEQ ID NO: 7) | IWSGGNT |
| Cetuximab Heavy Chain CDR3 (SEQ ID NO: 8) | ARALTYYDYEFAY |
| Cetuximab Kappa Light Chain CDR1 (SEQ ID NO: 9) | QSIGTN |
| Cetuximab Kappa Light Chain CDR2 (SEQ ID NO: 10) | YAS |
| Cetuximab Kappa Light Chain CDR3 (SEQ ID NO: 11) | QQNNNWPTT |
| Cetuximab Heavy Chain FW1 (SEQ ID NO: 12) | QVQLKQSGPGLVQPSQSLSITCTVS |
| Cetuximab Heavy Chain FW2 (SEQ ID NO: 13) | VHWVRQSPGKGLEWLGV |
| Cetuximab Heavy Chain FW3 (SEQ ID NO: 14) | DYNTPFTSRLSINKDNSKSQVFFKM NSLQSNDTAIYYC |
| Cetuximab Heavy Chain FW4 (SEQ ID NO: 15) | WGQGTLVTVSA |
| Cetuximab Kappa Light Chain FW1 (SEQ ID NO: 16) | DILLTQSPVILSVSPGERVSFSCRA S |
| Cetuximab Kappa Light Chain FW2 (SEQ ID NO: 17) | IHWYQQRTNGSPRLLIK |
| Cetuximab Kappa Light Chain FW3 (SEQ ID NO: 18) | ESISGIPSRFSGSGSGTDFTLSINS VESEDIADYYC |
| Cetuximab Kappa Light Chain FW4 (SEQ ID NO: 19) | FGAGTKLELK |
| Cetuximab Heavy chain CH1 constant domain (120-217) (SEQ ID NO: 20) | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKRV |
| Cetuximab Heavy chain hinge domain (218-232) (SEQ ID NO: 21) | EPKSCDKTHTCPPCP |
| Cetuximab Heavy chain CH2 constant domain (233-342) (SEQ ID NO: 22) | APELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALPA PIEKTISKAK |

TABLE II-continued

Cetuximab Sequences

| SEQ ID NO. | Sequence |
|---|---|
| Cetuximab Heavy chain CH3 constant domain (343-447) (SEQ ID NO: 23) | GQPREPQVYTLPPSREEMTKNQVSL TCLVKGFYPSDIAVEWESNGQPENN YKTTPPVLDSDGSFFLYSKLTVDKS RWQQGNVFSCSVMHEALHNHYTQKS LSLSP |
| Cetuximab Kappa Light Chain Constant Domain (108-214) (IMGT) (SEQ ID NO: 24) | RTVAAPSVFIFPPSDEQLKSGTASV VCLLNNFYPREAKVQWKVDNALQSG NSQESVTEQDSKDSTYSLSSTLTLS KADYEKHKVYACEVTHQGLSSPVTK SFNRGEC |
| Cetuximab Kappa Light Chain Constant Domain (108-214) (Ayoub et al.) (SEQ ID NO: 25) | RTVAAPSVFIFPPSDEQLKSGTASV VCLLNNFYPREAKVQWKVDNALQSG NSQESVTEQDSKDSTYSLSSTLTLS KADYEKHKVYACEVTHQGLSSPVTK SFNRGAC |

As used herein, the term "cetuximab antibody" encompasses cetuximab and any antibody or antibody fragment that recognizes and specifically binds EGFR and has at least a heavy chain variable domain or light chain variable domain having at least 80% identity (e.g., at least 85%, 90%, 91%, 92%, 93%, 94%, 95%, 96%, 97%, 98%, 99%, or 100% identity) to a corresponding sequence of cetuximab (i.e., SEQ ID NO:4 or SEQ ID NO: 5). In some instances, a cetuximab antibody includes two such variable domains, three such variable domains, four such variable domains, two such heavy chain variable domains, two such light chain variable domains, and/or two such heavy chain variable domains and two such light chain variable domains. In some instances, a cetuximab antibody includes a heavy chain or light chain having at least 80% identity (e.g., at least 85%, 90%, 91%, 92%, 93%, 94%, 95%, 96%, 97%, 98%, 99%, or 100% identity) to a corresponding sequence of cetuximab (i.e., one or more of SEQ ID NOs: 1-3). In some instances, a cetuximab antibody includes two such chains, three such chains, four such chains, two such heavy chains, two such light chains, and/or two such heavy chains and two such light chains. Thus, a cetuximab antibody may be, e.g., an intact antibody, antibody fragment (such as a Fab, Fab', F(ab')$_2$, Fd, or Fv), single chain Fv (scFv), or multispecific antibody such as a bispecific antibody.

In various instances of the present invention, a cetuximab antibody includes a heavy chain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 1.

In various instances of the present invention, a cetuximab antibody includes a light chain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 2 or SEQ ID NO: 3.

In various instances of the present invention, a cetuximab antibody includes a heavy chain that includes at least one heavy chain variable domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 4.

In various instances of the present invention, a cetuximab antibody includes a light chain that includes at least one light chain variable domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 5.

In various instances of the present invention, a cetuximab antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 6, SEQ ID NO: 7, or SEQ ID NO: 8. In certain instances a cetuximab antibody includes a heavy chain including such a CDR sequence. In certain instances a cetuximab antibody includes two such heavy chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 6 and SEQ ID NO: 7. In certain instances a cetuximab antibody includes a heavy chain including such CDR sequences. In certain instances a cetuximab antibody includes two such heavy chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 6 and SEQ ID NO: 8. In certain instances a cetuximab antibody includes a heavy chain including such CDR sequences. In certain instances a cetuximab antibody includes two such heavy chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 7 and SEQ ID NO: 8. In certain instances a cetuximab antibody includes a heavy chain including such CDR sequences. In certain instances a cetuximab antibody includes two such heavy chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 6, SEQ ID NO: 7, and SEQ ID NO: 8. In certain instances a cetuximab antibody includes a heavy chain including such CDR sequences. In certain instances a cetuximab antibody includes two such heavy chains.

In various instances of the present invention, a cetuximab antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 9, SEQ ID NO: 10, or SEQ ID NO: 11. In certain instances a cetuximab antibody includes a light chain including such a CDR sequence. In certain instances a cetuximab antibody includes two such light chains.

In various instances of the present invention, a cetuximab antibody includes a CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 9 and SEQ ID NO: 10. In certain instances a cetuximab antibody includes a light chain including such CDR sequences. In certain instances a cetuximab antibody includes two such light chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 9 and SEQ ID NO: 11. In certain instances a cetuximab antibody includes a light chain including such CDR sequences. In certain instances a cetuximab antibody includes two such light chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 10 and SEQ ID NO: 11. In certain instances a cetuximab antibody includes a light chain including such CDR sequences. In certain instances a cetuximab antibody includes two such light chains.

In various instances of the present invention, a cetuximab antibody includes CDR sequences having at least 80%, at least 85%, at least 90%, at least 91%, at least 92%, at least 93%, at least 94%, at least 95%, at least 96%, at least 97%, at least 98%, or at least 99% homology or identity to each of SEQ ID NO: 9, SEQ ID NO: 10, and SEQ ID NO: 11. In certain instances a cetuximab antibody includes a light chain including such CDR sequences. In certain instances a cetuximab antibody includes two such light chains.

In various instances of the present invention, a cetuximab antibody includes a heavy chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 12, SEQ ID NO: 13, SEQ ID NO: 14, or SEQ ID NO: 15.

In various instances of the present invention, a cetuximab antibody includes a light chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 16, SEQ ID NO: 17, SEQ ID NO: 18, or SEQ ID NO: 19.

In various instances of the present invention, a cetuximab antibody includes a heavy chain that includes at least one constant or hinge domain having at least 80%, at least 85%, at least 90%, at least 91%, at least 92%, at least 93%, at least 94%, at least 95%, at least 96%, at least 97%, at least 98%, or at least 99% identity to the sequence of one or more of SEQ ID NO: 20, SEQ ID NO: 21, SEQ ID NO: 22, or SEQ ID NO: 23.

In various instances of the present invention, a cetuximab antibody includes a light chain that includes at least one constant domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 24 or SEQ ID NO: 25.

Various cetuximab antibodies or antibody fragments as described herein incorporate one or more amino acid mutations, e.g., one or more amino acid substitutions, in a sequence corresponding to any of SEQ ID NOs: 1-25. In some embodiments the one or more amino acid substitutions may be conservative substitutions as is known in the art. Various heavy chains and light chains described herein can be utilized in the production of a cetuximab antibody, e.g., a monoclonal antibody including two heavy chains and light chains.

Trastuzumab and Trastuzumab Antibodies

Trastuzumab is an IgG1 mouse-human chimeric monoclonal antibody that targets HER2. Trastuzumab is indicated for the treatment of breast cancer and gastric cancer. Trastuzumab includes two heavy chains and two light chains. Trastuzumab heavy chain and light chain sequences are known in the art. For instance, a trastuzumab heavy chain or light chain can have a trastuzumab heavy chain sequence or trastuzumab light chain sequence as disclosed in any of (1) sequence variants described in patents (e.g. U.S. Pat. Nos. 5,821,337; 7,879,325; 8,937,159; U.S. Patent Publication No. 2006/0275305; EP Patent Publication No. EP2540745A9); and/or (2) the art-recognized IMGT database, sequence (available online at www.imgt.org/3Dstructure-DB/cgi/details.cgi?pdbcode=7637&Part=Chain& Chain=7637H). The contents of all of these are herein incorporated by reference in their entireties. Table 1 provides certain trastuzumab sequences that were obtained from these sources.

TABLE III

Trastuzumab Sequences

| SEQ ID NO. | Sequence |
|---|---|
| Trastuzumab IgG1 Heavy Chain (IMGT) (SEQ ID NO: 26) (CDRs underlined) | EVQLVESGGGLVQPGGSLRLSCAASGFNIK DTYIHWVRQAPGKGLEWVARIYPTNGYTRY ADSVKGRFTISADTSKNTAYLQMNSLRAED TAVYYCSRWGGDGFYAMDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Trastuzumab Kappa Light Chain (IMGT) (SEQ ID NO: 27) (CDRs underlined) | DIQMTQSPSSLSASVGDRVTITCRASQDVN TAVAWYQQKPGKAPKLLIYSASFLYSGVPS RFSGSRSGTDFTLTISSLQPEDFATYYCQQ HYTTPPTFGQGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC |
| Trastuzumab Heavy chain variable domain (SEQ ID NO: 28) (CDRs underlined) | EVQLVESGGGLVQPGGSLRLSCAASGFNIK DTYIHWVRQAPGKGLEWVARIYPTNGYTRY ADSVKGRFTISADTSKNTAYLQMNSLRAED TAVYYCSRWGGDGFYAMDYWGQGTLVTVSS |
| Trastuzumab Kappa Light Chain Variable Domain (SEQ ID NO: 29) (CDRs underlined) | DIQMTQSPSSLSASVGDRVTITCRASQDVN TAVAWYQQKPGKAPKLLIYSASFLYSGVPS RFSGSRSGTDFTLTISSLQPEDFATYYCQQ HYTTPPTFGQGTKVEIK |
| Trastuzumab Heavy Chain CDR1 (SEQ ID NO: 30) | GFNIKDTYIH |
| Trastuzumab Heavy Chain CDR2 (SEQ ID NO: 31) | RIYPTNGYTRYADSVKG |
| Trastuzumab Heavy Chain CDR3 (SEQ ID NO: 32) | WGGDGFYAMDY |

TABLE III-continued

Trastuzumab Sequences

| SEQ ID NO. | Sequence |
|---|---|
| Trastuzumab Kappa Light Chain CDR1 (SEQ ID NO: 33) | RASQDVNTAVA |
| Trastuzumab Kappa Light Chain CDR2 (SEQ ID NO: 34) | SASFLYS |
| Trastuzumab Kappa Light Chain CDR3 (SEQ ID NO: 35) | QQHYTTPPT |
| Trastuzumab Heavy Chain FW1 (SEQ ID NO: 36) | EVQLVESGGGLVQPGGSLRLSCAAS |
| Trastuzumab Heavy Chain FW2 (SEQ ID NO: 37) | WVRQAPGKGLEWVA |
| Trastuzumab Heavy Chain FW3 (SEQ ID NO: 38) | RFTISADTSKNTAYLQMNSLRAEDTAVYYCSR |
| Trastuzumab Heavy Chain FW4 (SEQ ID NO: 39) | WGQGTLVTVSS |
| Trastuzumab Kappa Light Chain FW1 (SEQ ID NO: 40) | DIQMTQSPSSLSASVGDRVTITC |
| Trastuzumab Kappa Light Chain FW2 (SEQ ID NO: 41) | WYQQKPGKAPKLLIY |
| Trastuzumab Kappa Light Chain FW3 (SEQ ID NO: 42) | GVPSRFSGSRSGTDFTLTISSLQPEDFATYYC |
| Trastuzumab Kappa Light Chain FW4 (SEQ ID NO: 43) | FGQGTKVEIK |
| Trastuzumab Heavy chain CH1 constant domain (SEQ ID NO: 44) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| Trastuzumab Heavy chain hinge domain (SEQ ID NO: 45) | EPKSCDKTHTCPPCP |
| Trastuzumab Heavy chain CH2 constant domain (SEQ ID NO: 46) | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |
| Trastuzumab Heavy chain CH3 constant domain (SEQ ID NO: 47) | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSP |
| Trastuzumab Kappa Light Chain Constant Domain (IMGT) (SEQ ID NO: 48) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

As used herein, the term "trastuzumab antibody" encompasses trastuzumab and any antibody or antibody fragment that recognizes and specifically binds HER2 and has at least a heavy chain variable domain or light chain variable domain having at least 80% identity (e.g., at least 85%, 90%, 91%, 92%, 93%, 94%, 95%, 96%, 97%, 98%, 99%, or 100% identity) to a corresponding sequence of trastuzumab (e.g., SEQ ID NO: 28 or SEQ ID NO: 29). In some instances, a trastuzumab antibody includes two such variable domains, three such variable domains, four such variable domains, two such heavy chain variable domains, two such light chain variable domains, and/or two such heavy chain variable domains and two such light chain variable domains. In some instances, a trastuzumab antibody includes a heavy chain or light chain having at least 80% identity (e.g., at least 85%, 90%, 91%, 92%, 93%, 94%, 95%, 96%, 97%, 98%, 99%, or 100% identity) to a corresponding sequence of trastuzumab (e.g., one or more of SEQ ID NO: 26 or SEQ ID NO: 27). In some instances, a trastuzumab antibody includes two such chains, three such chains, four such chains, two such heavy chains, two such light chains, and/or two such heavy chains and two such light chains. Thus, a trastuzumab antibody may be, e.g., an intact antibody, antibody fragment (such as a Fab, Fab', F(ab')$_2$, Fd, or Fv), single chain Fv (scFv), or multispecific antibody such as a bispecific antibody.

In various instances of the present invention, a trastuzumab antibody includes a heavy chain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 26.

In various instances of the present invention, a trastuzumab antibody includes a light chain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 27.

In various instances of the present invention, a trastuzumab antibody includes a heavy chain that includes at least one heavy chain variable domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 28.

In various instances of the present invention, a trastuzumab antibody includes a light chain that includes at least one light chain variable domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 29.

In various instances of the present invention, a trastuzumab antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 30, SEQ ID NO: 31, or SEQ ID NO: 32. In certain instances a trastuzumab antibody includes a heavy chain including such a CDR sequence. In certain instances a trastuzumab antibody includes two such heavy chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 30 and SEQ ID NO: 31. In certain instances a trastuzumab antibody includes a heavy chain including such CDR sequences. In certain instances a trastuzumab antibody includes two such heavy chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 30 and SEQ ID NO: 32. In certain instances a trastuzumab antibody includes a heavy chain including such CDR sequences. In certain instances a trastuzumab antibody includes two such heavy chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 31 and SEQ ID NO: 32. In certain instances a trastuzumab antibody includes a heavy chain including such CDR sequences. In certain instances a trastuzumab antibody includes two such heavy chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 30, SEQ ID NO: 31, and SEQ ID NO: 32. In certain instances a trastuzumab antibody includes a heavy chain including such CDR sequences. In certain instances a trastuzumab antibody includes two such heavy chains.

In various instances of the present invention, a trastuzumab antibody includes a CDR sequence having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 33, SEQ ID NO: 34, or SEQ ID NO: 35. In certain instances a trastuzumab antibody includes a light chain including such a CDR sequence. In certain instances a trastuzumab antibody includes two such light chains.

In various instances of the present invention, a trastuzumab antibody includes a CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 33 and SEQ ID NO: 34. In certain instances a trastuzumab antibody includes a light chain including such CDR sequences. In certain instances a trastuzumab antibody includes two such light chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 33 and SEQ ID NO: 35. In certain instances a trastuzumab antibody includes a light chain including such CDR sequences. In certain instances a trastuzumab antibody includes two such light chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% identity to each of SEQ ID NO: 34 and SEQ ID NO: 35. In certain instances a trastuzumab antibody includes a light chain including such CDR sequences. In certain instances a trastuzumab antibody includes two such light chains.

In various instances of the present invention, a trastuzumab antibody includes CDR sequences having at least 80%, at least 85%, at least 90%, at least 91%, at least 92%, at least 93%, at least 94%, at least 95%, at least 96%, at least 97%, at least 98%, or at least 99% homology or identity to each of SEQ ID NO: 33, SEQ ID NO: 34, and SEQ ID NO: 35. In certain instances a trastuzumab antibody includes a light chain including such CDR sequences. In certain instances a trastuzumab antibody includes two such light chains.

In various instances of the present invention, a trastuzumab antibody includes a heavy chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 36, SEQ ID NO: 37, SEQ ID NO: 38, or SEQ ID NO: 39.

In various instances of the present invention, a trastuzumab antibody includes a light chain that includes at least one FW domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 40, SEQ ID NO: 41, SEQ ID NO: 42, or SEQ ID NO: 43.

In various instances of the present invention, a trastuzumab antibody includes a heavy chain that includes at least one constant or hinge domain having at least 80%, at least 85%, at least 90%, at least 91%, at least 92%, at least 93%, at least 94%, at least 95%, at least 96%, at least 97%, at least 98%, or at least 99% identity to the sequence of one or more of SEQ ID NO: 44, SEQ ID NO: 45, SEQ ID NO: 46, or SEQ ID NO: 47.

In various instances of the present invention, a trastuzumab antibody includes a light chain that includes at least one constant domain having at least 80%, at least 85%, at least 90%, at least 91%, at least 92%, at least 93%, at least 94%, at least 95%, at least 96%, at least 97%, at least 98%, or at least 99% identity to the sequence of SEQ ID NO: 48.

Various antibodies or antibody fragments as described herein incorporate one or more amino acid mutations, e.g., one or more amino acid substitutions, in a sequence corresponding to any of SEQ ID NOs: 25-48. In some embodiments the one or more amino acid substitutions may be conservative substitutions as is known in the art. Various heavy chains and light chains described herein can be utilized in the production of an antibody, e.g., a monoclonal antibody including two heavy chains and light chains.

β-1,6-Glucan Oligomers

A β-1,6-glucan oligomer of the present invention can be derived from or synthesized from any source and/or by any procedure, e.g., any source and/or by any procedure known in the art.

In some embodiments, the β-1,6-glucan oligomer is derived from a lichen, which in one embodiment is from the genus Umbilicariaceae (e.g., from *U. pustulata* and *U. hirsute, U. angulata, U. caroliniana,* or *U. polyphylla*). In some embodiments, the β-1,6-glucan is derived from a fungus, which in one embodiment is from the genus *Candida* (e.g., from *C. albicans*). Other organisms from which the glucan may be derived include *Coccidioides immitis, Trichophyton verrucosum, Blastomyces dermatidis, Cryptococcus neoformans, Histoplasma capsulatum, Saccharomyces cerevisiae, Paracoccidioides brasiliensis, Botryosphaeria rhodina, Lasiodiplodia theobromae,* and *Pythiumn insidiosum*. Pure β-glucans are commercially available, e.g., pustulan is a β-1,6-glucan purified from *Umbilicaria papullosa* which is available from Calbiochem and Elicityl. β-glucans can also be purified from fungal cell walls in various ways, for example, as described in Tokunaka et al., *Carbohydr. Res.* 316:161-172, 1999, and the product may be enriched for β-1,6-glucan moieties by methods as are known in the art. In some embodiments, a β-1,6-glucan may be isolated from an organism and then chemically or enzymatically altered, for example, to increase solubility. Indeed, full-length native glucans are insoluble and have a molecular weight in the megadalton range. In some embodiments, this invention uses soluble β-1,6-glucan oligomers. In some embodiments, solubilization may be achieved by fragmenting long insoluble glucans. This may be achieved by, for example, hydrolysis or, in some embodiments, by digestion with a glucanase (e.g., with a β-1,3 glucanase or limited digestion with a β-1,6 glucanase).

In some embodiments, the β-1,6-glucan oligomer is chemically synthesized, as is known in the art. In an example embodiment, the β-1,6-glucan oligomer is synthesized from glucose monomers, gentiobiose dimers, or amygdalin joined via glycolysation reactions. The length of the β-1,6-glucan oligomer is controlled by selecting the number of "building blocks" to use. In an example embodiment, three different "building blocks" can be selected from:

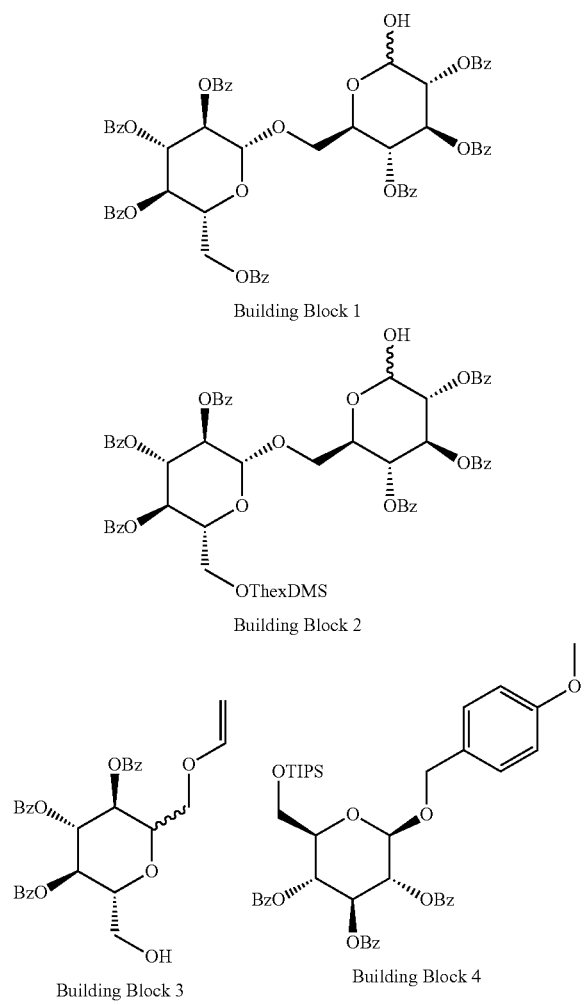

Building Block 1

Building Block 2

Building Block 3

Building Block 4

In an example embodiment, the glucose monomers or building blocks are joined via Schmidt reaction conditions. Exemplary Schmidt reaction conditions include, but are not limited to, converting a free hydroxyl group of the glucan monomer to its respective trichloroacetimidate and subsequent reaction with the free hydroxyl group of another glucose monomer or oligosaccharide in the presence of $BF_3 \cdot OEt_2$ or TMSOTf.

In another example embodiment, the free hydroxyl groups of the glucose monomer are selectively protected. In another example embodiment, the free hydroxyl groups are protected by reaction with benzoyl chloride or thexyldimethylsilyl chloride.

In another aspect, the present invention encompasses certain intermediate compounds which are represented by structural Formula V and that can be used in the chemical synthesis of certain β-1,6-glucan oligomers or oligomer precursors:

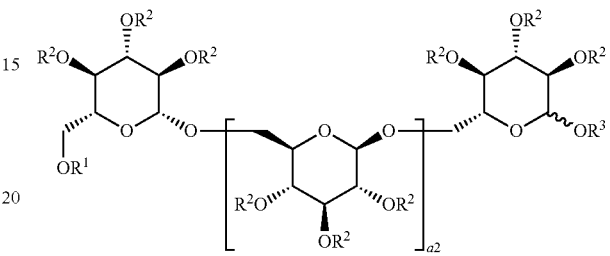

wherein
$R^1$ is hydrogen or a hydroxyl protecting group;
$R^2$ is hydrogen or a hydroxyl protecting group;
$R^3$ is hydrogen, a hydroxyl protecting group,

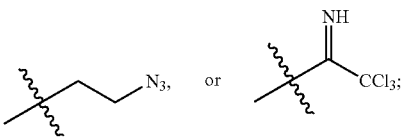

and
$a^2$ is between 0 and 8.

Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably hydroxyl protecting groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, dimethylthexyl silyl, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, 0-nitrobenzyl, p-nitrobenzyl, p-halobenzyl, 2,6-dichlorobenzyl, p-cyanobenzyl, 2- and 4-picolyl ethers. It is to be understood that any chemical terms used herein are intended to have their ordinary meaning as commonly used in the chemical arts.

Accordingly, in an example embodiment, $R^1$ is hydrogen. In another embodiment, $R^1$ is a hydroxyl protecting group. In another embodiment, $R^1$ is a hydroxyl protecting group, and the hydroxyl protecting group is dimethylthexyl silyl ("ThexDMS"). In another embodiment, $R^1$ is a hydroxyl protecting group, and the hydroxyl protecting group is benzoyl formate ("Bz"). In another embodiment, $R^2$ is hydrogen. In another embodiment, $R^2$ is a hydroxyl protecting group. In another embodiment, $R^2$ is a hydroxyl protecting group, and the hydroxyl protecting group is benzoyl formate.

In another embodiment, $R^3$ is hydrogen. In another embodiment, $R^3$ is

In another embodiment, $R^3$ is

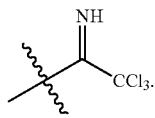

In another embodiment, $R^2$ is a hydroxyl protecting group. In another embodiment, $R^3$ is a hydroxyl protecting group, and the hydroxyl protecting group is benzoyl formate. In another embodiment, $R^3$ is a hydroxyl protecting group, and the hydroxyl protecting group is allyl ether.

In another embodiment $a^2$ is 0, 1, 2, 3, 4, 5, 6, 7, or 8.

As used herein, ~~~ appearing on a structure and joining a functional group to the structure in the position of a bond generally indicates a mixture of, or either of, the possible isomers, e.g., containing (R)- and (S)-stereochemistry. For example,

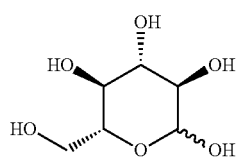

means containing either, or both of:

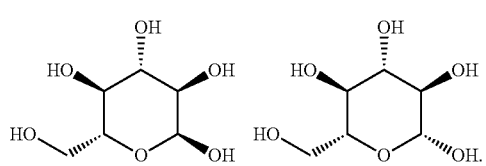

As used herein, ~~~ appearing across a bond indicates a point of attachment between two atoms. For example,

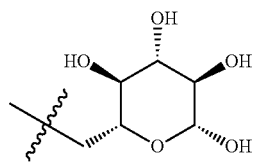 [SMILES: *C[C@H]1O[C@@H](O)[C@H](O)[C@@H](O)[C@@H]1O]

means that the glucose ring above is bound to an undepicted structure on which it is a substituent.

In some embodiments of the present invention, a β-1-6 glucan oligomer of the present invention includes a low molecular weight β-1-6 glucan oligomer, e.g., a β-1-6 glucan oligomer containing 10 or fewer (e.g., 9, 8, 7, 6, 5, 4, 3 or 2) glucose monomer units. In some embodiments, a composition of the present invention comprises β-1,6-glucan oligomers which comprise, consist essentially of or consist of low molecular weight β-1,6-glucan oligomers, e.g., β-1-6 glucan oligomers containing 10 or fewer (e.g., 9, 8, 7, 6, 5, 4, 3 or 2) glucose monomer units. In certain embodiments, at least 80%, 90%, 95%, 98%, 99% or 100% of the β-1,6-glucan oligomers contained in a composition of the invention by weight is low molecular weight β-1,6-glucan oligomers, e.g., β-1-6 glucan oligomers containing 10 or fewer (e.g., 9, 8, 7, 6, 5, 4, 3 or 2) glucose monomer units. In certain embodiments, "weight" refers to "dry weight".

In certain embodiments, at least 80%, 90%, 95%, 98%, 99% or 100% of the glucan contained in a composition of the invention by weight is β-1,6 glucan. In certain embodiments, "weight" refers to "dry weight". In certain embodiments, less than 20%, 10%, 5%, 2% or 1% of the glucan contained in a composition of the invention by weight is β-1,3 glucan. In certain embodiments, "weight" refers to "dry weight".

Conjugates

A therapeutic antibody disclosed herein may be conjugated to one or more β-1,6-glucan oligomers. The present application relates, among other things, to the length of β-1,6-glucan oligomers to be conjugated to a therapeutic antibody, the load of β-1,6-glucan oligomers to be conjugated to a therapeutic antibody (e.g., the number of β-1,6-glucan oligomers to be conjugated to each antibody), and to the type of conjugation by which β-1,6-glucan oligomers are linked with a therapeutic antibody. In some embodiments, the a therapeutic antibody disclosed herein may be conjugated to one or more β-1,6-glucan oligomers via a linker.

Glucan Length

In some embodiments, a conjugate of the present invention includes a β-1,6-glucan oligomer which is comprised of between 2 and 10 glucose monomer units (e.g., 2, 3, 4, 5, 6, 7, 8, 9, or 10 glucose monomer units). In particular embodiments, a conjugate of the present invention includes a β-1,6-glucan oligomer which is comprised of between 3 to 10, 3 to 9, 3 to 8, 3 to 7, 3 to 6, 3 to 5, 3 to 4,4 to 10, 4 to 9, 4 to 8, 4 to 7, 4 to 6, 4 to 5, 4 to 8, 5 to 8, 5 to 7, 5 to 6, 6 to 7, or 7 to 8 glucose monomer units.

In some embodiments, a conjugate of the present invention includes a β-1,6-glucan oligomer covalently linked to a therapeutic antibody via a linker L as shown in Formula I:

Accordingly, in some embodiments, the conjugates are formed from or derived from the following structural formula:

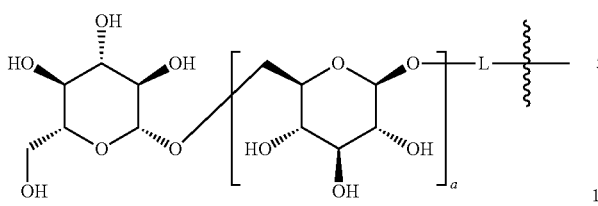

I

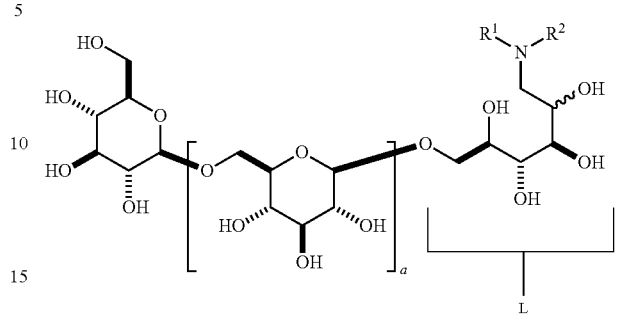

wherein a is between 1 and 9, 1 and 8, 1 and 7, 1 and 6, 1 and 5, 1 and 4 or 1 and 3, L is a linker, and "〰" represents a point of attachment between two atoms (e.g., an atom of the linker and an atom of a therapeutic antibody).

In some embodiments, the linker L can be a ring-opened glucose monomer as shown in Formula Ia:

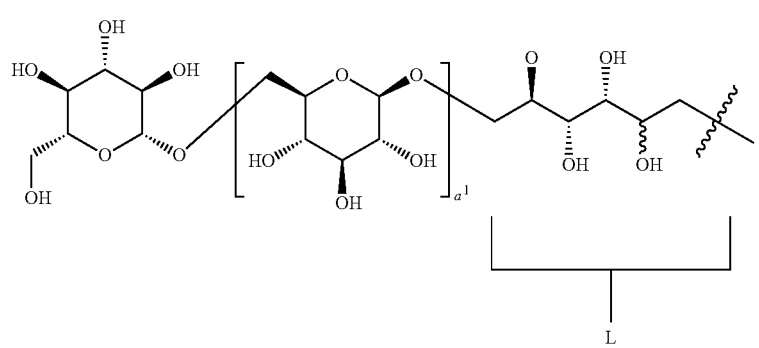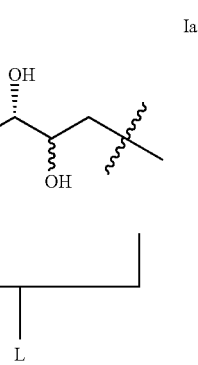

Ia wherein $a^1$ is between 1 and 9, 1 and 8, 1 and 7, 1 and 6, 1 and 5, 1 and 4 or 1 and 3, and "〰" represents a point of attachment between two atoms.

In some embodiments, the term "conjugate" and grammatical forms thereof refers to any association between the indicated molecules. In some embodiments, the conjugation is covalent. In other embodiments, the conjugation is non-covalent. In some embodiments, the conjugation is direct. In other embodiments, the conjugation is via a linker molecule. In some embodiments the conjugation will be via any means known in the art and as described herein. For example, the conjugation may be via amide formation, urethane, imine or disulfide linkage between the respective molecules, or between a linker moiety with the respective molecules. It is to be understood that there is no limitation with respect to the chemical backbone of the linker molecules. In some embodiments, the chemical backbone may be biocompatible, non-immunogenic and/or water soluble. In some embodiments, the linker may comprise poly ethylene glycol (PEG), further comprising active chemical groups which facilitate linkage as herein described.

In some embodiments, the linker L is alkyl, alkylenyl, alkynyl, aryl, heteroalkyl, heterocyclyl, or heteroaryl, optionally substituted with alkyl, aryl, heteroaryl, heteroalkyl, —N₃ (azidyl), —C(O)H, —C(O)OH, —C(O)-alkyl, —C(O)-aryl. In some embodiments, the linker L is polyester, polyimine, poly-acid, protein, or peptides. In other embodiments, the linker molecule comprises an alkylene, alkenylene, alkynylene, heteroalkylene, heteroalkenylene, or heteroalkynylene moiety.

wherein a is defined above, $R^1$ is H, alkyl, aryl, or heteroaryl; and $R^2$ is alkyl optionally substituted with azidyl, alkyl optionally substituted with $R^3$, —C(O)-alkyl, —C(O)-aryl, —C(O)O-alkyl, —C(O)O-aryl, or heteroaryl; $R^3$ is heteroaryl, optionally substituted with alkyl-C(O)H, aryl-C(O)H, alkyl-C(O)OH, or aryl-C(O)OH.

In some embodiments, the conjugates can comprise the following structural formula:

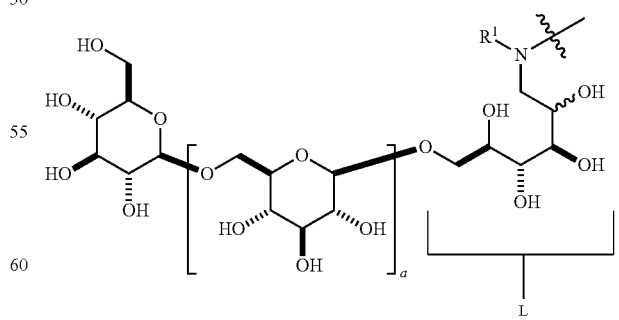

wherein a and $R^1$ are defined above.

In some embodiments, the conjugates can comprise the following structural formula:

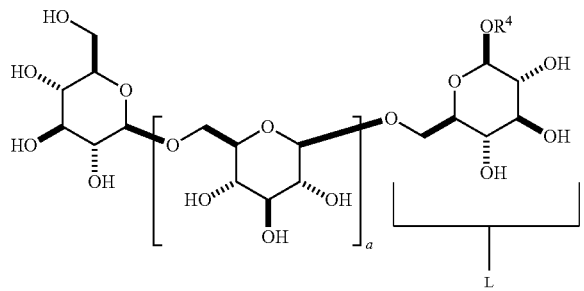

wherein a is defined above, $R^4$ is alkyl optionally substituted with $R^5$, —C(O)-alkyl, —C(O)-aryl, —C(O)O-alkyl, —C(O)O-aryl; $R^5$ is heteroaryl, optionally substituted with alkyl-C(O)H, aryl-C(O)H, alkyl-C(O)OH, or aryl-C(O)OH.

In some embodiments, the conjugates can comprise the following structural formula:

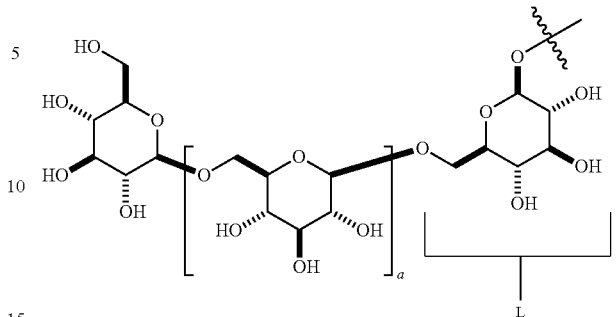

wherein a is defined above.

In some embodiments, the conjugates are formed from or derived from the following structural formula:

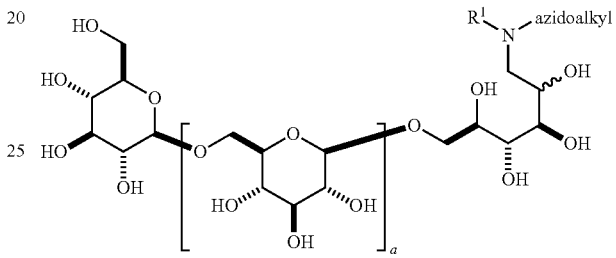

wherein a and $R^1$ are defined above.

In some embodiments, the conjugates are formed from or derived from the following structural formula:

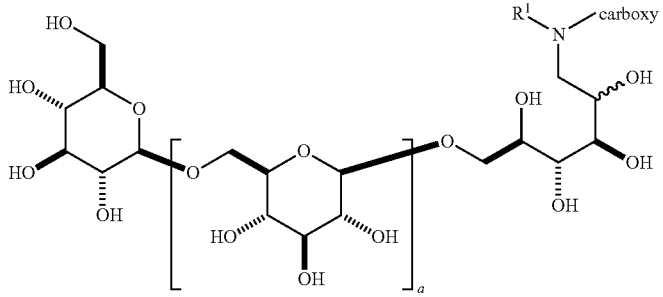

wherein a and $R^1$ are defined above.

In some embodiments, the conjugates are formed from or derived from the following structural formula:

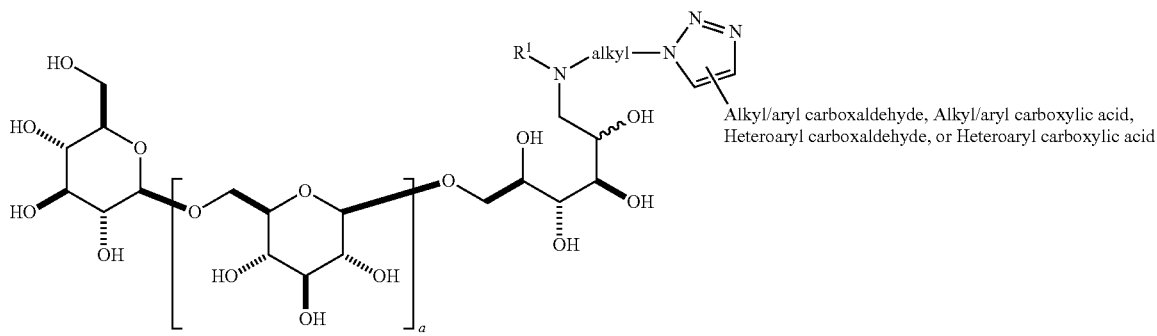

wherein a and $R^1$ are defined above.

In some embodiments, the conjugates are formed from or derived from the following structural formula:

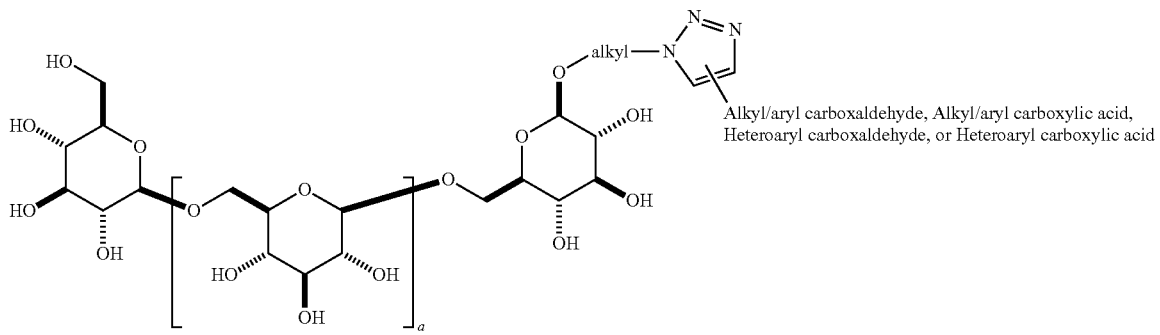

wherein a is defined above.

In some embodiments, the conjugates are formed from or derived from the following structural formula:

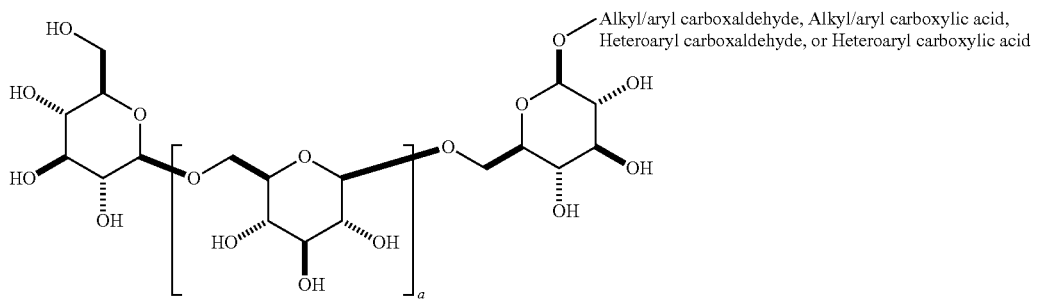

wherein a is defined above.

In some embodiments, the conjugates are formed from or derived from the following structural formula:

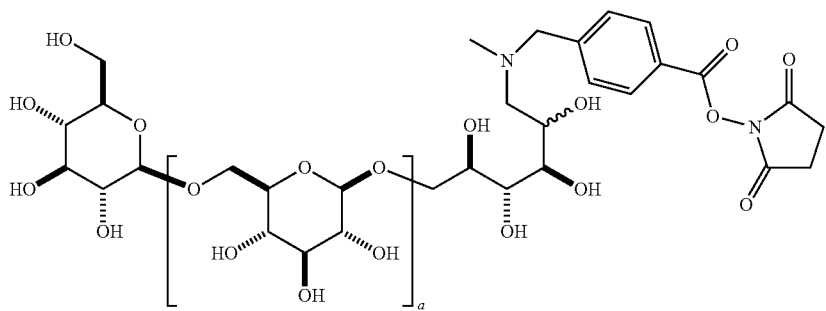

wherein a is defined above.

In some embodiments, the conjugates are formed from or derived from the following structural formula:

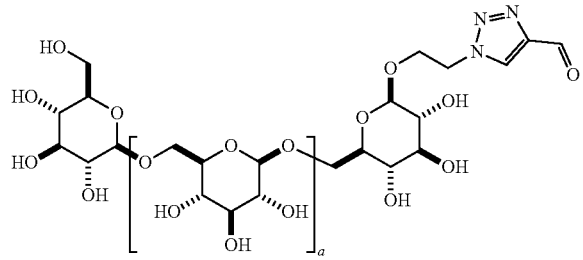

wherein a is defined above.

In some embodiments, the conjugates are formed from or derived from the following structural formula:

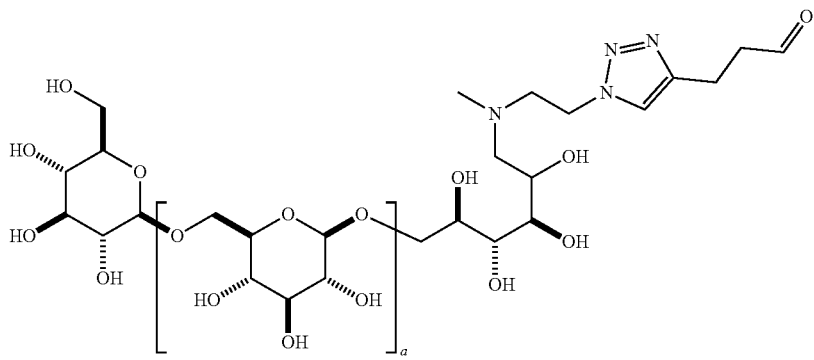

wherein a is defined above.

When a conjugate includes several β-1,6-glucan oligomers or when discussing a composition that includes a population of conjugates, it is to be understood that the aforementioned values and ranges may refer to the actual or average number of glucose monomer units that are present in the conjugated β-1,6-glucan oligomers. The length of the β-1,6-glucan oligomers (defined based on the number of glucose monomer units) may be a whole number, e.g., when referring to a single β-1,6-glucan oligomer or a population of β-1,6-glucan oligomers each having the same length. The length of the β-1,6-glucan oligomers may also be a whole number when referring to the length of a population of β-1,6-glucan oligomers wherein the whole number length is representative of the actual length of at least 90% of the β-1,6-glucan oligomers in the population (e.g., at least 91%, 92%, 93%, 94%, 95%, 96%, 97%, 98%, 99%, or 100% of the β-1,6-glucan oligomers in the population). The length of the β-1,6-glucan oligomers may be presented as a fraction when a population includes a mixture of β-1,6-glucan oligomers having two or more different lengths. The fraction may be indicative of a hypothetical, expected, approximate, or measured average length of β-1,6-glucan oligomers in the population. Accordingly, a length expressed as being between two whole numbers encompasses any intervening fraction of a whole number.

Various methods of determining the number of monomeric glucose units in a β-1,6-glucan oligomer are known in the art. In various instances, the number of monomeric glucose units in a β-1,6-glucan oligomer is provided or determined prior to conjugation with a therapeutic antibody. For instance, in some instances, a β-1,6-glucan oligomer or β-1,6-glucan oligomer precursor is synthesized to have a particular known length. Example 28 describes synthesis of gentiopentose. Example 29 describes synthesis of 2-azidoethylgentiotetrose. Example 30 describes synthesis of 2-azidoethylgentiohexose. It will be appreciated that β-1,6-glucan oligomers and other β-1,6-glucan oligomer precursors having different lengths can be made in accordance with known synthetic methods (e.g., those described herein) using these and other building blocks that are described herein. In certain instances, β-1,6-glucan oligomers having a particular number (or range) of monomeric glucose units are isolated from a population of oligomers, e.g., a population of oligomers derived from pustulan, e.g., by breakdown or modification of pustulan. In various instances a population of β-1,6-glucan oligomers each having a particular number of monomeric glucose units is provided and the number of monomeric glucose units per oligomer is determined by chromatography (e.g., size exclusion chromatograph) and/or mass spectrometry (e.g., MALDI). In various instances, a population of β-1,6-glucan oligomers including oligomers having various numbers of monomeric glucose units is provided and the number of monomeric glucose units per oligomer is determined by chromatography (e.g., size exclusion chromatograph) and/or mass spectrometry (e.g., MALDI). In various instances, one or more β-1,6-glucan oligomers having a particular number of monomeric glucose units are selected or isolated. In various instances, the number of monomeric glucose units in a β-1,6-glucan oligomer is provided or determined after conjugation with a therapeutic antibody for example by mass spectrometry (e.g., MALDI).

Glucan Load

In some embodiments, a therapeutic antibody molecule present in a conjugate of the present invention may be conjugated to one or more β-1,6-glucan oligomers. In certain embodiments, it is conjugated to between 1 and 6 β-1,6-glucan oligomers (e.g., between 1 and 5, 1 and 4 or 1 and 3 β-1,6-glucan oligomers, e.g., 1, 2, 3, 4, 5, or 6 β-1,6-glucan oligomers). In certain embodiments, it is conjugated to between 2 and 4 β-1,6-glucan oligomers. In certain embodiments, it is conjugated to 2 or 3 β-1,6-glucan oligomers. In certain embodiments, it is conjugated to 3 or 4 β-1,6-glucan oligomers. In certain embodiments, it is conjugated to 3 β-1,6-glucan oligomers. It is to be understood that when two or more β-1,6-glucan oligomers are conjugated to the same therapeutic antibody molecule, the two or more β-1,6-glucan oligomers may have the same or different lengths. In some embodiments, the two or more β-1,6-glucan oligomers have the same length.

As used herein, the term "glucan load" or the variable "b" in Formula II or Formula IIa refers to the actual or average number of individual β-1,6-glucan oligomers that are conjugated to each therapeutic antibody molecule. A glucan load may be a whole number, e.g., when referring to the load of a single conjugate or a population of conjugates each having the same load. A glucan load may also be a whole number when referring to the load of a population of conjugates wherein the whole number load is representative of the actual load found on at least 90% of conjugates in the population (e.g., at least 91%, 92%, 93%, 94%, 95%, 96%, 97%, 98%, 99%, or 100% of molecules in the population). A glucan load may be presented as a fraction when a population includes a mixture of conjugates having two or more different loads. The fraction may be indicative of a hypothetical, expected, approximate, or measured average load of conjugates in the population. Accordingly, a glucan load expressed as being between two whole numbers encompasses any intervening fraction of a whole number.

Various methods of determining load of β-1,6-glucan oligomers are known in the art. In various instances, a conjugate is synthesized to have a particular load. In various instances a conjugate or population of conjugates each having a particular load is provided and the load is determined by chromatography (e.g., size exclusion chromatograph) and/or mass spectrometry (e.g., MALDI) and/or SDS-PAGE. In various instances, a population of conjugates having various loads is provided and load is determined by chromatography (e.g., size exclusion chromatograph) and/or mass spectrometry (e.g., MALDI) and/or SDS-PAGE. In various instances, conjugates having a particular load are selected or isolated.

Conjugation

In various embodiments of the present invention, one or more of the aforementioned β-1,6-glucan oligomers are conjugated as described herein to a therapeutic antibody. In particular embodiments, one or more β-1,6-glucan oligomers are conjugated via a linker. In some embodiments, the one or more β-1,6-glucan oligomers are each independently conjugated to a therapeutic antibody, e.g., via a lysine residue.

In some embodiments, a conjugate of the present invention is of the Formula II:

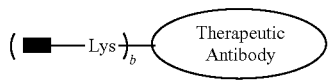

II wherein:

Lys is a lysine residue;

b is between 1 and 6, 1 and 5, 1 and 4 or 1 and 3; and

■ is a compound of Formula I or Formula Ia.

Formula II is intended to be a schematic illustration of the conjugation of a compound of Formula I or Formula Ia to a therapeutic antibody. Accordingly, when b is 1, and ■ is a compound of Formula Ia, the conjugate of Formula II can be drawn as:

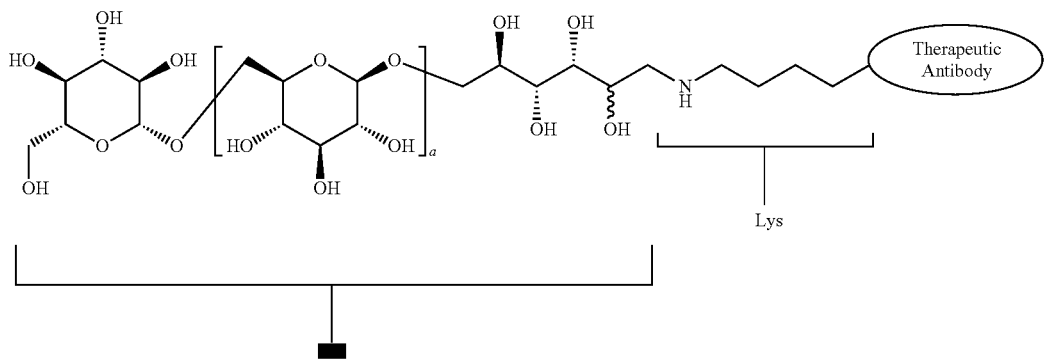

wherein "Lys" illustrates the aliphatic chain and terminal amine portion of the lysine residue.

Additionally, the structures above are intended to illustrate that multiple instances of the compound of Formula I or Formula Ia can be part of a conjugate. For example, when b is 2 in Formula II above, the conjugate is represented by the following schematic:

and when b is 3 in Formula II above, the conjugate is represented by the following schematic:

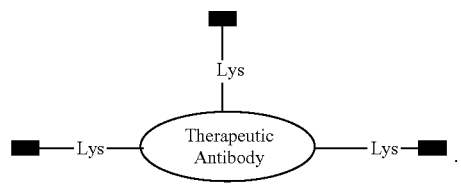

Exemplary Conjugates

A therapeutic antibody may be conjugated to one or more β-1,6-glucan oligomers. The present application relates, among other things, to the length of β-1,6-glucan oligomers to be conjugated to a therapeutic antibody, the load of β-1,6-glucan oligomers to be conjugated to a therapeutic antibody (e.g., the number of β-1,6-glucan oligomers to be conjugated to each antibody), and to the type of conjugation by which β-1,6-glucan oligomers are linked with a therapeutic antibody. In some embodiments, a therapeutic antibody may be conjugated to one or more β-1,6-glucan oligomers via a linker.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of between 2 and 10 glucose monomer units;
- a therapeutic antibody conjugated to between 1 and 5 β-1,6-glucan oligomers, wherein each β-1,6-glucan oligomer is independently comprised of between 2 and 10 glucose monomer units;
- a therapeutic antibody conjugated to between 1 and 4 β-1,6-glucan oligomers, wherein each β-1,6-glucan oligomer is independently comprised of between 2 and 10 glucose monomer units;
- a therapeutic antibody conjugated to between 1 and 3 β-1,6-glucan oligomers, wherein each β-1,6-glucan oligomer is independently comprised of between 2 and 10 glucose monomer units;
- a therapeutic antibody conjugated to between 2 and 4 β-1,6-glucan oligomers, wherein each β-1,6-glucan oligomer is independently comprised of between 2 and 10 glucose monomer units;
- a therapeutic antibody conjugated to between 2.5 and 3.5 β-1,6-glucan oligomers, wherein each β-1,6-glucan oligomer is independently comprised of between 2 and 10 glucose monomer units; or
- a therapeutic antibody conjugated to 3 β-1,6-glucan oligomers, wherein each β-1,6-glucan oligomer is independently comprised of between 2 and 10 glucose monomer units;
- a therapeutic antibody conjugated to 3 β-1,6-glucan oligomers, wherein each β-1,6-glucan oligomer is independently comprised of between 2 and 8 glucose monomer units;
- a therapeutic antibody conjugated to 3 β-1,6-glucan oligomers, wherein each β-1,6-glucan oligomer is independently comprised of between 3 and 7 glucose monomer units;
- a therapeutic antibody conjugated to 3 β-1,6-glucan oligomers, wherein each β-1,6-glucan oligomer is independently comprised of between 4 and 6 glucose monomer units;
- a therapeutic antibody conjugated to 3 β-1,6-glucan oligomers, wherein each β-1,6-glucan oligomer is independently comprised of 4 glucose monomer units;
- a therapeutic antibody conjugated to 3 β-1,6-glucan oligomers, wherein each β-1,6-glucan oligomer is independently comprised of 5 glucose monomer units;
- a therapeutic antibody conjugated to 3 β-1,6-glucan oligomers, wherein each β-1,6-glucan oligomer is independently comprised of 6 glucose monomer units;
- a therapeutic antibody conjugated to 3 β-1,6-glucan oligomers, wherein each β-1,6-glucan oligomer is independently comprised of 7 glucose monomer units;
- a therapeutic antibody conjugated to 3 β-1,6-glucan oligomers, wherein each β-1,6-glucan oligomer is independently comprised of 8 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of between 2 and 6 glucose monomer units;
- a therapeutic antibody conjugated to between 1 and 5 β-1,6-glucan oligomers, wherein each β-1,6-glucan oligomer is independently comprised of between 2 and 6 glucose monomer units;
- a therapeutic antibody conjugated to between 2 and 4 β-1,6-glucan oligomers, wherein each β-1,6-glucan oligomer is independently comprised of between 2 and 6 glucose monomer units;
- a therapeutic antibody conjugated to between 2.5 and 3.5 β-1,6-glucan oligomers, wherein each β-1,6-glucan oligomer is independently comprised of between 2 and 6 glucose monomer units; or
- a therapeutic antibody conjugated to 3 β-1,6-glucan oligomers, wherein each β-1,6-glucan oligomer is independently comprised of between 2 and 6 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of between 4 and 8 glucose monomer units;
- a therapeutic antibody conjugated to between 1 and 5 β-1,6-glucan oligomers, wherein each β-1,6-glucan oligomer is independently comprised of between 4 and 8 glucose monomer units;
- a therapeutic antibody conjugated to between 2 and 4 β-1,6-glucan oligomers, wherein each β-1,6-glucan oligomer is independently comprised of between 4 and 8 glucose monomer units;
- a therapeutic antibody conjugated to between 2.5 and 3.5 β-1,6-glucan oligomers, wherein each β-1,6-glucan oligomer is independently comprised of between 4 and 8 glucose monomer units; or
- a therapeutic antibody conjugated to 3 β-1,6-glucan oligomers, wherein each β-1,6-glucan oligomer is independently comprised of between 4 and 8 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of between 4 and 6 glucose monomer units;
- a therapeutic antibody conjugated to between 1 and 5 β-1,6-glucan oligomers, wherein each β-1,6-glucan oligomer is independently comprised of between 4 and 6 glucose monomer units;
- a therapeutic antibody conjugated to between 2 and 4 β-1,6-glucan oligomers, wherein each β-1,6-glucan oligomer is independently comprised of between 4 and 6 glucose monomer units;
- a therapeutic antibody conjugated to between 2.5 and 3.5 β-1,6-glucan oligomers, wherein each β-1,6-glucan oligomer is independently comprised of between 4 and 6 glucose monomer units; or
- a therapeutic antibody conjugated to 3 β-1,6-glucan oligomers, wherein each β-1,6-glucan oligomer is independently comprised of between 4 and 6 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of between 4.5 and 5.5 glucose monomer units;

a therapeutic antibody conjugated to between 1 and 5 β-1,6-glucan oligomers, wherein each β-1,6-glucan oligomer is independently comprised of between 4.5 and 6.5 glucose monomer units;

a therapeutic antibody conjugated to between 2 and 4 β-1,6-glucan oligomers, wherein each β-1,6-glucan oligomer is independently comprised of between 4.5 and 5.5 glucose monomer units;

a therapeutic antibody conjugated to between 2.5 and 3.5 β-1,6-glucan oligomers, wherein each β-1,6-glucan oligomer is independently comprised of between 4.5 and 5.5 glucose monomer units; or a therapeutic antibody conjugated to 3 β-1,6-glucan oligomers, wherein each β-1,6-glucan oligomer is independently comprised of between 4.5 and 5.5 glucose monomer units.

In some exemplary embodiments of the present invention, a conjugate may have (or a composition may comprise conjugates having) the following features:

a therapeutic antibody conjugated to between 1 and 6 β-1,6-glucan oligomers, wherein each β-1,6-glucan oligomer is independently comprised of 8 glucose monomer units;

a therapeutic antibody conjugated to between 1 and 5 β-1,6-glucan oligomers, wherein each β-1,6-glucan oligomer is independently comprised of 8 glucose monomer units;

a therapeutic antibody conjugated to between 2 and 4 β-1,6-glucan oligomers, wherein each β-1,6-glucan oligomer is independently comprised of 8 glucose monomer units;

a therapeutic antibody conjugated to between 2.5 and 3.5 β-1,6-glucan oligomers, wherein each β-1,6-glucan oligomer is independently comprised of 8 glucose monomer units; or a therapeutic antibody conjugated to 3 β-1,6-glucan oligomers, wherein each β-1,6-glucan oligomer is independently comprised of 8 glucose monomer units.

In some exemplary embodiments of the present invention, a conjugate may have (or a composition may comprise conjugates having) the following features:

a therapeutic antibody conjugated to between 1 and 6 β-1,6-glucan oligomers, wherein each β-1,6-glucan oligomer is independently comprised of 7 glucose monomer units;

a therapeutic antibody conjugated to between 1 and 5 β-1,6-glucan oligomers, wherein each β-1,6-glucan oligomer is independently comprised of 7 glucose monomer units;

a therapeutic antibody conjugated to between 2 and 4 β-1,6-glucan oligomers, wherein each β-1,6-glucan oligomer is independently comprised of 7 glucose monomer units;

a therapeutic antibody conjugated to between 2.5 and 3.5 β-1,6-glucan oligomers, wherein each β-1,6-glucan oligomer is independently comprised of 7 glucose monomer units; or a therapeutic antibody conjugated to 3 β-1,6-glucan oligomers, wherein each β-1,6-glucan oligomer is independently comprised of 7 glucose monomer units.

In some exemplary embodiments of the present invention, a conjugate may have (or a composition may comprise conjugates having) the following features:

a therapeutic antibody conjugated to between 1 and 6 β-1,6-glucan oligomers, wherein each β-1,6-glucan oligomer is independently comprised of 6 glucose monomer units;

a therapeutic antibody conjugated to between 1 and 5 β-1,6-glucan oligomers, wherein each β-1,6-glucan oligomer is independently comprised of 6 glucose monomer units;

a therapeutic antibody conjugated to between 2 and 4 β-1,6-glucan oligomers, wherein each β-1,6-glucan oligomer is independently comprised of 6 glucose monomer units;

a therapeutic antibody conjugated to between 2.5 and 3.5 β-1,6-glucan oligomers, wherein each β-1,6-glucan oligomer is independently comprised of 6 glucose monomer units; or a therapeutic antibody conjugated to 3 β-1,6-glucan oligomers, wherein each β-1,6-glucan oligomer is independently comprised of 6 glucose monomer units.

In some exemplary embodiments of the present invention, a conjugate may have (or a composition may comprise conjugates having) the following features:

a therapeutic antibody conjugated to between 1 and 6 β-1,6-glucan oligomers, wherein each β-1,6-glucan oligomer is independently comprised of 5 glucose monomer units;

a therapeutic antibody conjugated to between 1 and 5 β-1,6-glucan oligomers, wherein each β-1,6-glucan oligomer is independently comprised of 5 glucose monomer units;

a therapeutic antibody conjugated to between 2 and 4 β-1,6-glucan oligomers, wherein each β-1,6-glucan oligomer is independently comprised of 5 glucose monomer units;

a therapeutic antibody conjugated to between 2.5 and 3.5 β-1,6-glucan oligomers, wherein each β-1,6-glucan oligomer is independently comprised of 5 glucose monomer units; or a therapeutic antibody conjugated to 3 β-1,6-glucan oligomers, wherein each β-1,6-glucan oligomer is independently comprised of 5 glucose monomer units.

In some exemplary embodiments of the present invention, a conjugate may have (or a composition may comprise conjugates having) the following features:

a therapeutic antibody conjugated to between 1 and 6 β-1,6-glucan oligomers, wherein each β-1,6-glucan oligomer is independently comprised of 4 glucose monomer units;

a therapeutic antibody conjugated to between 1 and 5 β-1,6-glucan oligomers, wherein each β-1,6-glucan oligomer is independently comprised of 4 glucose monomer units;

a therapeutic antibody conjugated to between 4 and 6 β-1,6-glucan oligomers, wherein each β-1,6-glucan oligomer is independently comprised of 4 glucose monomer units;

a therapeutic antibody conjugated to 5 β-1,6-glucan oligomers, wherein each β-1,6-glucan oligomer is independently comprised of 4 glucose monomer units;

a therapeutic antibody conjugated to between 2 and 4 β-1,6-glucan oligomers, wherein each β-1,6-glucan oligomer is independently comprised of 4 glucose monomer units; or a therapeutic antibody conjugated to between 2 and 3 β-1,6-glucan oligomers, wherein each β-1,6-glucan oligomer is independently comprised of 4 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of 3 glucose monomer units;
- a therapeutic antibody conjugated to between 1 and 5 β-1,6-glucan oligomers, wherein each β-1,6-glucan oligomer is independently comprised of 3 glucose monomer units;
- a therapeutic antibody conjugated to between 4 and 6 β-1,6-glucan oligomers, wherein each β-1,6-glucan oligomer is independently comprised of 3 glucose monomer units;
- a therapeutic antibody conjugated to 5 β-1,6-glucan oligomers, wherein each β-1,6-glucan oligomer is independently comprised of 3 glucose monomer units;
- a therapeutic antibody conjugated to between 2 and 4 β-1,6-glucan oligomers, wherein each β-1,6-glucan oligomer is independently comprised of 3 glucose monomer units; or
- a therapeutic antibody conjugated to between 2 and 3 β-1,6-glucan oligomers, wherein each β-1,6-glucan oligomer is independently comprised of 3 glucose monomer units.

In some exemplary embodiments of the present invention, a conjugate may have (or a composition may comprise conjugates having) the following features:
- a therapeutic antibody conjugated to between 1 and 6 β-1,6-glucan oligomers, wherein each β-1,6-glucan oligomer is independently comprised of 2 glucose monomer units;
- a therapeutic antibody conjugated to between 1 and 5 β-1,6-glucan oligomers, wherein each β-1,6-glucan oligomer is independently comprised of 2 glucose monomer units;
- a therapeutic antibody conjugated to between 4 and 6 β-1,6-glucan oligomers, wherein each β-1,6-glucan oligomer is independently comprised of 2 glucose monomer units;
- a therapeutic antibody conjugated to 5 β-1,6-glucan oligomers, wherein each β-1,6-glucan oligomer is independently comprised of 2 glucose monomer units;
- a therapeutic antibody conjugated to between 2 and 4 β-1,6-glucan oligomers, wherein each β-1,6-glucan oligomer is independently comprised of 2 glucose monomer units; or
- a therapeutic antibody conjugated to between 2 and 3 β-1,6-glucan oligomers, wherein each β-1,6-glucan oligomer is independently comprised of 2 glucose monomer units.

In some exemplary embodiments of the present invention, a conjugate may be represented by Formula IIa:

wherein $a^1$ is between 1 and 9; and b is between 1 and 6. In other embodiments $a^1$ is 1, 2, 3, 4, 5, 6, 7, 8 or 9. In other embodiments, b is 1, 2, 3, 4, 5, or 6. In another exemplary embodiment, the conjugate is represented by Formula IIa, wherein $a^1$ is between 1 and 9, and b is between 2 and 4.

In another exemplary embodiment, the conjugate is represented by Formula IIa, wherein $a^1$ is between 1 and 9, and b is 3.

In another embodiment, the conjugate is represented by Formula IIa, wherein $a^1$ is between 1 and 3, and b is between 1 and 6. In other embodiments, a is 1, 2, or 3. In other embodiments, b is 1, 2, 3, 4, 5, or 6. In another exemplary embodiment, the conjugate is represented by Formula IIa, wherein $a^1$ is between 1 and 3, and b is between 2 and 4.

In another exemplary embodiment, the conjugate is represented by Formula IIa, wherein $a^1$ is between 1 and 3, and b is 3.

In another embodiment, the conjugate is represented by Formula IIa, wherein $a^1$ is between 2 and 4, and b is between 1 and 6. In other embodiments, $a^1$ is 2, 3, or 4. In other embodiments, b is 1, 2, 3, 4, 5, or 6. In another exemplary embodiment, the conjugate is represented by Formula IIa, wherein $a^1$ is between 2 and 4, and b is between 2 and 4.

In another exemplary embodiment, the conjugate is represented by Formula IIa, wherein $a^1$ is between 2 and 4, and b is 3.

In another embodiment, the conjugate is represented by Formula IIa, wherein $a^1$ is 3, and b is between 1 and 6. In other embodiments, b is 1, 2, 3, 4, 5, 6. In another exemplary embodiment, the conjugate is represented by Formula IIa, wherein $a^1$ is 3, and b is between 2 and 4. In another exemplary embodiment, the conjugate is represented by Formula IIa, wherein $a^1$ is 3, and b is 3.

In another embodiment, the conjugate is represented by Formula IIa, wherein $a^1$ is 4, and b is between 1 and 6. In other embodiments, b is 1, 2, 3, 4, 5, 6. In another exemplary embodiment, the conjugate is represented by Formula IIa, wherein $a^1$ is 4, and b is between 2 and 4 or between 4 and 6. In another exemplary embodiment, the conjugate is represented by Formula IIa, wherein $a^1$ is 4, and b is 3. In another exemplary embodiment, the conjugate is represented by Formula IIa, wherein $a^1$ is 4, and b is 5.

In another embodiment, the conjugate is represented by Formula IIa, wherein $a^1$ is 5, and b is between 1 and 6. In other embodiments, b is 1, 2, 3, 4, 5, 6. In another exemplary embodiment, the conjugate is represented by Formula IIa, wherein $a^1$ is 5, and b is between 2 and 4 or between 4 and 6. In another exemplary embodiment, the conjugate is represented by Formula IIa, wherein $a^1$ is 5, and b is 3. In another exemplary embodiment, the conjugate is represented by Formula IIa, wherein $a^1$ is 5, and b is 5.

In another embodiment, the conjugate is represented by Formula IIa, wherein $a^1$ is 6, and b is between 1 and 6. In other embodiments, b is 1, 2, 3, 4, 5, 6. In another exemplary

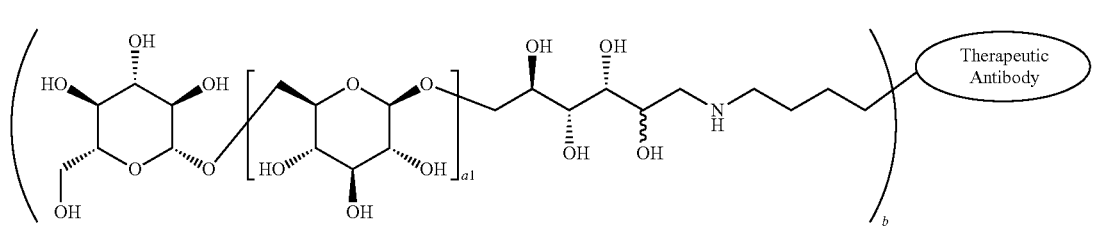

embodiment, the conjugate is represented by Formula IIa, wherein $a^1$ is 6, and b is between 2 and 4 or between 4 and 6. In another exemplary embodiment, the conjugate is represented by Formula IIa, wherein $a^1$ is 6, and b is 3. In another exemplary embodiment, the conjugate is represented by Formula IIa, wherein $a^1$ is 6, and b is 5.

In another embodiment, the conjugate is represented by Formula IIa, wherein $a^1$ is 7, and b is between 1 and 6. In other embodiments, b is 1, 2, 3, 4, 5, 6. In another exemplary embodiment, the conjugate is represented by Formula IIa, wherein $a^1$ is 7, and b is between 2 and 4 or between 4 and 6. In another exemplary embodiment, the conjugate is represented by Formula IIa, wherein $a^1$ is 7, and b is 3. In another exemplary embodiment, the conjugate is represented by Formula IIa, wherein $a^1$ is 7, and b is 5.

Conjugate Properties

In any of the various embodiments described herein, a therapeutic antibody conjugate of the present invention may be capable of binding its target. In some embodiments, the target is amplified and/or overexpressed by a cancer or tumor cell. In some embodiments, a therapeutic antibody conjugate of the present invention competes with its parent antibody for binding its target. In some embodiments, conjugation enhances complement (C3) deposition. C3 deposition can be assayed by any known method, including Western analysis or FACS analysis using monoclonal antibodies directed against the alpha or beta chains of C3. In some embodiments, conjugation enhances binding by anti-β-1,6-glucan antibodies. Binding by anti-β-1,6-glucan antibodies can be assayed by any known method, including ELISA analysis using anti-human IgG2 antibodies. In these various embodiments, the enhancement as compared to an unconjugated counterpart may be at least 5%, at least 10%, at least 20%, at least 30%, at least 40%, at least 50%, at least 75%, at least 100%, or more.

Uses and Administration

The following uses, and methods apply to any conjugate described herein. A therapeutic antibody conjugate of the present invention may be used, e.g., in the treatment of cancer, e.g., a cancer associated with amplification and/or overexpression of a target antigen (e.g., protein or other moiety). A conjugate of the present invention may be used, e.g., in the treatment of cancer. In some embodiments, the cancer is breast cancer. In some embodiments, the cancer is ovarian cancer. In some embodiments, the cancer is bladder cancer. In some embodiments, the cancer is salivary gland cancer. In some embodiments, the cancer is endometrial cancer. In some embodiments, the cancer is pancreatic cancer. In some embodiments, the cancer is prostate cancer. In some embodiments, the cancer is non-small-cell lung cancer (NSCLC). In some embodiments, the cancer is a blood cancer. In some embodiments, the cancer is a skin cancer.

In some embodiments, the cancer is metastatic. In various embodiments, a cancer or tumor treated by administration of a therapeutic antibody conjugate described herein is a recurrent or treatment-resistant cancer or tumor (e.g., a cancer or tumor resistant to treatment by unconjugated therapeutic antibody). Such treatment may be, e.g., in a subject having, suspected of having, or diagnosed as having such cancer. In various embodiments, a conjugate described herein, upon administration to a subject having, suspected of having, or diagnosed as having a cancer or tumor, is cytostatic, cytotoxic, or slows, delays, or inhibits growth of the cancer or tumor. In various embodiments, a conjugate described herein, upon administration to a subject having, suspected of having, or diagnosed as having a cancer or tumor, increases the length or likelihood survival of the subject. In various embodiments, a conjugate described herein, upon administration to a subject having, suspected of having, or diagnosed as having a cancer or tumor, induces regression or stasis of a cancer or tumor. In various embodiments, a conjugate described herein, upon administration to a subject having, suspected of having, or diagnosed as having a cancer or tumor, induces an immune response that is effective in inhibiting recurrence of a cancer or tumor. In various embodiments, a conjugate described herein recruits neutrophils, e.g., to a targeted cancer or tumor. In various embodiments, a conjugate described herein causes or promotes neutrophil infiltration, e.g., of a targeted cancer or tumor. In various embodiments, administration of a conjugate described herein to a subject having, suspected of having, or diagnosed as having a cancer or tumor does not elicit an adverse effect, e.g., a cytokine storm or sepsis.

In some embodiments, a conjugate of the present invention produces an enhanced therapeutic response in a subject with a tumor as compared to its unconjugated counterpart (e.g., a therapeutic antibody). For example, and in some embodiments, conjugation enhances phagocytosis and/or cytotoxic responses to tumor cells, or in some embodiments, enhances complement-mediated lysis of the tumor cells. In some embodiments, these responses are mediated by neutrophils and/or macrophages. Phagocytosis and/or lysis can be assessed by any known method, including time-lapse microscopy or Fluorescence-Activated Cell Sorting (FACS). In these various embodiments, the enhancement as compared to an unconjugated counterpart may be at least 5%, at least 10%, at least 20%, at least 30%, at least 40%, at least 50%, at least 75%, at least 100%, or more.

In various embodiments, conjugates described herein can be incorporated into a pharmaceutical composition. Such a pharmaceutical composition can be useful, e.g., for the treatment of a cancer or tumor, e.g., a cancer or tumor described herein. Pharmaceutical compositions of the present invention can be formulated by methods known to those skilled in the art (e.g., as described in Remington: The Science and Practice of Pharmacy, 22nd edition, ed. Lloyd Allen, Pharmaceutical Press and Philadelphia College of Pharmacy at University of the Sciences, 2012, the contents of which are incorporated herein by reference).

A pharmaceutical composition can include a therapeutically effective amount of a conjugate described herein. Such effective amounts can be readily determined by one of ordinary skill in the art based, in part, on the effect of the administered composition, or the combinatorial effect of the conjugate and one or more additional active agents, if more than one agent is used. A therapeutically effective amount of a conjugate described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the disease or disorder. Other factors affecting the dose administered to the subject include, e.g., the type or severity of the disease or disorder. Other factors can include, e.g., other medical disorders concurrently or previously affecting the subject, the general health of the subject, the genetic disposition of the subject, diet, time of administration, rate of excretion, etc. Suitable human doses of any of the compositions described herein can further be evaluated in, e.g., Phase I dose escalation studies.

The route of administration can be parenteral, for example, administration by injection. A pharmaceutical composition can be administered parenterally in the form of an injectable formulation comprising a sterile solution or suspension in water or another pharmaceutically acceptable liquid. For example, the pharmaceutical composition can be formulated by suitably combining the therapeutic molecule with pharmaceutically acceptable vehicles or media, such as sterile water and physiological saline, and other suitable excipients followed by mixing in a unit dose form required for generally accepted pharmaceutical practices. The amount of conjugate included in the pharmaceutical compositions is such that a suitable dose within the designated range is provided. The formulated injection can be packaged in a suitable ampule.

EXAMPLES

The examples described herein demonstrate, among other things, the purification of glucans from pustulan for use in making various mAbXcite-conjugates, (a therapeutic antibody linked to one or more β-1,6-glucan oligomers), the production and characterization of various mAbXcite-conjugates, methods of making synthetic β-1,6-glucans, and suitable linking chemistries for conjugating a therapeutic antibody to one or more β-1,6-glucan oligomers.

Also described herein are studies of HER2-mAbXcite-conjugates or mAbXcite-trastuzumab conjugates (trastuzumab linked to one or more β-1,6-glucan oligomers) relating to the effect of conjugation with β-1,6-glucan oligomers of different length, e.g., from 4 to 6 glucose monomer units with about 3 β-1,6-glucan oligomers per trastuzumab molecule. Binding of trastuzumab to HER2 when conjugated to β-1,6-glucan oligomers was tested and found to be similar to unconjugated trastuzumab. Among results described in the present Examples, include successful preclinical results in trastuzumab-resistant tumor xenograft mouse models treated with HER2-mAbXcite-conjugates.

Also described herein are studies of EGFR-mAbXcite or mAbXcite-cetuximab conjugates (cetuximab linked to one or more β-1,6-glucan oligomers) relating to the effect of conjugation with β-1,6-glucan oligomers of different length, e.g., from 4 to 9 glucose monomer units, and different loads, e.g., averaging from 1 to 6 β-1,6-glucan oligomers per cetuximab molecule. Binding of cetuximab to EGFR when conjugated to β-1,6-glucan oligomers as well as its antibody-dependent cell-mediated cytotoxicity (ADCC) was tested and found to be similar to unconjugated cetuximab. Among results described in the present Examples, mAbXcite-cetuximab conjugates were confirmed to recruit neutrophils by a live imaging technique and histology. Results described herein also include successful preclinical results in tumor xenograft mouse models with BRAF and KRAS mutations.

The present invention encompasses the realization that these results that were generated using two different therapeutic antibodies (trastuzumab and cetuximab), e.g., the improvements observed when using particular lengths of β-1,6-glucan oligomers and particular loads of β-1,6-glucan oligomers can be generalized to other therapeutic antibodies including those described herein.

In certain of the present Examples, mice were selected as a useful model for testing β-1,6-glucan conjugates, as these mammals have only low titers of endogenous anti-β-1,6-glucan. Levels of anti-β-1,6-glucan antibodies could therefore be controlled via administration of IVIG.

As used in the following Examples, the glucans are sometimes referred to as "#-mers" wherein "#" is the number of glucose monomer units that were present prior to conjugation with trastuzumab or cetuximab. For example, a glucan including three glucose monomer units prior to conjugation may be identified as a "3-mer" or "3mer", a glucan including four glucose monomer units may be identified as a "4-mer" or "4mer", a glucan including five glucose monomer units may be identified as a "5-mer" or "5mer", and so forth without limitation. When glucans are conjugated via reductive amination (direct conjugation) one of the glucose monomer units is ring-opened to form a "linker" between the remaining glucose monomer units and trastuzumab or cetuximab. Accordingly, references to conjugates that were prepared by direct conjugation using a "3-mer" would include the following structure:

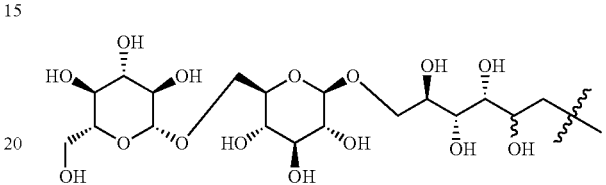

and when a non-glucose based linker such as, for example, NHS DBCO is used with, e.g., a "4-mer", the resulting conjugate would include the following structure:

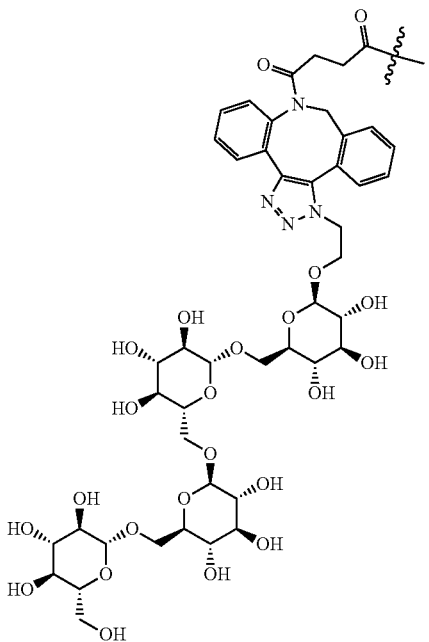 [SMILES: *C(=O)CCC(=O)N1Cc2ccccc2-c2c(nnn2CCO[C@@H]2O[C@H](CO[C@@H]3O[C@H](CO[C@@H]4O[C@H](CO[C@@H]5O[C@H](CO)[C@@H](O)[C@H](O)[C@H]5O)[C@@H](O)[C@H](O)[C@H]4O)[C@@H](O)[C@H](O)[C@H]3O)[C@@H](O)[C@H](O)[C@H]2O)-c2ccccc21]

Although exemplary embodiments are described in detail in these Examples, it should be understood that various changes, substitutions and alterations can be made herein without departing from the spirit and scope of the invention as defined in the appended claims.

Example 1: Purification of Oligomers from Pustulan

Degradation of Pustulan

Pustulan (Elicityl-Oligotech) was suspended in concentrated hydrochloric acid at 100 mg/ml. The resulting slurry was stirred vigorously at room temperature for 1.25 h, during which time the mixture's viscosity was noticeably reduced. The fine black slurry was then transferred to a beaker containing seven volumes of n-propanol, which led to the precipitation of a tan solid. After vigorous stirring for 15 min, the mixture was transferred to several tubes to separate the insoluble solids from the liquid by centrifugation (3600×g, 5 min). The supernatant was decanted leaving behind a light brown pellet. The pellets were successively washed with ethanol and n-propanol to remove traces of the lower order sugars (mono- and di-saccharides). Water was added to each tube and the subsequent mixture was stirred overnight at room temperature. Centrifugation (3600×g, 15 min) of these stirred mixtures yielded dark brown pellets and clear, lightly colored supernatant. The supernatants were pooled, frozen and lypholized yielding a ladder of β-1,6-glucans as a tan powder with a 15% by mass recovery based on starting pustulan. The resulting size of oligosaccharides ranged from 3mer to >14mer with the higher oligosaccharides (>14) present by LC but outside the detection limit of the MS, as determined by LC-MS analysis of the mixture via XBridge BEH HILIC Amide OBD Prep Column (XBridge BEH Amide HILIC OBD Prep Column, 130 Å, 5 µm, 19 mm×250 mm and) XBridge BEH Amide HILIC analytical column, 3.5 µm, 3 mm×100 mm acquired from Waters, pre-washed as described by the manufacturer prior to use; 95-40% acetonitrile/water w/0.1% formic acid, 50 C, 0.75 mL/min for 15 min). In addition, the bulk of material consisted of 3mer to 8mer, as determined by ELSD analysis.

Bulk Size Fractionation of the Oligosaccharide Ladder by P2

XK50 columns (P2 extra fine resin acquired from Biorad, prepared as described by the manufacturer, utilized to pack two XK50 100 cm long columns) were connected in parallel to an Agilent 1100 isocratic pump. An external pressure gauge was installed downstream of the pump to monitor the column pressure. All separations were carried out utilizing 0.1 M acetic acid with a flow rate of 3.5 ml/min. The oligosaccharide ladder was dissolved in water to a total volume of up to 12 mL and was injected onto the column via a manually injector possessing a 13 ml loop. The separation occurred over an approximately 500 minute period with the first 240 minutes diverted to waste. The remaining flow was collected as 6 mL fractions totaling 288 fractions. Fractions were analyzed by MALDI/TOF and fractions containing β-1,6-glucan of distinct sizes were pooled together, frozen and lypholized.

Final Purification of Oligosaccharides Via HILIC and C18/C18AQ Chromatography

The dried samples from the P2 purification were dissolved in minimal amount of water and further separated on a)(Bridge BEH Amide HILIC OBD Prep Column (XBridge BEH Amide HILIC OBD Prep Column, 130 Å, 5 µm, 19 mm×250 mm and XBridge BEH Amide HILIC analytical column, 3.5 µm, 3 mm×100 mm acquired from Waters, pre-washed as described by the manufacturer prior to use; 130 Å, 5 µm, 19 mm×250 mm, 95-40% acetonitrile/water w/ 0.1% formic acid, 25 mL/min for 30 min). The purified fractions containing oligosaccharides of distinct sizes as determined by LC/MS were frozen and lypholized. After drying to completion, the oligosaccharides were redissolved in minimal water containing 0.1% formic acid and passed through a C18 AQ and a C18 column (C18 and C18AQ cartridges acquired from Teledyne ISCO and pre-washed as recommended by the manufacturer prior to use; 10× wt/wt bed size) linked in sequence and the product was eluted with water with 0.1% formic acid (10 column volumes). The flow through was frozen and lypholized to a white powder.

Example 2: Conjugation of β-1,6-Glucan Oligomers to Trastuzumab

Conjugation of β-1,6-Glucan Oligomers to Trastuzumab Via Reductive Amination

β-1,6-glucan oligomers obtained from pustulan as described in Example 1 were conjugated to trastuzumab via reductive amination. The β-1,6-glucan oligomers were of Formula V:

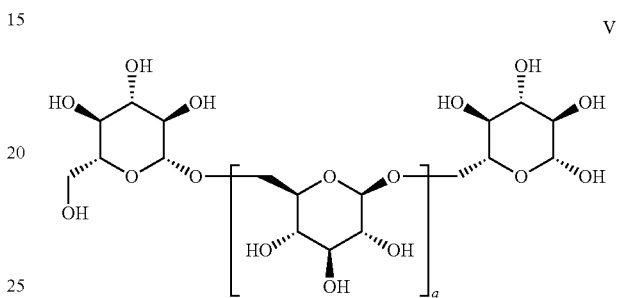

wherein a is between 3 and 5. Trastuzumab was buffer exchanged from storage solution into 0.2 M Na-Borate, pH 8.0 by TFF (50 kDa membrane) and making the concentration of Trastuzumab (10-20 mg/ml). The β-1,6-oligomers were prepared as a 0.1M solution in endotoxin-free water. To a solution of 0.3 M sodium cyanoborohydride in endotoxin-free water, and 10:90 PEG 2000:endotoxin-free water was added 0.1M sodium borate until the pH was about 8.0. Trastuzumab was added until the concentration of trastuzumab was 5 mg/mL. A 230× molar excess of the β-1,6-oligomer solution was added at 21° C. and the reaction was allowed to stir for 23 hours. The conjugation was stopped by adding a 100-fold molar ratio of lysine to oligosaccharide. Reaction quench solution was 1 M lysine in 0.1 M Na-Borate, pH 8.0.

Following conjugation, the reaction mixture was diluted 1 to 10 into 46.7% Trehalose dehydrate, 0.74% L-Histidine, and 1.15% L-Histidine hydrochloride monohydrate with a 50 kDa TFF membrane. Final trastuzumab-oligosaccharide conjugate was adjusted to 1 mg/ml. Storage buffer was 46.7% Trehalose dehydrate, 0.74% L-Histidine, 1.15% L-Histidine hydrochloride monohydrate, and 0.01% Polysorbate 20 at 4° C. Unconjugated oligosaccharide was <0.1% of the concentration of oligosaccharide-trastuzumab conjugate. PEG of average MW 2000 was <0.1% of the concentration of oligosaccharide-trastuzumab conjugate.

Methods of Analysis:
a) SEC separation
   a. Unmodified Trastuzumab
   b. Oligosaccharide-Trastuzumab conjugate
   c. SEC separation utilizes a TSKgel SuperSW3000, 4 mm, 250 Å silica, 4.6 mm ID×30 cm using as a mobile phase 0.4M $NaClO_4$, 0.05M $NaH_2PO_4$, pH 7.2 utilizing UV detection @ λ=280 nm
b) Load estimation by MALDI (AB Sciex MALDI/Q-TOF 4800 or comparable instrument). Note: HIC is not able to resolve individual loads due to hydrophilicity of oligosaccharides
   a. Utilize BSA (MW 66341) as the calibration standard (AB Sciex) in linear high mass positive mode b. Utilize sinapinic acid (Sigma) as matrix
c. Use native Trastuzumab as control
d. Estimate load by subtracting average m/z of Trastuzumab conjugate from that of unmodified Trastuzumab and divide by mass of a unit load to determine load of conjugate. Data has an average standard deviation of 0.2-0.3 load units c) Measure m/z of oligosaccharides by MALDI (AB Sciex 4800 or comparable instrument) using HABA (Sigma) as matrix.

d) Measure m/z of oligosaccharides by LC-MS using) (Bridge 3 mm×10 cm, 3.5 μm particle size (Waters) using as mobile phase A: Water/0.1% Formic acid, B: 100% Acetonitrile/0.1% Formic acid. We use a ZQ (Waters) for mass spectrometry.

Example 3: Binding Efficacy of HER2-mAbXcite by ELISA

Figure 1:
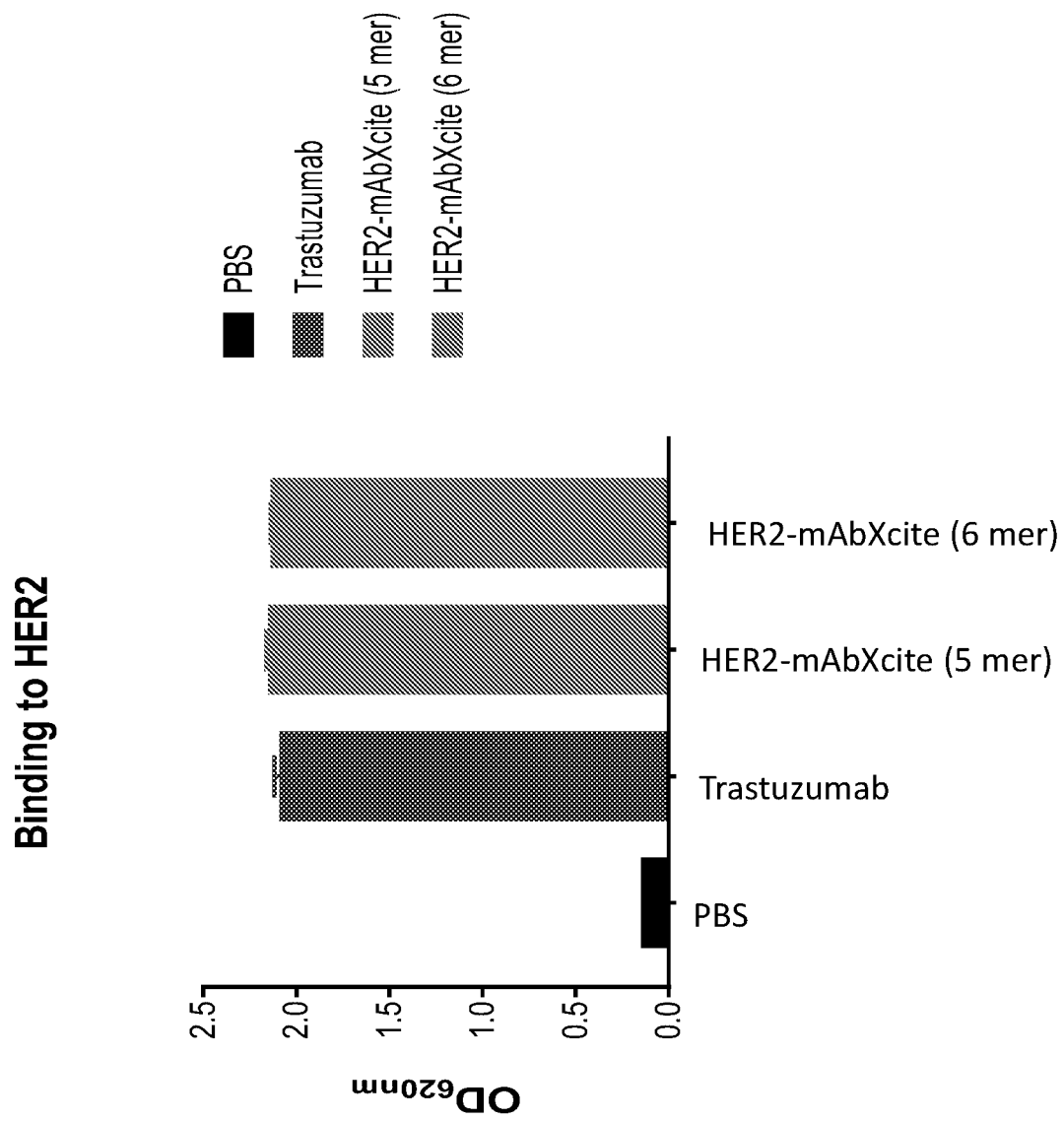
FIG. 1 depicts the results of an ELISA studying HER2 binding capability of trastuzumab, HER2-mAbXcite (5-mer), and HER2-mAbXcite (6-mer).

This example describes a study of the ability of HER2-mAbXcite conjugates, prepared as described in Example 2, to bind HER2. The wells of an ELISA plate were coated with HER2 antigen. PBS control, trastuzumab, HER2-mAbXcite (5-mer), and HER2-mAbXcite (6-mer) were added to wells and incubated. The wells were washed and labeled anti-human IgG antibodies were added to the wells. After incubation, the wells were washed, a detection reagent applied, and the plate read. As shown in FIG. 1, the PBS control was negative for signal, and binding of trastuzumab, HER2-mAbXcite (5-mer), and HER2-mAbXcite (6-mer) was detected.

Example 4: Detection of HER2-mAbXcite by ELISA

Figure 2:
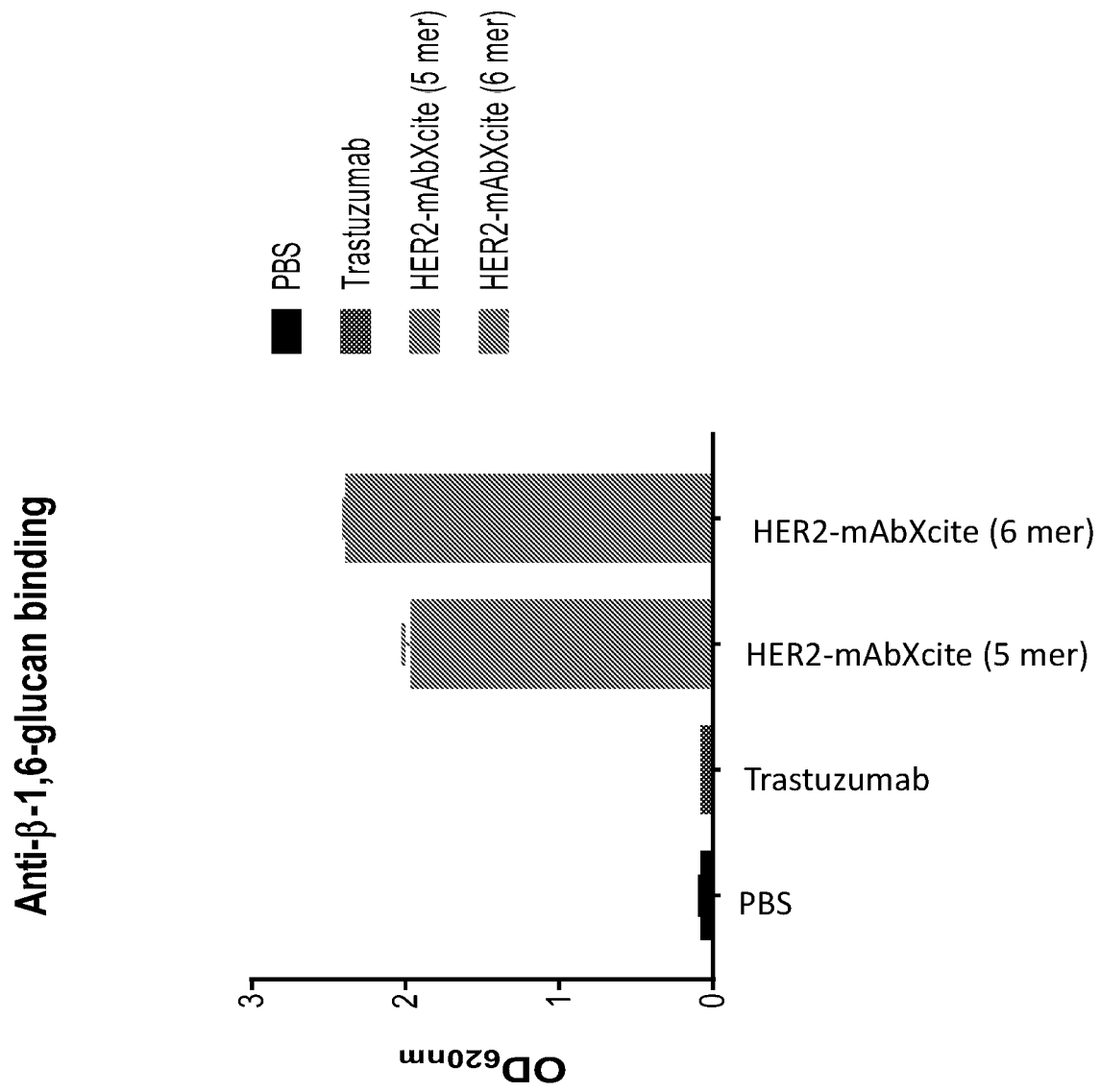
FIG. 2 depicts the results of an ELISA detecting the presence of human anti-β-1,6-glucan on trastuzumab, HER2-mAbXcite (5-mer) and HER2-mAbXcite (6-mer).

This example describes a selective ELISA for detection of HER2-mAbXcite conjugates, prepared as described in Example 2. The wells of an ELISA plate were coated with HER2 antigen. PBS control, trastuzumab, HER2-mAbXcite (5-mer), and HER2-mAbXcite (6-mer) were added to wells and incubated. The wells were washed and human anti-β-1,6-glucan polyclonal antibodies were added to the wells. After incubation, the wells were washed and labeled anti-human IgG2 antibodies were added to the wells. After incubation, the wells were washed, a detection reagent applied, and the plate read. As shown in FIG. 2, the PBS control and trastuzumab were negative for signal, and HER2-mAbXcite (5-mer), and HER2-mAbXcite (6-mer) were detected.

Example 5: Efficacy Study of HER2-mAbXcite (5-Mer) and (6-Mer) in Nude Mice

In this Example, the efficacy of HER2-mAbXcite conjugates, prepared as described in Example 2, was studied in a nude mouse model implanted with the trastuzumab-resistant human cell line JIMT-1. The study was of HER2-mAbXcite in which the conjugation utilized reductive amination (direct) chemistry, a 5-mer or 6-mer oligomer, with a load of about 3 oligomers per antibody.

In this Example, 7 week old female nude mice were implanted with 2.5×10$^6$ JIMT-1 cells. Once tumors reached a size of 150-182 mm$^3$, mice were randomly assigned into five study treatment groups, such that the mean tumor volume for each group was about 160 mm$^3$. Prior to each antibody administration, all mice received about 500 mg/kg (0.1 mL) intraperitoneal (IP) injection of pooled human antibodies (IVIG). Two hours post-IVIG administration, each group was administered one of the following treatments via an IP injection: PBS control; 15 mg/kg trastuzumab; 15 mg/kg HER2-mAbXcite (5-mer); 15 mg/kg HER2-mAbXcite (6-mer); or Kadcyla® (T-DMI).

Throughout the study, tumors were monitored twice weekly to determine tumor growth rates using external calipers. Tumors were measured prior to and following the first day of treatment. Body weights were also collected twice a week. Mice were euthanized when the maximum tumor volume reached 2000 mm$^3$. Mice were also euthanized if the tumor became ulcerated, if the tumor impeded ambulation, or there was a deterioration of body condition. Mice were also euthanized if they lost >15% of their original body weight.

Figure 3:
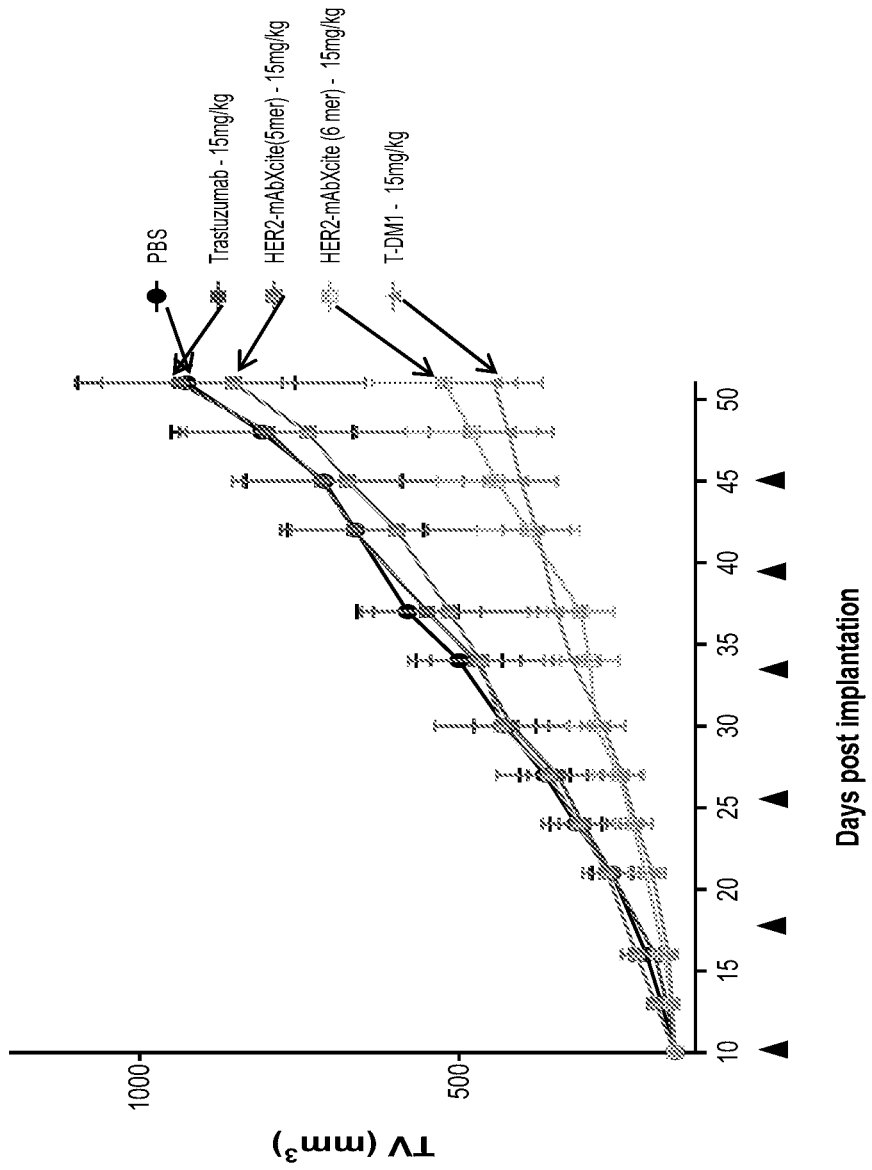
FIG. 3 depicts the mean tumor size results of a study of the efficacy of trastuzumab, HER2-mAbXcite (5-mer), HER2-mAbXcite (6-mer) and Kadcyla® (T-DM1) in a nude mouse model implanted with the trastuzumab-resistant human cell line JIMT-1.
Figure 4:
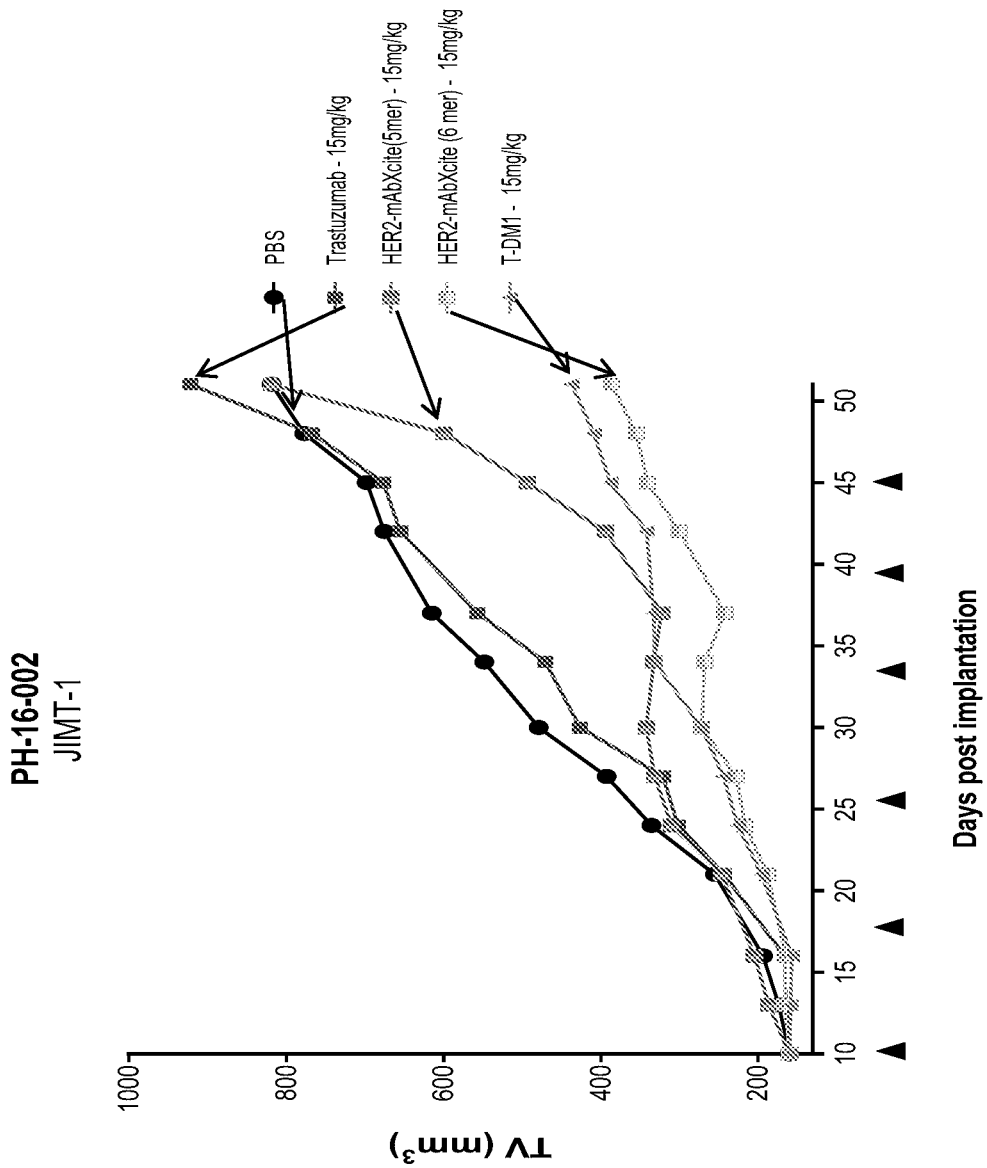
FIG. 4 depicts the median tumor size results of a study of the efficacy of trastuzumab, HER2-mAbXcite (5-mer), HER2-mAbXcite (6-mer) and Kadcyla® (T-DM1) in a nude mouse model implanted with the trastuzumab-resistant human cell line JIMT-1.

Analysis of the data collected from this experiment was performed. Tumor volume was calculated based on the following formula: TV (mm$^3$)={length (mm)×width (mm)$^2$}/2. FIG. 3 shows the results expressed as mean tumor size. FIG. 4 shows the results expressed as median tumor size.

Figure 5:
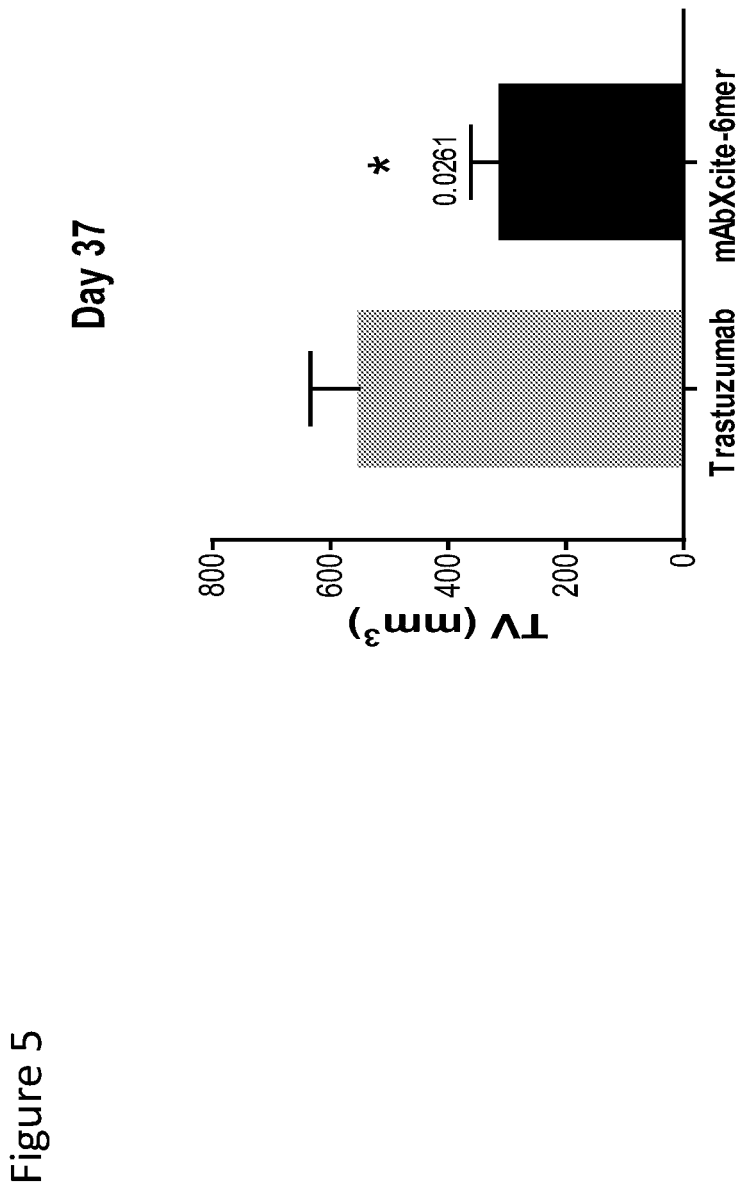
FIG. 5 depicts the mean tumor size of tumors in a nude mouse model implanted with the trastuzumab-resistant human cell line JIMT-1 on day 37 after treatment with trastuzumab and HER2-mAbXcite (6-mer).
Figure 6:
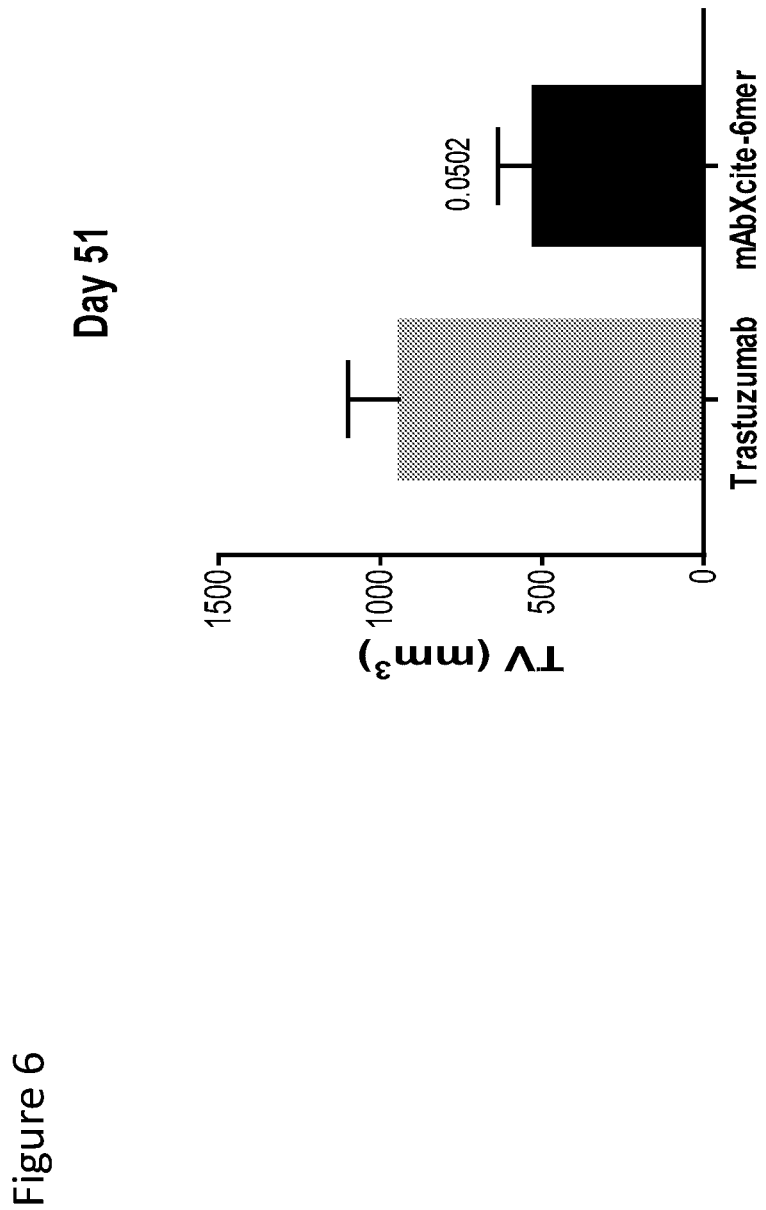
FIG. 6 depicts the mean tumor size of tumors in a nude mouse model implanted with the trastuzumab-resistant human cell line JIMT-1 on day 51 after treatment with trastuzumab and HER2-mAbXcite (6-mer).

HER2-mAbXcite (6-mer) was observed to be more effective than HER2-mAbXcite (5-mer) at reducing mean and median tumor size over the course of the study. As shown in FIGS. 5 and 6, HER2-mAbXcite (6-mer) was shown to be more effective than trastuzumab at 37 days and 51 days after treatment, respectively.

Example 6: Efficacy Study of HER2-mAbXcite (5-mer), (6-mer), and (7-mer) in Nude Mice In this Example, the efficacy of HER2-mAbXcite conjugates, prepared as described in Example 2, is studied in a nude mouse model implanted with the trastuzumab-resistant human cell line JIMT-1. The study is of HER2-mAbXcite in which the conjugation utilizes reductive amination (direct) chemistry, a 5-mer, 6-mer, or 7-mer oligomer, with a load of about 3 oligomers per antibody.

In this Example, 7-9 week old female nude mice are implanted with 2.5×10$^6$ JIMT-1 cells. Once tumors reach a size of about 150-180 mm$^3$, mice are randomly assigned into five study treatment groups. Prior to each antibody administration, all mice receive about 500 mg/kg (0.1 mL) intraperitoneal (IP) injection of pooled human antibodies (IVIG). Two hours post-IVIG administration, each group is administered one of the following treatments via an IP injection: PBS control; trastuzumab; HER2-mAbXcite (5-mer); HER2-mAbXcite (6-mer); or HER2-mAbXcite (7-mer).

Throughout the study, tumors are monitored twice weekly to determine tumor growth rates using external calipers. Tumors are measured prior to and following the first day of treatment. Body weights are also collected twice a week. Mice are euthanized when the maximum tumor volume reached 2000 mm$^3$. Mice are also euthanized if the tumor becomes ulcerated, if the tumor impedes ambulation, or there is a deterioration of body condition. Mice are also euthanized if they lost >15% of their original body weight. Analysis of the data collected form this experiment is performed. Tumor volume is calculated based on the following formula: TV (mm$^3$)={length (mm)×width (mm)$^2$}/2.

Example 7: Conjugation of β-1,6-Glucan Oligomers to Cetuximab

Strategy 1: Conjugation of β-1,6-Glucan Oligomers to Cetuximab Via NHS-DBCO The compound of Formula IV:

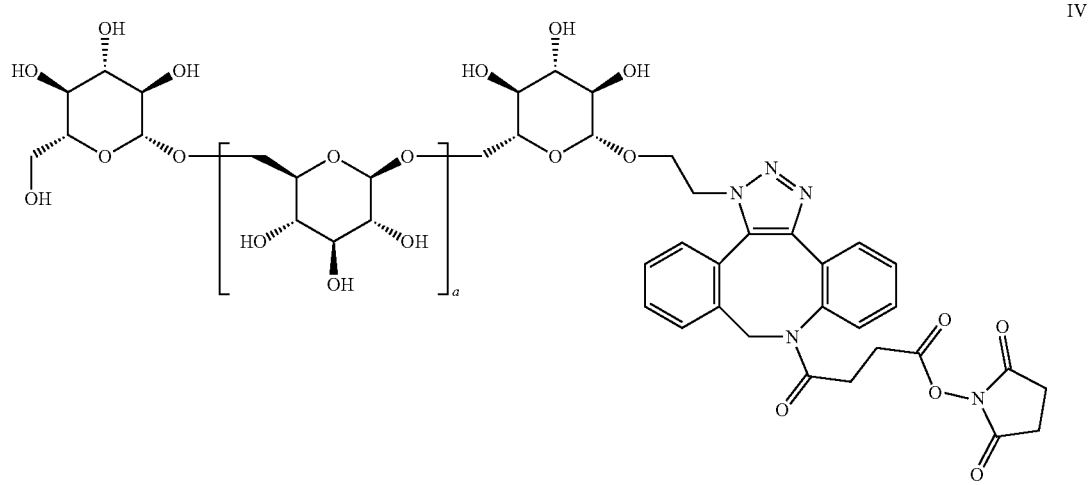

IV was conjugated to cetuximab (1 mg/mL in PBS, pH 7.2) by adding a 12× excess of the compound of the compound above to a reaction solution of PBS (pH 7.2 containing 3% DMSO) and allowing the reaction to stir for 30 minutes at 21° C. The reaction was quenched by adding a 100-fold ratio of lysine to NHS-DBCO-oligosaccharide. Then, the mixture was buffer-exchanged using PBS, pH 7.2 with a 50 kDa TFF membrane. Final cetuximab-oligosaccharide conjugate was adjusted to 1 mg/ml. Storage buffer is PBS, pH 7.2 at 4° C. Unconjugated oligosaccharide<0.1% of the concentration of oligosaccharide-cetuximab conjugate.

Strategy 2: Conjugation of β-1,6-Glucan Oligomers to Cetuximab Via Reductive Amination Alternatively, β-1,6-glucan oligomers were conjugated to cetuximab via reductive amination. The β-1,6-glucan oligomers were of the Formula V:

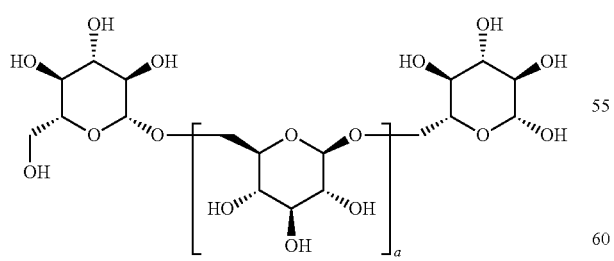

V wherein a is between 0 and 8. Cetuximab was buffer exchanged from storage solution into 0.2 M Na-Borate, pH 8.0 by TFF (50 kDa membrane) and making the concentration of Cetuximab (10-20 mg/ml). The β-1,6-oligomers were prepared as a 0.1M solution in endotoxin-free water.

To a solution of 0.3 M sodium cyanoborohydride in endotoxin-free water, and 10:90 PEG 2000:endotoxin-free water was added 0.1M sodium borate until the pH was about 8.0. Cetuximab was added until the concentration of cetuximab was 5 mg/mL. A 230× molar excess of the β-1,6-oligomer solution was added at 21° C. and the reaction was allowed to stir for 23 hours. The conjugation is stopped by adding a 100-fold molar ratio of lysine to oligosaccharide. Reaction quench solution is 1 M lysine in 0.1 M Na-Borate, pH 8.0.

Following conjugation, the reaction mixture was diluted 1 to 10 in PBS, pH 7.2 and buffer-exchanged using PBS, pH7.2 with a 50 kDa TFF membrane. Final Cetuximab-oligosaccharide conjugate was adjusted to 1 mg/ml. Storage buffer was PBS, pH 7.2 at 4° C. Unconjugated oligosaccharide<0.1% of the concentration of oligosaccharide-Cetuximab conjugate. PEG of average MW 2000<0.1% of the concentration of oligosaccharide-Cetuximab conjugate.

Methods of Analysis:
e) SEC separation
   d. Unmodified Cetuximab
   e. Oligosaccharide-Cetuximab conjugate
   f. SEC separation utilizes a TSKgel SuperSW3000, 4 mm, 250 Å silica, 4.6 mm ID×30 cm using as a mobile phase 0.4M NaClO$_4$, 0.05M NaH$_2$PO$_4$, pH 7.2 utilizing UV detection @ λ=280 nm
f) Load estimation by MALDI (AB Sciex MALDI/Q-TOF 4800 or comparable instrument). Note: HIC is not able to resolve individual loads due to hydrophilicity of oligosaccharides
   e. Utilize BSA (MW 66341) as the calibration standard (AB Sciex) in linear high mass positive mode
   f. Utilize sinapinic acid (Sigma) as matrix
   g. Use native Cetuximab as control
   h. Estimate load by subtracting average m/z of Cetuximab conjugate from that of unmodified Cetuximab and divide by mass of a unit load to determine load of conjugate. Data has an average standard deviation of 0.2-0.3 load units
g) Measure m/z of oligosaccharides by MALDI (AB Sciex 4800 or comparable instrument) using HABA (Sigma) as matrix.
h) Measure m/z of oligosaccharides by LC-MS using) (Bridge 3 mm×10 cm, 3.5 μm particle size (Waters)

using as mobile phase A: Water/0.1% Formic acid, B: 100% Acetonitrile/0.1% Formic acid. We use a ZQ (Waters) for mass spectrometry

Example 8: Conjugation of Cetuximab to Glucan does not Change Binding to EGFR Studies relating to whether conjugation affects cetuximab binding to EGFR were undertaken. These experiments were performed using cetuximab and rituximab as controls. Samples were detected using polyclonal human anti-β-1,6-glucan antibodies and mouse anti-human IgG-FITC. Also utilized were a blocking and staining buffer (PBS pH 7.2+ 2% BSA) and a washing buffer (PBS pH 7.2).

Figure 7:
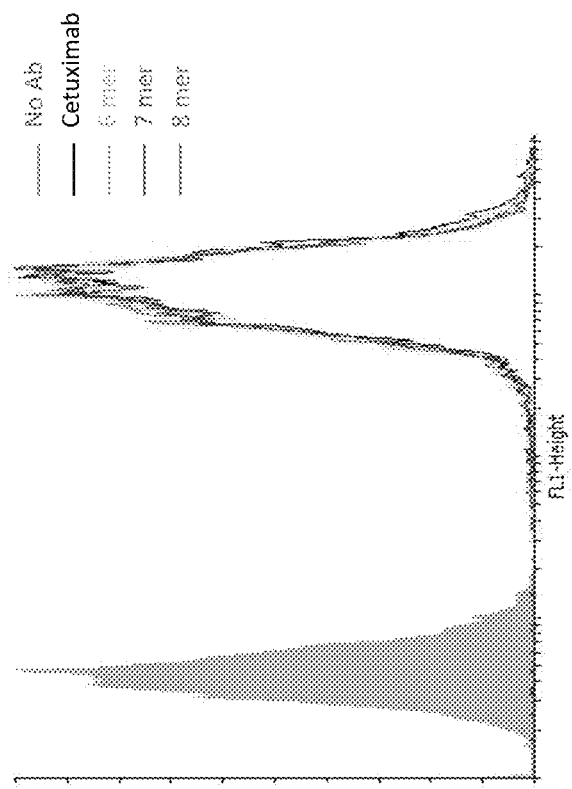
FIG. 7 is a graph showing that β-1,6-glucan conjugation does not affect cetuximab binding to EGF receptor.
Figure 8:
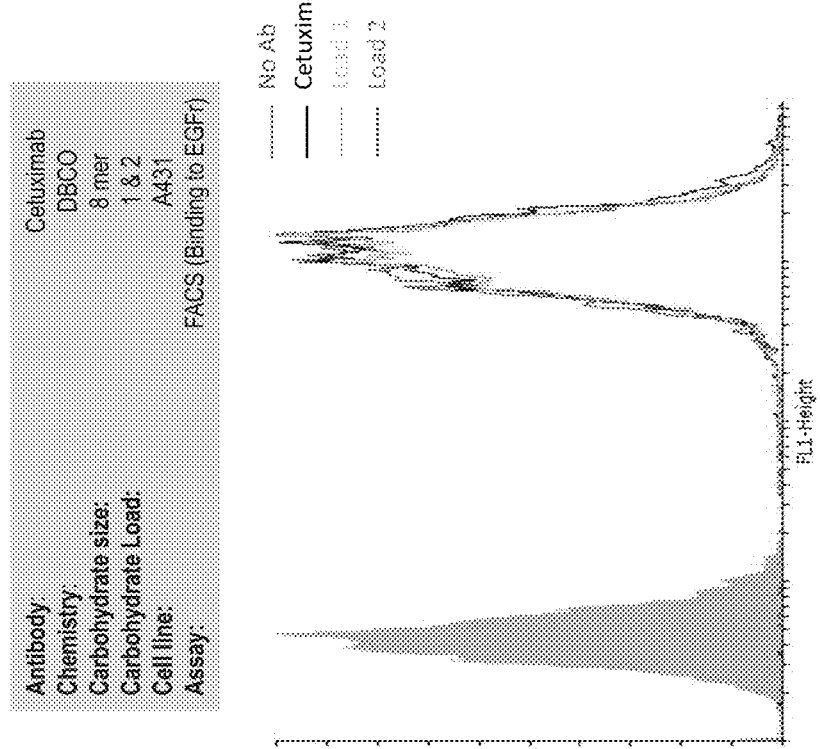
FIG. 8 is a graph showing that β-1,6-glucan conjugation does not affect cetuximab binding to EGF receptor.
Figure 9:
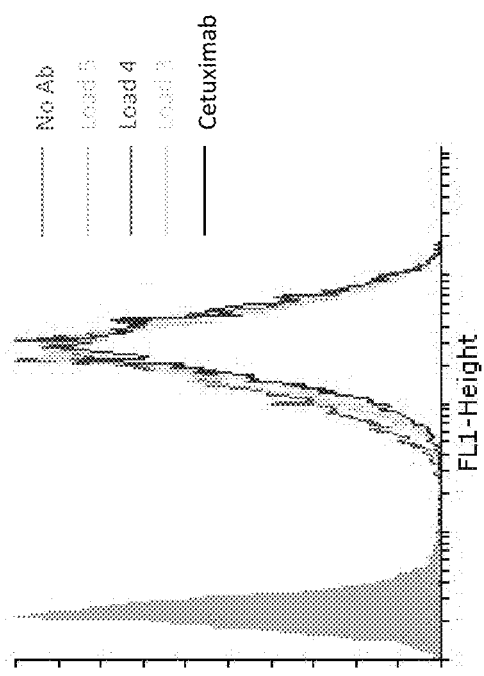
FIG. 9 is a graph showing that β-1,6-glucan conjugation does not affect cetuximab binding to EGF receptor.

$2 \times 10^5$ A431 (Epithelial cells, Epidermoid carcinoma) cells were blocked for 1 hour at room temperature in PBS-BSA, followed by an incubation with mAbXcite-cetuximab, cetuximab or rituximab (negative control) in staining buffer for 1 hour at RT. Cells were then washed (×3), and a detection antibody (mouse anti-human IgG-FITC) was added at 1:100 dilution. After three more washes, cells were spun down, re-suspended in PBS and analyzed by FACS using FACSCalibur (BD Biosciences). The cells were analyzed by FACS (FL1 for FITC).

β-1,6-glucan conjugation did not impair cetuximab binding to EGFR. mAbXcite-cetuximab binding to EGFR was assessed by FACS using rituximab as a non-specific control ("No Ab"), cetuximab and mAbXcite-cetuximab (6-mer, 7-mer, or 8-mer β-1,6-glucan oligomers), and for loads ranging from 1 to 5 β-1,6-glucan oligomers per antibody (FIGS. 7, 8, and 9). The results show that none of the conjugates or loads (in particular 1 or 2 load of 8-mer β-1,6-glucan oligomers or 3 to 5 load of 5-mer β-1,6-glucan oligomers) were impaired for binding to EGFR as compared to a cetuximab control. In this and other Examples discussed herein that involved direct conjugation, β-1,6-glucan oligomers were purified from pustulan. As described in Example 1, pustulan was treated to yield a ladder of β-1,6-glucans from which oligomers having the desired length were prepared, e.g., by fractionation and purification.

Example 9: Conjugation of Cetuximab to Glucan does not Change ADCC

We also studied whether conjugation with glucan affects cetuximab antibody-dependent cell-mediated cytotoxicity (ADCC). In this assay, the readout was luminescence signal from expression of firefly luciferase driven by an NFAT response element.

Figure 10:
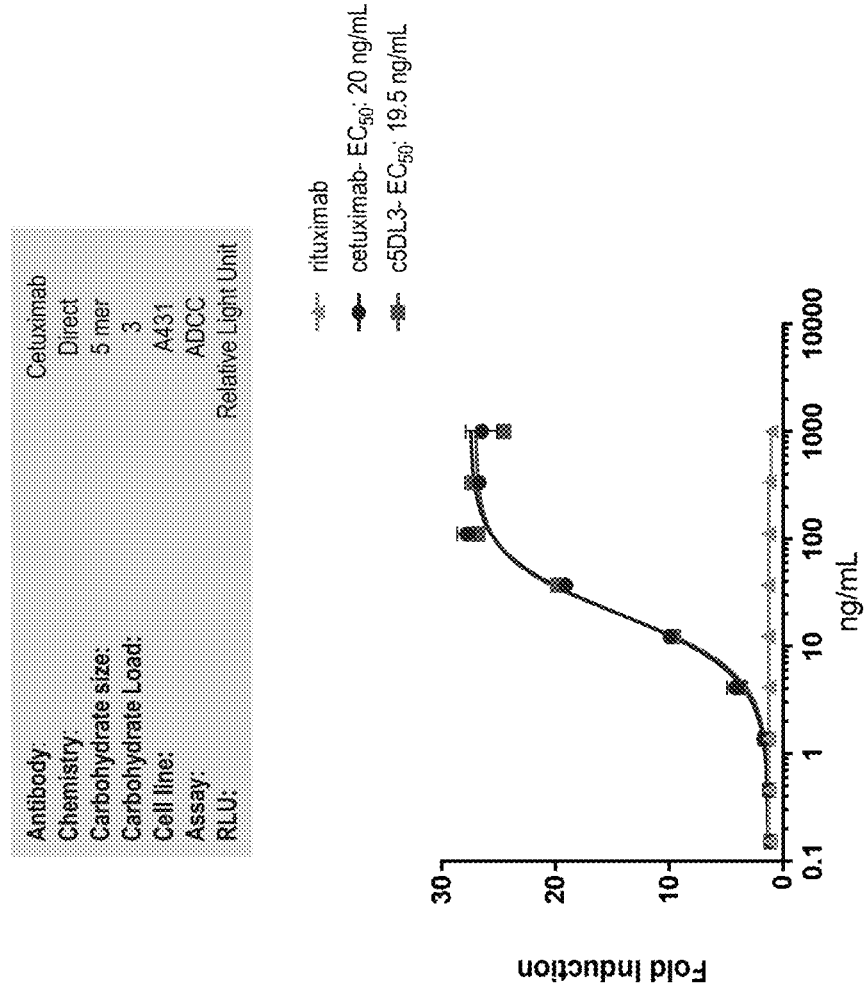
FIG. 10 is a graph showing that β-1,6-glucan conjugation does not affect cetuximab ADCC.
Figure 11:
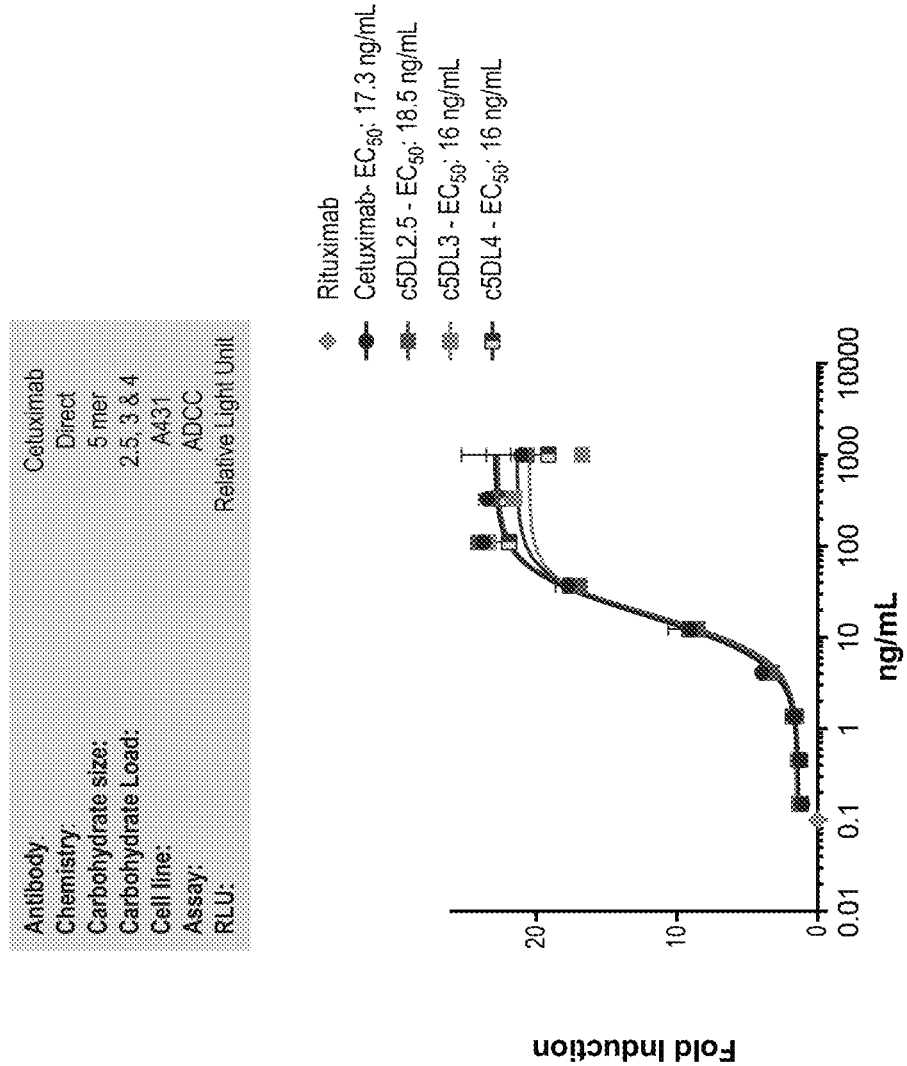
FIG. 11 is a graph showing that β-1,6-glucan conjugation does not affect cetuximab ADCC.

These experiments were also performed using cetuximab and rituximab as controls. ADCC Reporter Bioassay response to mAbXcite-cetuximab was studied using ADCC Bioassay Effector human and epithelial carcinoma cell line A431 as target cells. Experiments were performed using an ADCC Reporter Bioassay (Promega). Briefly, target cells (A431) were plated at the density of 5,000 cells per well in complete culture medium overnight. On the day of bioassay, antibodies (cetuximab, cetuximab-mAbXcite and rituximab as a control) were serially diluted. After carefully removing the cell medium, conjugate and antibodies, at various concentrations, were added to the cells, followed by addition of ADCC Bioassay Effector Cells. The E:T ratio was 15:1. After 6 hours of induction at 37° C., Bio-Glo™ Luciferase Assay Reagent was added and luminescence determined using an Envision luminometer (FIGS. 10 and 11).

The data were fitted to a 4PL curve using GraphPad Prism® software. The $EC_{50}$ of response using cetuximab/ A431 target cells was around 20 ng/ml. The results demonstrate that β-1,6-glucan conjugation did not change cetuximab ADCC (mAbXcite-cetuximab having a 2.5, 3, or 4 load of 5-mer oligomers) as compared to cetuximab control in an ADCC Reporter Bioassay using ADCC Bioassay Effector Cells and A431 Target Cells.

Example 10: β-1,6-Glucan Oligomer Length and Load with mAbXcite-Cetuximab Conjugates Two main potency assays were developed to assess antibody activity in vitro.

In the first such assay, antibody activity was assessed using an anti-β-1,6-glucan ELISA. In this ELISA, recombinant EGFR peptide was absorbed to an ELISA plate. Following the binding of cetuximab or mAbXcite-cetuximab the β-1,6-oligomer was detected by anti-β-1,6-glucan antibodies. The results of this assay correlate well with the average oligomer load as assayed by MALDI-TOF.

In the second such assay, antibody activity was assessed using anti-β-1,6-glucan FACS. In this assay the antibodies were added to live cells rather than to an EGFR peptide. The β-1,6-oligomer was detected by anti-β-1,6-glucan antibodies. The results of this assay also correlate well with the average oligomer load as assayed by MALDI-TOF.

ELISA Assay

The present studies were undertaken to evaluate the binding of anti-β-1,6-glucan antibodies to mAbXcite-cetuximab. In the present experiment, in order to assess the impact of 13-1,6-glucan oligomer length on mAbXcite-cetuximab activity, the oligomer load was 2 or 6, oligomer length was 4-mer to 9-mer, and the linkage of glucan to cetuximab was either DBCO or direct. Cetuximab was used as a control. Also utilized were a blocking and staining buffer (PBS pH 7.2+2% BSA) and a PBS-Tween buffer (PH 7.2, 0.05% Tween). ELISA was carried out using 1-Step™ Ultra TMB-ELISA (Pierce).

A recombinant EGFR peptide (rhEGFR/Fc Chimera peptide from R&D) was absorbed on an ELISA plate (MaxiSorp) overnight at 4° C. After 3 washes, non-specific binding sites were blocked for 1 hour at room temperature. Cetuximab or mAbXcite-cetuximab were then added and incubation performed on a plate shaker for 1 hour at room temperature, followed by 3 additional washes. To allow detection of the β-1,6-glucan oligomer, anti-β-1,6-glucan antibodies (polyclonal human anti-β-1,6-glucan antibodies) were added to the plate (3 ug/well) and incubated for 45 min at RT. The wells were washed 3 times and incubated with a 1:5000 dilution of anti-human IgG2 (Fc)-HRP antibody (mouse anti-human IgG2 (Fc)-HRP) for 45 min at RT. Extensive washes were performed (×5) and visualization was carried out with 100 uL of TMB substrate.

Figure 12:
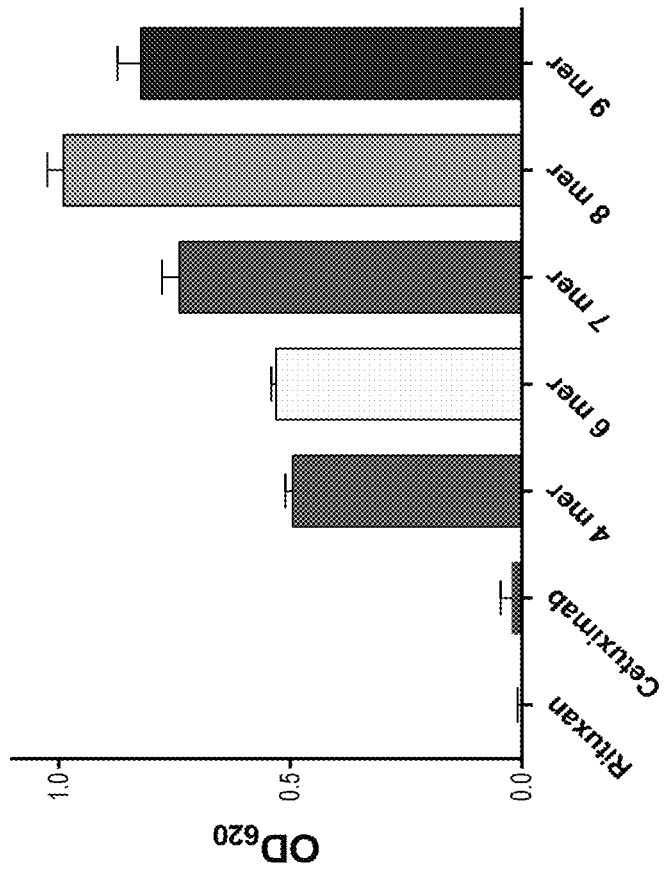
FIG. 12 is a chart showing an evaluation of anti-β-1,6-glucan IgG2 binding to a mAbXcite-cetuximab.
Figure 13:
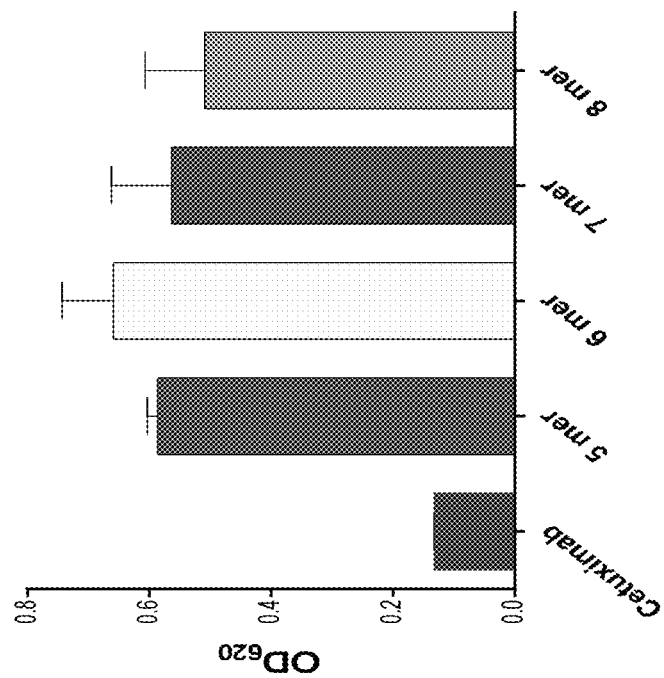
FIG. 13 is a chart showing an evaluation of anti-β-1,6-glucan IgG2 binding to a mAbXcite-cetuximab.

The plate was read immediately at OD620 nm—and reading occurred every minute for one hour. Data shown are the mean+/−standard deviation of 3 replicate wells (FIGS. 12 and 13). Binding to DBCO (A) and direct (B) conjugates was evaluated by ELISA. All mAbXcite-cetuximab conjugates tested were active in this assay. An increase in activity was observed with increases in oligomer length (up to 7-8-mer) where saturation was reached.

FACS Assay

The present studies were undertaken to identify whether all β-1,6-glucan oligomer lengths are recognized by anti-β-1,6-glucan antibodies when mAbXcite-cetuximab is bound to EGFR on live cells. Data was acquired using the conjugate mAbXcite-cetuximab with cetuximab as a control. In the present experiment, the β-1,6-glucan oligomer load was 1 to 6, the oligomer length ranges from 4-mer to 9-mer, and the linkage of glucan to cetuximab was DBCO.

Figure 14:
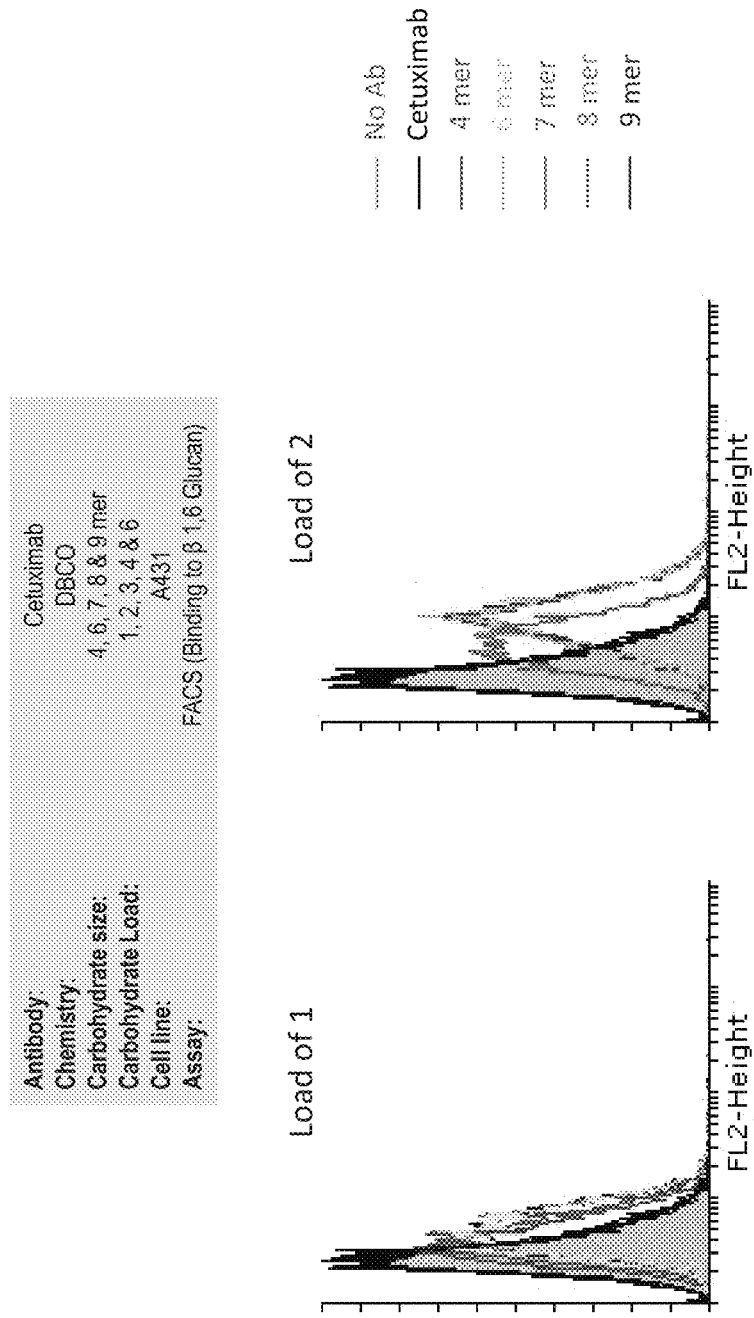
FIG. 14 is a set of two graphs showing an evaluation of anti-β-1,6-glucan IgG2 binding to a mAbXcite-cetuximab.
Figure 15:
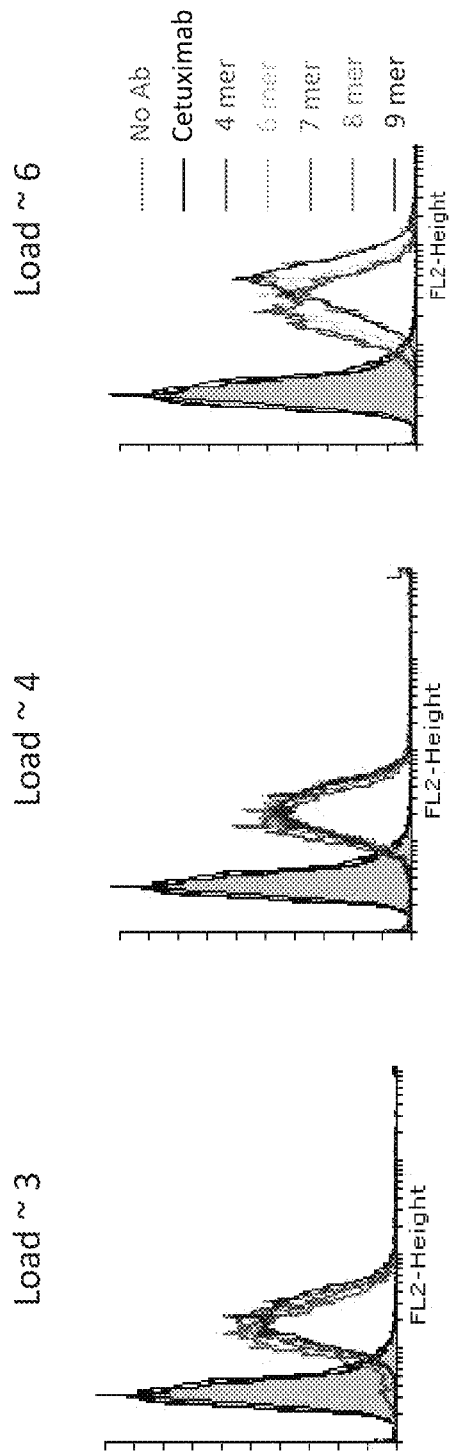
FIG. 15 is a set of three graphs showing an evaluation of anti-β-1,6-glucan IgG2 binding to a mAbXcite-cetuximab.

$2\times10^5$ A431 (Epithelial cells, Epidermoid carcinoma) cells were blocked for 1 hour at room temperature in PBS-BSA (PBS pH 7.2+2% BSA) followed by an incubation with mAbXcite-cetuximab and cetuximab or rituximab (negative control) in staining buffer for 1 hour at RT. After 3 washes (PBS pH 7.2), cells were incubated with purified anti-β-1,6-glucan antibodies (polyclonal human anti-β-1,6-glucan antibodies) for 1 hour at RT. Cell were then washed (×3), and a detection antibody (mouse anti-human IgG2-PE) was added at 1:100 dilution. After three more washes, cells were spun down, re-suspended in PBS and analyzed by FACS. The cells were analyzed by FACS (FL2) using FACSCalibur (BD Biosciences). mAbXcite-cetuximab binding was assessed by FACS using rituximab as a non-specific control ("No Ab"), cetuximab and mAbXcite-cetuximab (4-mer to 9-mer). Results are shown in FIGS. 14 and 15. All mAbXcite-cetuximab analyzed in this section for binding to EGFR on A431 cells and for deposition of anti-β-1,6-glucan antibody were functional in vitro.

Example 11: mAbXcite-Cetuximab Neutrophil Infiltration

The studies of this Example were undertaken to assess effect on pharmacodynamics (PD) in nude mice. Specifically, we evaluated the effect of conjugation with different oligomer lengths on neutrophil infiltration using 2 different approaches: live imaging using a luminol assay and histology using anti-neutrophil antibody.
Live Imaging Assay In this assay, luminol reacts with myeloperoxidase (which is a neutrophil-specific enzyme, and marker of activated neutrophils) and the resulting bioluminescence is detected by an IVIS imager. These experiments included mAbXcite-cetuximab with DBCO chemistry, 4-mer to 8-mer oligomer length, and a load of 2 oligomers per antibody. Cetuximab and pustulan (unconjugated β-1,6-glucan of undefined size) were used as a controls.

Mice were implanted SC with $2\times10^6$ A431 (Epithelial cells, Epidermoid carcinoma) cells. When the tumors reached a volume of 300-400 mm$^3$, which we have found to be ideal for imaging, mice were dosed with IVIG followed 2 hours later with mAbXcite-cetuximab, cetuximab, or vehicle control. 5 hours after treatment started, mice were anesthetized by isoflurane inhalation, administered with luminol (200 mg/kg IP) and imaged on IVIS 100 bioluminescence imaging system (Caliper Life sciences) within 7-15 minutes.

For quantification, total photon flux was calculated by the IVIS software and the background subtracted. All mice were imaged the day before treatment to assess the base line. After imaging, the tumors and blood were collected. The tumors were sent to histology (for correlation with imaging). Neutrophil activation was assessed by live imaging using PBS and cetuximab as negative controls, and pustulan (injected IT) as a positive control. A luminescent spot on the tumor indicates positives cells.

Figure 16:
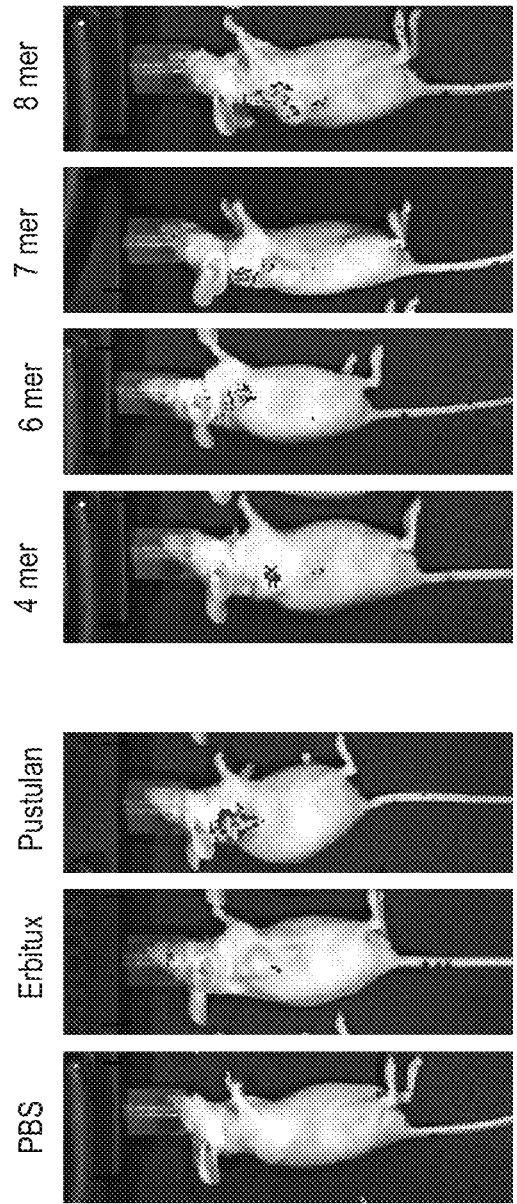
FIG. 16 is a set of seven images showing neutrophil activation by a mAbXcite-cetuximab. Neutrophil activation was observed with all β-1,6-glucan sizes.

All mAbXcite-cetuximab constructs tested (with 4-mer to 8-mer oligomers) led to neutrophil activation in this assay. See FIG. 16.
Histology Assay These studies were undertaken to assess neutrophil infiltration in tumor upon mAbXcite-cetuximab treatment. The glucan conjugation used direct chemistry. 5-mer oligomers were used with a load of 3 oligomers per antibody.

Figure 17:
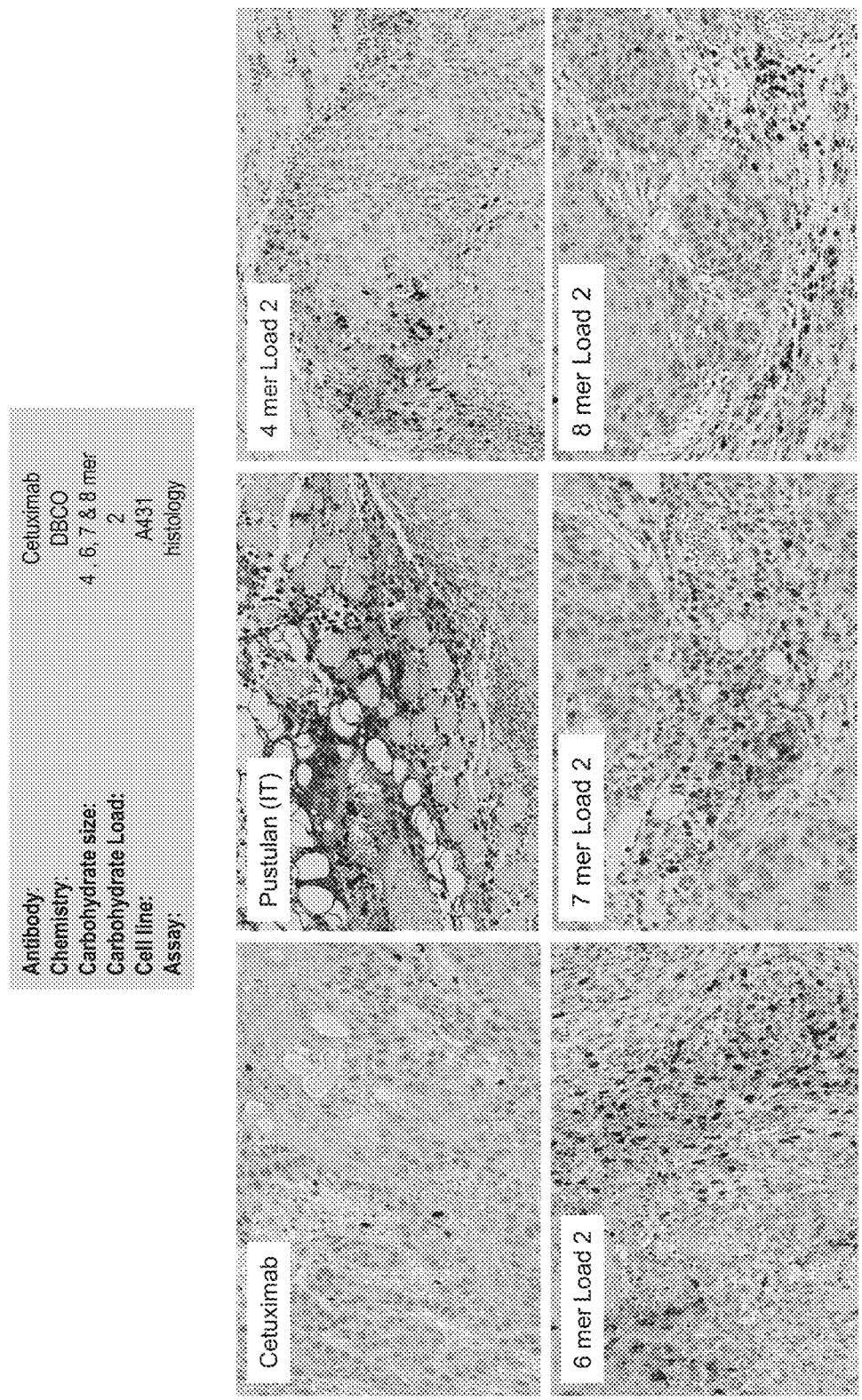
FIG. 17 is a set of six images showing neutrophil infiltration by a mAbXcite-cetuximab.

In this assay, mAbXcite-cetuximab was tested, with cetuximab and pustulan (unconjugated β-1,6-glucan of undefined size) as controls. Mice were implanted SC with $2\times10^6$ A431 (Epithelial cells, Epidermoid carcinoma) cells. When the tumors reached a volume of 300-400 mm$^3$, mice were dosed with IVIG followed 2 hours later with mAbXcite-cetuximab, cetuximab, or vehicle control. 5 hours after treatment started, tumor were collected and sent to histology for evaluating neutrophil infiltration. Tumors were fixed in formalin, embedded in paraffin blocks, and stained with a neutrophil-specific detection antibody (anti-neutrophil (Ly6G) antibody (Abcam No. 2557)). Neutrophil infiltration was assessed by immunohistochemistry (dark staining indicates positives cells). In correlation with the above live imaging study, neutrophil infiltration was also observed by histology upon treatment with all mAbXcite-cetuximab (with 4-mer to 8-mer oligomers) tested. See FIG. 17.

Example 12: Binding of mAbXcite-Cetuximab Having Various Oligomer Loads with Anti-β-1,6-Glucan Antibody or EGFR ELISA Assay ELISA was used to evaluate the binding of anti-β-1,6-glucan antibodies to mAbXcite-cetuximab, using cetuximab as a control. The present study utilized mAbXcite-cetuximab in which the conjugation utilized click chemistry (DBCO) using 6-mer oligomers at a load of 1-3 oligomers per antibody.

Figure 18:
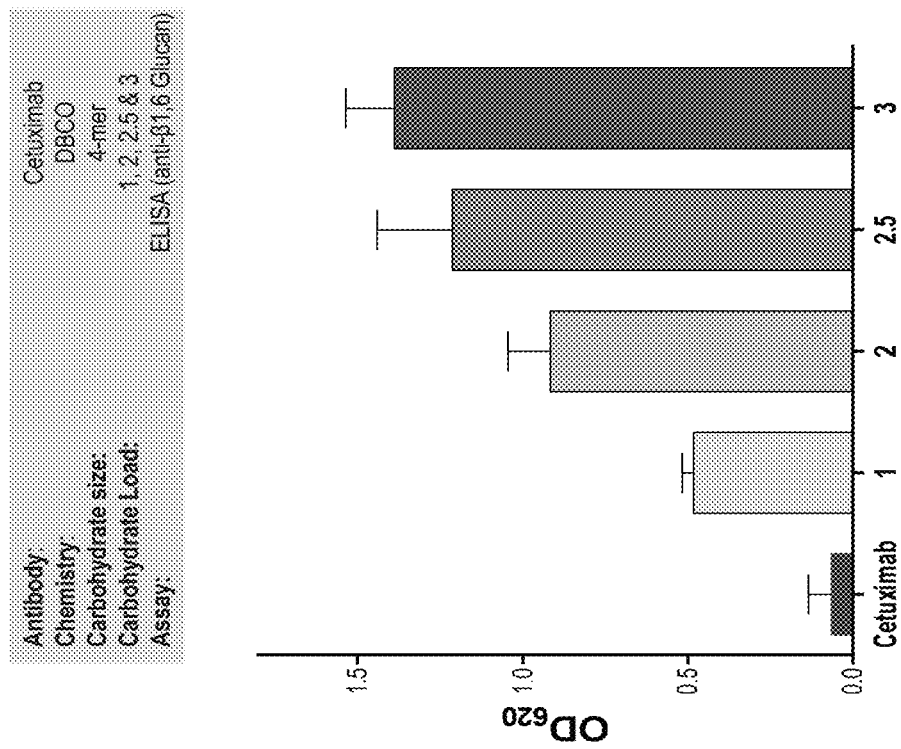
FIG. 18 is a chart showing an evaluation of anti-β-1,6-glucan IgG2 binding to a mAbXcite-cetuximab.
Figure 19:
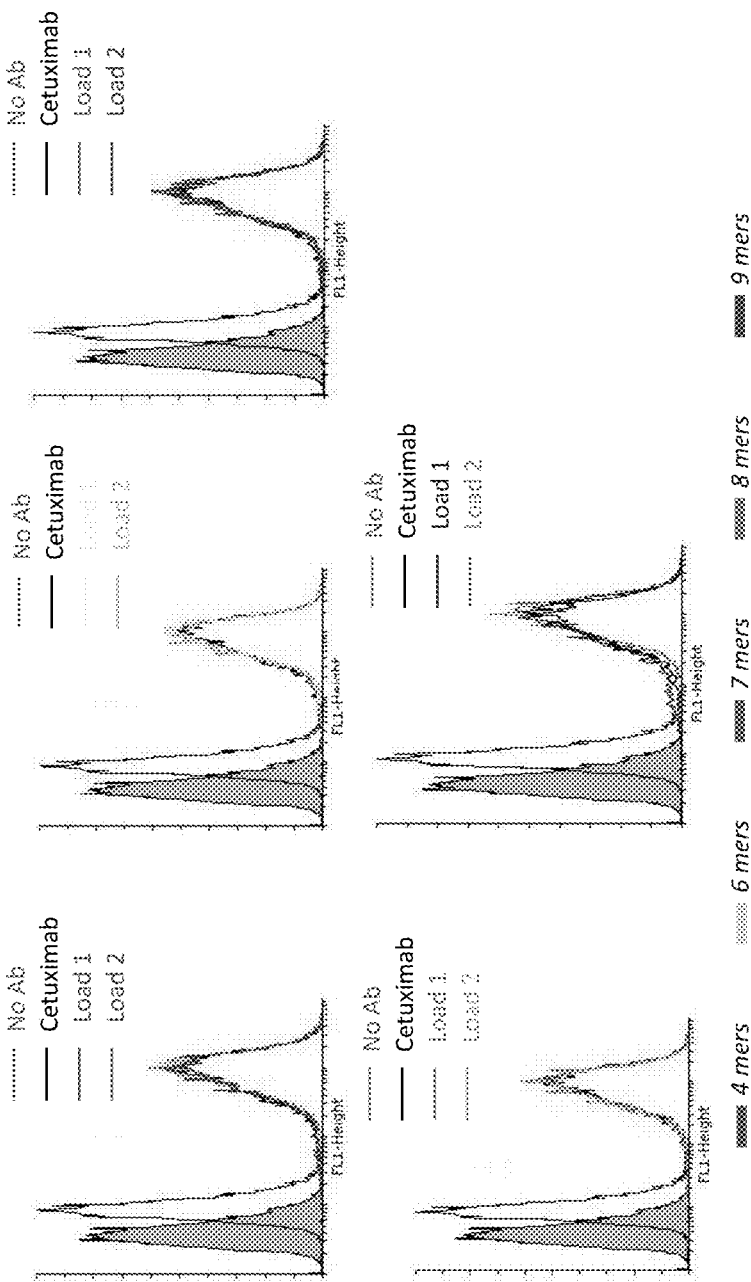
FIG. 19 is a set of five graphs showing that β-1,6-glucan conjugation does not affect cetuximab binding to EGFR.
Figure 20:
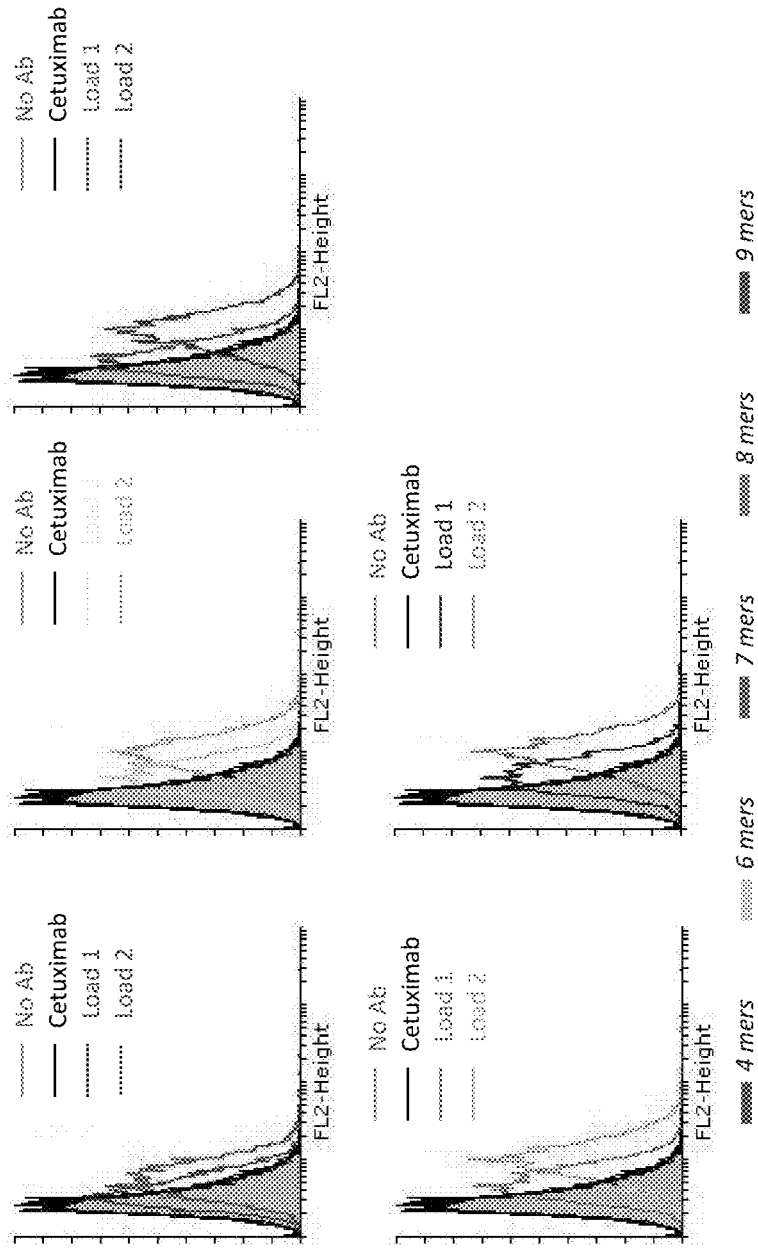
FIG. 20 is a set of five graphs showing an evaluation of anti-β-1,6-glucan IgG2 binding to a mAbXcite-cetuximab.
Figure 21:
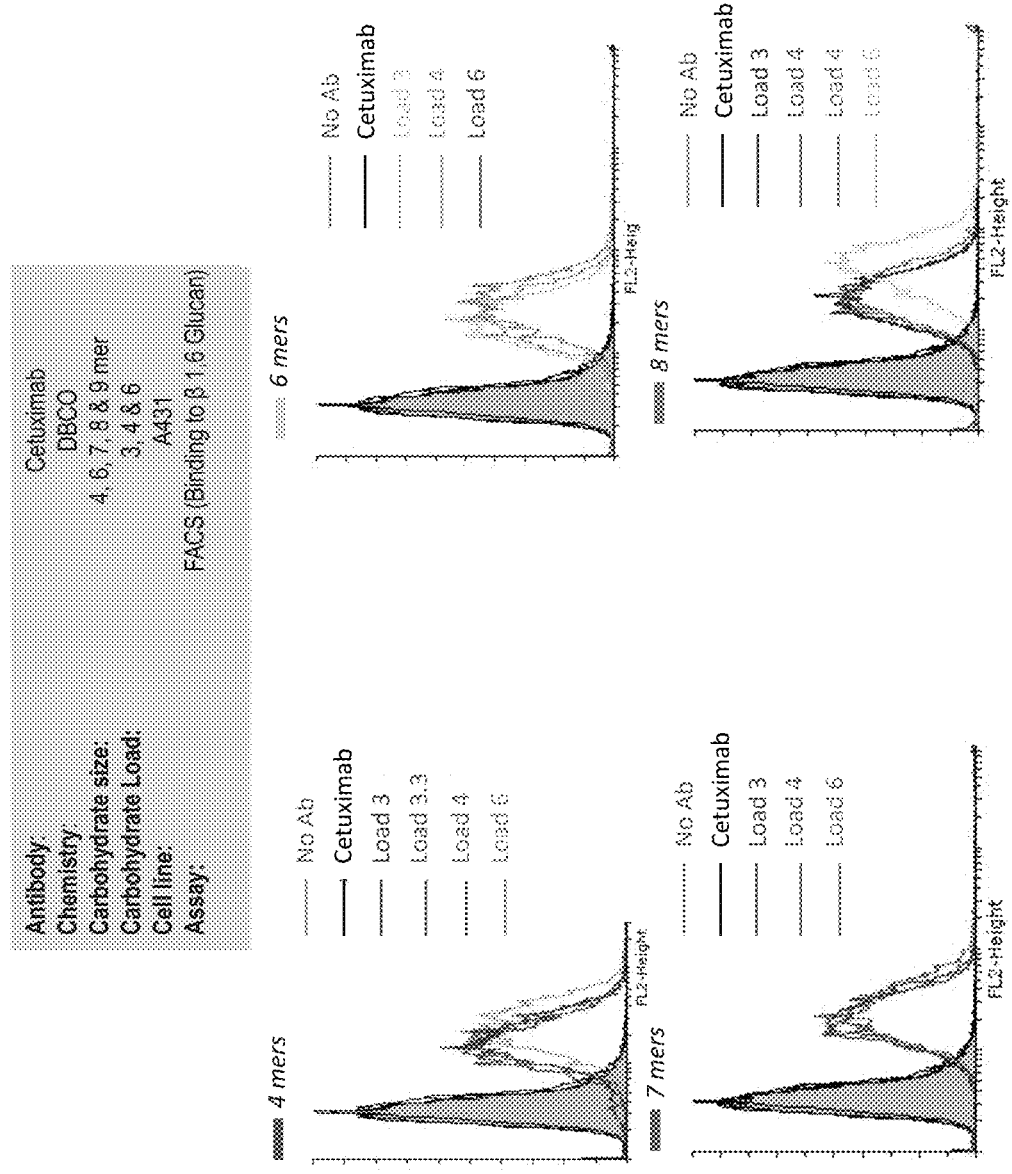
FIG. 21 is a set of four graphs showing an evaluation of anti-β-1,6-glucan IgG2 binding to a mAbXcite-cetuximab.

ELISA was carried out using 1-Step™ Ultra TMB-ELISA (Pierce). A human recombinant EGFR peptide (rhEGFR/Fc Chimera (peptide from R&D)) was absorbed on an ELISA plate (MaxiSorp) overnight at 4° C. Following a couple of washes, non-specific binding site were blocked in PBS-BSA buffer (blocking and staining buffer: PBS pH 7.2+2% BSA) for 1 hour at room temperature. Cetuximab or mAbXcite-cetuximab were then added and the plate placed in a plate shaker for 1 hour at room temperature, followed by 3 more washes. To allow detection of the β-1,6-glucan oligomers, anti-β-1,6-glucan antibodies (polyclonal human anti-β-1,6-glucan antibodies) were added to the plate (3 ug/well) and incubated for 45 min at RT. The well were washed 3 times (PBS-Tween buffer (PH 7.2, 0.05% Tween)) and incubated with a 1:5000 dilution of anti-human IgG2 (Fc)-HRP antibody (mouse anti-human IgG2 (Fc)-HRP) for 45 min at RT. Extensive washes were performed (×5) and visualization was carried out with 100 uL of TMB substrate. Plate was read immediately at OD 620 nm (for one hour, every minute). The results shown in FIG. 18 are the mean+/− standard deviation of 3 replicate wells. Binding was evaluated by ELISA. All mAbXcite-cetuximab, conjugated with various loads, were active in this assay, and the activity increased as the load increased.
FACS Assay FACS studies were undertaken to assess mAbXcite-cetuximab effect on EGFR binding and anti-β-1,6-glucan IgG2 deposition. The present study utilized mAbXcite-cetuximab in which the conjugation utilized click chemistry (DBCO) using 4-mer to 9-mer oligomers at a load of 1 to 6 oligomers per antibody. Cetuximab was used as a control. Detecting antibodies included polyclonal human anti-β-1,6-glucan antibodies and mouse anti-human IgG2-PE or mouse anti-human IgG-FITC.

$2\times10^5$ A431 (Epithelial cells, Epidermoid carcinoma) cells were blocked for 1 hour at room temperature in PBS-BSA followed by an incubation with mAbXcite-cetuximab, cetuximab or rituximab (negative control) in staining buffer (PBS pH 7.2+2% BSA) for 1 hour at RT. Cells were then washed (×3; PBS pH 7.2), and a detection antibody (mouse anti-human IgG2-PE or mouse anti-human IgG-FITC) was added at 1:100 dilution. After three more washes, cells were spun down, re-suspended in PBS and analyzed by FACS. The cells were analyzed by FACS (FL2 for PE or FL1 for FITC) in FACSCalibur (BD Biosciences).

mAbXcite-cetuximab binding was assessed by FACS using buffer as control ("No Ab"), cetuximab, and mAbXcite-cetuximab (loads ranging from 1 to 6). Conjugation of cetuximab with various loads of oligomer did not affect cetuximab binding to EGFR. In addition, deposition of anti-β-1,6-glucan antibody, was not impaired with either low or high load of oligomer. A minimum load of 1, was detected by anti-β-1,6-glucan IgG2 in these assays. See FIGS. 19, 20, 21, and 22.

Example 13: Binding of mAbXcite-Cetuximab Having Various Oligomer Loads with Anti-β-1,6-Glucan Antibody or EGFR ELISA Assay The present study utilized mAbXcite-cetuximab in which the conjugation was performed by direct reductive amination chemistry, a 5-mer oligomer, and a load of 1-5 oligomers per antibody. Anti-β-1,6-glucan binding to mAbXcite-cetuximab was assayed using ELISA. Cetuximab was used as a control. ELISA was carried out using 1-Step™ Ultra TMB-ELISA (Pierce). Detecting antibodies included polyclonal human anti-β-1,6-glucan antibodies and mouse anti-human IgG2 (Fc)-HRP.

Figure 23:
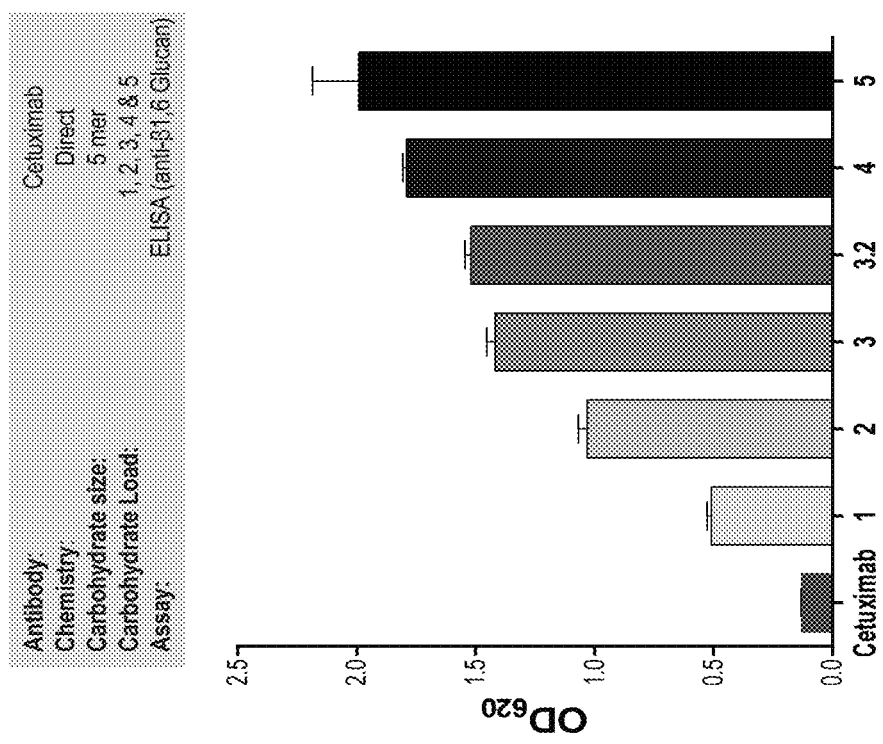
FIG. 23 is a chart showing an evaluation of anti-β-1,6-glucan IgG2 binding to a mAbXcite-cetuximab.
Figure 25:
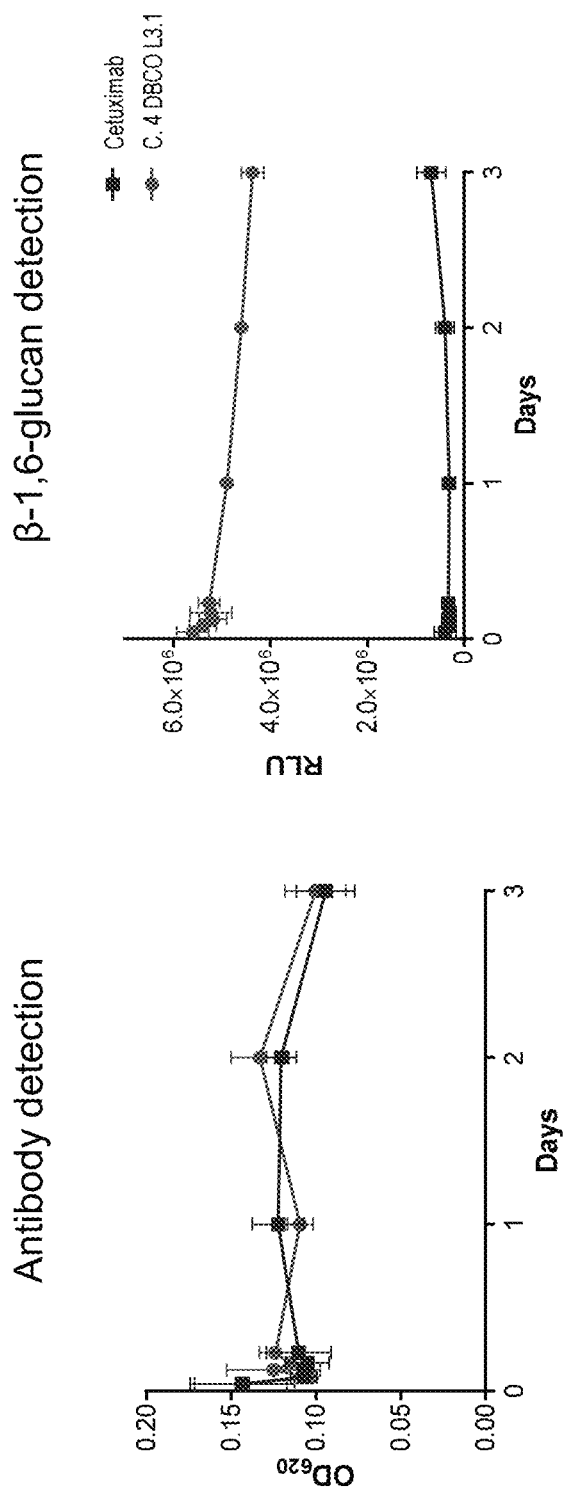
FIG. 25 is a set of two graphs showing that a mAbXcite-cetuximab is stable in human serum. The left graph of FIG. 19 shows antibody detection in human serum. The right graph of FIG. 19 shows β-1,6-glucan detection in human serum.
Figure 26:
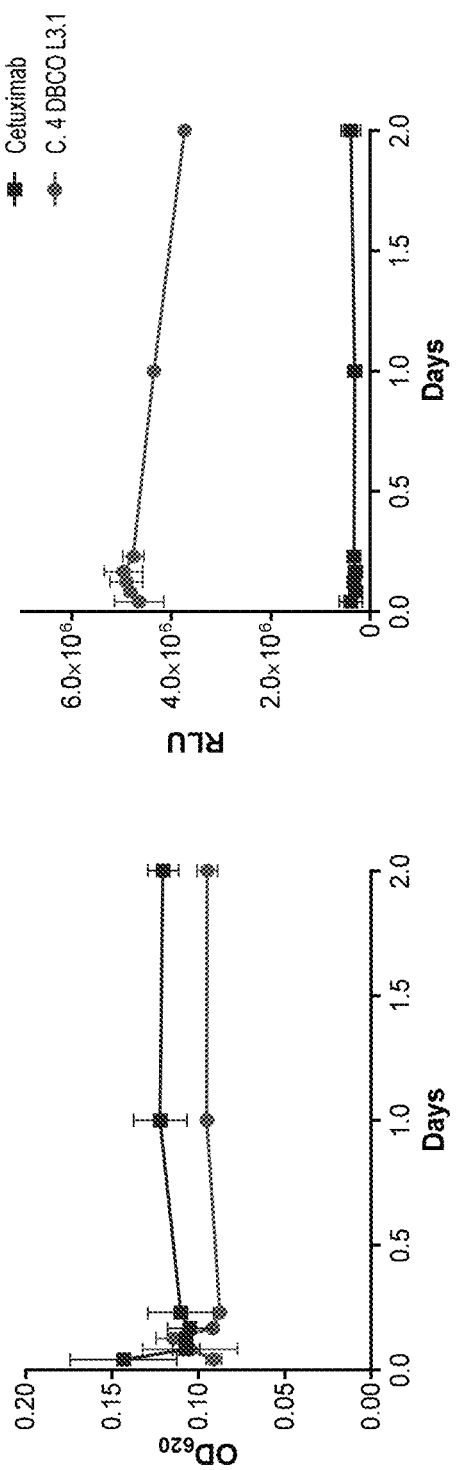
FIG. 26 is a is a set of two graphs showing that a mAbXcite-cetuximab is stable in mouse serum. The left graph of FIG. 20 shows antibody detection in mouse serum. The right graph of FIG. 20 shows β-1,6-glucan detection in mouse serum.
Figure 29:
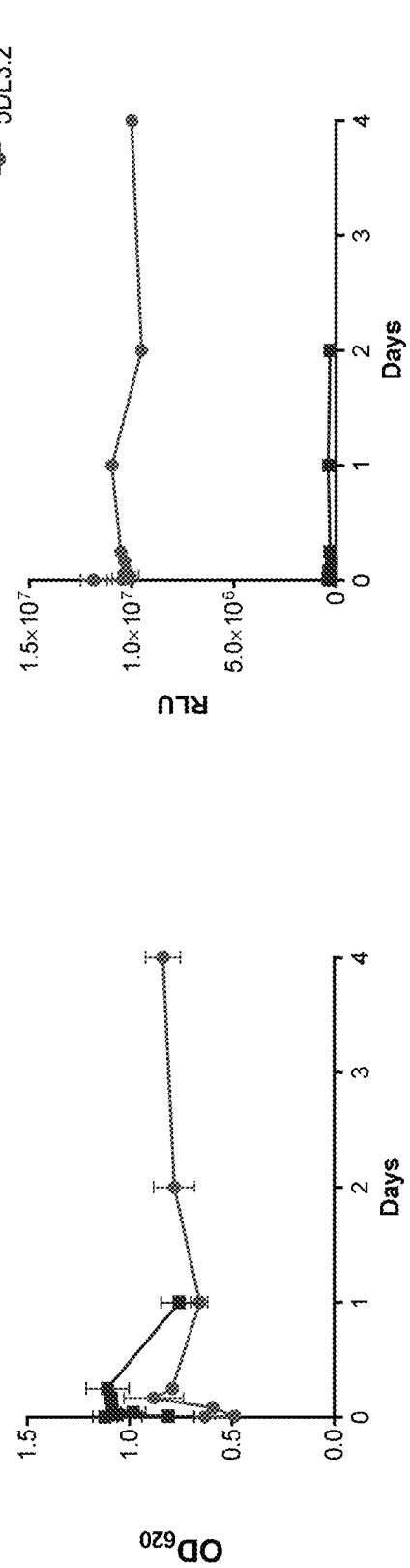
FIG. 29 is a set of two graphs showing that a mAbXcite-cetuximab is stable in mouse serum. The left graph of FIG. 23 shows antibody detection in mouse serum. The right graph of FIG. 23 shows β-1,6-glucan detection in mouse serum.

A human recombinant EGFR peptide (rhEGFR/Fc Chimera (peptide from R&D)) was absorbed on an ELISA plate (MaxiSorp) overnight at 4° C. Following a couple of washes, non-specific binding sites were blocked in PBS-BSA buffer (PBS pH 7.2+2% BSA) for 1 hour at room temperature. Cetuximab or mAbXcite-cetuximab were then added and the plate placed in a plate shaker for 1 hour at room temperature, followed by 3 more washes (pH 7.2, 0.05% Tween). To allow detection of the β-1,6-oligomers, anti-β-1,6-glucan antibodies were added to the plate (3 ug/well) and incubated for 45 min at RT. The wells were washed 3 times and incubated with a 1:5000 dilution of anti-human IgG2 (Fc)-HRP antibody for 45 min at RT. Extensive washes were performed (×5) and visualization was carried out with 100 uL of TMB substrate. Plate was read immediately at OD 620 nm (one hour, every minute). Data shown are the mean+/−standard deviation of 3 replicate wells. Similarly as what was observed with click chemistry (DBCO), all mAbXcite-cetuximab conjugates made using reductive amination were active in this assay, and activity increased as the oligomer load increased. See FIGS. 23 and 24.

FACS Assay

These studies were undertaken to assess mAbXcite-cetuximab effect on EGFR binding and anti-β-1,6-glucan IgG2 deposition. The present study utilized mAbXcite-cetuximab in which the conjugation was performed by direct reductive amination chemistry, a 5-mer oligomer, and a load of 3-5 oligomers per antibody. Cetuximab was used as a control. Detecting antibodies included polyclonal human anti-β-1,6-glucan antibodies and mouse anti-human IgG2-PE or mouse anti-human IgG-FITC.

$4 \times 10^5$ A431 (Epithelial cells, Epidermoid carcinoma) cells were blocked for 1 hour at room temperature in PBS-BSA followed by an incubation with mAbXcite-cetuximab, cetuximab or rituximab (negative control) in staining buffer (PBS pH 7.2+2% BSA) for 1 hour at RT. Cell were then washed (×3; PBS pH 7.2), resuspended in staining buffer and half of the cells were analyzed for binding to EGFR and half for deposition of the anti-β-1,6-glucan antibody. A detection antibody (mouse anti-human IgG2-PE or mouse anti-human IgG-FITC) was added to the cells at 1:100 dilution and incubated for 45 minutes at RT. After three more washes, cells were spin down re-suspend in PBS and analyzed by FACS using FACSCalibur (BD Biosciences). mAbXcite-cetuximab binding was assessed by FACS (FL1 for FITC; FL2 for PE) using buffer control ("No Ab"), cetuximab, and mAbXcite-cetuximab (various loads) (FIG. 24). The results demonstrate that conjugation of cetuximab with the various oligomer loads does not affect cetuximab binding to EGFR. In addition, the binding of anti-β-1,6-glucan IgG2 antibodies, was not impaired with either low or high load of oligomer. The detection was similar for loads of 4 and 5, and slightly weaker for conjugates with a load of 3.

Example 14: mAbXcite-Cetuximab Stability in Serum

In the present example, stability analysis was performed on mAbXcite-cetuximab, using cetuximab as a control. The present study utilized mAbXcite-cetuximab in which the conjugation utilized DBCO or direct chemistry, a 4-mer to 5-mer oligomer, and a load of 3 oligomers per antibody. ELISA was carried out using 1-Step™ Ultra TMB-ELISA (Pierce) detection kit. Detecting antibodies included polyclonal human anti-β-1,6-glucan antibodies, mouse anti-human IgG2 (Fc)-HRP, and goat anti-human IgG (H&L)-HRP. Also utilized were a blocking and staining buffer (casein in PBS (Pierce)) and a PBS-Tween buffer (PH 7.2, 0.05% Tween).

mAbXcite-cetuximab, or cetuximab control, were added to serum (human or mouse serum) at concentrations equivalent to a dosage of 5 mg/kg in mice (50 µg/mL) and incubated for 1, 2, 3, 4, 5, 14, 48, 72 or 96 hours at 37° C. The antibody (IgG concentration) and the presence of β-1, 6-glucan oligomers were then determined by ELISA.

Sera were incubated in 96-well plates coated with recombinant EGFR (hEGFR peptide from Sino Biological). Dilution was 1:500 for detection of the antibody and 1:10 in order to detect β-1,6-glucan conjugated to cetuximab. Total human antibody binding (cetuximab or mAbXcite-cetuximab) was detected using HRP-conjugated anti-human IgG (H&L). The color was developed by TMB Substrate Kit (Pierce).

To specifically detect the β-1,6-glucan oligomers conjugated to cetuximab, affinity purified human anti-β-1,6-glucan antibodies (polyclonal human anti-β-1,6-glucan antibodies) were used (3 µg per well for 1 hour at RT). The detection was carried out with anti-human IgG2 (Fc)-HRP antibody (mouse anti-human IgG2 (Fc)-HRP). SuperSignal ELISA Substrate (SuperSignal ELISA Pico Chemiluminescent Substrate (Pierce)) was added and luminescence determined using an Envision luminometer. OD at 620 nm was read for one hour, every minute. Results from 2 replicates were averaged and standard deviation determined. The antibody level was plotted as function of time for cetuximab or mAbXcite-cetuximab. The half-life of each antibody in serum was determined as the period of time it takes to decrease by half. Cetuximab or mAbXcite-cetuximab were stable in serum at 37° C. for up to 4 days. The β-1,6-glucan oligomers were also detected, suggesting that β-1,6-glucan oligomers are stable when conjugated to the antibody. See FIGS. 25 to 29.

Example 15: Evaluation of PK In Vitro and in Mice

The neutrophil recognition of β-1,6-glucan is opsonic, requiring endogenous IgGs, present in all human sera tested, as well as proteins of the complement system. The small size of the β-1,6-glucan oligomers that are linked to cetuximab is too short for unconjugated versions to bind these endogenous IgGs and complement proteins in circulation. They are however readily recognize by the endogenous antibodies when conjugated to cetuximab due to avidity either in plate assays or with high density of EGFR on cells. The following studies were performed to investigate the effect of oligomer length and load on PK.
Pharmacokinetics (PK) In Vitro This study utilized mAbXcite-cetuximab in which 5-mer to 8-mer oligomers were conjugated using direct chemistry at a load of 1, 2 and 2.5 oligomers per antibody. Cetuximab was used as a control. Detecting antibodies included polyclonal human anti-β-1,6-glucan antibodies and mouse anti-human IgG2 (Fc)-HRP. ELISA was carried out using 1-Step™ Ultra TMB-ELISA (Pierce).

A human recombinant EGFR peptide (rhEGFR/Fc Chimera (peptide from R&D)) was absorbed on an ELISA plate (MaxiSorp) overnight at 4° C. Following a couple of washes, non-specific binding sites were blocked in PBS-BSA buffer (PBS pH 7.2+2% BSA) for 1 hour at room temperature. Cetuximab or mAbXcite-cetuximab were then added and the plate placed in a plate shaker for 1 hour at room temperature, followed by 3 more washes (PBS-Tween buffer (PH 7.2, 0.05% Tween)). To allow detection of β-1,6-oligomers, anti-β-1,6-glucan antibodies were added to the plate (3 ug/well) and incubated for 45 min at RT. The wells were washed 3 times and incubated with a 1:5000 dilution of anti-human IgG2 (Fc)-HRP antibody for 45 min at RT. Extensive washes were performed (×5) and visualization was carried out with 100 uL of TMB substrate. Plate was read immediately at OD620 nm.

Figure 30:
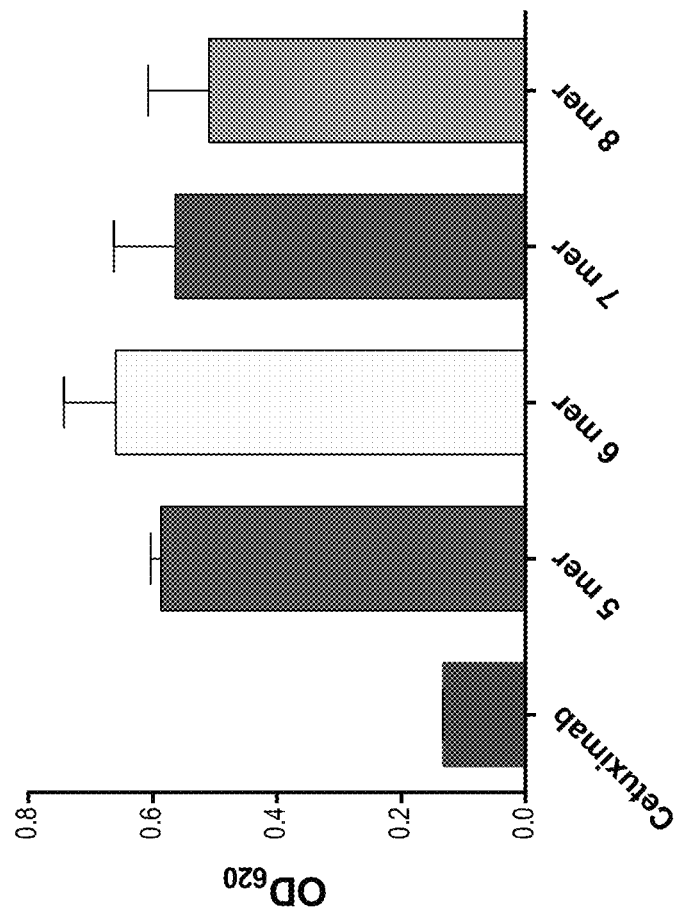
FIG. 30 is a chart showing an evaluation of in vitro activity (anti-β-1,6-glucan IgG2 binding) of a mAbXcite-cetuximab tested in pharmacokinetic study.
Figure 31:
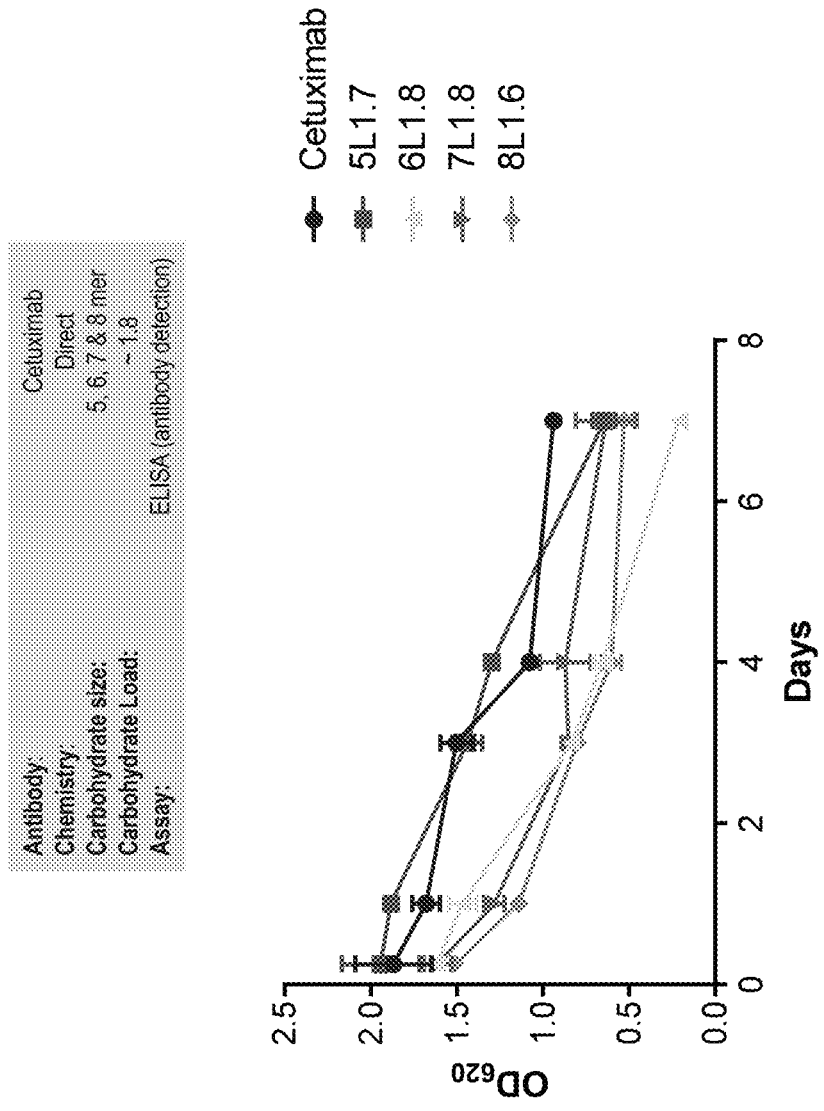
FIG. 31 is a graph showing pharmacokinetic antibody stability of a mAbXcite-cetuximab in the absence of tumor.

OD was read at 620 nm for one hour, every minute. Data shown are the mean+/−standard deviation of 3 replicate wells. All direct conjugates tested were active in this in vitro assay and therefore tested for their PK properties. See FIG. 30; this graph is representative of what was also observed with a load of 1 and 2.5 oligomers per antibody.
Pharmacokinetics (PK) of mAbXcite-Cetuximab in Tumor-Free Nude Mice The present study utilized mAbXcite-cetuximab in which 5-mer to 8-mer oligomers were conjugated using direct chemistry at different loads of oligomer per antibody. Cetuximab was used as a control. The experiment further utilized a blocking and staining buffer: Casein in PBS (Pierce) and a PBS-Tween buffer (PH 7.2, 0.05% Tween). Elisa was carried out using 1-Step™ Ultra TMB-ELISA (Pierce) with SuperSignal ELISA Pico Chemiluminescent Substrate (Pierce).

PK of mAbXcite-cetuximab conjugates was determined in tumor-free nude mice in the presence of anti-β-1,6-glucan antibodies (IVIG), as they might affect the half-life of the conjugates. In these experiments, 7 week old female nude mice were injected IP with anti-β-1,6-glucan antibodies (polyclonal human anti-β-1,6-glucan antibodies) and, 2 hours later, with 5 mg/kg of mAbXcite-cetuximab or of cetuximab (three mice per group). To assess circulating levels of total and conjugated antibody, blood was collected by terminal bleeding at various time points post injection (from 1 hour to 96 hours). Plasma was obtained using anticoagulant-treated tubes (EDTA-treated rubes) and stored at −70° C. The antibody (IgG concentration) and the presence of the β-1,6-glucan oligomers were then determined by ELISA.

Plasma or mAbXcite-cetuximab control (as a standard) were incubated in 96-well plates coated with recombinant EGFR (hEGFR (peptide from SinoBiological)). Dilutions were 1:500 for detection of the antibody and 1:10 in order to detect β-1,6-glucan oligomers conjugated to cetuximab.

Total human antibody binding (cetuximab or mAbXcite-cetuximab) were detected using HRP-conjugated anti-human IgG (goat anti-human IgG (H&L)-HRP). To specifically detect the β-1,6-glucan oligomers linked to cetuximab, affinity purified human anti-β-1,6-glucan antibodies were used (3 µg per well for 1 hour at RT). The detection was carried out with anti-human IgG2 (Fc)-HRP antibody (mouse anti-human IgG2 (Fc)-HRP). The color was developed by TMB Substrate Kit (Pierce). OD was read at 620 nm for one hour, every minute. Results from three mice in each time point were averaged and standard error determined. See FIGS. 31 to 35. The antibody level was plotted as function of time for cetuximab or mAbXcite-cetuximab. The half-life of each antibody was determined as the period of time it takes to decrease by half. The half-life of mAbXcite-cetuximab—conjugated with a 5-mer oligomer—was similar to the half-life of cetuximab. However, mAbXcite-cetuximab clearance increased when longer oligomers were conjugated to the antibody, even at a low load level. This result suggests that mAbXcite-cetuximab conjugates with shorter oligomers may have certain advantages in vivo. Longer oligomers (5 to 8-mer) were also detected and were stable when conjugated to cetuximab.

Example 16: Pharmacokinetics (PK) of mAbXcite-Cetuximab with Various Loads in Tumor-Free Mice This study utilized mAbXcite-cetuximab in which 5-mer to 8-mer oligomers were conjugated using direct chemistry at different loads of oligomer per antibody. Cetuximab was used as a control. The present experiment included a blocking and staining buffer: Casein in PBS (Pierce) and a PBS-Tween buffer (PH 7.2, 0.05% Tween).

In this Example, 7 week old female nude mice were injected IP with anti-β-1,6-glucan antibodies (polyclonal human anti-β-1,6-glucan antibodies) and, 2 hours later, with 5 mg/kg of mAbXcite-cetuximab or cetuximab (three mice per group). To assess circulating levels of total and conjugated antibody, blood was collected by terminal bleeding at various time points post injection (from 1 hour to 96 hours). Plasma was obtained using anticoagulant-treated tubes (EDTA-treated rubes) and stored at −70° C. The antibody (IgG concentration) and the presence of the β-1,6-glucan oligomers were then determined by ELISA (1-Step™ Ultra TMB-ELISA (Pierce)).

Plasma or mAbXcite-cetuximab control (as a standard) were incubated in 96-well plates coated with recombinant EGFR (hEGFR (peptide from SinoBiological)). Dilutions were 1:500 for detection of the antibody and 1:10 in order to detect β-1,6-glucan conjugated to cetuximab.

Total human antibody binding (cetuximab or mAbXcite-cetuximab) were detected using HRP-conjugated anti-human IgG (goat anti-human IgG (H&L)-HRP). To specifically detect the β-1,6-glucan oligomers linked to cetuximab, affinity purified human anti-β-1,6-glucan antibodies were used (3 µg per well for 1 hour at RT). The detection was carried out with anti-human IgG2 (Fc)-HRP antibody (mouse anti-human IgG2 (Fc)-HRP). The color was developed by TMB Substrate Kit (SuperSignal ELISA Pico Chemiluminescent Substrate (Pierce)). OD was read at 620 nm for one hour, every minute. Results from three mice in each time point were averaged and standard error determined. The antibody level was plotted as function of time for cetuximab or mAbXcite-cetuximab. The half-life of each antibody was determined as the period of time it takes to decrease by half. See FIGS. 36 to 41. The PK profile of mAbXcite-cetuximab conjugated with a 5-mer at different loads was similar to the PK profile of cetuximab. mAbXcite-cetuximab clearance was however increased when longer oligomers were conjugated to the antibody, even at low load level. β-1,6-glucan (5 to 8-mer) were stable when conjugated cetuximab. mAbXcite-cetuximab conjugates were stable with load of around 3. Oligomers were also stable with a load of around 3.

Example 17: Pharmacokinetics (PK) of mAbXcite-Cetuximab in Tumor Bearing Mice

A large body of work has shown that the plasma clearance of many therapeutic monoclonal antibodies is dramatically enhanced in tumor bearing compared to tumor-free mice, suggesting the presence of a target mediated elimination pathway. In order to assess target mediated degradation of conjugates of the present invention, we also evaluated mAbXcite-cetuximab plasma disposition in mice bearing HCT-116 human colorectal cancer xenografts, which express EGFR.

The present study utilized mAbXcite-cetuximab in which 5-mer oligomers were conjugated using direct chemistry at a load of 3 and 4 oligomers per antibody. Cetuximab was used as a control. This study further included a blocking and staining buffer: Casein in PBS (Pierce) and a PBS-Tween buffer (PH 7.2, 0.05% Tween). ELISA was carried out using a 1-Step™ Ultra TMB-ELISA (Pierce) detection kit with SuperSignal ELISA Pico Chemiluminescent Substrate (Pierce). HCT-116 (KRAS mutant colorectal cancer) cells were used.

In this experiment, 7 week old female nude mice were implanted SC with $2.5 \times 10^6$ HCT-116 cells. When tumor reached a volume superior to 120 mm³, mice were randomly divided into groups (3 mice/group) and treated with IVIG (as a source for polyclonal human anti-β-1,6-glucan antibodies) followed 2 hours later by vehicle control, cetuximab or mAbXcite-cetuximab (5 mg/kg, IP). mAbXcite-cetuximab plasma pharmacokinetics were studied at various time points (1 to 96 hours) following treatment.

Plasma or mAbXcite-cetuximab control (as a standard) were incubated in 96-well plates coated with recombinant EGFR (hEGFR (peptide from SinoBiological)). Dilutions were 1:500 for detection of the antibody and 1:10 in order to detect β-1,6-glucan oligomers conjugated to cetuximab. Total human antibody binding (cetuximab or mAbXcite-cetuximab) were detected using HRP-conjugated anti-human IgG (Goat anti-human IgG (H&L)-HRP). To specifically detect β-1,6-glucan oligomers linked to cetuximab, affinity purified human anti-β-1,6-glucan antibodies were used (3 µg per well for 1 hour at RT). The detection was carried out with anti-human IgG2 (Fc)-HRP antibody (mouse anti-human IgG2 (Fc)-HRP). The color was developed by TMB Substrate Kit (Pierce).

Analysis of data collected form this experiment was performed. Tumor Volume was calculated based on the following formula TV (mm3)={length (mm)×width (mm) 2}/2. For ELISA analysis, OD was read at 620 nm for one hour, every minute. Results from three mice at each time point were averaged and standard error determined. See FIGS. 42 to 44. The antibody level was plotted as function of time for cetuximab or mAbXcite-cetuximab. The half-life of each antibody was determined as the period of time it takes to decrease by half. FIG. 44 provides a comparison of mAbXcite-cetuximab PK in tumor-free and tumor bearing mice. Stability of the antibody and β-1,6-glucan detection were assessed by ELISA. FIG. 45 provides a comparison of mAbXcite-cetuximab conjugated with 3 or 4 β-1,6-oligomers in tumor bearing mice. Stability of the antibody and β-1,6-glucan detection were assessed by ELISA. PK of mAbXcite-cetuximab directly conjugated to a 5-mer oligomer was more stable with a load of 3 than with a load of 4 oligomers per antibody. Tumor-dependent degradation may explain lower PK in tumor bearing animals with higher load of oligomers.

Example 18: Accumulation of mAbXcite-Cetuximab in Tumor Bearing Mice

The studies of the present Example were undertaken to identify dosing regimens that do not result in antibody accumulation over time.

The present Example utilized mAbXcite-cetuximab in which 5-mer oligomers were conjugated using direct chemistry at a load of 3 oligomers per antibody. Cetuximab was used as a control. Also utilized were a blocking and staining buffer (casein in PBS (Pierce)) and a PBS-Tween buffer (pH 7.2, 0.05% Tween). ELISA was carried out using a 1-Step™ Ultra TMB-ELISA (Pierce) detection kit.

In this Example, 7 week old female nude mice were implanted SC with $2.5 \times 10^6$ HCT-116 (KRAS mutant colorectal cancer) cells. When tumor reached a volume of 120 mm³, mice were randomly divided into groups (3 mice/group) and treated with IVIG (as a source for polyclonal human anti-β-1,6-glucan antibodies) followed 2 hours later by vehicle control, cetuximab, or mAbXcite-cetuximab. The dosing was determined by the half-life and was twice weekly (5 mg/kg). Mice were dosed 3 times and mAbXcite-cetuximab plasma collected to study conjugate accumulation following treatment.

Plasma or mAbXcite-cetuximab control (as a standard) were incubated in 96-well plates coated with recombinant EGFR (hEGFR (peptide from SinoBiological)). Dilutions were 1:500 for detection of the antibody and 1:10 in order to detect β-1,6-glucan oligomers conjugated to cetuximab. Total human antibody binding (cetuximab or mAbXcite-cetuximab) was detected using HRP-conjugated anti-human IgG (goat anti-human IgG (H&L)-HRP). To specifically detect the β-1,6-glucan oligomers linked to cetuximab, affinity purified human anti-β-1,6-glucan antibodies were used (3 µg per well for 1 hour at RT). The detection was carried out with anti-human IgG2 (Fc)-HRP antibody (mouse anti-human IgG2 (Fc)-HRP). The color was developed by TMB Substrate Kit (SuperSignal ELISA Pico Chemiluminescent Substrate (Pierce)). For ELISA analysis, OD was read at 620 nm for one hour, every minute.

Analysis of data collected from this experiment was performed. Tumor volume was calculated based on the following formula: TV (mm³)={length (mm)×width (mm)²}/2. Results from three mice at each time point were averaged and standard error determined. See FIG. 46. The antibody level was plotted as function of time for cetuximab or mAbXcite-cetuximab. The half-life of each antibody was determined as the period of time it takes to decrease by half. A twice weekly dosing regimen, based on the half-life determined by PK, does not lead to either antibody or oligomer accumulation. This treatment schedule was used in subsequent examples to assess mAbXite-cetuximab efficacy in a mouse xenograft model.

Example 19: Pharmacokinetic Stability of mAbXcite-Cetuximab in Tumor-Free and Tumor-Bearing Mice Stability of the antibody and β-1,6-glucan detection were assessed by ELISA. The present study utilized mAbXcite-cetuximab in which the conjugation utilized click chemistry (DBCO), a 4-mer oligomer and a load of 3 oligomers per antibody. Cetuximab was used as a control. Also utilized were a blocking and staining buffer: Casein in PBS (Pierce) and a PBS-Tween buffer (PH 7.2, 0.05% Tween). ELISA was carried out using a 1-Step™ Ultra TMB-ELISA (Pierce) detection kit.

In this Example, 7 week old female nude mice were implanted SC with $2.5\times10^6$ HCT-116 (KRAS mutant colorectal cancer) cells. When tumor reached a volume superior to 120 mm$^3$, mice were randomly divided into groups (3 mice/group) and treated with IVIG (as a source for polyclonal human anti-β-1,6-glucan antibodies) followed 2 hours later by vehicle control, cetuximab or mAbXcite-cetuximab (5 mg/kg, IP). mAbXcite-cetuximab plasma pharmacokinetics were studied at various time points (1 to 96 hours) following treatment.

Plasma or mAbXcite-cetuximab control (as a standard) were incubated in 96-well plates coated with recombinant EGFR (hEGFR (peptide from SinoBiological)). Dilutions were 1:500 for detection of the antibody and 1:10 in order to detect β-1,6-glucan oligomers conjugated to cetuximab.

Total human antibody binding (cetuximab or mAbXcite-cetuximab) were detected using HRP-conjugated anti-human IgG (goat anti-human IgG (H&L)-HRP). To specifically detect the β-1,6-glucan oligomers linked to cetuximab, affinity purified human anti-β-1,6-glucan antibodies were used (3 μg per well for 1 hour at RT). The detection was carried out with anti-human IgG2 (Fc)-HRP antibody (mouse anti-human IgG2 (Fc)-HRP). The color was developed using SuperSignal ELISA Pico Chemiluminescent Substrate (Pierce). For ELISA analysis, OD was read at 620 nm for one hour, every minute.

Analysis of data collected from this experiment was performed. Tumor Volume was calculated based on the following formula: TV (mm$^3$)={length (mm)×width (mm)$^2$}/2. Results from three mice at each time point were averaged and standard error determined. See FIGS. 47 to 50. The antibody level was plotted as function of time for cetuximab or mAbXcite-cetuximab. The half-life of each antibody was determined as the period of time it takes to decrease by half. Contrary to what was observed with the directly conjugated mAbXcite-cetuximab, PK profile of this mAbXcite-cetuximab was dramatically decreased in tumor bearing mice. Antibody remained relatively stable but β-1, 6-glucan oligomer was not stable even with a small oligomer (4-mer) and a load of 3.

Example 20: Efficacy Study in Nude Mice with BRAF Colorectal Cancer Cell (CRC)

The present study utilized mAbXcite-cetuximab in which the conjugation of the glucan utilized click chemistry (DBCO), 4-mer and 6-mer oligomers, and loads of 3 and 4 oligomer per antibody.

In this Example, 7 week old female nude mice were implanted with $1\times10^6$ HT-29 cells (a human BRAF mutant colorectal adenocarcinoma cell line) into the dorsal region. Once tumors reached approximately 118-383 mm$^3$, mice were randomly assigned into four study treatment groups (n=5), such that the mean tumor volumes for each group were similar (mean=255.8±0.8 mm$^3$). Prior to each antibody administration, all mice received a 500 mg/kg (~0.1 mL) intraperitoneal (IP) injection of pooled human antibodies (IVIG). mAbXcite-cetuximab, cetuximab (5 mg/kg) and control were administered via an IP injection a minimum of 2 hours post-IVIG administration. Throughout the study, tumors were monitored twice weekly to determine tumor growth rates using external calipers. Tumors were measured prior to and following the first day of treatment. Body weights were also collected twice a week. Mice were euthanized when the maximum tumor volume reached 2000 mm$^3$. Mice were also to be euthanized if the tumor became ulcerated, if the tumor impeded ambulation, or there was a deterioration of body condition. Mice were also to be euthanized if they lost >15% of their original body weight. Animals were euthanized via carbon dioxide ($CO_2$) inhalation.

Analysis of data collected form this experiment was performed. Tumor volume was calculated based on the following formula: TV (mm$^3$)={length (mm)×width (mm)$^2$}/2. Results are shown in FIGS. 51 to 53. mAbXcite-cetuximab treatment with a 4-mer DBCO linked oligomer delayed the growth of HT-29 tumor. Borderline activity was seen with a 6-mer DBCO linked oligomer. It is to be noted that in that experimental setting, cetuximab also slows tumor growth.

Example 21: Efficacy Study in Nude Mice with KRAS Colorectal Cancer Cell (CRC)

In this Example, the efficacy of mAbXcite-cetuximab was studied in nude mice that were treated with KRAS CRC. The present study utilized mAbXcite-cetuximab in which the conjugation of the glucan utilized click chemistry (DBCO) or direct chemistry, 4-mer to 6-mer oligomers, and a load of 3 oligomers per antibody.

In this Example, 7 week old female nude mice were implanted SC with $2.5\times10^6$ HCT-116 cells (HCT-116 is a human KRAS mutant colorectal cancer cell line). When tumor volume was in the range of 67±1.3 mm$^3$ mice were randomly divided into groups (10 mice/group) and treated with IVIG (as a source for anti-β-1,6-glucan antibodies) followed 2 hours later by vehicle control, cetuximab or mAbXcite-cetuximab. The dosing was determined by the half-life and was twice weekly (5 mg/kg). Tumor volumes were assessed by caliper measurement twice weekly. Body weights were monitored twice weekly. Mice were euthanized after tumors reached a volume of 2000 mm$^3$ or if their body weight dropped by more than 15%.

Analysis of data collected form this experiment was performed. Tumor volume was calculated based on the following formula: TV (mm$^3$)={length (mm)×width (mm)$^2$}/2. Results are shown in FIGS. 54 and 55. mAbXcite-cetuximab treatment with a 4-mer DBCO linked oligomers delays the growth of HCT-116 tumor. However, 6-mer DBCO linked oligomers had no effect on tumor growth in that experiment. These results confirm the results obtained in the HT-29 xenograft model and suggest that shorter oligomers may have certain advantages which may be explained by the better PK profile of these mAbXcite-cetuximab conjugates. The growth inhibition was similar in this experiment with mAbXcite-cetuximab with a 4-mer DBCO linked oligomer and 5-mer direct conjugates.

Example 22: Efficacy Study in Nude Mice with KRAS CRC

In this Example, the efficacy of mAbXcite-cetuximab was studied in nude mice with KRAS CRC. The present study utilized mAbXcite-cetuximab in which the conjugation utilized reductive amination (direct) chemistry, a 5-mer oligomer, and a load of 3 oligomers per antibody.

In this Example, 7 week old female nude mice implanted with $2.5\times10^6$ HCT-116 cells (HCT-116 is a human KRAS mutant colorectal cancer cell line). Once tumors reached approximately 46-79 mm$^3$, mice were randomly assigned into four study treatment groups (n=9), such that the mean tumor volumes for each group were similar (mean=57±3.5 mm$^3$). Prior to each antibody administration, all mice received a 500 mg/kg (~0.1 mL) intraperitoneal (IP) injection of pooled human antibodies (IVIG). mAbXcite-cetuximab, cetuximab (5 mg/kg) and control were administered via an IP injection a minimum of 2 hours post-IVIG administration. Throughout the study, tumors were monitored twice weekly to determine tumor growth rates using external calipers. Tumors were measured prior to and following the first day of treatment. Body weights were also collected twice a week. Mice were euthanized when the maximum tumor volume reaches 2000 mm$^3$. Mice were also to be euthanized if the tumor became ulcerated, if the tumor impeded ambulation, or there was a deterioration of body condition. Mice were also to be euthanized if they lost >15% of their original body weight.

Analysis of data collected form this experiment was performed. Tumor volume was calculated based on the following formula: TV (mm$^3$)={length (mm)×width (mm)$^2$}/2. Results are shown in FIGS. 56 and 57. mAbXcite-cetuximab treatment with a 5-mer direct conjugate showed enhanced tumor growth delay on average and also by looking at the median.

Example 23: Dose Response in Nude Mice with KRAS CRC

In this Example, the dose response of mAbXcite-cetuximab was studied. The present study utilized mAbXcite-cetuximab in which the conjugation utilized reductive amination (direct) chemistry, a 5-mer oligomer, and a load of about 3 oligomers per antibody.

In this Example, 7 week old female nude mice were implanted SC with $2.5\times10^6$ HCT-116 cells (HCT-116 is a human KRAS mutant colorectal cancer cell line). When tumor volume wan in the range of 51-80 mm$^3$ mice were randomly divided into groups (9 mice/group) and treated with IVIG (as a source for anti-β-1,6-glucan antibodies) followed 2 hours later by vehicle control, cetuximab or mAbXcite EGFR. The dosing was determined by the half-life and was twice weekly. Various doses were assessed: 5, 10, 15 mg/kg for each antibody. Tumor volume was assessed by caliper measurement twice weekly. Body weight was monitored twice weekly. Mice were euthanized after tumors reached a volume of 2000 mm$^3$ or if their body weight dropped by more than 15%.

Analysis of data collected form this experiment was performed. Tumor volume was calculated based on the following formula: TV (mm$^3$)={length (mm)×width (mm)$^2$}/2. Results are shown in FIGS. 58 to 61.

Example 24: Dose Response in Nude Mice with KRAS CRC

In this Example, mAbXcite-cetuximab treatment with a 5-mer direct conjugate demonstrated a dose-dependent tumor growth delay. The present study utilized mAbXcite-cetuximab in which the conjugation utilized reductive amination (direct) chemistry, a 5-mer oligomer, and a load of about 3 oligomers per antibody. This study utilized nude mice with KRAS CRC—repeat.

In this Example, 7 week old female nude mice implanted with $3\times10^6$ HCT-116 cells (HCT-116 is a human KRAS mutant colorectal cancer cell line). Once tumors reached approximately 65-89 mm$^3$, mice were randomly assigned into four study treatment groups (n=7), such that the mean tumor volumes for each group were similar (mean=74±1.2 mm$^3$). Prior to each antibody administration, all mice received a 500 mg/kg (~0.1 mL) intraperitoneal (IP) injection of pooled human antibodies (IVIG). mAbXcite-cetuximab, cetuximab (5 mg/kg) and control were administered via an IP injection a minimum of 2 hours post-IVIG administration. Throughout the study, tumors were monitored twice weekly to determine tumor growth rates using external calipers. Tumors were measured prior to and following the first day of treatment. Body weights were also collected twice a week. Mice were euthanized when the maximum tumor volume reached 2000 mm$^3$. Mice were also to be euthanized if the tumor became ulcerated, if the tumor impeded ambulation, or there was a deterioration of body condition. Mice were also to be euthanized if they lost >15% of their original body weight.

Analysis of data collected form this experiment was performed. Tumor volume was calculated based on the following formula: TV (mm$^3$)={length (mm)×width (mm)$^2$}/2. Tumor Growth Inhibition (TGI) was calculated based on the following formula: % TGI=(TVvehicle day x−TVvehicle day initial)−(TVtreatment day x−TVtreatment day initial)×100/(TVvehicle day x−TVvehicle day initial). A TGI greater than 50% is considered to be significant. Tumor volume results (see FIGS. 62 and 63) and a survival curve (see FIG. 64) are provided. mAbXcite-cetuximab treatment with a 5-mer direct conjugate showed enhanced tumor growth delay on average and also by looking at the median. This efficacy study in these HCT-116 tumor-bearing mice, receiving either cetuximab or mAbXcite-cetuximab showed longer survival in mice receiving mAbXcite-cetuximab compared to mice treated with cetuximab. This data suggests that mAbXcite-cetuximab specifically delivered to EGFR-positive tumors by cetuximab can suppress tumor growth despite the KRAS mutant status and present opportunities for personalized clinical treatment strategies in colorectal cancer.

Example 25: Tumor Re-Challenge Assays in Nude Mice with KRAS CRC

Efficacy study in HCT-116 tumor-bearing mice, receiving mAbXcite-cetuximab (5-mer direct conjugation) showed longer survival in mice receiving mAbXcite-cetuximab than in mice treated with cetuximab. This survival was associated with mice exhibiting either regression or stasis of their tumors.

Since the generation of an adaptive immune memory response is essential for preventing tumor relapse and metastasis, we sought to address whether mAbXcite-cetuximab could also induce effective antitumor immune memory. To do so, we used tumor-rechallenge assays, as they are a robust readout not only for established memory responses but also for the ability of the host immune system to control systemic cancer relapse. Upon cessation of mAbXcite-cetuximab treatment, mice were re-challenged the with HCT-116 cells.

17 days after treatment cessation, nude mice were re-implanted subcutaneously (SC) with 2.5×10⁶ HTC-116 cells. Tumor volumes were assessed by caliper measurement twice weekly. Body weight monitored twice weekly. Mice were euthanized after tumors reached a volume of 2000 mm³ or if their body weight dropped by more than 15%.

Tumor Volume was calculated based on the following formula: TV (mm³)={length (mm)×width (mm)²}/2. Results are shown in FIGS. 65 and 66 and show that mAbXcite-cetuximab inhibits tumor growth and protects mice from rechallenge with HCT-116. The primary tumor and secondary tumor are shown. Growth curves are shown for individual mice that were treated with 5 mg/kg of cetuximab (FIGS. 65 and 66), mAbXcite-cetuximab (5-mer direct conjugate in FIG. 65), or other constructs (FIG. 66).

Despite low levels of T cells present in nude mice, we showed that cetuximab directly conjugated to a 5-mer with a load of 3, leads to lasting effects in some of the mice. Specifically, we have demonstrated that mice that exhibit either regression or stasis of their tumors are not growing secondary tumors upon rechallenge with cancer cells, suggesting that neutrophils initiate a response that confers memory. This effect was not observed in mice initially treated with cetuximab or mAbXcite-cetuximab conjugated utilizing the click DBCO linker.

Example 26: T-Cell Depletion in Nude Mice with BRAF CRC

Since mAbXcite-cetuximab shows efficacy and antitumor immune memory, we sought to address whether the overall antitumor effect of mAbXcite-cetuximab direct conjugate depends on cytotoxic T-lymphocyte (CTL). CD8⁺ T lymphocytes are the major cell population involved in controlling the growth of many tumors. However, to address whether CTL are essential for the therapeutic effect of mAbXcite-cetuximab, both CD8 and a CD4-depleting antibody were administered.

CD8⁺ CD4⁺-depleting antibody were administered to three mice, two of which had tumors that completely regressed and one whose tumor still showed stasis over 40 days upon treatment cessation and after being re-challenged. CD8 and a CD4-depleting antibody were administered twice weekly for the duration of the experiment. Tumor volume was assessed by caliper measurement twice weekly. Body weight was monitored twice weekly. Mice were euthanized after tumors reached a volume of 2000 mm³ or if their body weight dropped by more than 15%.

Tumor Volume was calculated based on the following formula: TV (mm³)={length (mm)×width (mm)²}/2. The two mice whose tumors regressed were not affected by the depletion. However, the one slow growing tumor grew exponentially following the depletion. Results are shown in FIG. 67. Results demonstrate that loss of CD8⁺ CD4⁺-cells significantly impaired the therapeutic effect of mAbXcite-cetuximab, suggesting that the antitumor effect of mAbXcite-cetuximab direct conjugate is indeed dependent on adaptive immune T cells, and that activation of neutrophils of the innate immune system progresses to activation of T cells of the adaptive immune system.

Example 27: Efficacy Study in Nude Mice with KRAS CRC

In this Example, the efficacy of mAbXcite-cetuximab was studied in nude mice with KRAS CRC. The present study utilized mAbXcite-cetuximab in which the conjugation utilized reductive amination (direct) chemistry, a 4-mer or 6-mer oligomer, and a load of 2.3, 2.5, or 5 oligomers per antibody.

In this Example, 7 week old female nude mice implanted with 2.5×10⁶ HCT-116 cells (HCT-116 is a human KRAS mutant colorectal cancer cell line). Once tumors reached approximately 46-79 mm³, mice were randomly assigned into four study treatment groups, such that the mean tumor volumes for each group were similar. Prior to each antibody administration, all mice received a 500 mg/kg (~0.1 mL) intraperitoneal (IP) injection of pooled human antibodies (IVIG). mAbXcite-cetuximab, cetuximab (10 mg/kg) and control were administered via an IP injection a minimum of 2 hours post-IVIG administration. Throughout the study, tumors were monitored twice weekly to determine tumor growth rates using external calipers. Tumors were measured prior to and following the first day of treatment. Body weights were also collected twice a week. Mice were euthanized when the maximum tumor volume reaches 2000 mm³. Mice were also to be euthanized if the tumor became ulcerated, if the tumor impeded ambulation, or there was a deterioration of body condition. Mice were also to be euthanized if they lost >15% of their original body weight.

Analysis of data collected form this experiment was performed. Tumor volume was calculated based on the following formula: TV (mm³)={length (mm)×width (mm)²}/2. Results are shown in FIGS. 68 to 73.

Example 28: Synthesis of Gentiopentose

In addition to purifying oligomers from pustulan, suitable glucans may be prepared by synthetic methods. For example, gentiopentose may be prepared by the following method.

The synthesis of the exemplary sugars below begin with the preparation of three "building blocks" (building block 1, building block 2, and building block 3). Two of the building blocks (building block 1 and building block 2) are protected dimers prepared from D-amygdalin. Building block 3 is prepared from glucose.

Scheme 1 illustrates the synthesis of building block 1.

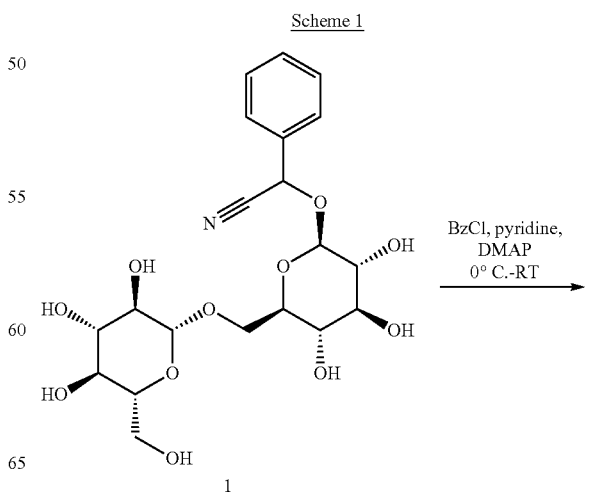

Scheme 1

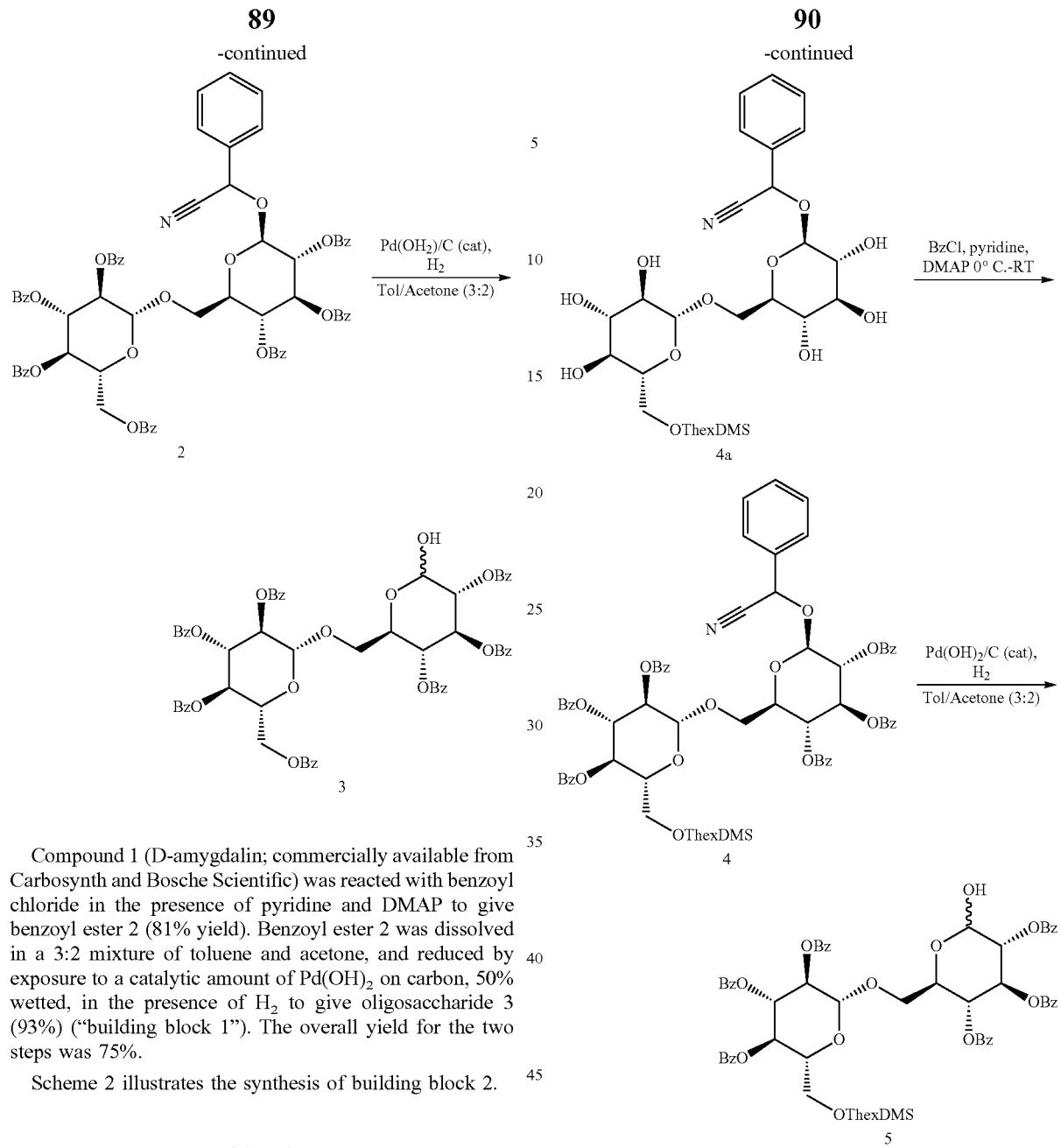

Compound 1 (D-amygdalin; commercially available from Carbosynth and Bosche Scientific) was reacted with benzoyl chloride in the presence of pyridine and DMAP to give benzoyl ester 2 (81% yield). Benzoyl ester 2 was dissolved in a 3:2 mixture of toluene and acetone, and reduced by exposure to a catalytic amount of Pd(OH)$_2$ on carbon, 50% wetted, in the presence of H$_2$ to give oligosaccharide 3 (93%) ("building block 1"). The overall yield for the two steps was 75%.

Scheme 2 illustrates the synthesis of building block 2.

Scheme 2

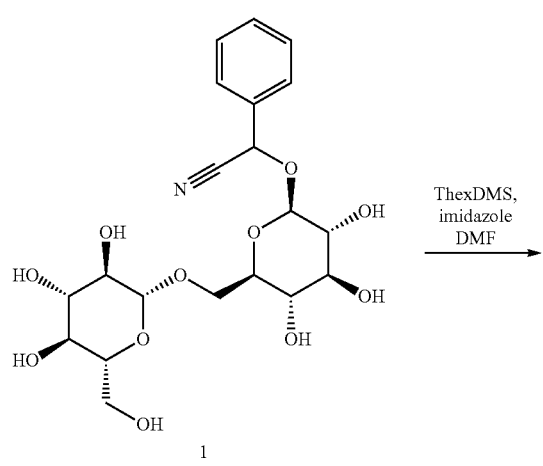

Compound 1 was first reacted with dimethylthexyl silyl chloride (ThexDMS-Cl) in the presence of imidazole and DMF to selectively protect the 6-hydroxyl moiety, giving compound 4a (82% yield). Compound 4a was then reacted with benzoyl chloride in the presence of pyridine and DMAP to give benzoyl ester 4 (81% yield). Without being bound to any particular theory, it is believed that use of ThexDMS was advantageous because the dimethyl-tert-butylsilyl moiety is easily cleaved during glycolysation. Benzoyl ester 4 was then dissolved in a toluene/acetone mixture (3:2 ratio), and reduced by exposure to a catalytic amount of Pd(OH)$_2$ on carbon, 50% wetted, in the presence of H$_2$ to give oligosaccharide 5 (93%) ("building block 2"). The overall yield for the process was 61%.

Scheme 3 illustrates the synthesis of building block 3.

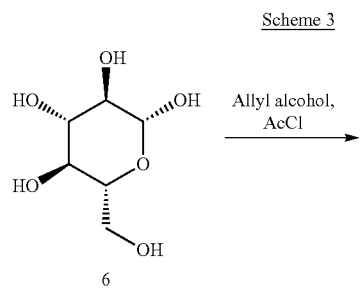

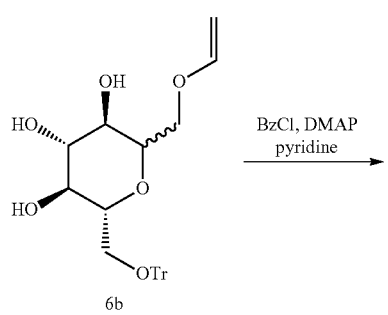

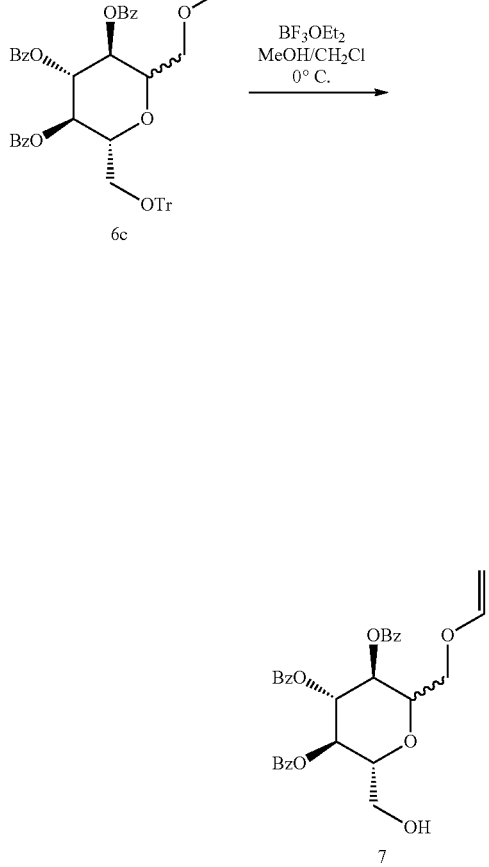

Compound 6 (glucose, commercially available from VWR) was first reacted with allylic alcohol in the presence of acetyl chloride to give compound 6a. Compound 6a was protected at the 6-hydroxyl position by reacting compound 6a with tritylchloride in the presence of pyridine and heat to give compound 6b. The remaining hydroxyl moieties of compound 6b were protected by reacting compound 6b with benzoyl chloride in the presence of pyridine and DMAP to give benzoyl ester 6c. Compound 6c was reacted with borontrifluoride etherate in a mixture of methanol and dichloromethane at 0° C. to give compound 7 ("building block 3"). The synthesis of building block 3 was performed with 42% overall yield.

Scheme 4 illustrates the synthesis of gentiotriose.

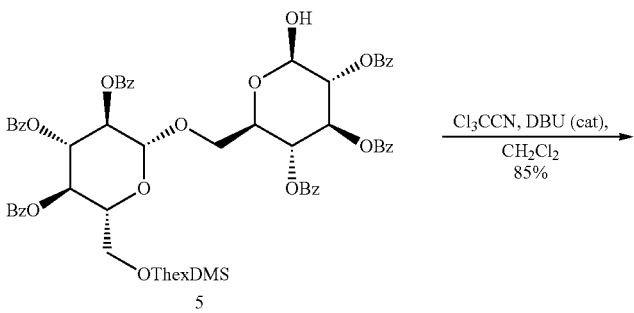

-continued

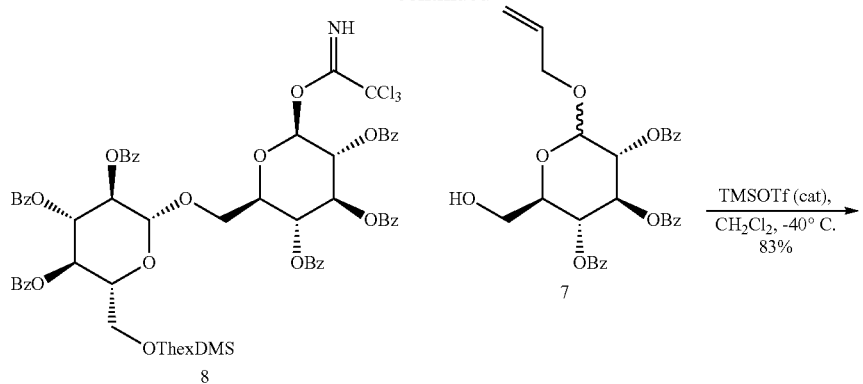

8

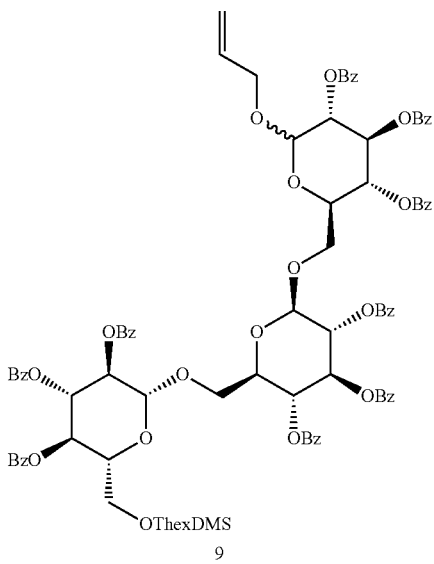

9

Compound 5 was reacted with Cl₃CCN in the presence of catalytic DBU in dichloromethane to give trichloroimidate 8. Compound 8 was repassed through a plug of base deactivated silica to remove base-line materials and carried forward without any further manipulation. Compound 8 was reacted with compound 7 (building block 3) under Schmidt glycosylation conditions (reacting the components with catalytic trimethylsilyl trifluoromethanesulfonate at −40° C.) to give compound 9 (gentiotriose). The overall yield for this two-step process was 70%.

Scheme 5 illustrates the glycosylation to form gentiopentose 12.

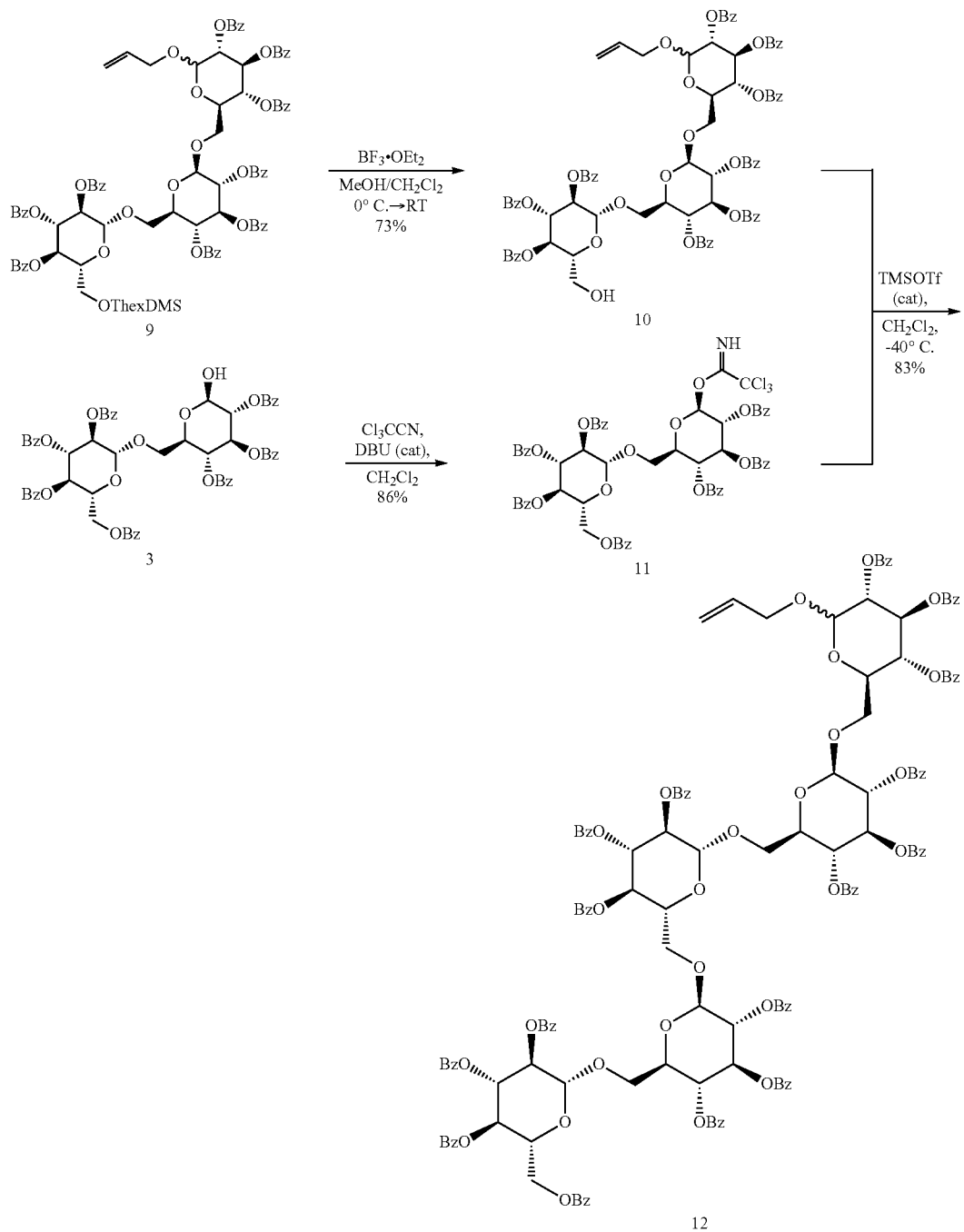

Gentiotriose 9 was treated with borontrifluoride etherate in methanol at 0° C. followed by warming to room temperature to afford the compound 10. Compound 3 (building block 1) was reacted with Cl₃CCN in the presence of catalytic DBU in dichloromethane to give trichloroimidate 11. Trichloroimidate 11 and compound 10 were reacted under Schmidt glycosylation conditions to afford the fully protected gentiopentose 12. The overall yield for these steps were 60%.

Scheme 6 illustrates the deprotection of gentiopentose 12.

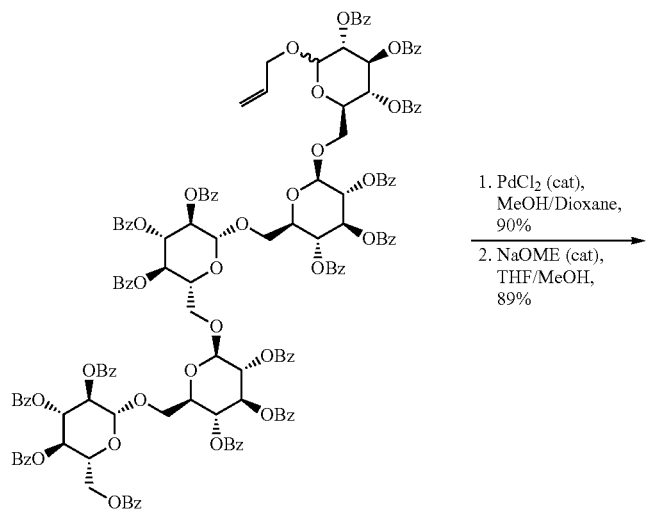

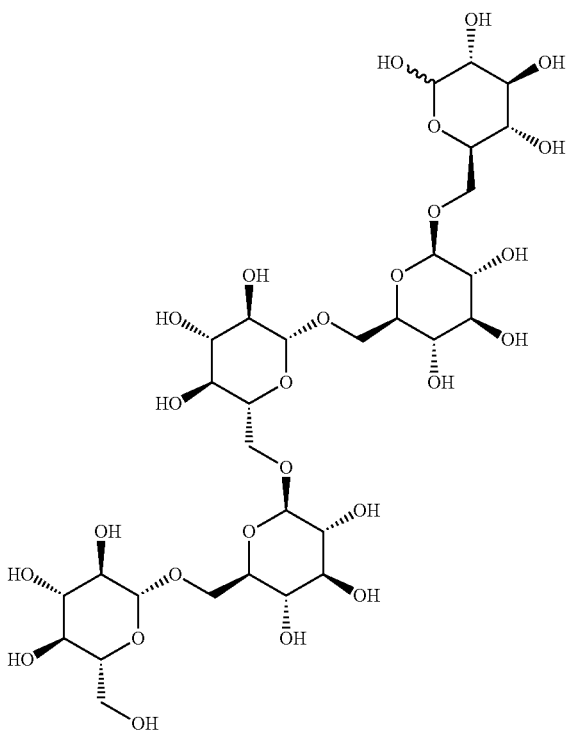

Gentiopentose 12 was contacted with a catalytic amount of palladium chloride in a mixture of methanol and dioxane to remove the allyl moiety. The resulting product was globally deprotected by reacting the product with a catalytic amount of sodium methoxide in a mixture of methanol and THF to provide gentiopentose 13. The overall yield for the 10 linear steps (16 total steps) was 14%.

Example 29: Synthesis of 2-azidoethylgentiotetrose

Scheme 7 illustrates the incorporation of the azido moiety into building block 2, prepared as described in example 7.

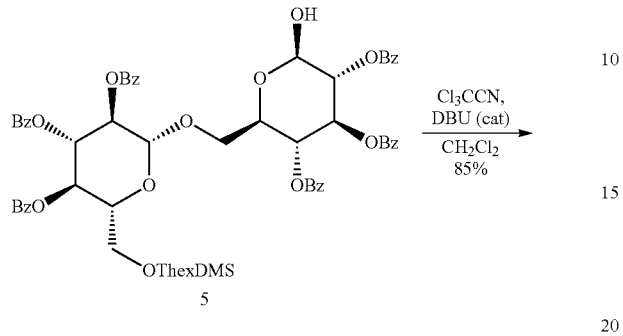

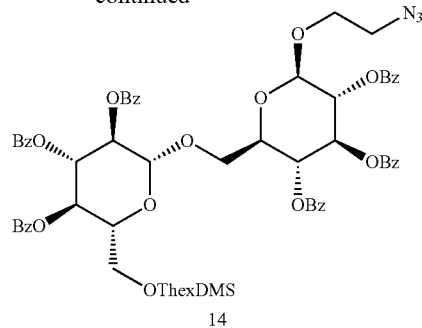

Compound 5 (building block 2) was reacted with Cl₃CCN in the presence of a catalytic amount of DBU in the presence of dichloromethane to give trichloroimidate 8. Trichloroimidate 8 was reacted under Schmidt glycosylation conditions to give compound 14. Compound 14 was synthesized in 70% overall yield.

Scheme 8 illustrates the synthesis of 2-azidoethylgentiotetrose.

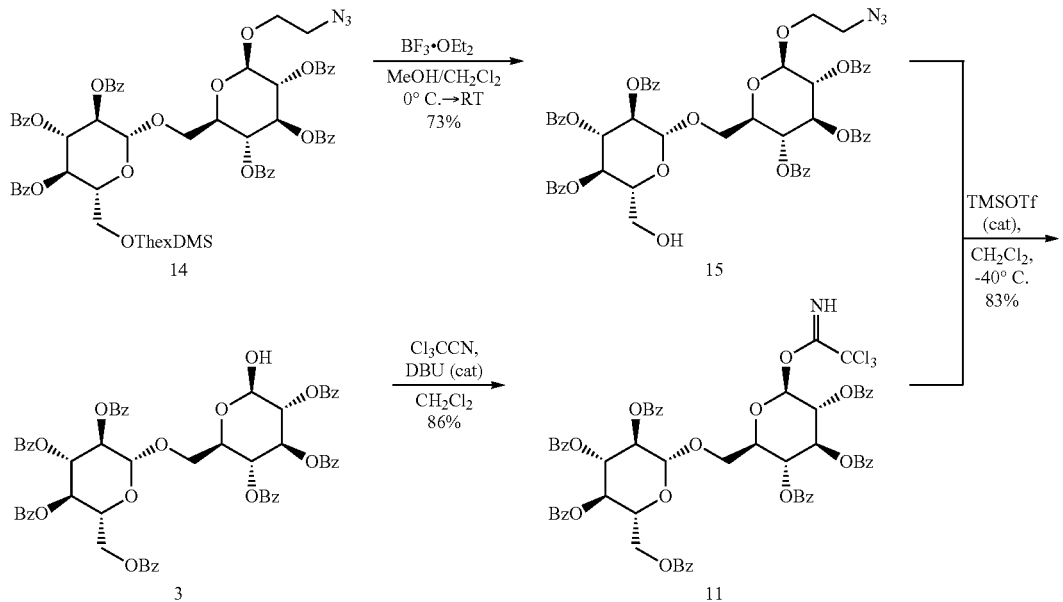

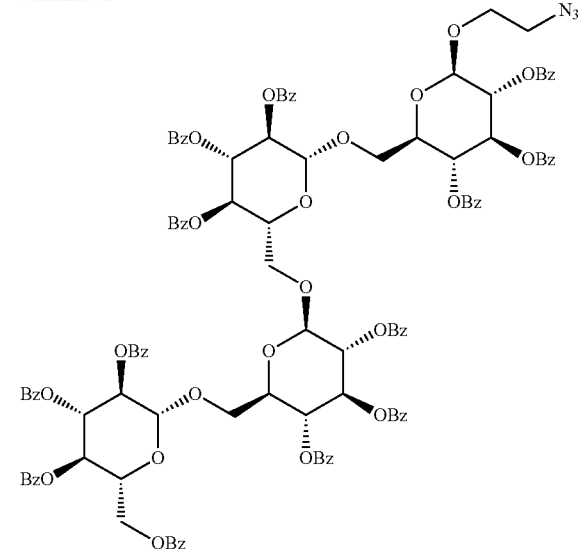

16

Compound 14 was deprotected by treatment of borontrifluoride etherate complex in methanol to give compound 15. Compound 3 (building block 1) was treated with trichloroacetonitrile and catalytic DBU to give compound 11. Compound 14 and compound 11 then subjected to the Schmidt glycosylation conditions to afford the gentiotetrose product 16. The overall yield of the sequence was 60%.

Example 30: Synthesis of 2-azidoethylgentiohexose

This Example provides further methods for glucan synthesis. Scheme 9 illustrates the synthesis of gentiotriose 17.

Scheme 9

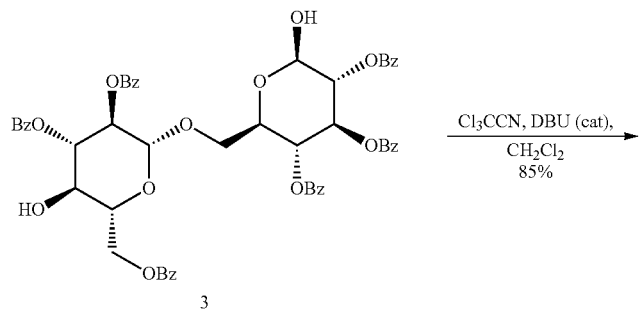

3

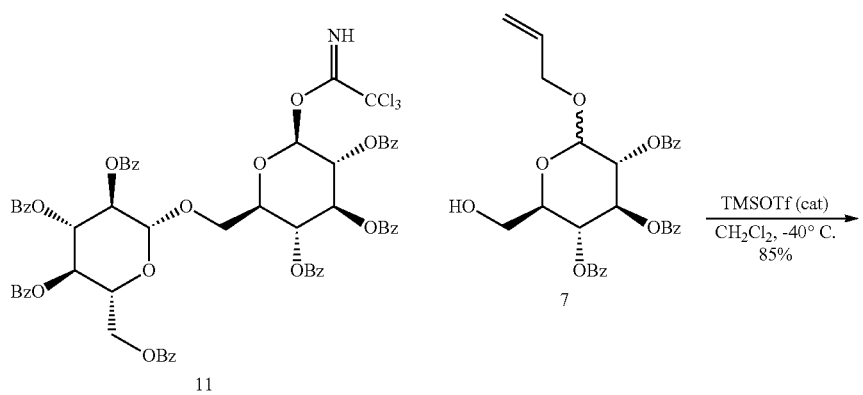

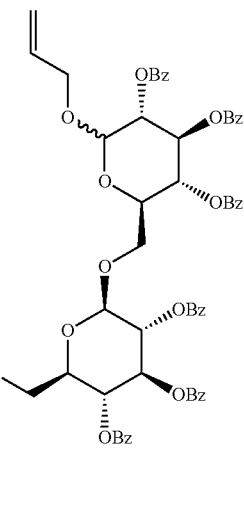
17
Compound 3 (building block 1) was reacted with Cl₃CCN in the presence of catalytic DBU in dichloromethane to give trichloroimidate 11. Trichloroimidate 11 was reacted with compound 7 (building block 3) under Schmidt glycosylation condition to give gentiotriose 17 (72% overall yield).
Scheme 10 illustrates incorporate of the 2-azidoethyl moiety into gentiotriose 9.
Scheme 10
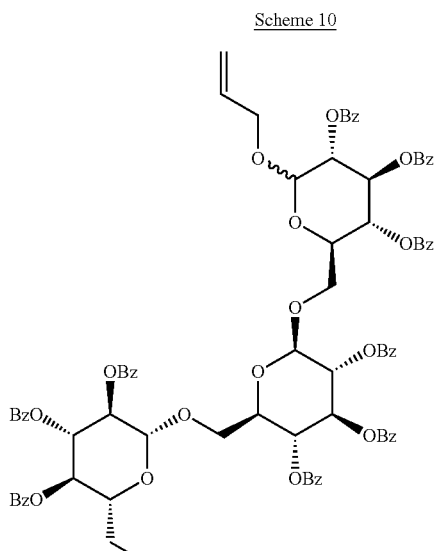
9
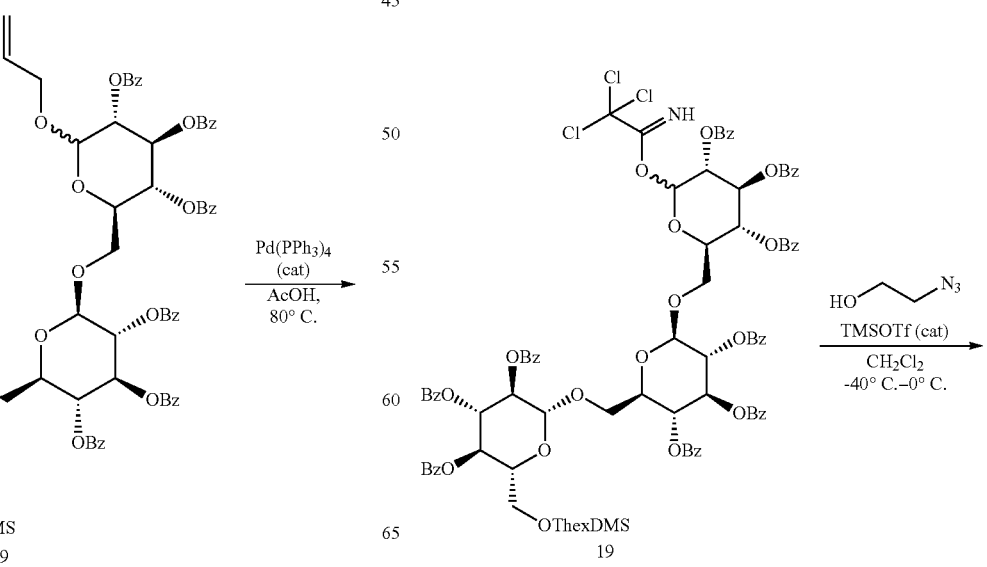
18
19

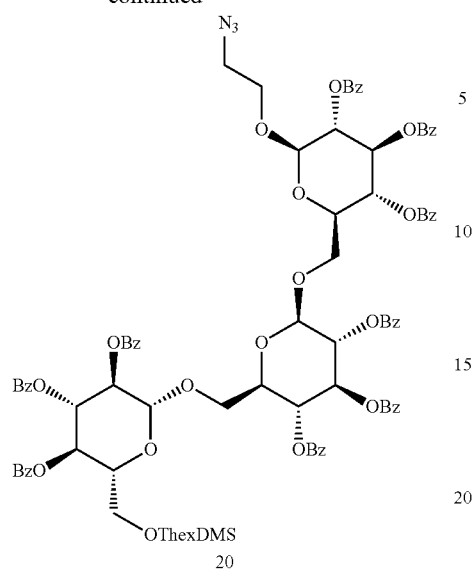

20

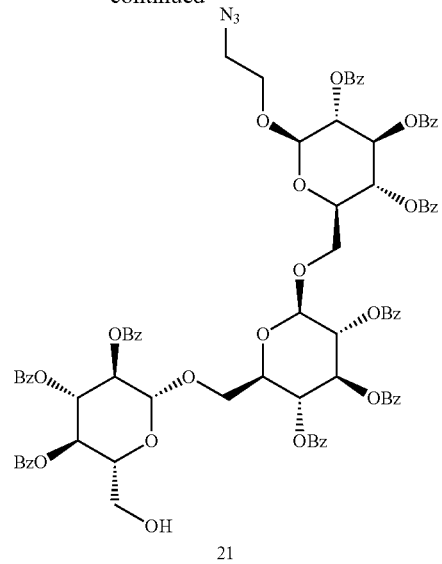

21

Gentiotriose 9 was deprotected by exposure to a catalytic amount of palladium (0) tetrakistriphenylphosphine in acetic acid at 80° C. to afford the compound 18. Utilization of palladium chloride in methanol resulted in the loss of the silyl moiety in addition to reduction of the allyl moiety. The glycosylation of the 2-azidoethanol under typical lewis acid conditions occurs after functionalization of the free hydroxyl moiety as the trichloroimidate 19 to afford the product 20. This sequence yielded 56% overall yield of 2-azidoethyl-gentiotriose.

Schemes 11a-c illustrates the synthesis of 2-azidoethyl-gentiohexose 24.

As illustrated in Scheme 11a, compound 20 was reacted with a borontrifluoride etherate complex in methanol to afford compound 21 (75% yield).

Scheme 11b

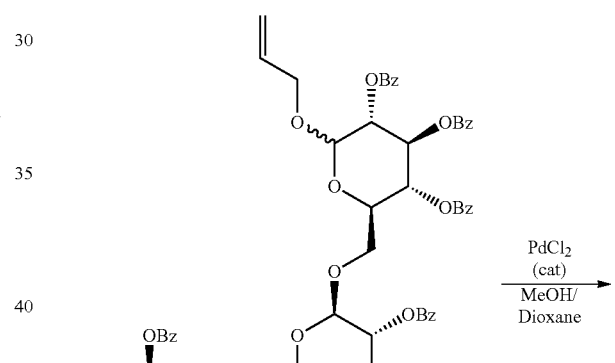

Scheme 11a

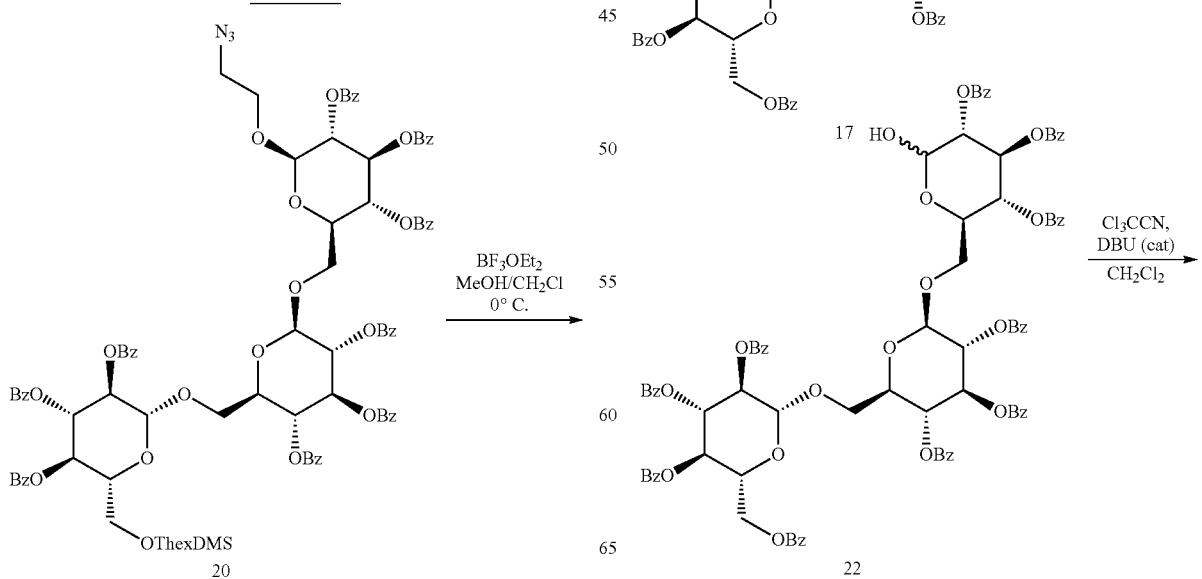

107

-continued

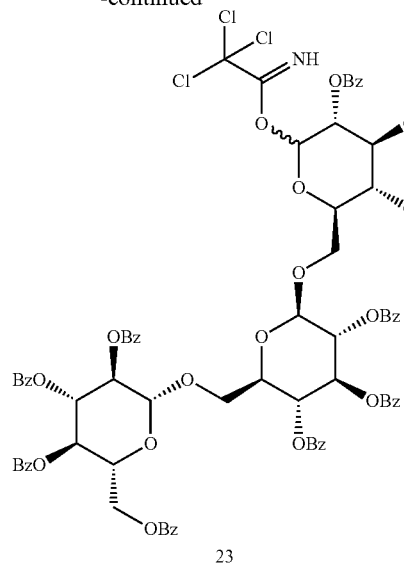

23

As illustrated in Scheme 11b, compound 17 was reduced with palladium (II) chloride in a mixture of methanol and dioxane to provide compound 22 (92% yield). Compound 22 was reacted with Cl₃CCN in the presence of catalytic DBU in dichloromethane to give trichloroimidate 23 (86% yield).

Scheme 11c

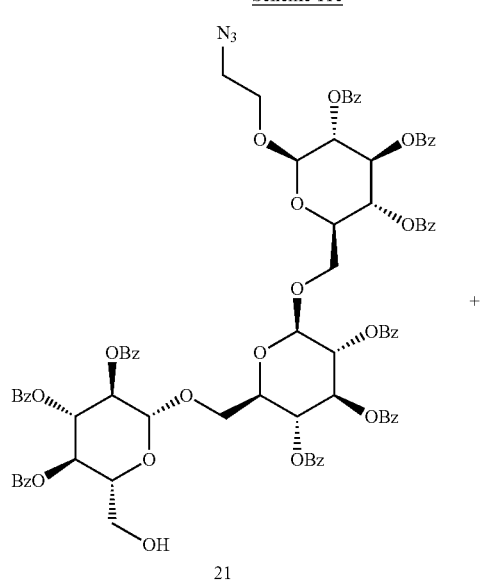

21

108

-continued

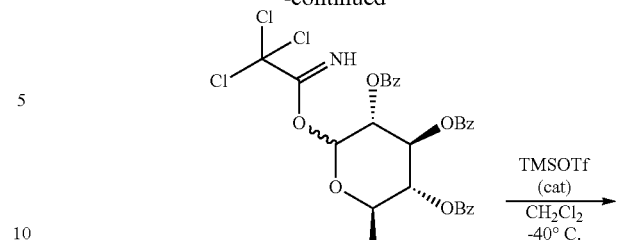

23

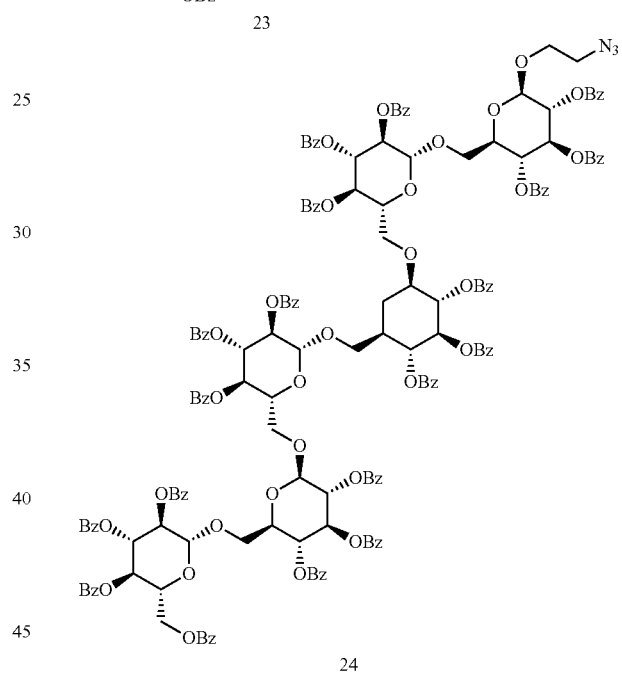

24

As illustrated in Scheme 11c, compounds 21 and 23 were under Schmidt glycosylation conditions to afford the desired product 24 (83% yield). The total synthetic process provided compounds 24 in 62% yield.

Example 31: Synthesis of Conjugate Precursors

In some embodiments, the sugar oligomers can further comprise a linker moiety bound to a functional group useful in conjugating the oligomer to the antibody. Therefore, the following synthetic examples illustrate methods of using sugar oligomers (for example, the sugar oligomers isolated from pustulan as in Example 1 or prepared as described above in Examples 7-9), and adding functionality to assist with the conjugation of the oligomer to the antibody. Because the compounds have not yet been conjugated to the antibody, they are referred to herein as "Conjugate Precursors." Below are provided three exemplary precursors suitable for conjugating with the antibodies described above.

Conjugate Precursor B
The synthesis of Conjugate Precursor B can be prepared according to Scheme 12:
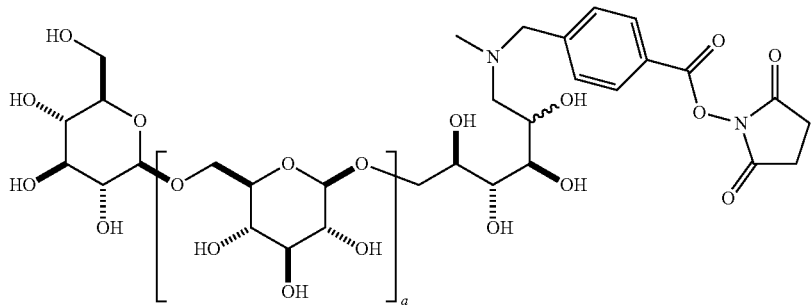
Conjugate Precursor B
Scheme 12
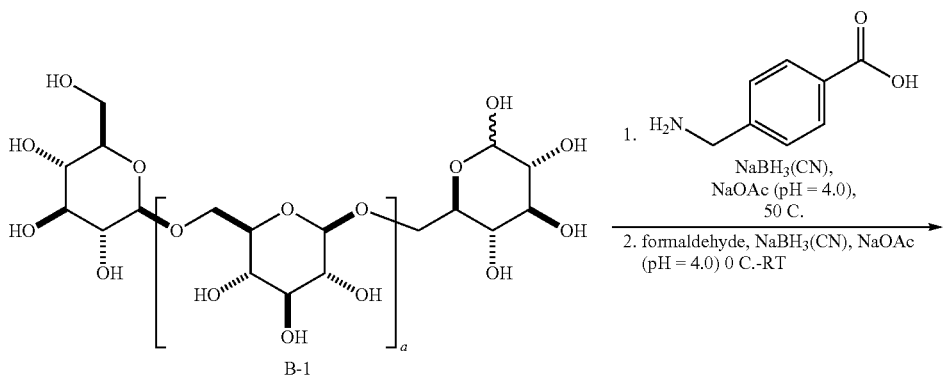
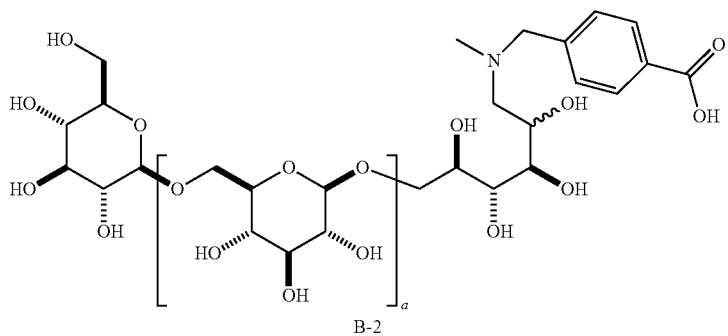
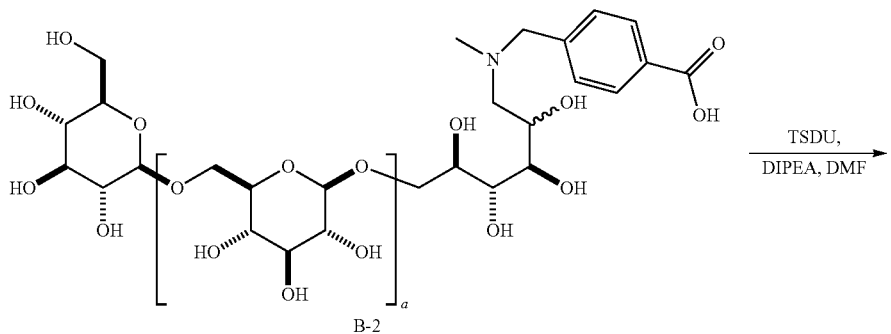

-continued

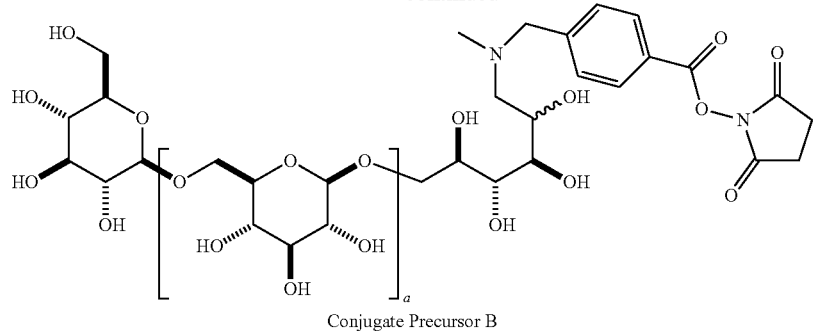

Conjugate Precursor B

B-1 was contacted with 4-(aminomethyl)benzoic acid in the presence of NaBH$_3$(CN) and sodium acetate. The reaction was stirred at 50° C. until the reaction was completed. The product was then treated with formaldehyde, NaBH$_3$(CN), and sodium acetate at 0° C. The reaction was allowed to stir and warm to room temperature to afford product B-2.

B-2 was dissolved in DMF. TSDU was added to the solution, followed by DIPEA. The solution was allowed to stir until the reaction was complete to yield Conjugate Precursor B.

Conjugate Precursor C

The synthesis of Conjugate Precursor C can be prepared according to Scheme 13:

Conjugate Precursor C

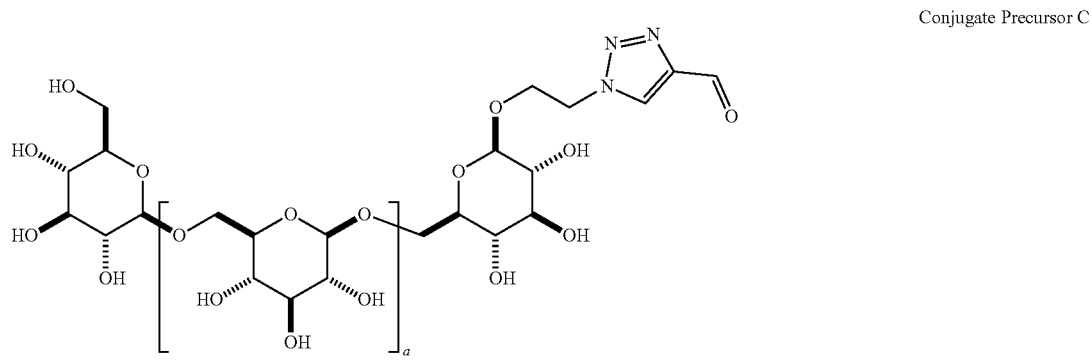

Scheme 13

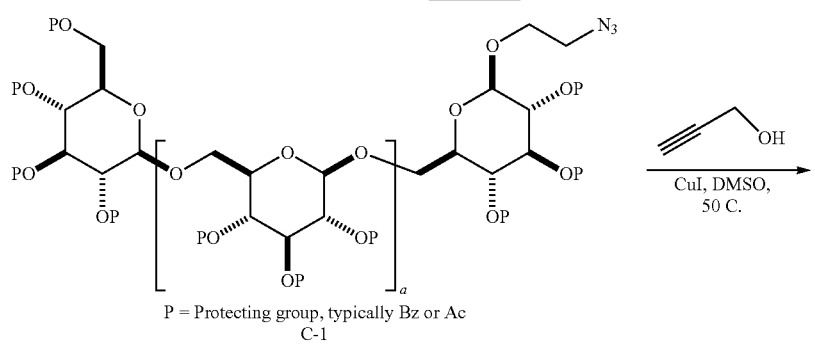

P = Protecting group, typically Bz or Ac
C-1

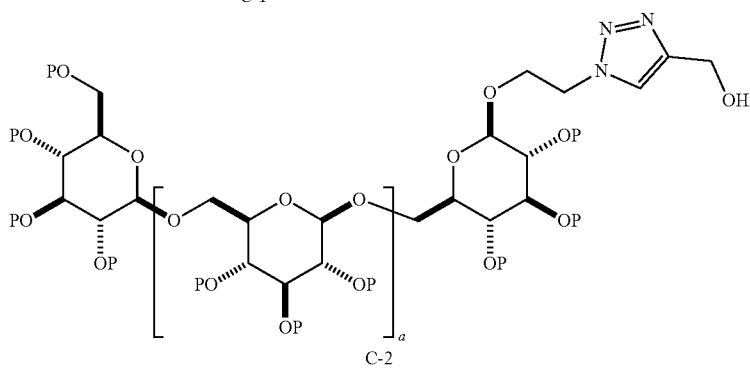

C-2

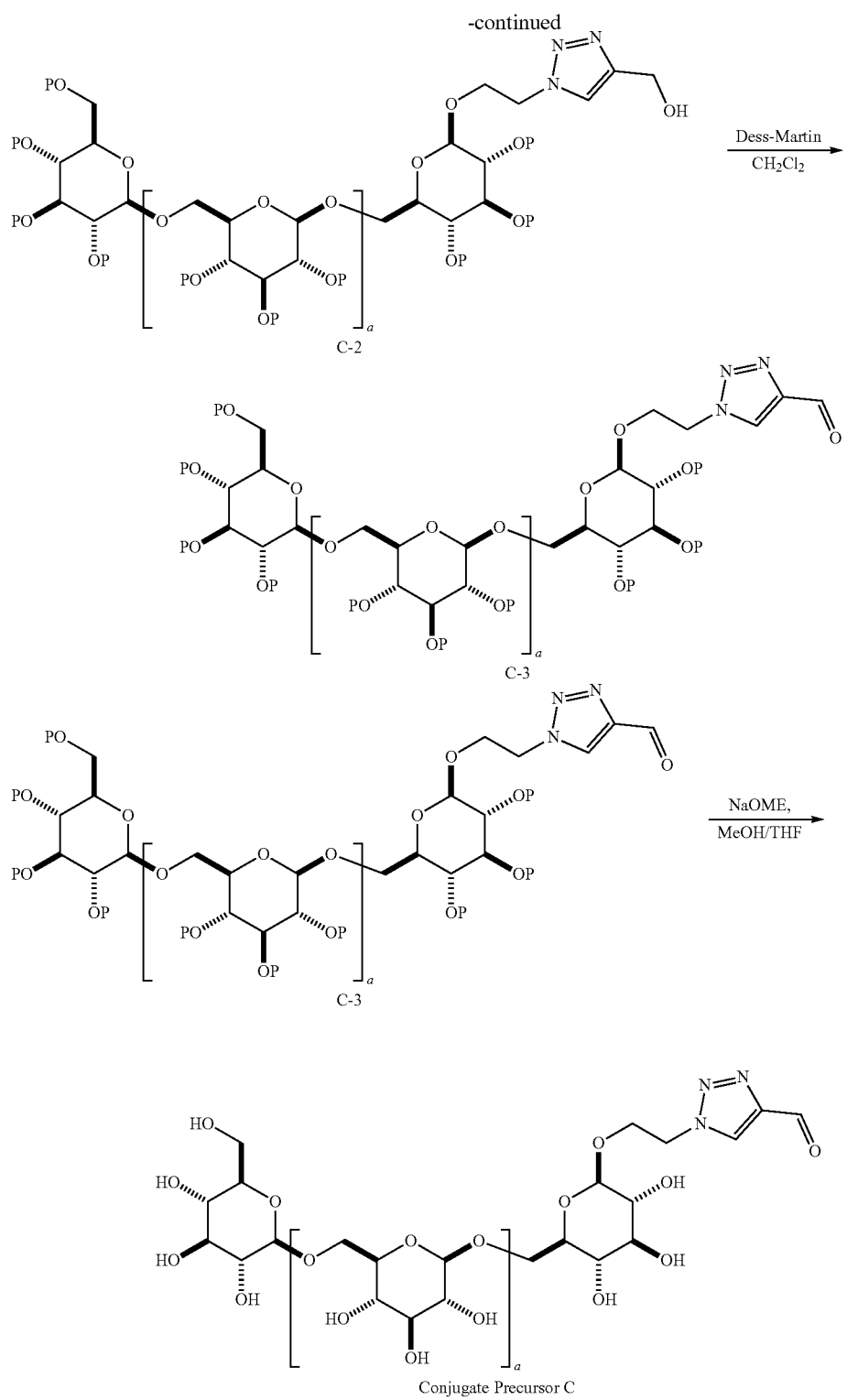
C-1 was dissolved in DMSO and contacted with prop-2-yn-1-ol and CuI at 50° C. The reaction was allowed to stir until the reaction was complete, yielding C-2. C-2 was dissolved in DCM in the presence of Dess-Martin reagent to provide C-3. C-3 was dissolved in a solution of methanol and THF and contacted with sodium methoxide to provide Conjugate Precursor C.

Conjugate Precursor D
The synthesis of Conjugate Precursor D can be prepared according to Scheme 14:
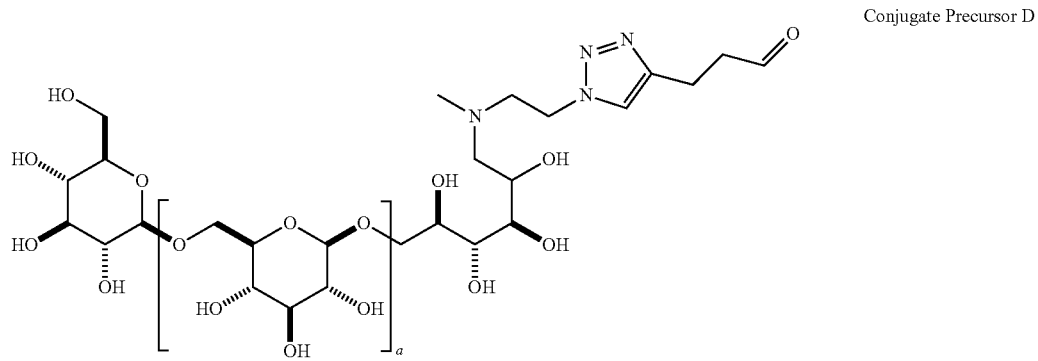
Conjugate Precursor D
Scheme 14
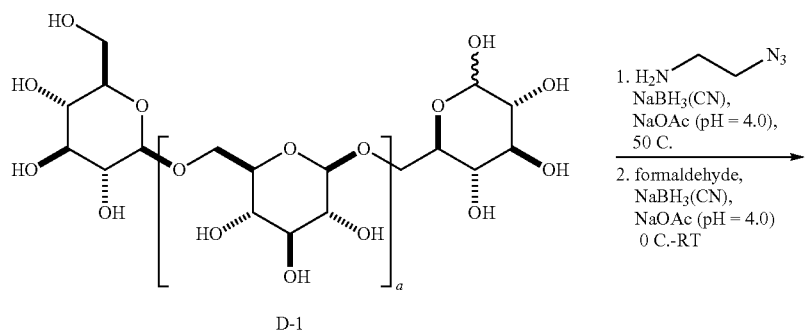
D-1
1. H₂N⁓N₃
   NaBH₃(CN),
   NaOAc (pH = 4.0),
   50 C.
2. formaldehyde,
   NaBH₃(CN),
   NaOAc (pH = 4.0)
   0 C.-RT
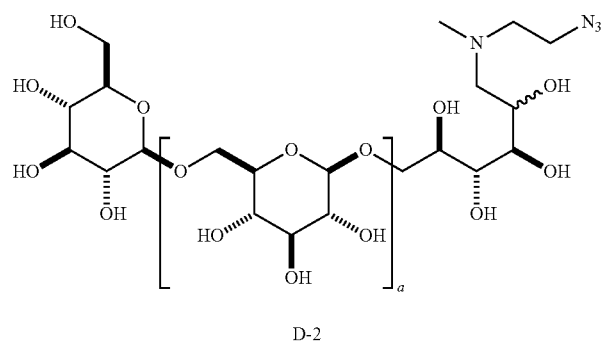
D-2
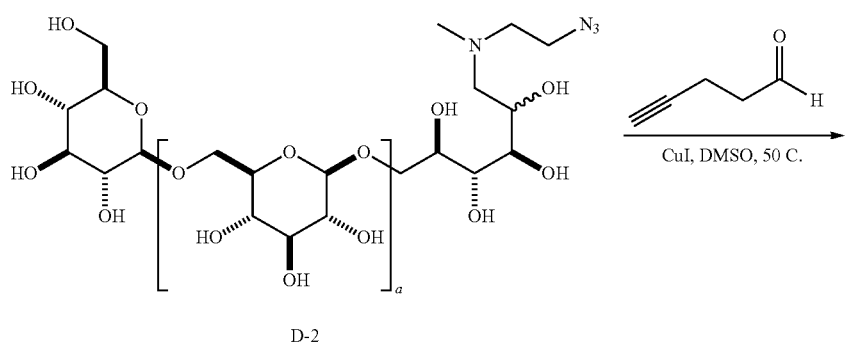
D-2
CuI, DMSO, 50 C.

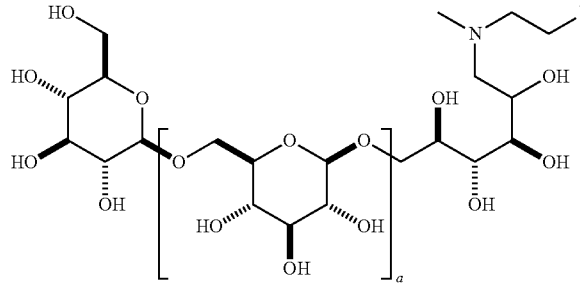

Conjugate Precursor D

D-1 was contacted with 2-azidoethan1-amine in the presence of $NaBH_3(CN)$ and sodium acetate. The reaction was stirred at 50° C. until the reaction was completed. The product was then treated with formaldehyde, $NaBH_3(CN)$, and sodium acetate at 0° C. The reaction was allowed to stir and warm to room temperature to afford product D-2.

D-2 was dissolved in DMSO and contacted with pent-4-ynal and CuI at 50° C. The solution was allowed to stir until the reaction was complete to yield Conjugate Precursor D.

OTHER EMBODIMENTS

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

What is claimed is:

1. A composition comprising conjugates according to Formula II:

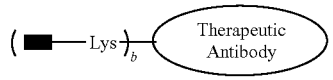

wherein:

each Lys is a different lysine residue present in the Therapeutic Antibody;

b represents the average number of individual β-1,6-glucan oligomers that are conjugated to each Therapeutic Antibody molecule in the composition and is between 2 and 4; and each ■ is a β-1,6-glucan oligomer of Formula Ia:

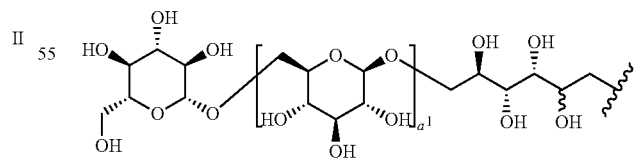

wherein:

$a^1$ is 4; and

"⸹" represents a point of attachment between the β-1,6-glucan oligomer and one lysine residue of the Therapeutic Antibody.

2. The composition of claim 1, wherein the Therapeutic Antibody comprises a heavy chain variable domain comprising the complementarity determining region (CDR) amino acid sequences of SEQ ID NO: 30, SEQ ID NO:31, and SEQ ID NO:32; and a light chain variable domain comprising the complementarity determining region (CDR) amino acid sequences of SEQ ID NO: 33, SEQ ID NO:34, and SEQ ID NO:35.

3. The composition of claim 2, wherein the Therapeutic Antibody is trastuzumab.

4. The composition of claim 1, wherein the Therapeutic Antibody comprises a heavy chain variable domain comprising the complementarity determining region (CDR) amino acid sequences of SEQ ID NO: 6, SEQ ID NO:7, and SEQ ID NO:8; and a light chain variable domain comprising the complementarity determining region (CDR) amino acid sequences of SEQ ID NO: 9, SEQ ID NO:10, and SEQ ID NO:11.

5. The composition of claim 4, wherein the Therapeutic Antibody is cetuximab.

6. The composition of claim 1, wherein the β-1,6-glucan oligomers are chemically synthesized.

7. The composition of claim 1, wherein at least 90% of the dry weight of glucan contained in the composition is β-1,6-glucan.

8. The composition of claim 1, wherein less than 10% of the dry weight of glucan contained in the composition is β-1,3-glucan.

9. The composition of claim 8, wherein the composition is substantially free of β-1,3-glucan.

10. A method of inhibiting tumor growth in a cancer associated with overexpression and/or amplification of a target moiety in a subject in need thereof, the method comprising administering to the subject a therapeutically effective amount of a composition of claim 1, wherein the target moiety is recognized by the Therapeutic Antibody.

11. The method of claim 10, wherein the target moiety is selected from the group consisting of CEACAM5, CD20, CD33, CD52, EGFR, EGFRVIII, FAP, Glycipan-3, HER2/neu, Her3, IGF1R (insulin-like growth factor-1 receptor), Mucl (CanAg), MUC18, Phosphatidyl Serine (PS), PSMA (prostate specific membrane antigen), RSV (A antigenic site of the F protein), and VEGF-A.

12. The method of claim 11, wherein the target moiety is EGFR.

13. The method of claim 12, wherein the cancer is a colorectal cancer, a non-small cell lung cancer, or a head and neck cancer.

14. The method of claim 11, wherein the target moiety is a HER2/neu.

15. The method of claim 14, wherein the cancer is a gastric cancer, or a breast cancer.

16. The method of claim 11, wherein the cancer is a bladder cancer, a prostate cancer, an endometrial cancer, a gastric cancer, a breast cancer, a lung cancer, a non-small cell lung cancer, an ovarian cancer, a salivary gland cancer, a pancreatic cancer, a blood cancer, a skin cancer, a head and neck cancer, or a colorectal cancer.

17. The composition of claim 1, wherein the Therapeutic Antibody is selected from the group consisting of cetuximab, cergutuzumab; ibritumomab tiuxetan; rituximab; tositumomab; gemtuzumab; alemtuzumab; panitumumab; depatuxizumab; sibrotuzumab; codrituzumab; trastuzumab; patritumab; figitumumab; ganitumab; cantuzumab; ABX-MA1; bavituximab; J591; palivizumab; and bevacizumab.

* * * * *

SEQUENCE LISTING

```
<160> NUMBER OF SEQ ID NOS: 88

<210> SEQ ID NO 1
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60
```

```
Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Leu Leu Thr Gln Ser Pro Val Ile Leu Ser Val Ser Pro Gly
  1               5                  10                  15

Glu Arg Val Ser Phe Ser Cys Arg Ala Ser Gln Ser Ile Gly Thr Asn
                 20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Ala Cys
        210

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 6

Gly Phe Ser Leu Thr Asn Tyr Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Trp Ser Gly Gly Asn Thr
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Ala Leu Thr Tyr Tyr Asp Tyr Glu Phe Ala Tyr
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ile Gly Thr Asn
1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ala Ser
1

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln Asn Asn Asn Trp Pro Thr Thr
1               5

<210> SEQ ID NO 12

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Val Gln Leu Lys Gln Ser Gly Pro Gly Leu Val Gln Pro Ser Gln
1               5                   10                  15

Ser Leu Ser Ile Thr Cys Thr Val Ser
            20                  25

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val His Trp Val Arg Gln Ser Pro Gly Lys Gly Leu Glu Trp Leu Gly
1               5                   10                  15

Val

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Tyr Asn Thr Pro Phe Thr Ser Arg Leu Ser Ile Asn Lys Asp Asn
1               5                   10                  15

Ser Lys Ser Gln Val Phe Phe Lys Met Asn Ser Leu Gln Ser Asn Asp
            20                  25                  30

Thr Ala Ile Tyr Tyr Cys
        35

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Gly Gln Gly Thr Leu Val Thr Val Ser Ala
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Ile Leu Leu Thr Gln Ser Pro Val Ile Leu Ser Val Ser Pro Gly
1               5                   10                  15
```

Glu Arg Val Ser Phe Ser Cys Arg Ala Ser
            20                  25

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile His Trp Tyr Gln Gln Arg Thr Asn Gly Ser Pro Arg Leu Leu Ile
1               5                   10                  15

Lys

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ser Ile Ser Gly Ile Pro Ser Arg Phe Ser Gly Ser Gly Ser Gly
1               5                   10                  15

Thr Asp Phe Thr Leu Ser Ile Asn Ser Val Glu Ser Glu Asp Ile Ala
            20                  25                  30

Asp Tyr Tyr Cys
            35

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Gly Ala Gly Thr Lys Leu Glu Leu Lys
1               5                   10

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Arg Val

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Pro Lys Ser Cys Asp Lys Thr His Thr Cys Pro Pro Cys Pro
1               5                  10                  15

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 23
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95
```

Thr Gln Lys Ser Leu Ser Leu Ser Pro
            100             105

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Ala Cys
            100                 105

<210> SEQ ID NO 26
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                      55                  60

Lys Gly Arg Phe Thr Ile Ser Ala Asp Thr Ser Lys Asn Thr Ala Tyr
65                      70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                    420                 425                 430

Glu Ala Leu His Asn His Tyr Thr Gln Lys Ser Leu Ser Leu Ser Pro
            435                 440                 445

Gly Lys
    450

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
        115                 120

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
                100                 105

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Phe Asn Ile Lys Asp Thr Tyr Ile His
 1               5                  10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ile Tyr Pro Thr Asn Gly Tyr Thr Arg Tyr Ala Asp Ser Val Lys
 1               5                  10                  15

Gly
```

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Gly Gly Asp Gly Phe Tyr Ala Met Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Asp Val Asn Thr Ala Val Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ala Ser Phe Leu Tyr Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln His Tyr Thr Thr Pro Pro Thr
1               5

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 37
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 37

Trp Val Arg Gln Ala Pro Gly Lys Gly Leu Glu Trp Val Ala
1               5                   10

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Gly Gln Gly Thr Leu Val Thr Val Ser Ser
1               5                   10

<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Tyr Gln Gln Lys Pro Gly Lys Ala Pro Lys Leu Leu Ile Tyr
1               5                   10                  15

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 42

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Gly Gln Gly Thr Lys Val Glu Ile Lys
1               5                   10

<210> SEQ ID NO 44
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Pro Lys Ser Cys Asp Lys Thr His Thr Cys Pro Pro Cys Pro
1               5                   10                  15

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Pro Glu Leu Leu Gly Gly Pro Ser Val Phe Leu Phe Pro Pro Lys
```

```
                1               5                   10                  15
       Pro Lys Asp Thr Leu Met Ile Ser Arg Thr Pro Glu Val Thr Cys Val
                        20                  25                  30

Val Val Asp Val Ser His Glu Asp Pro Glu Val Lys Phe Asn Trp Tyr
                        35                  40                  45

Val Asp Gly Val Glu Val His Asn Ala Lys Thr Lys Pro Arg Glu Glu
                50                  55                  60

Gln Tyr Asn Ser Thr Tyr Arg Val Val Ser Val Leu Thr Val Leu His
       65                   70                  75                  80

Gln Asp Trp Leu Asn Gly Lys Glu Tyr Lys Cys Lys Val Ser Asn Lys
                        85                  90                  95

Ala Leu Pro Ala Pro Ile Glu Lys Thr Ile Ser Lys Ala Lys
                        100                 105                 110

<210> SEQ ID NO 47
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Gln Pro Arg Glu Pro Gln Val Tyr Thr Leu Pro Pro Ser Arg Glu
       1               5                   10                  15

Glu Met Thr Lys Asn Gln Val Ser Leu Thr Cys Leu Val Lys Gly Phe
                        20                  25                  30

Tyr Pro Ser Asp Ile Ala Val Glu Trp Glu Ser Asn Gly Gln Pro Glu
                        35                  40                  45

Asn Asn Tyr Lys Thr Thr Pro Pro Val Leu Asp Ser Asp Gly Ser Phe
                50                  55                  60

Phe Leu Tyr Ser Lys Leu Thr Val Asp Lys Ser Arg Trp Gln Gln Gly
       65                   70                  75                  80

Asn Val Phe Ser Cys Ser Val Met His Glu Ala Leu His Asn His Tyr
                        85                  90                  95

Thr Gln Lys Ser Leu Ser Leu Ser Pro
                        100                 105

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Thr Val Ala Ala Pro Ser Val Phe Ile Phe Pro Pro Ser Asp Glu
       1               5                   10                  15

Gln Leu Lys Ser Gly Thr Ala Ser Val Val Cys Leu Leu Asn Asn Phe
                        20                  25                  30

Tyr Pro Arg Glu Ala Lys Val Gln Trp Lys Val Asp Asn Ala Leu Gln
                        35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
       65                   70                  75                  80

Lys His Lys Val Tyr Ala Cys Glu Val Thr His Gln Gly Leu Ser Ser
```

```
                    85                  90                  95
Pro Val Thr Lys Ser Phe Asn Arg Gly Glu Cys
                100                 105

<210> SEQ ID NO 49
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
                100                 105                 110

Gln Gly Thr Thr Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335
```

```
Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 50
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 51
```

<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
    115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
    195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
    275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
    355                 360                 365

Val Thr Asp Phe Met Pro Glu Asp Ile Tyr Val Glu Trp Thr Asn Asn

```
                370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
            435                 440

<210> SEQ ID NO 52
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 53
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Gln Pro Gly Ala Glu Leu Val Lys Pro Gly Ala
1               5                   10                  15
```

```
Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 54
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 55
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

-continued

```
Gly Ala Ile Tyr Pro Gly Asn Gly Asp Thr Ser Tyr Asn Gln Lys Phe
         50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                     85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 56
<211> LENGTH: 210
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 56

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 57
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Arg Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Gly Gly Gly Val Phe Asp Tyr Trp Gly Gln Gly Thr Thr Leu
```

```
                    100                 105                 110

Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Glu Tyr Asn Gly Gly Leu
            100                 105                 110

Val Thr Val Ser Ser
        115

<210> SEQ ID NO 59
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
            20                  25                  30

His Trp Phe Gln Gln Lys Pro Gly Thr Ser Pro Lys Leu Trp Ile Tyr
        35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ile Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asp Ser Lys
                85                  90                  95

Met Phe Gly Gln Gly Thr Lys Val Glu Val Lys
            100                 105

<210> SEQ ID NO 61
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly

```
            225                 230                 235                 240
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 62
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 63
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270
```

```
Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 64
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 65
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
                20                  25                  30

Ile Gly Trp Leu Gln Gln Lys Pro Gly Lys Ser Phe Lys Gly Leu Ile
            35                  40                  45

Tyr His Gly Thr Asn Leu Asp Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
```

```
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
```

```
                     370                 375                 380
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
            450

<210> SEQ ID NO 68
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 69
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 69

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Glu Met His Trp Val Arg Gln Ala Pro Gly Gln Gly Leu Glu Trp Met
        35                  40                  45
Gly Ala Leu Asp Pro Lys Thr Gly Asp Thr Ala Tyr Ser Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Phe Tyr Ser Tyr Thr Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 70
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 71
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45
```

```
Gly Glu Ile Asn His Ser Gly Ser Thr Asn Tyr Asn Pro Ser Leu Lys
 50                  55                  60

Ser Arg Val Thr Ile Ser Val Glu Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 72
<211> LENGTH: 220
```

<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 72

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 73
<211> LENGTH: 450
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
            210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                    325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 74
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 75
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Thr Gly Arg Thr Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 76
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 77
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 77

Xaa Val Gln Leu Val Gln Ser Gly Ala Glu Val Lys Lys Pro Gly Glu
1               5                   10                  15

Thr Val Lys Ile Ser Cys Lys Ala Ser Asp Tyr Thr Phe Thr Tyr Tyr
            20                  25                  30

Gly Met Asn Trp Val Lys Gln Ala Pro Gly Gln Gly Leu Lys Trp Met
        35                  40                  45

Gly Trp Ile Asp Thr Thr Thr Gly Glu Pro Thr Tyr Ala Gln Lys Phe
 50                  55                  60

Gln Gly Arg Ile Ala Phe Ser Leu Glu Thr Ser Ala Ser Thr Ala Tyr
65                  70                  75                  80

Leu Gln Ile Lys Ser Leu Lys Ser Glu Asp Thr Ala Thr Tyr Phe Cys
                85                  90                  95

Ala Arg Arg Gly Pro Tyr Asn Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 78
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Val Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Val Ser Gly Val Pro
    50                  55                  60
```

```
Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Leu Gln His
             85                  90                  95

Leu Glu Tyr Pro Phe Thr Phe Gly Pro Gly Thr Lys Leu Glu Leu Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 79
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Trp Thr Ser Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
             85                  90                  95

Arg Asp Gln Gly Gln Trp Leu Leu Pro Asp Ala Phe Asp Ile Trp Gly
            100                 105                 110

Gln Gly Thr Met Val Thr Val Ser Ser
            115                 120

<210> SEQ ID NO 80
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu Arg Ser
                20                  25                  30

Asn Gly Tyr Asn Tyr Leu Asp Trp Tyr Leu Gln Lys Pro Gly Gln Ser
            35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Ser Pro Ile Thr Phe Gly Gln Gly Thr Arg Leu Glu Ile Lys
            100                 105                 110

<210> SEQ ID NO 81
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Gln Gln Ser Gly Pro Glu Leu Glu Lys Pro Gly Ala
1               5                   10                  15

Ser Val Lys Leu Ser Cys Lys Ala Ser Gly Tyr Ser Phe Thr Gly Tyr
                20                  25                  30

Asn Met Asn Trp Val Lys Gln Ser His Gly Lys Ser Leu Glu Trp Ile
            35                  40                  45

Gly His Ile Asp Pro Tyr Tyr Gly Asp Thr Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Val Lys Gly Gly Tyr Tyr Gly His Trp Tyr Phe Asp Val Trp Gly Ala
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
                260                 265                 270
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 82
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Gly Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Val Ser Ser Pro Pro
                85                  90                  95

Thr Phe Gly Ala Gly Thr Lys Leu Glu Leu Lys Arg Ala Asp Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Lys Ala Asp Tyr Glu Lys His Lys Val Tyr Ala Cys Glu Val Thr His
            180                 185                 190

Gln Gly Leu Ser Ser Pro Val Thr Lys Ser Phe Asn Arg Gly Glu Cys
        195                 200                 205

<210> SEQ ID NO 83
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Gln Gln Ser Gly Pro Glu Leu Lys Lys Pro Gly Thr
1               5                   10                  15

Ser Val Arg Ile Ser Cys Lys Thr Ser Trp Val Lys Gln Ser His Gly
            20                  25                  30

Lys Ser Leu Glu Trp Ile Gly Lys Ala Thr Leu Thr Val Asp Lys Ser
        35                  40                  45

Ser Ser Thr Ala Tyr Met Glu Leu Arg Ser Leu Thr Ser Glu Asp Ser
    50                  55                  60

Ala Val Tyr Tyr Cys Ala Ala Trp Gly Gln Gly Thr Thr Leu Thr Val
65                  70                  75                  80

Ser Ser

<210> SEQ ID NO 84
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Ser His Lys Phe Met Ser Thr Ser Val Gly
1               5                   10                  15

Asp Arg Val Ser Ile Ile Cys Trp Tyr Gln Gln Lys Pro Gly Gln Ser
            20                  25                  30

Pro Lys Leu Leu Ile Tyr Gly Val Pro Asp Arg Phe Thr Gly Ser Gly
        35                  40                  45

Ser Gly Thr Asp Phe Thr Leu Thr Ile Thr Asn Val Gln Ser Glu Asp
    50                  55                  60

Leu Ala Asp Tyr Phe Cys Phe Gly Ala Gly Thr Met Leu Asp Leu Lys
65                  70                  75                  80

<210> SEQ ID NO 85
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30
```

```
Gly Met Ser Val Gly Trp Ile Arg Gln Pro Gly Lys Ala Leu Glu
        35                  40                  45
Trp Leu Ala Asp Ile Trp Trp Asp Asp Lys Lys Asp Tyr Asn Pro Ser
 50                  55                  60
Leu Lys Ser Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                 85                  90                  95
Cys Ala Arg Ser Met Ile Thr Asn Trp Tyr Phe Asp Val Trp Gly Ala
            100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 86
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 87
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 88
<211> LENGTH: 214
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```